(12) United States Patent
Alexander et al.

(10) Patent No.: US 11,959,838 B2
(45) Date of Patent: Apr. 16, 2024

(54) REPRESENTATIVE DIAGNOSTICS

(71) Applicant: Ventana Medical Systems, Inc., Tucson, AZ (US)

(72) Inventors: Nelson Alexander, Marana, AZ (US); Aoune Barhoumi, Tucson, AZ (US); Melinda Day, Oro Valley, AZ (US); Lisa Gallegos, Tucson, AZ (US); Katherine Leith, Tucson, AZ (US); Samantha Rajkovich, Marana, AZ (US); Esteban Roberts, Tucson, AZ (US); Stacey Stanislaw, Tucson, AZ (US); Eric Walk, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 15/965,786

(22) Filed: Apr. 27, 2018

(65) Prior Publication Data
US 2020/0049599 A1 Feb. 13, 2020

Related U.S. Application Data

(63) Continuation of application No. PCT/US2016/060861, filed on Nov. 7, 2016.

(60) Provisional application No. 62/418,146, filed on Nov. 4, 2016, provisional application No. 62/354,622, filed on Jun. 24, 2016, provisional application No. 62/279,405, filed on Jan. 15, 2016, provisional application No. 62/252,153, filed on Nov. 6, 2015.

(51) Int. Cl.
| | | |
|---|---|---|
| *G01N 1/28* | (2006.01) | |
| *A01N 1/02* | (2006.01) | |
| *G01N 1/30* | (2006.01) | |
| *G01N 1/36* | (2006.01) | |
| *G01N 33/483* | (2006.01) | |

(52) U.S. Cl.
CPC ........... *G01N 1/286* (2013.01); *A01N 1/0226* (2013.01); *A01N 1/0278* (2013.01); *G01N 1/30* (2013.01); *G01N 1/36* (2013.01); *G01N 33/4833* (2013.01); *G01N 2001/2866* (2013.01); *G01N 2001/368* (2013.01)

(58) Field of Classification Search
CPC .............................. G01N 1/30; G01N 33/4833
See application file for complete search history.

(56) References Cited

U.S. PATENT DOCUMENTS

| | | | |
|---|---|---|---|
| 3,130,101 A | 4/1964 | Gittins et al. | |
| 4,469,797 A | 9/1984 | Albarella | |
| 4,616,658 A | 10/1986 | Shell et al. | |
| 4,683,195 A | 7/1987 | Mullis et al. | |
| 4,774,339 A | 9/1988 | Haugland et al. | |
| 4,811,741 A | 3/1989 | Shell et al. | |
| 5,132,432 A | 7/1992 | Haugland et al. | |
| 5,187,288 A | 2/1993 | Kang et al. | |
| 5,198,537 A | 3/1993 | Huber et al. | |
| 5,248,782 A | 9/1993 | Haugland et al. | |
| 5,262,357 A | 11/1993 | Alivisatos et al. | |
| 5,274,113 A | 12/1993 | Kang et al. | |
| 5,338,854 A | 8/1994 | Kang et al. | |
| 5,433,896 A | 7/1995 | Kang et al. | |
| 5,451,663 A | 9/1995 | Kang et al. | |
| 5,505,928 A | 4/1996 | Alivisatos et al. | |
| 5,571,018 A | 11/1996 | FitzGerald | |
| 5,690,807 A | 11/1997 | Clark, Jr. et al. | |
| 5,696,157 A | 12/1997 | Wang et al. | |
| 5,753,485 A | 5/1998 | Dwulet et al. | |
| 5,800,996 A | 9/1998 | Lee et al. | |
| 5,830,912 A | 11/1998 | Gee et al. | |
| 5,843,644 A | 12/1998 | Liotta et al. | |
| 5,866,366 A | 2/1999 | Kallender | |
| 5,990,479 A | 11/1999 | Weiss et al. | |
| 6,048,616 A | 4/2000 | Gallagher et al. | |
| 6,114,038 A | 9/2000 | Castro et al. | |
| 6,130,101 A | 10/2000 | Mao et al. | |

(Continued)

FOREIGN PATENT DOCUMENTS

| | | |
|---|---|---|
| CA | 2694050 A1 | 2/2009 |
| CN | 1488639 A | 4/2004 |

(Continued)

OTHER PUBLICATIONS

De Petris et al. "A novel method for sample preparation of fresh lung cancer tissue proteomics analysis by tumor cell enrichment an dremoval of blood contaminants" Proteome Science 2010, 8: 9 (Year: 2010).*
Burden "Guide to the Disruption of Biological Samples" Random Primers, Issue No. 12, 2012, pp. 1-25) (Year: 2012).*
Koutna "Flow Cytometry Analysis of Intracellular Protein" Flow Cytometry Recent Perspectives (Year: 2012).*
Jordanova et al. "Flow cytometric sorting of paraffin-embedded tumor tissues considerably improves molecular genetic analysis." American Journal of Clinical Pathology 120.3 (2003): 327-334. (Year: 2003).*

(Continued)

*Primary Examiner* — Emily A Cordas
(74) *Attorney, Agent, or Firm* — Charney IP Law LLC; Thomas M. Finetti

(57) ABSTRACT

The disclosure generally relates to the preparation of representative samples from clinical samples, e.g., tumors (whole or in part), lymph nodes, metastases, cysts, polyps, or a combination or portion thereof, using mechanical and/or biochemical dissociation methods to homogenize intact samples or large portions thereof. The resulting homogenate provides the ability to obtain a correct representative sample despite spatial heterogeneity within the sample, increasing detection likelihood of low prevalence subclones, and is suitable for use in various diagnostic assays as well as the production of therapeutics, especially "personalized" anti-tumor vaccines or immune cell based therapies.

43 Claims, 78 Drawing Sheets
(67 of 78 Drawing Sheet(s) Filed in Color)
Specification includes a Sequence Listing.

(56) References Cited

U.S. PATENT DOCUMENTS

| | | |
|---|---|---|
| 6,207,229 B1 | 3/2001 | Bawendi et al. |
| 6,207,392 B1 | 3/2001 | Weiss et al. |
| 6,225,198 B1 | 5/2001 | Alivisatos et al. |
| 6,238,922 B1 | 5/2001 | Uchida |
| 6,274,323 B1 | 8/2001 | Bruchez et al. |
| 6,306,736 B1 | 10/2001 | Alivisatos et al. |
| 6,500,622 B2 | 12/2002 | Bruchez, Jr. et al. |
| 6,593,100 B2 | 7/2003 | Bobrow et al. |
| 6,602,671 B1 | 8/2003 | Bawendi et al. |
| 6,610,488 B2 | 8/2003 | Danenberg et al. |
| 6,649,138 B2 | 11/2003 | Adams |
| 6,682,596 B2 | 1/2004 | Zehnder et al. |
| 6,689,338 B2 | 2/2004 | Kotov |
| 6,709,929 B2 | 3/2004 | Zhang et al. |
| 6,716,979 B2 | 4/2004 | Diwu et al. |
| 6,815,064 B2 | 11/2004 | Treadway et al. |
| 6,818,395 B1 | 11/2004 | Quake et al. |
| 6,855,202 B2 | 2/2005 | Alivisatos et al. |
| 6,914,256 B2 | 7/2005 | Zhang et al. |
| 6,927,069 B2 | 8/2005 | Weiss et al. |
| 7,049,141 B1 | 5/2006 | Uchida |
| 7,169,560 B2 | 1/2007 | Lapidus et al. |
| 7,588,890 B2 | 9/2009 | Chu |
| 7,803,637 B2 | 9/2010 | Terman |
| 8,262,900 B2 | 9/2012 | Rothberg et al. |
| 8,673,241 B2 | 3/2014 | Groelz et al. |
| 9,029,138 B2 | 5/2015 | Groelz et al. |
| 9,192,629 B2 | 11/2015 | Presnell et al. |
| 9,719,986 B2 | 8/2017 | Kosmeder, II et al. |
| 9,850,311 B2 | 12/2017 | Gurney et al. |
| 10,105,392 B2 | 10/2018 | Presnell et al. |
| 10,109,052 B2 | 10/2018 | Chefd'hotel et al. |
| 10,132,796 B2 | 11/2018 | Stauber et al. |
| 10,650,221 B2 | 5/2020 | Chukka et al. |
| 11,085,079 B2 | 8/2021 | Sanders et al. |
| 2002/0164629 A1 | 11/2002 | Quake et al. |
| 2003/0165518 A1 | 9/2003 | Berd |
| 2003/0165951 A1 | 9/2003 | Bruchez, Jr. et al. |
| 2005/0112141 A1 | 5/2005 | Terman |
| 2005/0233367 A1* | 10/2005 | Chu ................. B01L 3/502753 435/6.15 |
| 2006/0199197 A1* | 9/2006 | Danenberg ......... C12N 15/1003 435/6.12 |
| 2008/0227695 A1 | 9/2008 | Akiyama et al. |
| 2009/0026082 A1 | 1/2009 | Rothberg et al. |
| 2009/0047656 A1 | 2/2009 | Baden et al. |
| 2009/0127589 A1 | 5/2009 | Rothberg et al. |
| 2009/0191565 A1 | 7/2009 | Lapidus et al. |
| 2010/0029498 A1 | 2/2010 | Gnirke et al. |
| 2010/0035252 A1 | 2/2010 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0267081 A1* | 10/2010 | Groelz ..................... G01N 1/36 435/40.5 |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0027275 A1 | 2/2011 | Ferrara et al. |
| 2011/0033854 A1 | 2/2011 | Drmanac et al. |
| 2011/0293637 A1 | 12/2011 | Hacohen et al. |
| 2012/0207856 A1 | 8/2012 | Goel et al. |
| 2012/0219948 A1 | 8/2012 | Yun et al. |
| 2012/0238463 A1 | 9/2012 | Goel et al. |
| 2013/0109019 A1 | 5/2013 | Murillo et al. |
| 2013/0115628 A1 | 5/2013 | Isaacson et al. |
| 2013/0252240 A1 | 9/2013 | Cutler et al. |
| 2013/0260385 A1 | 10/2013 | Dylla et al. |
| 2013/0302852 A1 | 11/2013 | Barnes et al. |
| 2013/0345087 A1 | 12/2013 | Yamagata et al. |
| 2014/0106391 A1 | 4/2014 | Stauber et al. |
| 2014/0234959 A1 | 8/2014 | McGrath et al. |
| 2014/0242576 A1 | 8/2014 | Cuppens |
| 2014/0242611 A1 | 8/2014 | Bazin et al. |
| 2014/0278461 A1 | 9/2014 | Artz |
| 2015/0045232 A1 | 2/2015 | Han et al. |
| 2015/0093416 A1 | 4/2015 | Hanna, Jr. |
| 2015/0276563 A1 | 10/2015 | Carrigan et al. |
| 2016/0130558 A1 | 5/2016 | Baer |
| 2017/0010194 A1 | 1/2017 | Showalter et al. |
| 2017/0120213 A1 | 5/2017 | Drmanac et al. |
| 2017/0173180 A1 | 6/2017 | Li |
| 2019/0272891 A1 | 9/2019 | Kural |
| 2020/0049599 A1 | 2/2020 | Alexander et al. |
| 2021/0270857 A1 | 9/2021 | Durrant et al. |
| 2022/0389523 A1 | 12/2022 | Demichelis et al. |

FOREIGN PATENT DOCUMENTS

| | | |
|---|---|---|
| CN | 1659287 A | 8/2005 |
| CN | 101955541 A | 1/2011 |
| CN | 101955541 B | 10/2012 |
| CN | 101778672 B | 2/2013 |
| CN | 103045467 A | 4/2013 |
| CN | 103688151 B | 5/2016 |
| CN | 103858010 B | 11/2016 |
| CN | 103937737 B | 5/2023 |
| EP | 1733739 A1 | 12/2006 |
| ES | 2319039 A1 | 5/2009 |
| JP | S62221334 A | 9/1987 |
| JP | H09508026 | 8/1997 |
| JP | H09508026 A | 8/1997 |
| JP | H10500205 A | 1/1998 |
| JP | 2002536991 A | 11/2002 |
| JP | WO2005094887 A1 | 2/2008 |
| JP | WO2008150001 A1 | 8/2010 |
| JP | 2010535332 A | 11/2010 |
| JP | WO2012124338 A1 | 7/2014 |
| JP | 2014519816 A | 8/2014 |
| RU | 2521239 C1 | 6/2014 |
| WO | 1992020781 A1 | 11/1992 |
| WO | 1996000283 A1 | 1/1996 |
| WO | WO9600283 | 1/1996 |
| WO | 1999026299 A1 | 5/1999 |
| WO | 2000050572 A1 | 8/2000 |
| WO | 2003063802 A2 | 8/2003 |
| WO | 2003087766 A2 | 10/2003 |
| WO | 2005094887 A1 | 10/2005 |
| WO | 2007053577 A2 | 5/2007 |
| WO | 2008063378 A2 | 5/2008 |
| WO | 2008150001 A1 | 12/2008 |
| WO | 2009016254 A1 | 2/2009 |
| WO | 2009099602 A1 | 8/2009 |
| WO | 2010056328 A1 | 5/2010 |
| WO | 2012003476 A2 | 1/2012 |
| WO | 2012031280 A2 | 3/2012 |
| WO | 2012096842 A1 | 7/2012 |
| WO | 2012116949 A1 | 9/2012 |
| WO | 2012124338 A1 | 9/2012 |
| WO | 2012152747 A2 | 11/2012 |
| WO | 2012154552 A1 | 11/2012 |
| WO | 2012164221 A1 | 12/2012 |
| WO | 2013004970 A1 | 1/2013 |
| WO | 2013019945 A2 | 2/2013 |
| WO | 2013068528 A1 | 5/2013 |
| WO | 2013079606 A1 | 6/2013 |
| WO | 2013139555 A1 | 9/2013 |
| WO | 2014056812 A1 | 4/2014 |
| WO | 2014086465 A1 | 6/2014 |
| WO | 2014086765 A2 | 6/2014 |
| WO | 2014106076 A2 | 7/2014 |
| WO | 2014139979 A1 | 9/2014 |
| WO | 2014144478 A2 | 9/2014 |
| WO | 2014202199 A1 | 12/2014 |
| WO | 2015048305 A1 | 4/2015 |
| WO | 2015052128 A1 | 4/2015 |
| WO | 2015058093 A1 | 4/2015 |
| WO | 2015148879 A1 | 10/2015 |

(56) References Cited

FOREIGN PATENT DOCUMENTS

| | | |
|---|---|---|
| WO | 2015150278 A1 | 10/2015 |
| WO | 2015197742 A1 | 12/2015 |

OTHER PUBLICATIONS

Shioyama et al. "Intraoperative flow cytometry analysis of glioma tissue for rapid determination of tumor presence and its histopathological grade." Journal of Neurosurgery 118.6 (2013): 1232-1238. (Year: 2013).*

Garaud et al. "A simple and rapid protocol to non-enzymatically dissociate fresh human tissues for the analysis of infiltrating lymphocytes." Journal of Visualized Experiments: JoVE 94 (2014). (Year: 2014).*

Khattar, Mithun "Dissociate Tissues for Cell Recovery", from Biocompare webpage, accessed Nov. 29, 2022<< Dissociate Tissues for Cell Recovery | Biocompare Product Review. >>, published online May 13, 2015 (Year: 2015).*

Mørkve et al. "Influence of tissue preparation techniques on p53 expression in bronchial and bladder carcinomas, assessed by immunofluorescence staining and flow cytometry." Cytometry: The Journal of the International Society for Analytical Cytology 12.7 (1991): 622-627. (Year: 1991).*

Hardt et al. "Highly sensitive profiling of CD44+/CD24− breast cancer stem cells by combining global mRNA amplification and next generation sequencing: evidence for a hyperactive PI3K pathway." Cancer letters 325.2 (2012): 165-174. (Year: 2012).*

Blaud-Rotureau et al, 2002, "A Comparative Analysis of FISH, RT-PCR, PCR, and Immunohistochemistry for the Diagnosis of Mantle Cell Lymphomas", Modern Pathology, 15(5): 517-525.

Burden, David W., Ph.D., 2012, "Guide to the Disruption of Biological Samples", Random Primers, Jan. 2012, 12:1-25.

Bzhalava et al, 2014, "Deep sequencing extends the diversity of human papillomaviruses in human skin", Scientific Reports, 4(24):5807.

Casbon et al., 2011, "A method for counting PCR template molecules with application to next-generation sequencing", Nucleic Acids Research, 39(12):e81.

Cottrell et al, 2014, "Validation of a Next-Generation Sequencing Assay for Clinical Molecular Oncology", The Journal of Molecular Diagnostics, 16(1):89-105.

International Search Report and Written Opinion dated Apr. 20, 2017 in corresponding PCT/US2016/060861 filed Nov. 7, 2016, pp. 1-18.

Kim et al, 2013, "A Microfluidic DNA Library Preparation Platform for Next-Generation Sequencing", PLOS One, 8(7):e68988.

Mansour et al, 2014, "A novel xylene-free deparaffinization method for the extraction of proteins from human derived formalin-fixed paraffin embedded (FFPE) archival tissue blocks", MethodsX, 1:90-95.

Mattsson et al, 2007, "Detection of Genetic Alterations by ImmunoFISH Analysis of Whole Cells Extracted from Routine Biopsy Material", Journal of Molecular Diagnostics, 9(4): 479-489, vol. 9, No. 4.

Pareek et al, 2011, "Sequencing technologies and genome sequencing", Journal of Applied Genetics, 52 (4):413-435.

Thaitrong et al, 2012, "Quality control of next-generation sequencing library through an integrative digital microfluidic platform", Electrophoresis, 2012, 33:3506-3513.

Ural State Medical Academy of the Fed Agency for Health Care and Social Development, 2007 (also available at https://studfile.net/preview/6460816/page:11/).

Yu, W. et al, Microbiology and Inspection Technology, -, (2008), 1st edition, pp. 42-44,, -, Heilongjiang Science and Technology Press.

Yu, W. et al., Microbiology and Inspection Technology, Section 11 Operational specifications for tissue specimen culture, (2008), 1st edition, pp. 42-44 / EN-Abstract, -, Heilongjiang Science and Technology Press.

Jordanova et al., Am Journ Clincal Pathology, 120:3 (2003): 327-334.

Koutna_Flow Cytometry—Recent Perspectives_2012_421.pdf.

De Petris_Proteome Science_8_2010_1.

Shioyama, T. et al. Journal of Neurosurgery 118.6 (2013): 1232-1238.

Sprung R W et al., Equivalence of Protein Inventories Obtained from Formalin-fixed Paraffin-embedded and Frozen Tissue in Multidimensional Liquid Chromatography-Tandem Mass Spectrometry Shotgun Proteomic Analysis, Molecular & Cellular Proteomics, Apr. 12, 2022 pp. 1988-1998.

Ralhan R et al., Discovery and Verification of Head-and-neck Cancer Biomarkers by Differential Protein Expression Analysis Using iTRAQ Labeling, Multidimensional Liquid Chromatography, and Tandem Mass Spectrometry, Molecular & Cellular Proteomics, Apr. 12, 2022 pp. 1162-1173.

Qiang, Cellular DNA content, tumor-associated antigen and tumor heterogeneity in gastric carcinoma, Chin J New Gastroenterol, 1997;5( 8) :500-501.

Fowler, et al_An Ultra-Sensitive Immunoassay for Quantifying Biomarkers in Breast Tumor Tissue_Journal of Cancer_2014 pp. 115-124.

Gutierrez, Maria Laura, et al., Cytogenetic heterogeneity of pancreatic ductal adenocarcinomas: identification of intratumoral pathways of clonal evolution, Histopathology, 2011, pp. 486-497, vol. 58.

Sayagues, Jose Maria et al., Intratumoural cytogenetic heterogeneity of sporadic colorectal carcinomas suggests several pathways to liver metastasis, Journal of Pathology, 2010, pp. 308-319, vol. 221.

Search Report and Written Opinion dated Oct. 13, 2023 in Patent Appl. No. 10202203644T.

* cited by examiner

Protocol # 145 : Rep Dia-DAB-Her2 (11/18/2015)
Procedure: Rep Dia BXT v1-DAB
BenchMark XT IHC/ISH Staining Module

| Step No | Procedure Step |
|---|---|
| 1 | ***** Select EZ Prep ***** |
| 2 | ***** Start Timed Steps ***** |
| 3 | ***** Mixers On ***** |
| 4 | Rinse Slide With Reaction Buffer |
| 5 | Adjust Slide Volume With Reaction Buffer |
| 6 | Apply Long Cell Conditioner #1 |
| 7 | Apply CC Coverslip Long |
| 8 | Warmup Slide to 90 Deg C, and Incubate for 4 Minutes |
| 9 | Apply Cell Conditioner #1 |
| 10 | Incubate for [4 Minutes] ( Cell Conditioner #1 ) |
| 11 | Disable Slide Heater |
| 12 | Incubate for [4 Minutes] ( Cell Conditioner #1 ) |
| 13 | Apply 350ul of Reaction Buffer |
| 14 | Apply Coverslip |
| 15 | Warmup Slide to 37 Deg C |
| 16 | ***** Procedure Synchronization ***** |
| 17 | ***** Select SSC Wash ***** |
| 18 | Warmup Slide to 37 Deg C |
| 19 | Rinse Slide With Reaction Buffer |
| 20 | Adjust Slide Volume With Reaction Buffer |
| 21 | Apply One Drop of CV PEROX INHTR, Apply Coverslip, and Incubate for 4 Minutes |
| 22 | Rinse Slide With Reaction Buffer |
| 23 | Adjust Slide Volume With Reaction Buffer |
| 24 | Apply Coverslip |
| 25 | [ If not selected, temperature will default to 37°C. ] |
| 26 | Warmup Slide to 37 Deg C, and Incubate for 4 Minutes |
| 27 | Rinse Slide With Reaction Buffer |
| 28 | Adjust Slide Volume With Reaction Buffer |
| 29 | Apply Coverslip, One Drop of (ANTIBODY 6) ( Antibody ), and Incubate for [0 Hr 4 Min] |
| 30 | [ Titration will only happen if selected ] |
| 31 | Warmup Slide to 37 Deg C |
| 32 | Rinse Slide With Reaction Buffer |
| 33 | Apply 450ul + VA Reaction Buffer |
| 34 | Apply Coverslip |
| 35 | Rinse Slide With Reaction Buffer |
| 36 | Apply 450ul + VA Reaction Buffer |
| 37 | Apply Coverslip |
| 38 | Rinse Slide With Reaction Buffer |
| 39 | [ If not selected, HQ Universal Linker will dispense and incubate 8 min in normal slide volume. ] |
| 40 | Adjust Slide Volume With Reaction Buffer |
| 41 | Apply Coverslip, One Drop of CV HQ UNIV LNKR, and Incubate for 8 Minutes |
| 42 | Rinse Slide With Reaction Buffer |
| 43 | Apply 450ul + VA Reaction Buffer |
| 44 | Apply Coverslip |
| 45 | Rinse Slide With Reaction Buffer |

FIG. 10

Protocol # 145 : Rep Dia-DAB-Her2 (11/18/2015)
Procedure: Rep Dia BXT v1-DAB
BenchMark XT IHC/ISH Staining Module

| Step No. | Procedure Step |
|---|---|
| 46 | Apply 450uL + VA Reaction Buffer |
| 47 | Apply Coverslip |
| 48 | Rinse Slide With Reaction Buffer |
| 49 | ( If not selected, HRP Multimer will dispense and incubate 8 min in normal slide volume. ) |
| 50 | Adjust Slide Volume With Reaction Buffer |
| 51 | Apply Coverslip, One Drop of OV HRP MULTIMER, and Incubate for 8 Minutes |
| 52 | Rinse Slide With Reaction Buffer |
| 53 | Apply 900uL of Reaction Buffer |
| 54 | Apply Coverslip |
| 55 | ( OptiView Amplifier and OptiView Amplification H2O2 incubation time ) |
| 56 | Rinse Slide With Reaction Buffer |
| 57 | Adjust Slide Volume With Reaction Buffer |
| 58 | Apply One Drop of OV AMP H2O2 and One Drop of OV AMPLIFIER, Apply Coverslip, Incubate for (4 Minutes |
| 59 | Rinse Slide With Reaction Buffer |
| 60 | Apply 900uL of Reaction Buffer |
| 61 | Apply Coverslip |
| 62 | ( OptiView Amplification Multimer incubation time ) |
| 63 | Rinse Slide With Reaction Buffer |
| 64 | Adjust Slide Volume With Reaction Buffer |
| 65 | Apply One Drop of OV AMP MULTIMER, Apply Coverslip, and Incubate for (4 Minutes |
| 66 | Rinse Slide With Reaction Buffer |
| 67 | Apply 900uL of Reaction Buffer |
| 68 | Apply Coverslip |
| 69 | Rinse Slide With Reaction Buffer |
| 70 | Apply 450uL + VA Reaction Buffer |
| 71 | Apply Coverslip |
| 72 | Rinse Slide With Reaction Buffer |
| 73 | Apply 450uL + VA Reaction Buffer |
| 74 | Apply Coverslip |
| 75 | Rinse Slide With Reaction Buffer |
| 76 | Adjust Slide Volume With Reaction Buffer |
| 77 | Apply One Drop of OV H2O2 and One Drop of OV DAB, Apply Coverslip, Incubate for 8 Minutes |
| 78 | Rinse Slide With Reaction Buffer |
| 79 | Adjust Slide Volume With Reaction Buffer |
| 80 | Apply One Drop of OV COPPER, Apply Coverslip, and Incubate for 4 Minutes |
| 81 | Rinse Slide With Reaction Buffer |
| 82 | Adjust Slide Volume With Reaction Buffer |
| 83 | Apply Coverslip |
| 84 | Disable Slide Heater |
| 85 | \*\*\*\* Select Optional Wash \*\*\*\* |
| 86 | \*\*\*\* Select SSC Wash \*\*\*\* |
| 87 | Warmup Slide to 37 Deg C |
| 88 | Rinse Slide With Reaction Buffer |
| 89 | Adjust Slide Volume With Reaction Buffer |
| 90 | Apply One Drop of (HEMATOXYLIN II) ( Counterstain ), Apply Coverslip, and Incubate for (8 Minutes |

\* one drop is one reagent dispense
Ventana Medical Systems, Inc., 1910 Innovation Park Drive Tucson, Arizona USA
NexES v10.6

Printed 12/07/2015 3:03:20 PM
Page 2 of 3

FIG. 10 (CONT)

Protocol # 145 : Rep Dia-DAB-Her2 (11/18/2015)
Procedure: Rep Dia BXT v1-DAB
BenchMark XT IHC/ISH Staining Module

| Step No. | Procedure Step |
|---|---|
| 91 | Rinse Slide With Reaction Buffer |
| 92 | Adjust Slide Volume With Reaction Buffer |
| 93 | Apply Coverslip |
| 94 | Rinse Slide With Reaction Buffer |
| 95 | Adjust Slide Volume With Reaction Buffer |
| 96 | Apply One Drop of [BLUING REAGENT] ( Post Counterstain ), Apply Coverslip, and Incubate for [8 Minutes] |
| 97 | Rinse Slide With Reaction Buffer |
| 98 | Adjust Slide Volume With Reaction Buffer |
| 99 | Apply Coverslip |
| 100 | Disable Slide Heater |
| 101 | ***** Start Timed Steps ***** |
| 102 | Rinse Slide With Reaction Buffer |

FIG. 10 (CONT)

Protocol # 150 : Rep Dia Fluorescence-4min/16min (11/18/2015)
Procedure: Rep Dia BXT v2-Fluorescence
BenchMark XT IHC/ISH Staining Module

| Step No. | Procedure Step |
|---|---|
| 1 | ***** Select EZ Prep ***** |
| 2 | ***** Start Timed Steps ***** |
| 3 | ***** Mixers On ***** |
| 4 | Rinse Slide With Reaction Buffer |
| 5 | Adjust Slide Volume With Reaction Buffer |
| 6 | Apply Long Cell Conditioner #1 |
| 7 | Apply CC Coverslip Long |
| 8 | Warmup Slide to 95 Deg C, and Incubate for 4 Minutes |
| 9 | Apply Cell Conditioner #1 |
| 10 | Incubate for [4 Minutes] ( Cell Conditioner #1 ) |
| 11 | Disable Slide Heater |
| 12 | Incubate for [4 Minutes] ( Cell Conditioner #1 ) |
| 13 | Apply 300ul of Reaction Buffer |
| 14 | Apply Coverslip |
| 15 | Warmup Slide to 37 Deg C |
| 16 | ***** Procedure Synchronization ***** |
| 17 | Warmup Slide to 37 Deg C |
| 18 | ***** Hand Apply ( Titration ), and Incubate for [0 Hr 4 Min] ***** |
| 19 | Rinse Slide With Reaction Buffer |
| 20 | Adjust Slide Volume With Reaction Buffer |
| 21 | Apply Coverslip |
| 22 | Rinse Slide With Reaction Buffer |
| 23 | Adjust Slide Volume With Reaction Buffer |
| 24 | Apply Coverslip |
| 25 | Warmup Slide to 37 Deg C |
| 26 | ***** Hand Apply ( Primary Antibody ), and Incubate for [0 Hr 16 Min] ***** |
| 27 | Rinse Slide With Reaction Buffer |
| 28 | Adjust Slide Volume With Reaction Buffer |
| 29 | Apply Coverslip |
| 30 | Rinse Slide With Reaction Buffer |
| 31 | Adjust Slide Volume With Reaction Buffer |
| 32 | Apply One Drop of [COUNTERSTAIN I] ( Counterstain ), Apply Coverslip, and Incubate for [4 Minutes] |
| 33 | Rinse Slide With Reaction Buffer |
| 34 | Adjust Slide Volume With Reaction Buffer |
| 35 | Apply Coverslip |
| 36 | ***** Start Timed Steps ***** |
| 37 | Rinse Slide With Reaction Buffer |
| 38 | Rinse Slide With Reaction Buffer |

* one drop is one reagent dispense
Ventana Medical Systems, Inc., 1910 Innovation Park Drive, Tucson, Arizona, USA
NexES v10.6

Protocol # 66 : Rep Dia BXT-multiplex (12/08/2015)
Procedure: Res IHC MultiplexSequentialAP-ER
BenchMark XT IHC/ISH Staining Module

| Step No. | Procedure Step |
|---|---|
| 91 | Apply Coverslip |
| 92 | Rinse Slide With Reaction Buffer |
| 93 | Adjust Slide Volume With Reaction Buffer |
| 94 | Apply Coverslip |
| 95 | Rinse Slide With Reaction Buffer |
| 96 | Adjust Slide Volume With Reaction Buffer |
| 97 | Apply Coverslip |
| 98 | ( Detection #2 ) |
| 99 | ( Tyr-Rhodamine Detection ) |
| 100 | Adjust Slide Volume With Reaction Buffer |
| 101 | Apply Two Drops of FIXATIVE 10, Apply Coverslip, and Incubate for 4 Minutes |
| 102 | Apply One Drop of OPTION 1, and Incubate for [0 Hr 20 Min] |
| 103 | Rinse Slide With Reaction Buffer |
| 104 | Adjust Slide Volume With Reaction Buffer |
| 105 | Apply Coverslip |
| 106 | Rinse Slide With Reaction Buffer |
| 107 | Adjust Slide Volume With Reaction Buffer |
| 108 | Apply Coverslip |
| 109 | ( Research Park #12 - denaturation w/ CC3 at 100C ) |
| 110 | ( Kill Step #2 ) |
| 111 | Rinse Slide With Reaction Buffer |
| 112 | Apply Short Cell Conditioner #2 |
| 113 | Apply Coverslip |
| 114 | Warmup Slide to [95 Deg C], and Incubate for [0 Hr 12 Min] ( Extra Pretreatment #2 Incubation ) |
| 115 | Warmup Slide to 37 Deg C |
| 116 | Disable Slide Heater |
| 117 | Warmup Slide to 37 Deg C |
| 118 | Rinse Slide With Reaction Buffer |
| 119 | Adjust Slide Volume With Reaction Buffer |
| 120 | Apply Coverslip |
| 121 | ( Primary Antibody #3 ) |
| 122 | Rinse Slide With Reaction Buffer |
| 123 | Adjust Slide Volume With Reaction Buffer |
| 124 | Apply Coverslip |
| 125 | Apply One Drop of [ANTIBODY 3] ( D3 Primary Antibody ), and Incubate for [16 Minutes] |
| 126 | Rinse Slide With Reaction Buffer |
| 127 | Adjust Slide Volume With Reaction Buffer |
| 128 | Apply Coverslip |
| 129 | ( Research Park #3 - Detection #3 ) |
| 130 | ( Secondary Antibody #3 ) |
| 131 | ( GAR/GAM AP enzyme conjugate ) |
| 132 | Rinse Slide With Reaction Buffer |
| 133 | Adjust Slide Volume With Reaction Buffer |
| 134 | Apply One Drop of [DETECTION 3] ( Detection #3 ), Apply Coverslip, and Incubate for [0 Hr 12 Min] |
| 135 | Adjust Slide Volume With Reaction Buffer |

FIG. 14 (CONT)

Protocol # 66 : Rep Dia BXT-multiplex (12/08/2015)
Procedure: Res IHC MultiplexSequentialAP-ER
BenchMark XT IHC/ISH Staining Module

FIG. 14 (CONT)

Protocol # 66 : Rep Dia BXT-multiplex (12/08/2015)
Procedure: Res IHC MultiplexSequentialAP-ER
BenchMark XT IHC/ISH Staining Module

FIG. 14 (CONT)

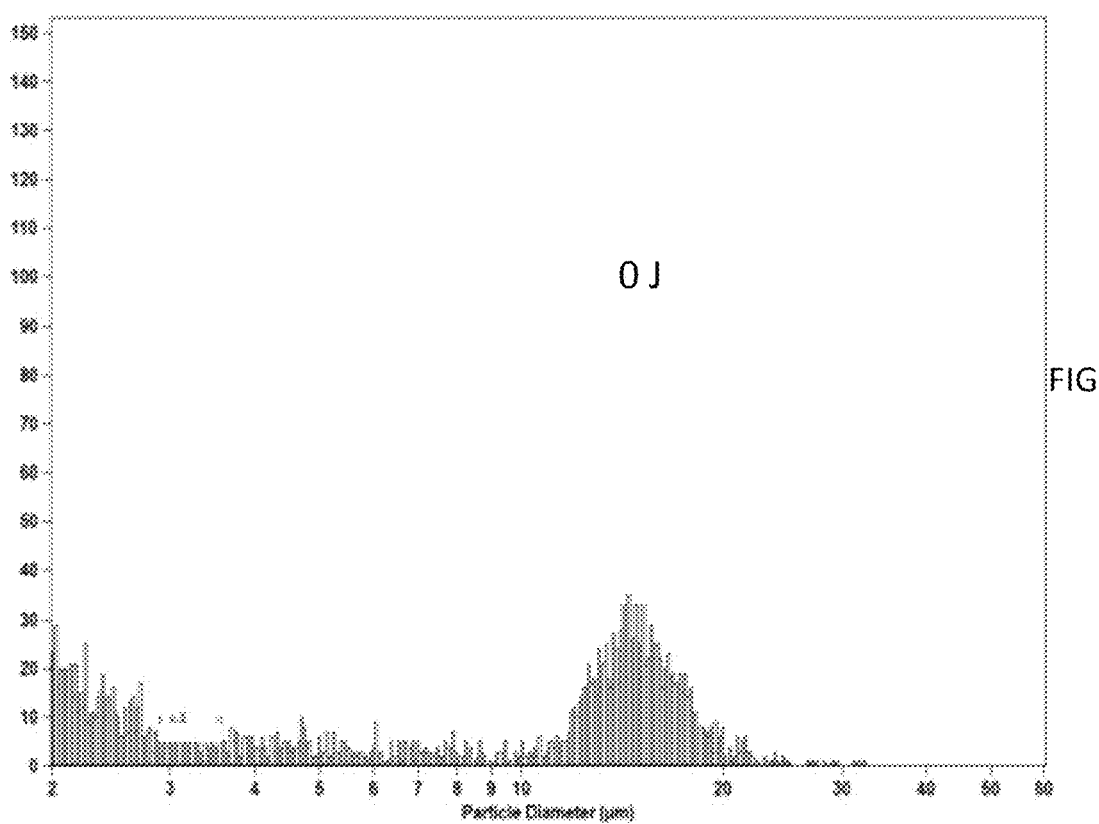
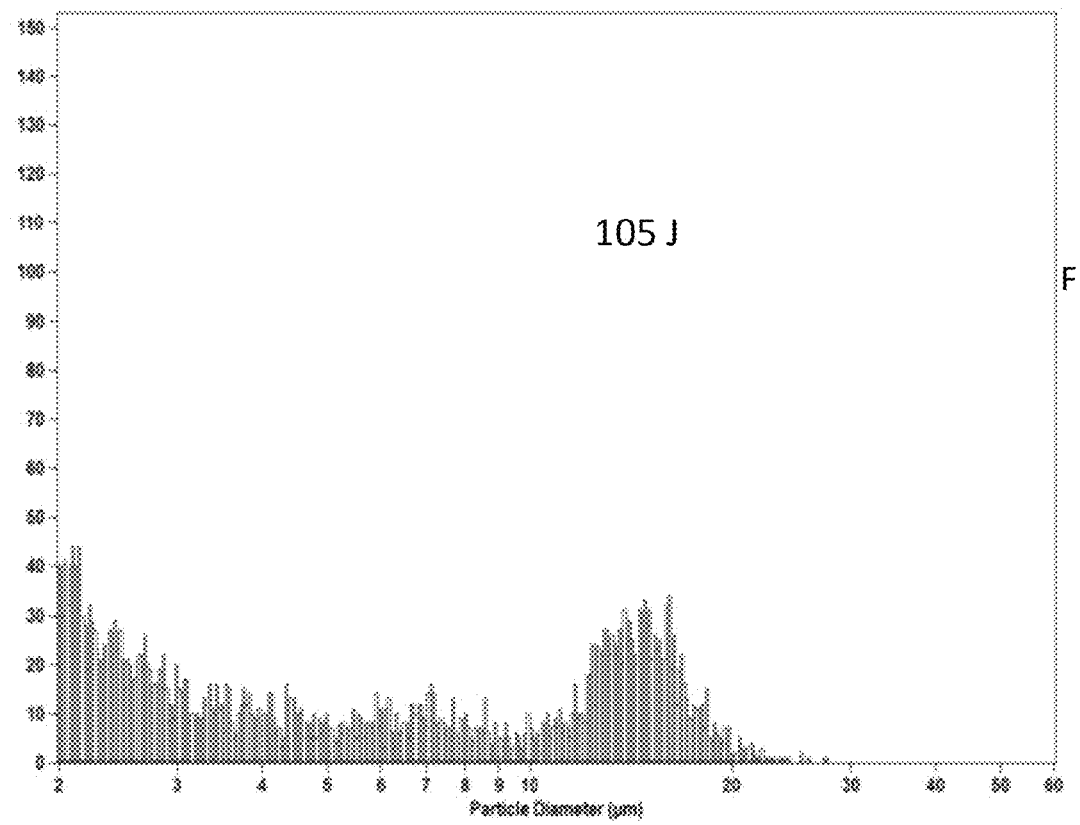
FIG. 32

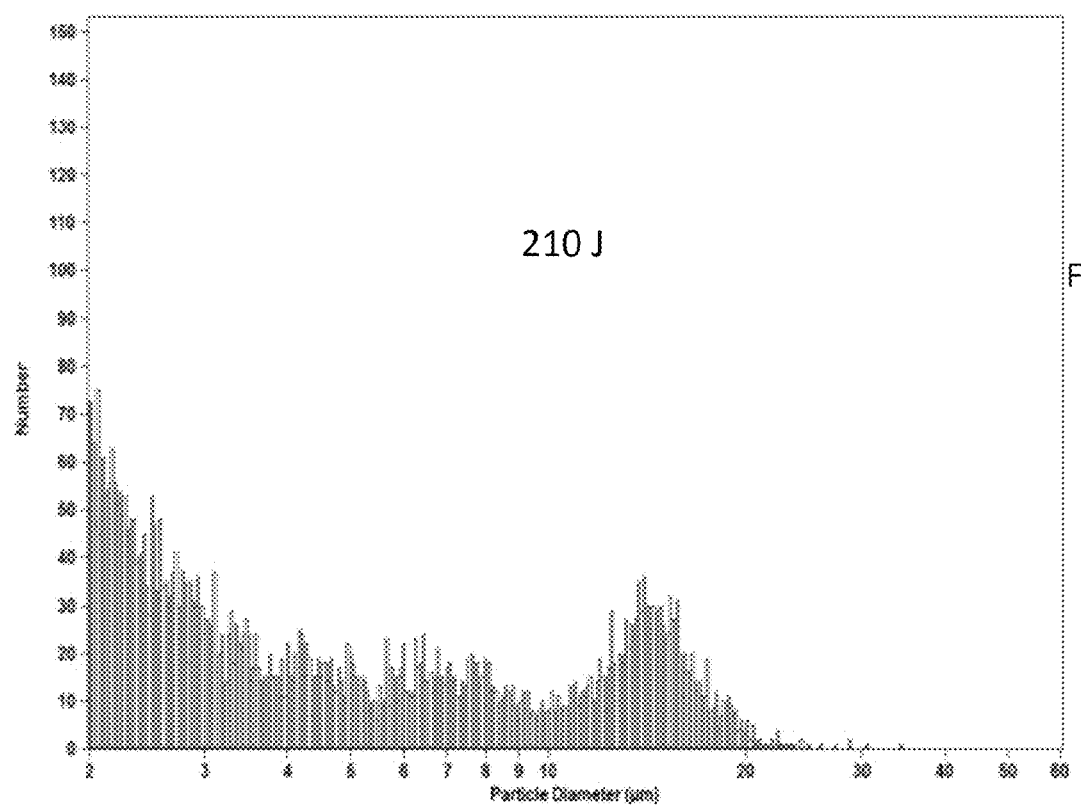
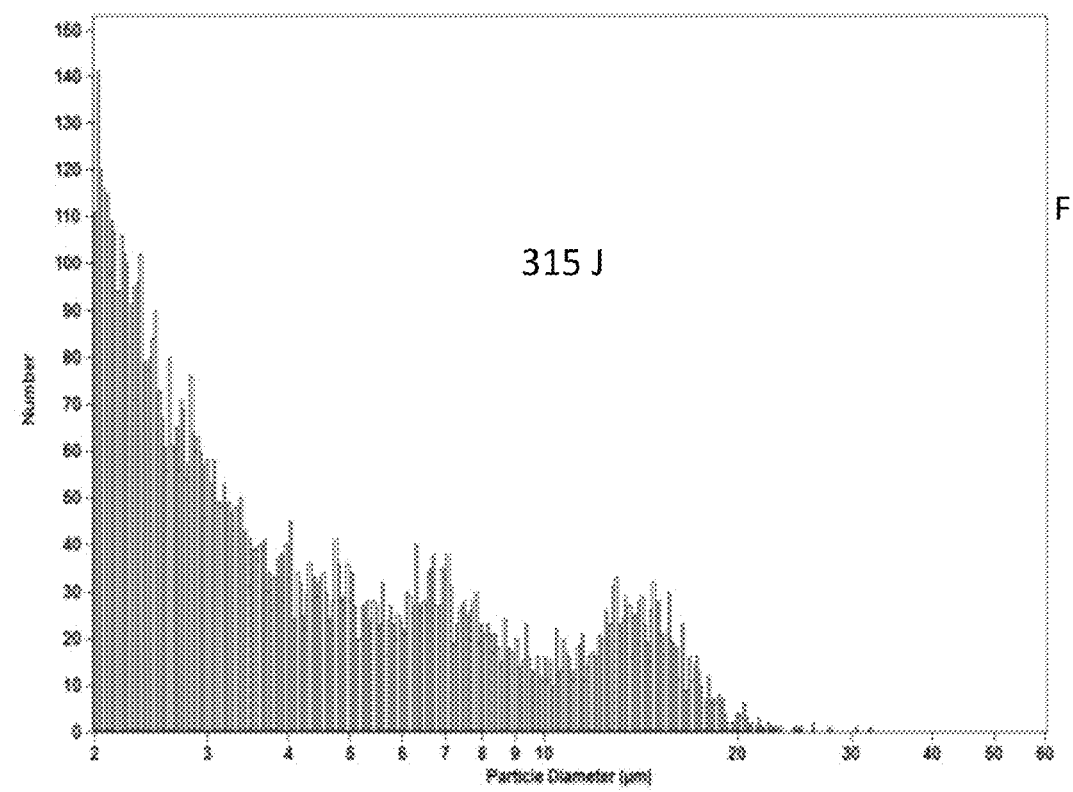
FIG. 32 (...cont.)

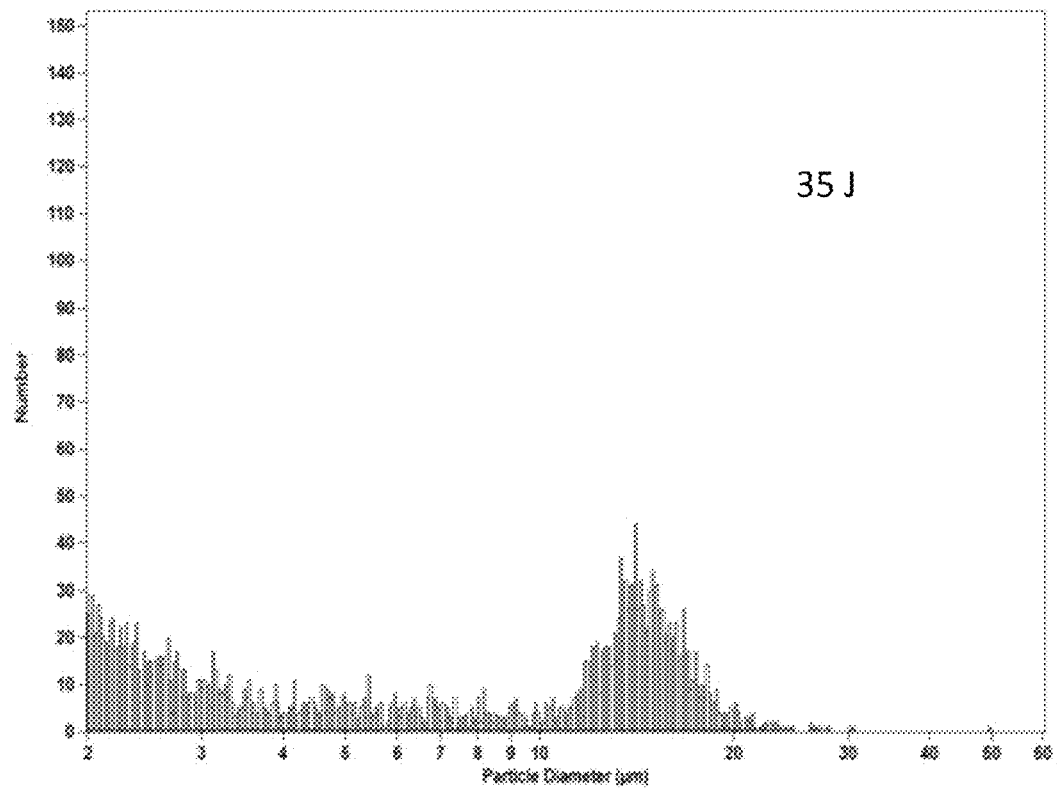
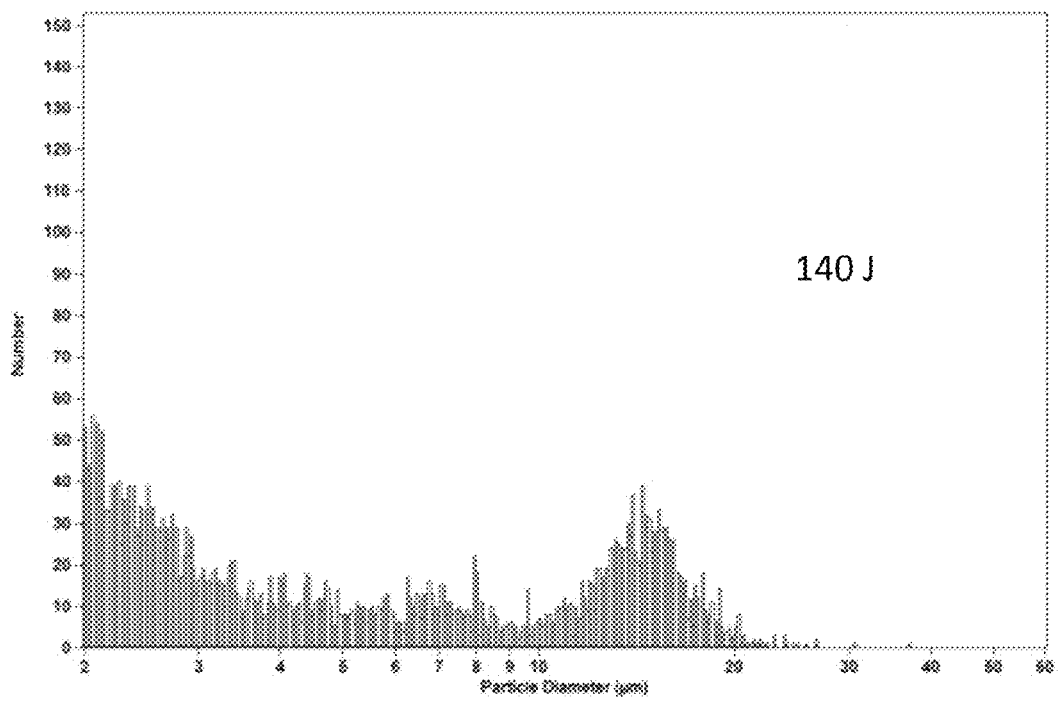
FIG. 32 (...cont.)

FIG. 42 A
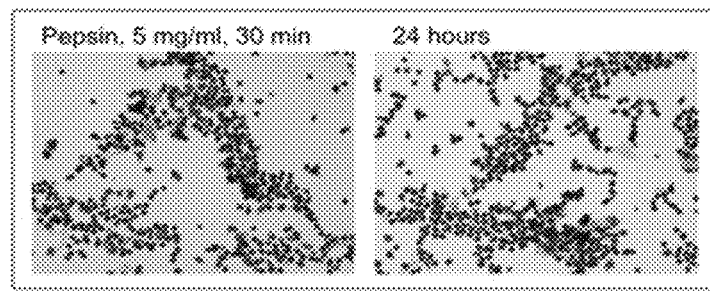
FIG. 42 B
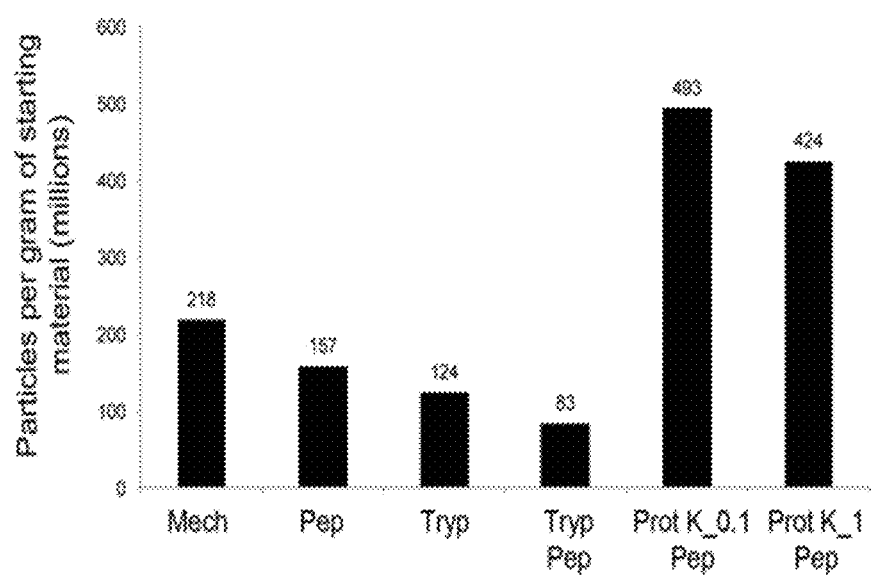
FIG. 43

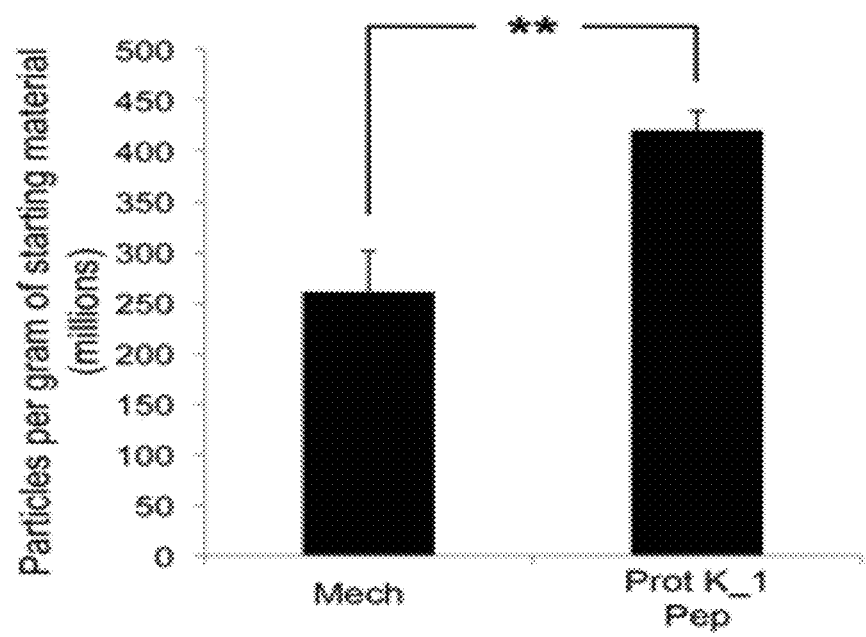
FIG. 44A
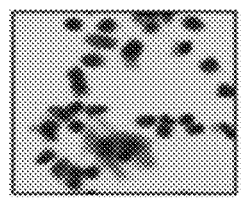
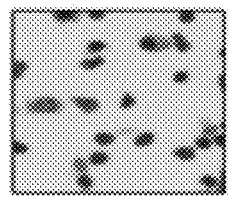
FIG. 44B  FIG. 44C

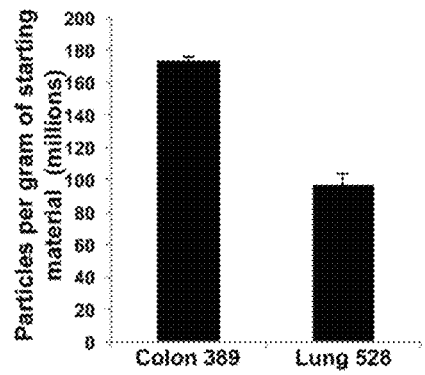
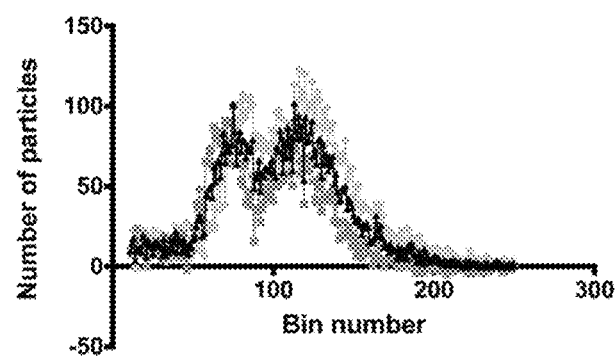
FIG. 45A          FIG. 45B
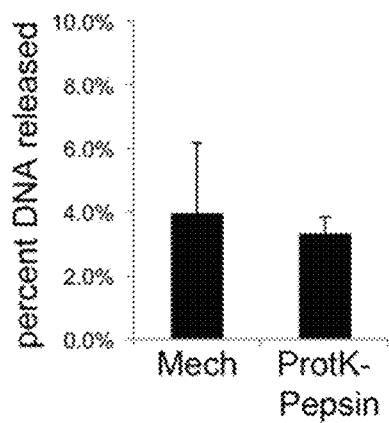
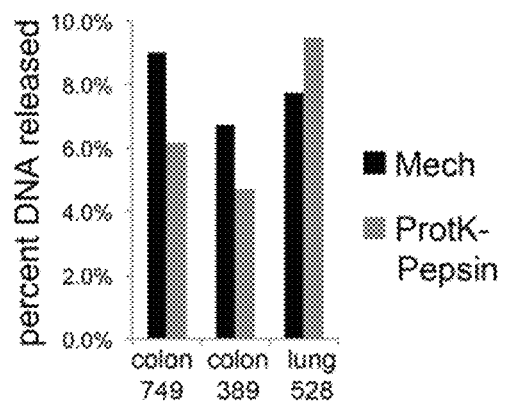
FIG. 46A          FIG. 46B

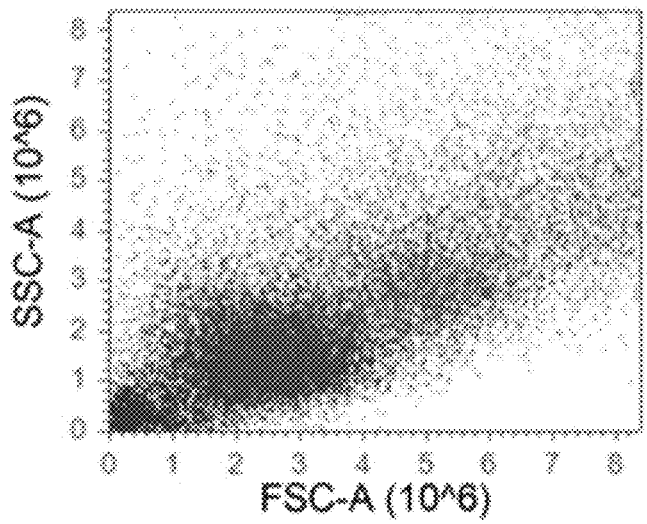
FIG. 47A
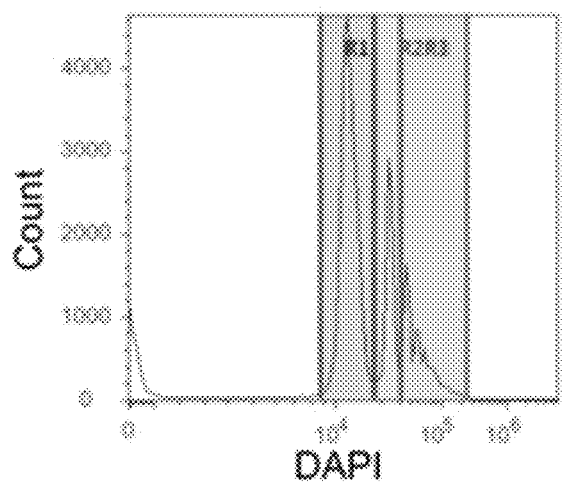
FIG. 47B
FIG. 47C

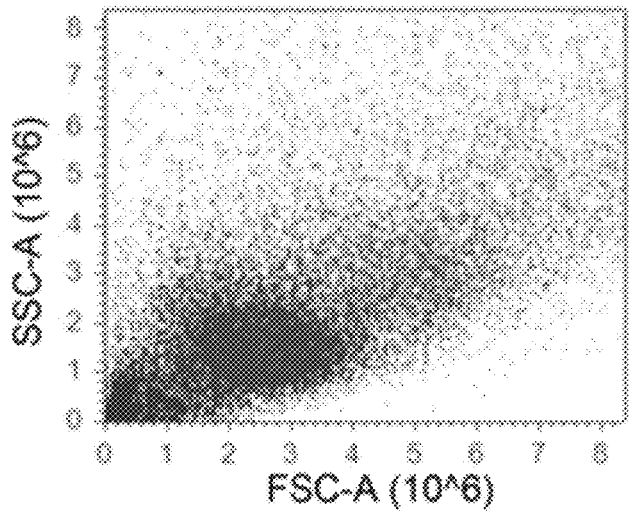
FIG. 47D
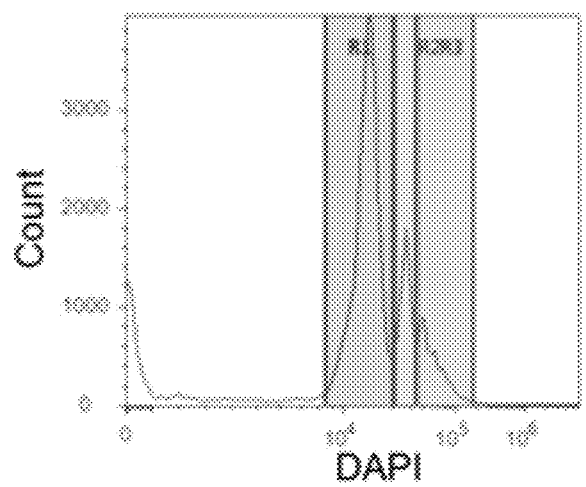
FIG. 47E
FIG. 47F

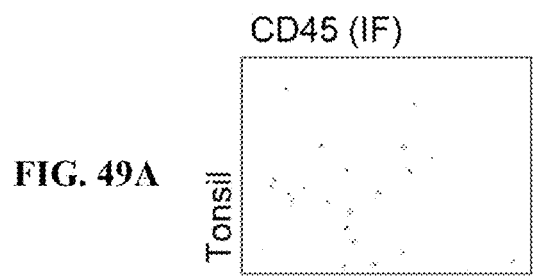
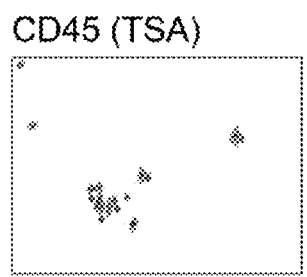
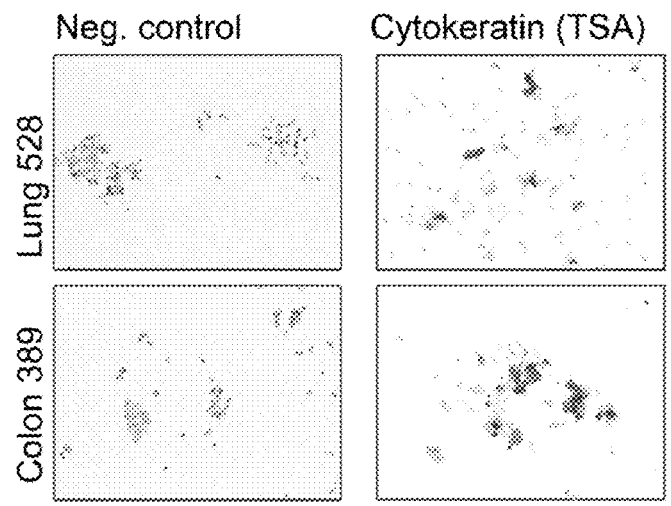
FIG. 49A  FIG. 49B  FIG. 49C  FIG. 49D  FIG. 49E  FIG. 49F

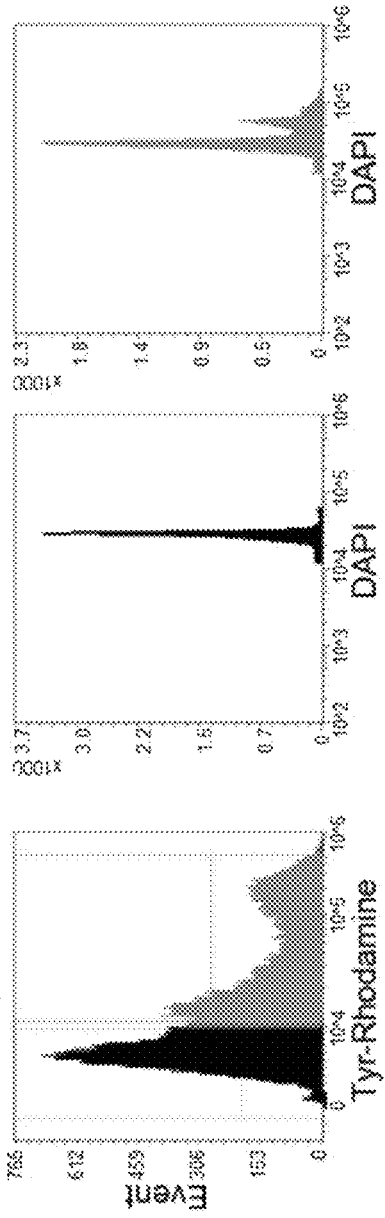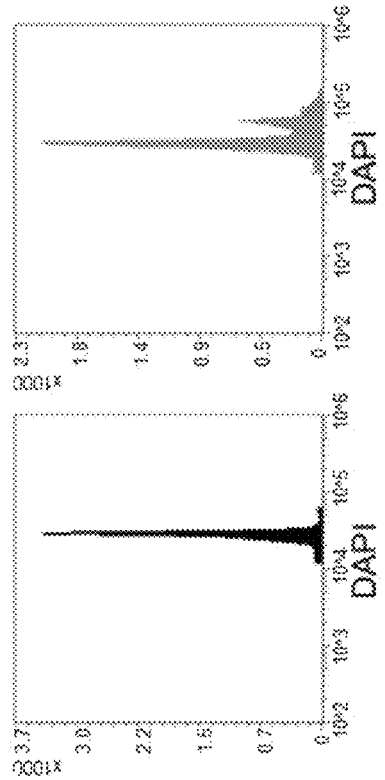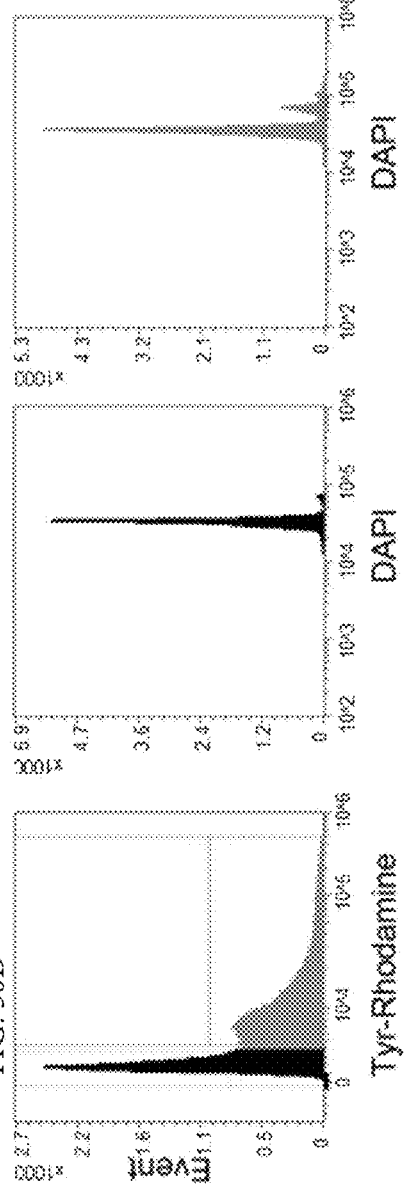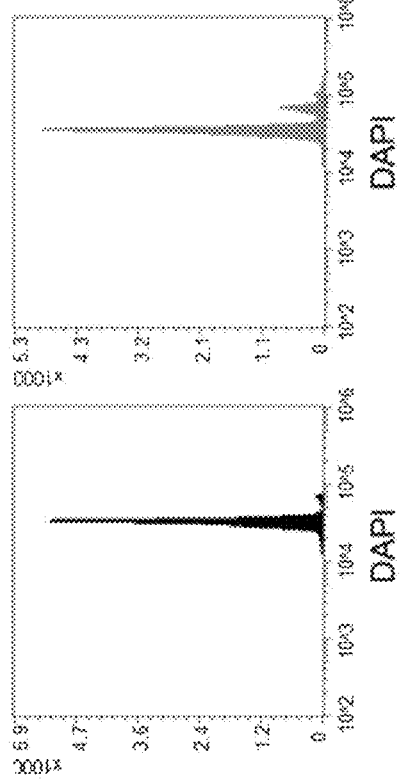

REPRESENTATIVE DIAGNOSTICS

CROSS-REFERENCE TO RELATED APPLICATIONS

The present application is a continuation of PCT Application Serial Number PCT/US2016/060861, filed Nov. 7, 2016, which claims priority to and the benefit of U.S. Provisional Application Ser. No. 62/418,146, filed Nov. 4, 2016; U.S. Provisional Application Ser. No. 62/354,622, filed Jun. 24, 2016; U.S. Provisional Application Ser. No. 62/279,405, filed Jan. 15, 2016 and U.S. Provisional Application Ser. No. 62/252,153 filed Nov. 6, 2015 the disclosures of which are hereby incorporated by reference in their entireties.

TECHNICAL FIELD

The disclosure generally relates to the development of a methodology for generating representative tissue samples, e.g., whole organs, tumors, lymph nodes, metastasizes, or combinations thereof, in order to address the issue of tissue heterogeneity in clinical samples, especially samples for use in clinical oncology. More particularly, the disclosure relates to applying mechanical, chemical and/or biochemical, e.g., enzymatic, dissociation methods to intact fixed (or preserved) tissue samples, e.g., whole organs, tumors, lymph nodes, metastasized tissues or combinations of any of the foregoing in order to create a homogeneous sample that provides the ability to obtain a correct representative sample despite spatial heterogeneity within the tissue, e.g., a tumor, increasing detection likelihood for minor sub-clone populations and/or low prevalence events. The representative tissue sample, e.g., a tumor sample, is suitable for use in various diagnostic assays. Particularly, these representative tumor samples and portions thereof are useful in assay methods for assessing cancer prognosis (e.g., tumor staging) and in the selection and design of appropriate treatment regimens. The representative tissue samples, e.g., tumor samples and portions thereof, may be used as therapeutics or to generate therapeutics, e.g., as vaccines or in the manufacture of cancer vaccines or immune cell-based therapies, as the representative samples contain a diverse array of the antigens expressed by a given tumor or tumors.

BACKGROUND

Tumor sampling techniques used for all diagnostic testing in medical oncology are rooted in the co-evolution of anatomical pathology and surgical oncology in the late 1800s. Prior to the discovery of ether based anesthesia in 1842 and the invention of antiseptic surgical techniques in 1867 pathology samples were typically acquired from autopsies. Preceding to these two significant advances in surgical techniques the tissue samples obtained by pathologists typically came from patients that had died on the operating table due to shock or soon thereafter due to infection. The high mortality rates of surgery, therefore, did not allow pathologists to correlate the anatomic and microscopic characterization of tumor structures with patient survival statistics. The impact of anesthesia and antiseptic techniques brought about an immediate and dramatic increase in the number of patients surviving surgeries and led to a substantial increase in the number of complicated surgical procedures.

The above described advancements in the surgical suite coincided with the advent of paraffin embedding of tissue in 1869 and the widespread utilization of formalin fixation beginning in 1893. With these two innovations, anatomic pathologists had unprecedented clarity of tissue architecture and microscopic morphology. Beginning in the early 1900s, insights were made that connected distinct patterns of tissue architecture and morphology with specific tumor types. Over time, anatomic pathologists and surgical oncologists were able to link these specific anatomic and microscopic features within the same tumor type with differences in overall survival. The correlations between the histological features of tumors and patient prognosis were ultimately codified into the TNM staging system in the early 1950s.

The TNM staging system aims to determine the prognosis of a cancer patient by evaluating the morphological aspects of the tumor (T), the extent to which tumor cells have spread to the regional lymph nodes (N), and whether or not the tumor has metastasized to distant organs (M). The information that is necessary for the "T" portion of the TNM staging analysis requires that a handful (typically 3-5) of very small samples of tumor be taken at the interface of the tumor and the surrounding normal tissue. The samples should be a consistent size (about 20×20×3 millimeters) to enable proper formalin fixation and paraffin embedding. A four micron section of the formalin fixed, paraffin embedded (FFPE) sample is cut by a microtome and placed on a glass slide to be reviewed by a pathologist. Most pathology labs will have the basic instrumentation that enables TNM staging of tumors: plastic tissue cassettes, formalin fixation buffer, a tissue processor to dehydrate and embed the tissue in paraffin, a microtome to cut thin sections (generally four microns thick), and glass slides on which to place the tissue sections.

The TNM staging system became the internationally recognized method for cancer staging in 1987 and is now governed by the American Joint Commission on Cancer (AJCC) and the Union Internationale Contre le Cancer (UICC). The AJCC and UICC, as well as the College of American Pathologists (CAP), review and periodically update the guidelines for the worldwide TNM staging criteria. The histological and anatomical features that are the inputs into the TNM rubric are contingent on surgical pathologists acquiring consistent tissue samples worldwide. Therefore, the sampling techniques required for the TNM staging system, based on technology and methods developed in the late 1800s, have become fixed in medical oncology.

Gaining the "correct" tissue samples for the TNM staging of tumors is the primary goal of surgical pathology, as evidenced by the fact that multiple textbooks describe and illustrate how surgical pathologists are to address a surgical sample. Generally, sections are taken that best demonstrate the features seen on gross examination. Many of these textbooks set forth the AJCC-, UICC- and CAP-approved procedures from recognized medical institutions and contain illustrations detailing the exact portions of the tumor to be sampled (see FIGS. 1A-1C). The goal of these textbooks is to train surgical pathologists across the world to take specific regions of resected solid tumors in a consistent and reproducible manner so as to avoid random sampling. See, e.g., Surgical Pathology Dissection: An Illustrated Guide, Second Edition, at p. 29 stating: "The key to an approach that is both economical and thorough is selective sampling. Selective sampling is a strategic approach which attempts to maximize the information that can be obtained from a given tissue section. As opposed to random and indiscriminant sampling of a specimen, tissue sampling that is selective increases the information that can be obtained histologically, and it requires fewer sections to do so". These references dictate that specific regions of solid tumors should be collected in a consistent and reproducible manner to facilitate TNM staging. Generally, the section with the highest grade is used for all diagnostic tests and the remaining sample is discarded.

Surgical pathologists are taught to refrain from increasing the total number of samples taken from a surgical specimen as there is no further information gained from increases in tumor sampling. There is no recognition that more diagnostic information may be available within the residual tumor that is not sampled.

Tumor metastasis to the local draining lymph nodes is a significant indicator of prognosis (i.e., the "N" of the prognostic TNM staging system). Presence of tumor cells within the regional lymph nodes may be the deciding factor as to whether a patient receives adjuvant chemotherapy. Conventionally, tumor cells are detected in lymph nodes following surgical removal and microscopic examination of a single, thin section of FFPE tissue. Metastatic growths in lymph nodes can fill the entire organ, or may be microscopic, containing only a handful of cancer cells. Small metastatic growths can be missed in lymph nodes, as only a single thin section of the excised lymph node will be examined for the presence of a metastatic tumor. Depending on the size on the lymph node, a single FFPE tissue section may contain only a few tenths of a percent of the total volume of the excised node. A metastatic tumor growing in the area of the lymph node that was not sampled will not be identified, resulting in a false negative analysis. This may result in the patient receiving a less aggressive therapy regimen than is necessary for an individual with regionally advanced cancer (i.e. lymph node metastasis, N-positive).

A case report is finalized by the pathology department and submitted to the oncologist after the tumor sample have been cut from the resected tumor material and the TNM stage calculated. The remaining surgical material containing the residual tumor tissue that was not utilized in the TNM staging is then destroyed, typically by incineration as required under the Health Insurance Portability and Accountability Act (HIPAA) of 1996. However, CAP recommends that all paraffin blocks and cut slides be maintained for 10 years. A worldwide system exists in which all diagnostic information derived from solid tumors is based on the minority of the tumor itself. See e.g., De Petris, *Proteome Science*, 8:9 (2010) ("De Petris"). In De Petris, only "[t]he biopsy from a region representative of the tumor" was taken for further examination, with the hemolysis and non-fixture requirements rendering the sample unsuitable for the follow-up histological study.

The discovery of tumor heterogeneity is contrary to conventional theories regarding tumor development. In the 1950s, the prevailing wisdom was that the final, clinically detectable tumor was a product of sequential selection of specific subpopulations of tumor "stemlines". In this theory, the bulk of the tumor is dominated by a single "stemline" that outperformed other "stemlines" due to natural selection. The TNM staging system was developed during the same period as the concepts of tumor "stemlines", where the majority of the tumor will be composed of a single "type" of tumor. See Peter Nowel, Science (1976) 194:23-28.

Rather than being uniform in composition, solid tumors are in fact heterogeneous. It has been reported that some solid tumors are composed of multiple genetically distinct, spatially segregated populations of cancer cells. See Gerlinger et al., NEJM (2012) 366:883-92; and Yachida et al. nature (2010) 467(7319):1114-1117. As further described herein, the inventors have shown that the conventional sampling methods for histological analysis of tumors provides an inadequate sample of a tumor (or tissue potentially containing cancer cells, such as a lymph node) and can be improved upon.

Doctors and scientists, guided by the modern-day pathology, do not normally attribute any meaningful medical value to the remaining tumor tissue once the samples have been taken for the TNM staging system, hence its destruction. Morphological and biomarker based analysis of histological sections are also limited by the phenotypic, morphological, and genetic heterogeneities displayed by the malignant populations within a tumor or between tumors. A small population of tumor cells may comprise the main source of malignancy and metastasis and constitute an insignificant amount of genetic makeup of the whole tumor. As a result, the biomarkers developed against a bulk mass of the tumor may not capture the very reasons for cancer mortality that is often caused by a small proportion of the tumor.

The heterogeneous genetic makeup within a given tumor poses significant challenges for therapy decisions in diagnostic oncology which utilizes information taken from the minority of a tumor on the assumption that tumors are composed of cells that are uniform in their composition. For example, spatial location of genetic subtypes within the sample is greatly influence the clinical outcome. Traditional routine tissue section procedures, even if based on the selective sampling guided by recognized literature, are unable to sample the entire surgical specimen. Moreover, current sampling procedures can only test the minority of the tumor, thereby leaving the vast majority of the tumor unexamined in any way, and eventually destroyed.

Under AJCC-, UICC- and CAP-approved procedures, the pathologists will use only small fractions of the surgically resected tissue specimen and discard the remaining sample. Because a tumor sample may harbor multiple genetically and spatially distinct populations of tumor cells, the 3 to 5 small samples taken by even the most experienced pathologist cannot represent all the genetically diverse groups of malignancies or metastasis within the entire specimen. Moreover, the location of any genomically distinct populations of cancer cells cannot be known a priori, as the DNA sequence of tumor cells is not apparent upon gross examination. In fact it is the discarded residual tumor material that contains the vast majority of all the cellular, genomic, and proteomic heterogeneity within the primary tumor, yet there is no time and cost effective methodology or instrumentation that enables whole tumor sampling.

Current pathological practice requires more thorough sampling and processing methods for the entire tumor that can help to ensure that the cellular, genomic, and proteomic heterogeneity within the entire primary tumor is captured in a diagnostic sample.

SUMMARY

The disclosure provides a processed homogenate composition that is derived from a heterogeneous tissue sample comprising substantially homogeneously distributed cellular structures, wherein a ratio of cellular structures in each subset of the homogenate is substantially similar to the ratio of cellular structures in the original heterogeneous tissue sample. The homogenate composition is a new, unique tissue sample that represents key characteristics of the original heterogeneous tissue sample. The disclosed composition addresses and overcomes the limitations of prior art methods that fail to account for tissue heterogeneity in clinical samples, especially samples for use in clinical oncology.

The homogenate composition is derived or sourced from various tissues, organs or samples thereof, for example a lymph node, a metastasis, a polyp, a cyst, a resection, an organ, or a fraction thereof, or spatially segregated cells. In one aspect, the homogenate comprises from about 25% to about 100% of the cellular structures of the tissue sample. The homogenate may comprise a protein fraction, lipid, nucleic acids or other moieties which are present in the starting tissue, e.g., a whole tumor, lymph nodes or metastases used to derive the homogenate thereof, wherein the relative proportions of such substituents components are representative of the starting tissue. The substantially homogenous cellular structures may comprise single cells or a plurality of cell clusters isolated from a normal or abnormal tissue. In certain aspects, the homogenate may comprise a liquid or non-liquid tissue sample, obtained by a variety of methods such as a cytology needle aspirate, effusion sample or a pap smear.

In other aspects, the homogenate may be isolated from preserved tissue, for example formalin fixed tissue. In other aspects the tissue sample is not preserved or fixed, and/or comprises live cells. The heterogeneous tissue sample may be isolated from one or more tissues obtained from one or more patients.

The homogenate is suitable for use in various diagnostic, prognostic and clinical applications, including but not limited to generating representative data including representative oncology data, cancer staging, identification and assessment of prognosis of diseases (e.g., tumor staging), selection and design of appropriate treatment regimens, clinical trial matching, marker identification and characterization, tissue profiling, and storage of the homogenate composition. The homogenate composition is also useful for screening therapeutics or to generate therapeutics in treating patients, e.g., as vaccines or in the manufacture of cancer vaccines or immune cell-based therapies, as the representative samples contain a diverse array of the antigens expressed by a given tumor or tumors.

The disclosure also provides methods for generating a homogenate composition that is representative of the heterogeneous tissue sample, e.g., a representative sample. More particularly, the disclosure comprise applying mechanical, chemical and/or biochemical, e.g., enzymatic, dissociation methods to intact tissue-containing samples, e.g., whole organs, tumors, lymph nodes, metastasized tissues or combinations of any of the foregoing (from the same or different patients) in order to provide an accurate representative sample despite spatial heterogeneity within the original tissue or organ, e.g., a tumor, thereby increasing detection likelihood for minor sub-clone populations and/or low prevalence events.

In one aspect, the disclosure generally relates to the development of a methodology for generating representative tissue samples of, for example, whole organs, tumors, lymph nodes, metastases, or combinations thereof in order to address the issue of heterogeneity, e.g., tumor heterogeneity, in clinical specimens, especially clinical specimens for use in clinical oncology, and the use of such representative samples or portions thereof in various diagnostic and therapeutic methods as well as compositions comprising such representative samples for use in diagnosis and therapy, especially oncology.

Moreover, representative samples from different patients or different tissues of single or different patients may each be labeled with unique identifying labels, e.g., a hapten, and the labeled samples of different patients or tissues combined and used in desired assay methods.

Representative samples derived by exemplary embodiments of the disclosure may be utilized to improve the accuracy of detecting, diagnosing, and/or staging of different tumor types, irrespective of tumor tissue type, location, size or volume. The presently disclosed methods are useful for the production of a representative sample from normal tissue or putative precancerous tissues (e.g., obtained from subjects at higher risk of developing cancer because of a genetic risk or a prior cancer) to identify rare cell.

In one aspect, the disclosure provides a method for producing a biological sample suitable for assessing heterogeneity of cells within a tumor, lymph node, or metastases and/or assessing the prognosis of a particular cancerous condition in a subject and/or determining an appropriate therapeutic protocol for a subject with a cancerous condition. This method comprises (i) obtaining a tissue (such as a tumor sample or a lymph node or metastases) that comprises spatially distinct regions of the tissue or which comprises a whole tumor or a substantial portion thereof, and (ii) homogenizing the tissue such that the heterogeneity of the cells is substantially homogeneously distributed within the resultant homogenate or a portion or fraction thereof. The sample or samples optionally may be fixed and/or preserved, e.g., formalin fixed, ethanol fixed, frozen or freeze-dried, stored in wax (such as paraffin), etc. before or after homogenization of an entire or substantially entire tumor, lymph node, metastases, or even an entire organ such as a kidney.

In another aspect, the disclosure provides a method for producing a biological sample suitable for assessing heterogeneity of cells within a sample (such as a tumor sample, lymph node, metastases or a combination thereof) and/or assessing the prognosis of a particular cancerous condition in a subject comprising: (i) obtaining one or more intact samples from a solid tumor or a lymph node, preferably wherein each intact sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells, or alternatively at least 1,000; 10,000; 100,000; 1,000,000; 5,000,000; 10,000,000; 50,000,000; 100,000,000; 500,000,000; 1,000,000,000; 5,000,000,000; 10,000,000,000; 50,000,000,000; 100,000,000,000; 500,000,000,000; 1,000,000,000,000; 5,000,000,000,000; 10,000,000,000,000; 50,000,000,000,000; 100,000,000,000,000 or more cells, and optionally fixed or preserved (such as a formalin, paraffin, or ethanol fixed or preserved sample), and (ii) separately or in combination homogenizing the one or more samples, wherein the one or more homogenates each substantially homogeneously express the heterogeneity of the respective sample or samples. In one embodiment, the intact sample or samples from the solid tumor or the lymph node comprise or alternatively consist essentially of, or yet further consist of a portion of the solid tumor or the lymph node. In another embodiment, the intact sample or samples from the solid tumor or the lymph node comprise, or alternatively consist essentially of, or yet further consist of substantially portions of the solid tumor or the lymph node. In a further embodiment, the intact sample or samples from the solid tumor or the lymph node comprise, or alternatively consist essentially of, or yet further consist of the entire solid tumor or the entire lymph node.

The representative samples optionally may be further dissociated and/or treated to remove or isolate specific types of molecules such as specific cell types, proteins, nucleic acids, or lipids, and the like and using, for example, CAVA computational analysis of the Illumina sequencing output to be used in diagnostic and therapeutic methods.

In yet another aspect, the disclosure provides a method for producing a biological sample suitable for assessing heterogeneity of cells within a tumor or lymph node or metastases or combination thereof comprising (i) obtaining one or more biopsy samples from a solid tumor or a lymph node or metastases, preferably wherein each biopsy sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or alternatively at least 1,000; 10,000; 100,000; 1,000,000; 5,000,000; 10,000,000; 50,000,000; 100,000,000; 500,000,000; 1,000,000,000; 5,000,000,000; 10,000,000,000; 50,000,000,000; 100,000,000,000; 500,000,000,000; 1,000,000,000,000; 5,000,000,000,000; 10,000,000,000,000; 50,000,000,000,000; 100,000,000,000,000 or more cells, and optionally fixed or preserved (such as a formalin, paraffin, or ethanol fixed or preserved sample), and (ii) separately or in combination homogenizing the one or more biopsy samples, under conditions wherein the resultant homogenate or homogenates are substantially dissociated into individual cells and the resultant homogenate or homogenates are substantially homogeneous.

In another aspect, the disclosure provides a method for producing a biological sample suitable for assessing whether a subject has or is at risk of developing a virulent form of a particular cancer and/or whether a has a virulent form cancer comprising (i) obtaining one or more intact biopsy samples from a solid tumor or a lymph node or metastases or precancerous cyst, preferably wherein each biopsy sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells, or alternatively at least 1,000; 10,000; 100,000; 1,000,000; 5,000,000; 10,000,000; 50,000,000; 100,000,000; 500,000,000; 1,000,000,000; 5,000,000,000; 10,000,000,000; 50,000,000,000; 100,000,000,000; 500,000,000,000; 1,000,000,000,000; 5,000,000,000,000; 10,000,000,000,000; 50,000,000,000,000; 100,000,000,000,000 or more cells, and optionally fixed or preserved (such as a formalin, paraffin, or ethanol fixed or preserved sample), and (ii) separately or in combination homogenizing the one or more biopsy samples, wherein the resultant one or more homogenates each substantially homogeneously contains the heterogeneity of the respective biopsy sample or samples, and optionally isolating or detecting the presence of at least one biomarker. In this aspect, the presence or absence of the biomarker is indicative of a virulent form of cancer, or alternatively the upregulation or downregulation of the biomarker is associated with a virulent form of the particular cancer.

In yet another aspect, the disclosure provides a method for characterizing a landscape within a heterogeneous tumor, lymph nodes or metastases or precancerous cyst and/or detecting genetically distinct subclones within a heterogeneous tumor lymph nodes or metastases or precancerous cyst and/or identifying low prevalence events within a tumor lymph nodes or metastases or precancerous cyst and/or determining the prevalence of targets within a tumor lymph nodes or metastases or precancerous cyst comprising (i) obtaining a sample or samples of the tumor lymph nodes or metastases or precancerous cyst that encompasses spatially distinct regions of the tumor lymph nodes or metastases or precancerous cyst, which is or are optionally fixed or preserved prior to homogenization e.g., with formalin, paraffin and/or ethanol, and (ii) homogenizing the tumor lymph nodes or metastases or precancerous cyst sample or samples separately, thereby producing a set of homogenates that is representative of the landscape of the heterogeneity within the tumor, lymph nodes, metastases, or precancerous cyst and is suitable for characterizing the landscape of the tumor and/or detecting genetically distinct subclones within a heterogeneous tumor lymph nodes or metastases or precancerous cyst and/or identifying low prevalence events within a tumor or lymph nodes or metastases or precancerous cyst and/or determining the prevalence of targets within a tumor lymph nodes or metastases or precancerous cyst. These landscapes relate to the genomic diversity (eg. the number of point mutations, insertions, and deletions within the tumor), the diversity in tumor phenotypes (eg. amount of the tumor that has undergone epithelial to mesenchymal transition), diversity in the host immune response (eg. the diversity of the expression of immune checkpoint regulators in the tumor and immune cells), the diversity of all potential resistance mechanisms (eg. the number and diversity of the tumor mutations that confer resistance to targeted therapy), the diversity of tissue histologies (eg. amount of the tumor that is squamous vs. adenocarcinoma in lung cancer), the diversity of neo-antigens expressed by the tumor, and/or other complex phenotypic, morphological, histological, genomic, proteomic, metabolomic landscapes across all affected, or potentially affected tissue that is resected from a subject.

In yet another aspect, the disclosure provides a method for detecting precancerous cells or cancerous cells in supposed normal tissues or putative precancerous tissues in a patient, e.g., one at risk of developing cancer because of a genetic mutation or previous cancer, or a patient with precancerous cysts or polyps comprising (i) obtaining a sample or samples of supposed normal tissues or putative precancerous tissues such as precancerous cysts or polyps that encompass spatially distinct regions of the supposed normal tissues or putative precancerous tissues of the patient, which is optionally fixed or preserved prior to homogenization, and (ii) homogenizing the sample or samples, thereby producing a homogenate that is representative of the supposed normal tissues or putative precancerous tissues and which is suitable for detecting rare cancerous cells or cancer stem cells, e.g., even before any sign of disease has manifested in the patient.

In another aspect, the disclosure provides methods of using representative samples and portions thereof produced by the any of the foregoing methods in different assay formats, wherein these assays may be effected in high throughput, performed simultaneously or at different times or different locations, and/or by automation (fully automated or semi-automated).

In another aspect, the disclosure provides for representative samples or portions thereof produced by the any of the foregoing methods which are stored for future use, non-limiting examples of such include e.g., frozen, formalin-fixed, paraffin-embedded, processed with ethanol, or freeze-dried.

In another aspect, the disclosure provides for representative samples or portions thereof produced by the any of the foregoing methods are used to derive (and optionally purify) antibodies or antigens specific to a particular antigen from a cancer cell or cell types in a patient sample, which antibodies or antigens potentially may be used in personalized medicine, i.e., in the production of therapeutic or prophylactic cancer vaccines.

The homogenization step in all of the above-mentioned methods may be effected by a method which preserves the integrity of the cells within the sample, i.e., the bulk of the cells within the homogenized sample or samples are not lysed and whereby the resultant homogenate and portions thereof are "representative" of the sample or samples. Therefore, the cells within the sample or a portion thereof reflect the percentages of the different cell types within the entirety of the tissue sample or samples, e.g., a solid tumor or a lymph node. This may be accomplished, for example, by mechanical dissociation of the tumor sample or a portion thereof (such as mechanical dissociation performed with or without the addition of liquid to the tumor sample or a portion thereof) and/or chemical or enzymatic dissociation of the tumor sample or a portion thereof (such as treatment with an enzyme that selectively or preferentially or primarily acts upon extracellular matrix proteins as compared to membrane-associated proteins). Alternatively, the homogenization methods may result in the dissociation of the cells while still generating a sample that is representative of the starting tissue, such as a whole tumor. The homogenized representative samples optionally may be further dissociated and/or treated to remove or isolate specific types of molecules such as specific cell types, proteins, nucleic acids or lipids, and the like thereby generating other representative samples which may be used in diagnostic and therapeutic methods.

Any of the above methods may include detecting the expression of at least one biomarker, e.g., at least one lipid, protein, or nucleic acid biomarker, in the homogenate or a portion or fraction thereof. Additionally, the methods may further include detecting the percentage of tumor cells in the homogenate or a portion or fraction thereof that express a particular biomarker or combination of biomarkers. Optionally, tumor stem cells and/or the relative frequency or percentage of tumor subclones in the homogenate or a portion or fraction thereof are detected and/or isolated. Additionally, the methods may also include detecting a genetic target (such as a point mutation, a deletion, an insertion, a translocation, a genetic fusion, or an amplification of a gene).

Any of the above methods may also be used to detect, isolate, and/or quantify specific immune cells (such as B lymphocytes, T lymphocytes, macrophages, NK cells, monocytes, or a combination thereof) present in the homogenate or a portion or fraction thereof, which provides valuable clinical information, e.g., immune status and disease state, and also in order to select suitable treatment protocols such as checkpoint inhibitors, cytokines, or other immune modulators.

The resultant homogenates or representative samples may comprise, consist essentially of, or yet further consist of about 100-200; 200-1,000; 1,000-5,000; 10,000-100,000; 100,000-1,000,000; 1,000,000-5,000,000; 5,000,000-1,000,000,000; 1,000,000,000-5,000,000,0000 cells or alternatively, at least 1,000; 10,000; 100,000; 1,000,000; 5,000,000; 10,000,000; 50,000,000; 100,000,000; 500,000,000; 1,000,000,000; 5,000,000,000; 10,000,000,000; 50,000,000,000; 100,000,000,000; 500,000,000,000; 1,000,000,000,000; 5,000,000,000,000; 10,000,000,000,000; 50,000,000,000,000; 100,000,000,000,000 or more cells.

The resultant homogenates or a fraction or portion thereof optionally may be frozen or freeze-dried, embedded in wax (such as paraffin) or, alternatively, used in further steps without such freezing or freeze-drying or wax. For example, a representative paraffin block, i.e., produced from a homogenate or a fraction or portion thereof embedded in paraffin, is suitable for use in the current anatomic pathology workflow, e.g., sectioning, preparing slides, staining, microscopy, antigen retrieval, etc.

The homogenates may be derived from two or more tumors taken from one or more subjects at the same of different time points (e.g., the same subject before or after treatment or multiple subjects before and after the same or different treatments from each other), and the resultant homogenates or fractions thereof of each tumor are used to assess the similarities and/or differences of the two or more tumors or disease condition of different patients. In a further aspect, the homogenates from one or more subjects can be combined for the purposes of a multiple-subject representative sample.

The homogenates may be derived from two or more putative normal or precancerous tissues, e.g., breast, cervical, colorectal, or precancerous cysts or polyps obtained from a subject or multiple subjects, e.g., one with a BRCA mutation, and the resultant homogenates or fractions thereof used to assess whether any abnormal cells or disease biomarkers are present.

In addition, non-human cells (such as insect cells and/or mouse cells) or other foreign proteins, nucleic acids, or small molecules may be added to the homogenate to create an internal control for positive protein or nucleic acid detection.

Small molecules (such as haptens, peptide tags, protein tags, fluorescent tags, and/or nucleic acid tags) may be added to the sample and used to provide spatial information in the representative sample. For example, a sample (such a tumor or lymph node) may be sectioned, e.g., cut into quadrants, and a different hapten (or other suitable small molecule) may be "doped" into each section prior to homogenizing the sections to generate a representative sample. It should be understood that the number of sections that can be generated from each sample for "doping" prior to homogenization is not limited but, rather, likely selected in scale with the size of the sample, i.e., the larger the sample, the greater the number of sections that can be "tagged" with a small molecule prior to homogenization. In this way, spatial information can be maintained in the resultant homogenates or fractions thereof.

In one embodiment, small molecules can also be added to the sample prior to combining the sample with a different sample from another patient or the same patient and, thus, provides a means to differentiate samples when run in a multiplex assay format.

The samples which are homogenized may be preserved, e.g., formalin fixed, or may or treated with ethanol before or after homogenization. Because of safety concerns, tissue samples are generally formalin or otherwise fixed prior to processing in using CAVA computational analysis of the Illumina sequencing output a pathology lab prior to use in most diagnostic methods. Formalin or other fixation methods may be accomplished by techniques that are generally known in the art. In such cases, the formalin fixed tumor sample may be soaked in water or buffered saline solution (such as PBS) prior to homogenization in step (ii).

Alternatively, or in addition, the tumor sample used in the disclosed methods may be preserved in ethanol prior to homogenization. However formalin fixation, methanol or ethanol fixation, or other preservation procedures are not essential to the subject methods, and may be eliminated without compromising the suitability of the resultant homogenized representative sample.

The homogenization of unfixed tissue may be utilized to produce a representative live sample. A live representative sample may be cultured to create a representative tissue culture sample from individual patients. Such a representative sample can be split numerous times to create multiple representative culture samples, which can be used to determine the efficacy of chemotherapy (such as an antibody, nucleic acid, small molecule, or polypeptide, which antagonizes, inhibits, or blocks the expression or functional activity of at least one known or unknown biomarker). Moreover, specific cell types (such as immune cells or tumor cells) can be selected using FACS analysis. For example, tumor infiltrated immune cells can be selected and cultured to determine the tumor specific antibodies being secreted by the immune system.

Also, as shown herein the disclosed methods for producing representative samples and their use in diagnostic and therapeutic methods is suitable for both fixed and unfixed tissue samples.

Any of the disclosed methods for preparing a representative sample may include the addition of at least one collagenase (or other suitable enzyme or enzyme combination or other chemical such as a salt that itself breaks down or which facilitates the breakdown of the extracellular matrix) before, during, or after homogenization; the use of elevated temperature and/or buffer conditions (such as a cell conditioning buffer, e.g., CC1 or CC2, that disrupts cellular cross-links); and/or the use of a device for mechanical shearing (such as an IKA® blender, a gentleMACs™ Disassociator, or a functional equivalent). Again, these methods may or may not be affected under conditions that maintain the viability and integrity of the cells within the sample, e.g., under some homogenization conditions the cells are substantially not lysed.

In one aspect, homogenization processes comprise the use of a mechanical process, non-limiting examples of such include mortar & pestle, a dounce homogenizer or tissue grinder, a hand held electronic rotary blade tissue homogenizer (such as Omni-TH available from Thomas Scientific), a bead beating homogenizer (such as a bullet blender or a Burton Precellys® 24 Tissue Homogenizer or a Bead Ruptor available from OMNI), optionally at a speed of between about 100 and about 75,000 RPM for rotational homogenizers or a speed of about 0.5 m/s to about 2.5 m/s for bead beaters, and for a length of about 30 second to about 5 minutes, about 5 minutes to about 10 minutes, about 10 minutes to about 30 minutes, or about 30 minutes to about 60 minutes. As noted herein, the mechanical homogenization process can be used alone or in combination with other processes.

In another embodiment, homogenization comprises, alone or in combination with other processes, the use of an enzyme preparation, non-limiting examples of such include for example, interstitial collagenase, Gelatinase-A, Stromelysin 1, Matrilysin, Neutrophil collagenase, Gelatinase-B, Stromelysin 2, Stromelysin 3, Macrophage metalloelastase, Collagenase 3, MT1-MMP, MT2-MMP, MT3-MMP, MT4-MMP, Collagenase 4, Enamelysin, X-MMP, CA-MMP, MT5-MMP, MT6-MMP, Matrilysin-2, MMP-22, endoproteinase, trypsin, chymotrypsin, endoproteinase Asp-N, endoproteinase Arg-C, endoproteinase Glu-C (V8 protease), endoproteinase Lys-C, pepsin, thermolysin, elastase, papain, proteinase K, subtilisin, clostripain, exopeptidase, carboxypeptidase A, carboxypeptidase B, carboxypeptidase P, carboxypeptidase Y, cathepsin C, acylamino-acid-releasing enzyme, pyroglutamate aminopeptidase, or any combination thereof, optionally at a concentration of about 0.001 µg/ml to about 1000 mg/ml, and for a length of about 1 minute to about 120 minutes.

The tumor or other sample used in the disclosed methods that encompasses spatially distinct regions of the tumor or other tissue may comprise at least 10%, 20%, 30%, 40%, 50%, 60%, 70%, 75%, at least 85%, at least 95%, at least 96%, at least 97%, at least 98%, at least 99% or, preferably, the entirety of a tumor or tissue sample surgically removed from a patient. The tumor sample may be at least 1, 5, 10, 20, 50, 100 or more millimeters (mm) or centimeters (cm) in diameter.

The samples used in the subject methods generally will be derived from any appropriate tissue sample, e.g., a solid tumor or tumors (including primary tumors and metastatic tumors), lymph nodes, metastases, or precancerous tissues such as cysts or polyps. Alternatively, or in addition, the methods may also be effective with non-solid tumors, e.g., blood cancers. For example, the tissue samples or solid tumor samples which are homogenized optionally may be combined with liquid patient samples, e.g., blood, lymphatic fluid, effusion specimens, cerebrospinal fluid, bile, mucus, and/or urine samples from the patient. The samples that are homogenized may in addition or alternatively comprise complete or partial samples, e.g., a biopsied "normal" or precancerous tissue, e.g., in order to detect diseased cells prior to disease manifestation.

Such tumor or other tissue sample or samples used in the disclosed methods may be derived from any source, e.g., from breast, colon, lung, pancreas, gall bladder, skin, bone, muscle, liver, kidney, cervix, ovarian, prostate, esophageal, stomach, or other organs, e.g., a breast cancer tumor, a lung cancer tumor, liver tumor, a prostate cancer tumor, a colon cancer tumor, a bladder cancer tumor, or a kidney cancer tumor. In one embodiment, the tumor sample or other tissue used in the disclosed methods is of human origin but can be of any appropriate tissue source.

The tumor or other tissue sample used in the disclosed methods may have a volume of at least 1 $cm^3$, at least 2 $cm^3$, at least 3 $cm^3$, at least 4 $cm^3$, at least 5 $cm^3$, at least 6 $cm^3$, at least 7 $cm^3$, at least 8 $cm^3$, at least 9 $cm^3$, at least 10 $cm^3$, at least 15 $cm^3$, at least 20 $cm^3$, at least 25 $cm^3$, at least 50 $cm^3$, at least 100 $cm^3$, at least 250 $cm^3$, at least 500 $cm^3$, at least 1,000 $cm^3$, at least 2,500 $cm^3$, at least 5,000 $cm^3$, at least 7,500 $cm^3$, at least 10,000 $cm^3$ or larger.

The tumor or other tissue sample used in the disclosed method may have a width at the widest point of at least 0.5 cm, at least 1 cm, at least 1.5 cm, at least 2 cm, at least 2.5 cm, at least 3 cm, at least 3.5 cm, at least 4 cm, at least 4.5 cm, at least 5 cm, at least 6 cm, at least 7 cm, at least 10 cm, at least 25 cm, at least 50 cm or larger.

In an additional embodiment, representative samples can be made of tissue that has previously been formalin fixed and embedded in paraffin wax. In particular, the wax can be melted, the tissue recovered and hydrated, and then methods described herein, i.e., homogenization, applied to the sample, which is suitable for use in any number of assays. In this way, the disclosed methods can be used to generate a representative sample using a sample or samples already prepared for TNM staging, by melting the wax, recovering the sample, rehydrating the tissue and homogenizing accordingly.

Any of the above methods may further comprise (iii) distributing the homogenate or a portion or fraction thereof onto one or more slides or other solid supports and, optionally, staining the one or more slides or other solid supports containing the homogenate or a portion or fraction thereof with hematoxylin and eosin stain; performing immunohistochemical staining on the slide or other solid support containing the homogenate or a portion or fraction thereof; or performing in situ hybridization on the slide or other solid support containing the homogenate or a portion or fraction thereof, i.e., any one of which would be considered step (iv)

in the methods. For example, the homogenate or a portion thereof can be analyzed on an automated platform for analysis. Such platforms are known in the art, and commercially available from Ventana® Medical Systems, Inc. (see Ventana.com for exemplary automated platforms).

Moreover, any of the above methods may further comprise (iii) purifying nucleic acids (such as DNA or mRNA) from the homogenate or a portion or fraction thereof. The purified nucleic acids may be subject to Northern blot, DNA sequencing, PCR, RT-PCR, microarray profiling, differential display, or in situ hybridization. Alternatively, the purified nucleic acid may be conjugated to a nanoparticle (such as quantum dots, paramagnetic nanoparticles, superparamagnetic nanoparticles, and metal nanoparticles, preferably alloyed quantum dots, including by way of example and without limitation, CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN, by way of example).

It is also contemplated that any of the above methods may further comprise purifying lipids or exosomes or other organelles from the homogenate or a portion or fraction thereof. The purified lipids may be subject to mass spectrometry or histochemistry.

Additionally, it is also contemplated that any of the above methods may further comprise purifying proteins from the homogenate or a portion or fraction thereof. The purified proteins may be subject to Western blot, enzyme-linked immunosorbent assay (ELISA), immunoprecipitation, chromatography, mass spectrometry, microarray profiling, interferometry, electrophoretic staining, or immuno-histochemical staining. Alternatively, or in addition to the foregoing, the purified proteins may be used to produce antisera specific to the tumor or tissue sample.

Moreover, it is contemplated that any of the above methods further comprise (iii) performing a genomic, epigenomic, transcriptomic, proteomic and/or metabolomic analysis on the homogenate or a portion or fraction thereof.

Furthermore, it is contemplated that any of the above methods further comprise (iii) affinity purifying specific cell types from the homogenate or a portion or fraction thereof. The specific cell types may contain a biomarker of interest. Exemplary biomarkers of interest may include Her2, bRaf, an ERBB2 amplification, a P13KCA mutation, a FGFR2 amplification, a p53 mutation, a BRCA mutation, a CCND1 amplification, a MAP2K4 mutation, an ATR mutation, or any other biomarker the expression of which is correlated to a specific cancer; at least one of AFP, ALK, BCR-ABL, BRCA1/BRCA2, BRAF, V600E, Ca-125, CA19.9, EGFR, Her-2, KIT, PSA, S100, KRAS, ER/Pr, UGT1A1, CD30, CD20, F1P1L1-PDGRFα, PDGFR, TMPT, and TMPRSS2; or at least one biomarker selected from ABCB5, AFP-L3, Alpha-fetoprotein, Alpha-methyl acyl-CoA racemase, BRCA1, BRCA2, CA 15-3, CA 242, Ca 27-29, CA-125, CA15-3, CA19-9, Calcitonin, Carcinoembryonic antigen, Carcinoembryonic antigen peptide-1, Des-gamma carboxy prothrombin, Desmin, Early prostate cancer antigen-2, Estrogen receptor, Fibrin degradation product, Glucose-6-phosphate isomerase, an HPV antigen such as vE6, E7, L1, L2 or p16INK4a Human chorionic gonadotropin, IL-6, Keratin 19, Lactate dehydrogenase, Leucyl aminopeptidase, Lipotropin, Metanephrines, Neprilysin, NMP22, Normetanephrine, PCA3, Prostate-specific antigen, Prostatic acid phosphatase, Synaptophysin, Thyroglobulin, TNF, a transcription factor selected from ERG, ETV1 (ER81), FLI1, ETS1, ETS2, ELK1, ETV6 (TEL1), ETV7 (TEL2), GABPα, ELF1, ETV4 (E1AF; PEA3), ETV5 (ERM), ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or FEV, Tumor-associated glycoprotein 72, c-kit, SCF, pAKT, pc-kit, and Vimentin.

Alternatively, or in addition the biomarker of interest may be an immune checkpoint inhibitor such as, but not limited to, CTLA-4, PDL1, PDL2, PD1, B7-H3, B7-H4, BTLA, HVEM, KIR, TIM3, GAL9, GITR, LAG3, VISTA, KIR, 2B4, TRPO2, CD160, CGEN-15049, CHK 1, CHK2, A2aR, TL1A, and B-7 family ligands or a combination thereof or is a ligand of a checkpoint protein selected from the group consisting of CTLA-4, PDL1, PDL2, PD1, B7-H3, B7-H4, BTLA, HVEM, TIM3, GALS, LAG3, VISTA, KIR, 2B4, CD160, CGEN-15049, CHK1, CHK2, A2aR, B-7 family ligands, or a combination thereof.

The methods of this disclosure can also comprise or include the detection of at least one biomarker associated with acute lymphoblastic leukemia (etv6, am11, cyclophilin b), B cell lymphoma (Ig-idiotype), glioma (E-cadherin, .alpha.-catenin, .beta.-catenin, .gamma.-catenin, p120 ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-C017-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkin's lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and/or T cell leukemia (HTLV-1 epitopes).

The methods of this disclosure further comprise (iii) treating the homogenate or a portion or fraction thereof with collagenase or other enzyme or chemical or combination thereof that breaks down extracellular matrices, incubating the homogenate or a portion or fraction thereof under high temperature conditions, and/or mechanically agitating the homogenate or a portion or fraction thereof in order to dissociate the cells within the homogenate or a portion or fraction thereof. Generally, these methods will generate a population of individual cells, or small clusters of cells from the representative sample that may be used in the disclosed analytic or therapeutic methods or a combination thereof.

Additionally any of the above mentioned methods further comprise (iii) filtering or sizing the homogenate or a portion or fraction thereof, which may result in obtaining single cells or small cell clusters, such as doublets or triplets.

The cellular componentry of the representative sample may be separated by one or multiple filtration steps. For example, following homogenization and disassociation of the homogenate through physical and/or biochemical means, the disassociated sample may be filtered through a 1 micron filter to remove all intact cellular material. It is expected that the non-cellular representative sample will contain secreted factors from the tumor and normal stroma from within the tumor that will be of clinical utility, i.e., antibodies, growth factors, immunomodulators, and other unknown factors. The non-cellular representative sample may be analyzed by ELISA, mass spectrometry, next generation sequencing, and other diagnostic methods. To the extent that single cells derived from the representative sample are obtained following filtration, such cells may be analyzed using fluorescent activated cell sorting (FACS) and flow cytometry analysis.

Given the representative nature of the homogenate generated by the disclosed methods, the homogenate or a portion or fraction thereof can be used to detect a low prevalence genetic event (such as a genetic event that occurs at 20% prevalence, 15% prevalence, 10% prevalence, 5% prevalence, 2% prevalence, 1% prevalence, 0.5% prevalence, 0.1% prevalence, 0.001% prevalence, 0.001% prevalence, 0.0001% prevalence, 0.00001% prevalence, 0.000001% prevalence or less). Exemplary genetic events include a point mutation, a deletion, an addition, a translocation, a genetic fusion, or an amplification of a gene. Likewise, the methods can also involve detecting genetic or epigenetic heterogeneity within the tumor sample or a portion thereof and/or detecting cells comprising rare genetic or epigenetic variations. Such cells may be present in the tumor sample at a frequency of less than 5%, less than 1%, less than 0.5%, less than 0.1%, less than 0.05%, or less than 0.01%.

The detected rare cells may comprise one or more genetic or epigenetic differences that confer resistance to a therapy, a sensitivity to one therapy over another, an anti-cancer therapy and/or promote metastasis. Therefore, in one aspect, the detection of such cells will facilitate cancer prognosis as well as the selection of an appropriate therapeutic regimen such as chemotherapy, combination targeted therapy, and/or the use of biologics.

The foregoing methods may also include the use of at least one detectable label selected from fluorescent molecules or fluorochromes such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo) benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives, thiol-reactive europium chelates which emit at approximately 617 nm The disclosed methods may be automated, in whole or in part. For example, steps (i) and (ii) may be automated, but any subsequent steps, e.g., steps (iii) and (iv), are manual. Alternatively, by way of example, steps (i) and (ii) may be manual, whereas subsequent steps, e.g., steps (iii) and (iv), are automated. Additionally, all steps encompassed by the methods may be automated, such that the methods are fully automated.

The disclosed methods may be used, alone or in combination with other known methods (such as TNM), for tumor staging. In one aspect, the methods further comprise evaluating one or more aspects of the representative sample of the tumor, and the extent to which tumor cells have spread to the regional lymph nodes through analysis of the representative sample of the resected lymph nodes to predict the likelihood of the disease recurrence and/or progression.

The disclosed methods may further comprise employing an algorithm to calculate the percentage of sampled cells, e.g., tumor cells with or without a specific biomarker. The relative risk of metastatic (or virulent subclone) progression may be determined based on the percentage of cells within a representative tumor sample and/or representative lymph node sample with a specific detectable biomarkers, or combination of biomarkers.

The disclosed methods may further comprise development of a personalized dosage or treatment regimen based on the biomarker profile, the antigen profile, the mutational profile, the lipid profile, the protein profile, and/or the exosome profile contained in the representative sample. For example, based on the information contained in the representative sample, or in combination with information obtained from a representative lymph node sample, the selection of one or more drugs and/or dosage (amount, length of administration, etc.) of such drugs administered to a patient may be modified to personalize the treatment based upon the patient's individual tissue or cancer profile.

The disclosed methods may further comprise comparing the genomic profile of the representative sample to the genomic profile of a representative tissue sample from the same patient or other patient, e.g., lymph node sample, and further optionally comparing these profiles to circulating tumor DNA from any distant metastases or a representative metastatic tumor sample.

The disclosed methods may further comprise development of inclusion criteria for a clinical trial based on the biomarker profile, the antigen profile, the mutational profile, the lipid profile, the protein profile, and/or the exosome profile contained in the representative sample.

The present disclosure also encompasses the representative homogenate compositions produced by any of the foregoing methods, alone or in combination with other compositions and carriers.

Additionally, the results of the foregoing methods (such as the detection of rare genetic and/or epigenetic events, rare cells, etc.) or compositions produced by any of the foregoing methods, which involve homogenization of a sample such as a tumor sample to prepare a representative sample suitable for further analysis using any number of standard diagnostic assays, can be used in the selection of an appropriate therapeutic regimen for a cancer patient The therapeutic regimen can include gene therapy, chemotherapy, a targeted small molecule, other targeted therapies, immunomodulator administration, radiation, cytokine administration, surgery, or a combination thereof.

Moreover, the disclosed methods can be used to select at least one therapeutic agent (such as gene therapy (e.g., CRISPR), T cell therapy (e.g., CAR T cell), an antibody, nucleic acid, small molecule, or polypeptide, which antagonizes, inhibits, or blocks the expression or functional activity of at least one detected biomarker) suitable for use in a subject whose sample or tumor was the source for the representative sample generated by the methods provided.

In an additional aspect, the present disclosure pertains to a method for preparing a representative sample for analysis, comprising (1) obtaining a surgical resection tissue sample from at least one subject; and (2) homogenizing the surgical resection tissue sample to obtain a homogenized sample. In one embodiment, at least a portion of the surgical resection tissue sample is fixed. In an additional embodiment, the method further comprises processing a first portion of the surgical resection sample and generating one or more fixed, embedded tissue blocks and further homogenizing a second portion of the remaining surgical tissue resection sample. A portion of the one or more fixed, embedded tissue blocks may be processed by micrototomy to produce one or more tissue thin sections for morphological analysis. In addition, the at least one of the one or more fixed, embedded tissue blocks may be homogenized. In one aspect the surgical resection tissue sample includes one or more separate pieces of tissue. In an additional embodiment, the one or more separate pieces of tissue comprise at least a portion of one or more primary solid tumor tissue masses resected from a subject to obtain the surgical resection sample. In another aspect, the one or more separate pieces of tissue comprise at least a portion of one or more lymph nodes resected from the subject.

In an additional embodiment, the method further comprises separately homogenizing at least a portion of the separate pieces of tissue to yield separate homogenized samples. In an additional embodiment, the surgical resection tissue sample comprises a single tissue mass which may be further divided into two or more pieces of the single tissue mass. Additionally, at least one of the two or more pieces of the single tissue mass may be homogenized and preserved. In one aspect, the homogenization may comprise physical separation, such as cutting, dicing, or mincing. In another aspect, the homogenization may comprise mechanical disassociation, such as blending or juicing. In yet another aspect, the homogenization is accomplished by biochemical disassociation, for instance with a protease.

In an additional aspect, one or more biomolecules may be purified from at least a portion of the homogenate, such biomolecules may include DNA, RNA, proteins, lipids, and metabolites. The biomolecules may then be analyzed, for instance by PCR, mass spectrometry, next generation sequencing, or ELISA. Such analysis produces at least one dataset.

In an additional embodiment, at least a portion of the homogenized sample may be embedded in paraffin. In an additional aspect, the method further comprises preparing one or more thin sections of the paraffin embedded homogenized sample and performing histological analysis on the sample. Such histological analysis may include H&E staining, IHC staining, ISH staining, and FISH staining. The histological analysis may be interpreted by a human or quantified on an automated device. In an additional embodiment, the interpretation or quantification produces at least one dataset.

In one aspect, the disclosure also pertains to further processing at least a portion of the homogenate to generate cellular fragments. Such processing may include physical, mechanical, chemical, or enzymatic methods. Such cellular fragments may include nuclei, cellular membranes, and cellular organelles. In another aspect, at least a portion of the cellular fragments are affixed to at least one glass slide and optionally subjected to histological analysis. Such histological analysis may include H&E staining, IHC staining, ISH staining, or FISH staining. The analysis may be interpreted by a human or quantified by an automated device. The interpretation or quantification results in the creation of at least one dataset.

In an additional aspect, at least a portion of the cellular fragments is analyzed by flow cytometry, FACS, or particle analyzer, wherein such analysis produces a data set. In one aspect, at least one cellular fragment from the at least a portion of the cellular fragments is purified. Such purification may occur, for example, by FACS, affinity purification, size exclusion differential centrifugation, filtration, or electrophoresis. In another embodiment, biomolecules may be isolated from the purified at least one cellular fragment from the at least a portion of the cellular fragments. The biomolecules may be analyzed by PCR, mass spectrometry, next generation sequencing, or ELISA. In one aspect the analysis produces at least one dataset.

In yet another embodiment, the method of the present disclosure further comprises further processing at least a portion of the homogenate to generate at least one disassociated cell, for instance by physical, mechanical, chemical, or enzymatic. The disassociated cell is a normal cell, a cancer cell, or a bacterial cell. In one aspect, the disassociated cell is affixed to at least one glass slide and subjected to histological analysis. Such analysis may include, for example, H&E staining, IHC staining, ISH staining, or FISH staining. In an additional embodiment, the analysis is interpreted by a human or quantified by an automated device. In an additional embodiment, the interpretation or quantification produces at least one dataset. In an additional aspect, at least one cell from the at least one disassociated cell is purified by such means as FACS, affinity purification, size exclusion differential centrifugation, filtration, or electrophoresis. In an additional embodiment, biomolecules may be isolated from the purified at least one cell from the at least one disassociated cell. In an additional aspect, the biomolecules may be analyzed, for example by PCR, mass spectrometry, next generation sequencing, or ELISA. In an additional embodiment, such analysis produces at least one dataset.

In an additional aspect, the purified at least one cell from the at least one disassociated cell is affixed to at least one glass slide, and optionally is subjected to histological analysis. In an additional embodiment, the histological analysis is H&E staining, IHC staining, ISH staining, or FISH staining. Such analysis may be interpreted by a human or quantified by an automated device. In an additional aspect, the analysis or interpretation produces at least one dataset.

In an additional embodiment, the datasets produced by the above-disclosed methods are further analyzed. In one aspect, the analysis comprises the determination of a biomarker diversity or phenotypic diversity. In an additional embodiment, the analyzing comprises the determination of at least one clinical decision. Such clinical decision, in one aspect, includes determining disease prognosis, predicting recurrence of disease, predicting targets of therapy of disease, inclusion of subjects of clinical trials, or therapeutic treatment strategy for at least one subject.

Sequence Listing

The nucleic acid sequence provided herein is shown using standard letter abbreviations for nucleotide bases as defined in 37 C.F.R. 1.822. The sequence listing is submitted as an ASCII text file, named "Ventana-0155_ST25.txt" created on Mar. 26, 2019, 1 KB, which is incorporated by reference herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 illustrates an exemplary DAB ICC protocol, set forth in steps 1-102, for protein detection in representative samples. In this particular example, the protocol was used to detect Her2.

FIG. 11 provides an exemplary fluorescence ICC protocol (set forth in steps 1-38) for protein detection in representative samples.

FIG. 20A illustrates H&E staining of a first section taken from a papillary urothelial kidney tumor.

FIG. 20B illustrates H&E staining of a second different section taken from the papillary urothelial kidney tumor of FIG. 20A. Each of the sections illustrated in FIGS. 20A and 20B were obtained by a pathologist. The difference in H&E staining shows the variation within the same tumor.

FIG. 20C illustrates H&E staining of a representative sample prepared from the papillary urothelial kidney tumor of FIGS. 20A and 20B.

FIG. 22A illustrates Alk DAB staining of a first section taken from a papillary urothelial kidney tumor;

FIG. 22B illustrates Alk DAB staining of a second different section taken from the papillary urothelial kidney tumor. Each of the sections illustrated in FIGS. 22A and 22B were obtained by a pathologist. The difference in Alk DAB staining shows the variation within the same tumor.

FIG. 22C illustrates Alk DAB staining of a representative sample prepared from the papillary urothelial kidney tumor.

FIG. 25A illustrates an H&E image of stained histological slides made of hand cut (~2 mm²) tonsil tissue.

FIG. 25B illustrates an additional H&E image of stained histological slides made of hand cut (~2 mm²) tonsil tissue.

FIG. 25C illustrates an H&E image of stained histological slides made of tonsil tissue minced with a "juicer" (~200 um²).

FIG. 25D illustrates an additional H&E image of stained histological slides made of tonsil tissue minced with a "juicer" (~200 um²).

FIG. 27A shows size distribution of mechanically dissociated and filtered single cells from colon tumor sample.

FIG. 27B shows cells mechanically dissociated and filtered immune cells from tonsils; and FIG. 27C shows EpCAM positive cells (tumor cells) sorted from mechanically dissociated and filtered cells from colon tumor sample.

FIG. 31A shows dissociated tonsil cells sorted using magnetic beads. FSC-A vs. FSC-H was used for doublet discrimination. Fluorescent cells above certain threshold were used in the comparison.

FIG. 31B illustrates bar graphs showing the percentage of fluorescent cells (CD3 or CD8 positive cells) in the total cell population (FIG. 31A) before and after depletion.

FIGS. 32A-J shows sonication of multicellular aggregates. The sonication of multicellular aggregates (population size between 12 and 18 um) gives single cells (population size between 5.5 and 9.3 um). The size of the generated single cells corresponds to that of tumor cells. FIG. 32A shows the result of sonication where the system received 0J of energy at sonication. FIG. 32B shows the result of sonication where the system received 105 J of energy at sonication. FIG. 32C shows the result of sonication where the system received 210 J of energy at sonication. FIG. 32D shows the result of sonication where the system received 315 J of energy at sonication. FIG. 32E shows the result of sonication where the system received 35 J of energy at sonication. FIG. 32F shows the result of sonication where the system received 140 J of energy at sonication. FIG. 32G shows the result of sonication where the system received 245 J of energy at sonication. FIG. 32H shows the result of sonication where the system received 70 J of energy at sonication. FIG. 32I shows the result of sonication where the system received 175 J of energy at sonication. FIG. 32J shows the result of sonication where the system received 280 J of energy at sonication.

FIG. 33A shows size distribution of collagenase treated cell aggregates with sonication.

FIG. 33B shows size distribution of collagenase treated cell aggregates without sonication.

FIG. 33C illustrates images of the samples displayed in FIG. 33A.

FIG. 33D illustrates images of the samples displayed in FIG. 33B.

FIG. 42A illustrates H&E stained slides of tissue digested with Pepsin, 5 mg/ml, at 37 degrees C., for 30 min (left panel) or 24 hours (right panel).

FIG. 42B illustrates H&E stained slides of tissue digested with Trypsin, 0.25%, at 37 degrees C. for 30 min (left panel) or 24 hours (right panel).

FIG. 43 is a graph of sub-100 micron particles isolated from parallel representative tonsil samples using different enzymatic methods listed in Table 6.

FIG. 44A shows a graph illustrating sub-100 micron particles isolated from representative tonsil samples dissociated by mechanical or proteinase K-pepsin methods. Error bars represent S.D. of three independent experiments **p=0.0037 using unpaired T-test.

FIG. 44B shows brightfield images of H&E stained slides of particles isolated using mechanical disassociation.

FIG. 44C shows brightfield images of H&E stained slides of particles isolated using proteinase K pepsin dissociation methods.

FIG. 45A is a bar graph showing average yield of nuclear particles isolated from aliquots of representative samples from a colon (N=3) and a lung tumor (N=4).

FIG. 45B is a graph showing the distribution of nuclear particles prepared from aliquots of a representative colon tumor sample into sized particle bins.

FIG. 46A is a bar graph showing average percentage of DNA released by dissociation of representative tonsil samples using mechanical (Mech) or Proteinase K (ProtK)-Pepsin methods.

FIG. 46B is a bar graph showing percentage of DNA released by dissociation of representative tumor samples.

FIG. 47A provides a dot plot of side scatter vs. forward scatter for samples prepared using autoMACS® buffer.

FIG. 47B provides initial flow cytometry experiments where the were samples prepared using autoMACS® buffer. The experiments revealed that ~35% of the particles existed in an aggregated state, as evidenced by the presence of particles in peaks of higher DAPI staining intensity (R2 (green) and R3 (pink). When back-gated onto the dot plot of side scatter vs. forward scatter FIG. 47A, these particles fall in peaks of higher DAPI intensity when compared to regions with higher forward and side scatter, indicating a larger size.

FIG. 47C provides a chart summarizing data from the flow cytometry experiments.

FIG. 47D provides a dot plot of side scatter vs. forward scatter samples prepared using autoMACS® with 1% Tween™ 20.

FIG. 47E visualizes the discovery that the addition of 1% Tween™ 20 reduced the number of aggregated particles from ~35% to ~23% (compare R2+R3 of plots in B to the same regions of plots in A).

FIG. 47F provides a chart summarizing data from the flow cytometry experiments.

FIG. 49A illustrates show tyramide Signal Amplification (TSA) images (20×) of mechanically isolated cells from fixed tonsil tissue stained for CD45 (red) by standard immunofluorescence. DAPI staining (blue) marks nuclei. 100 ms exposure was used for both images.

FIG. 49B illustrates show tyramide Signal Amplification (TSA) images (20×) of mechanically isolated cells from fixed tonsil tissue stained for CD45 (red) by TSA. DAPI staining (blue) marks nuclei. 100 ms exposure was used for both images.

FIG. 49C illustrates images show tyramide Signal Amplification (TSA) (40×) of nuclei isolated from fixed tumor tissue stained using TSA. The image shows stained without primary antibody (lung tissue) (Neg. control). DAPI staining (blue) marks nuclei. 2 ms exposure was used for all images.

FIG. 49D illustrates images show tyramide Signal Amplification (TSA) (40×) of nuclei isolated from fixed tumor tissue stained using TSA. The image shows stained without primary antibody (colon tissue) (Neg. control). DAPI staining (blue) marks nuclei. 2 ms exposure was used for all images.

FIG. 49E illustrates images show tyramide Signal Amplification (TSA) (40×) of nuclei isolated from fixed tumor tissue stained using TSA. The image shows staining with anti-cytokeratin (red) primary antibodies (lung tissue). DAPI staining (blue) marks nuclei. 2 ms exposure was used for all images.

FIG. 49F illustrates images show tyramide Signal Amplification (TSA) (40×) of nuclei isolated from fixed tumor tissue stained using TSA. The image shows staining with anti-cytokeratin (red) primary antibodies (colon tissue). DAPI staining (blue) marks nuclei. 2 ms exposure was used for all images.

FIG. 50A shows how positive cytokeratin (CK) staining distinguishes tumor nuclei from normal. Histograms of flow cytometry data for nuclei isolated from a colon tumor representative samples.

FIG. 50B shows how positive cytokeratin (CK) staining distinguishes tumor nuclei from normal. Histograms of flow cytometry data for nuclei isolated from a colon tumor representative samples.

FIG. 50C shows positive cytokeratin (CK) staining distinguishes tumor nuclei from normal. Histograms of flow cytometry data for nuclei isolated from a lung tumor representative samples.

FIG. 50D shows positive cytokeratin (CK) staining distinguishes tumor nuclei from normal. Histograms of flow cytometry data for nuclei isolated from a lung tumor representative samples.

FIG. 50E shows how positive cytokeratin (CK) staining distinguishes tumor nuclei from normal. Histograms of flow cytometry data for nuclei isolated from a colon tumor representative samples.

FIG. 50F shows how positive cytokeratin (CK) staining distinguishes tumor nuclei from normal. Histograms of flow cytometry data for nuclei isolated from a colon tumor representative samples.

Figure 50G:
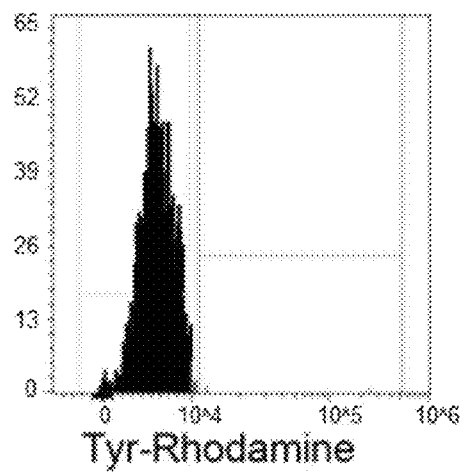

FIG. 50G shows how positive cytokeratin (CK) staining distinguishes tumor nuclei from normal. Histograms of flow cytometry data for nuclei isolated from a colon tumor representative samples.

Figure 50H:
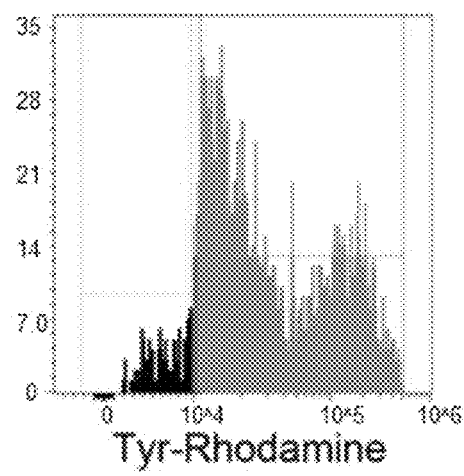

FIG. 50H shows positive cytokeratin (CK) staining distinguishes tumor nuclei from normal. Histograms of flow cytometry data for nuclei isolated from a lung tumor representative samples.

Figure 50I:
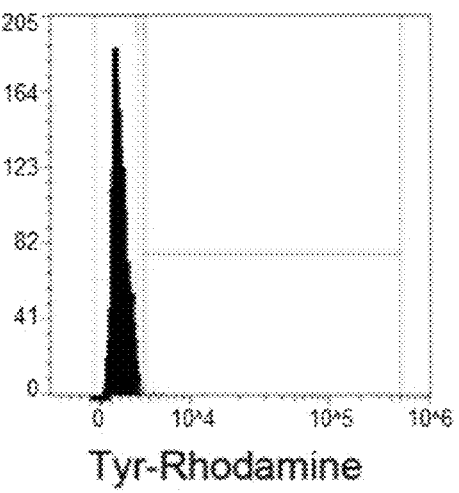

FIG. 50I shows positive cytokeratin (CK) staining distinguishes tumor nuclei from normal. Histograms of flow cytometry data for nuclei isolated from a lung tumor representative samples.

Figure 50J:
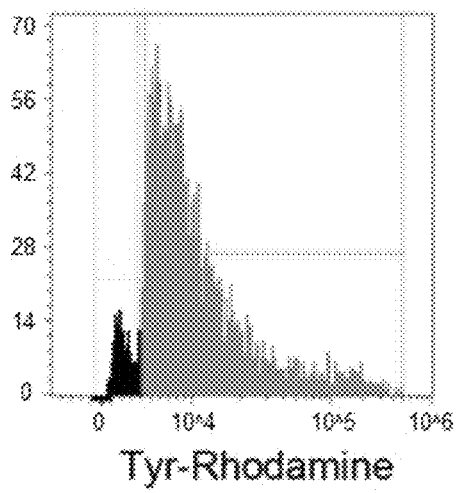

FIG. 50J shows positive cytokeratin (CK) staining distinguishes tumor nuclei from normal. Histograms of flow cytometry data for nuclei isolated from a lung tumor representative samples.

Figure 51A:
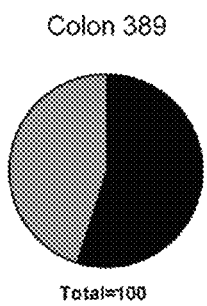

FIG. 51A illustrates a fraction of nuclei isolated from a colon adenocarcinoma (389).

Figure 51B:
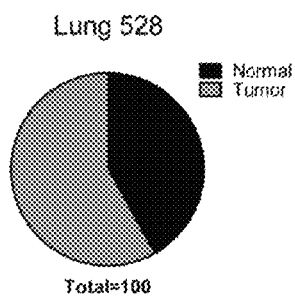

FIG. 51B illustrates a fraction of nuclei isolated from a lung squamous carcinoma (528) that were designated normal vs. tumor using flow cytometry.

Figure 51C:
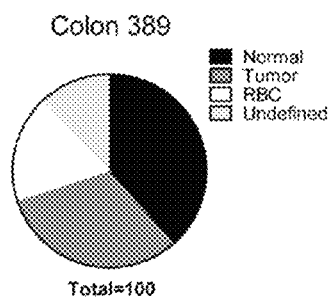

FIG. 51C illustrates a fraction of normal and tumor cells isolated from a colon adenocarcinoma (389).

Figure 52:
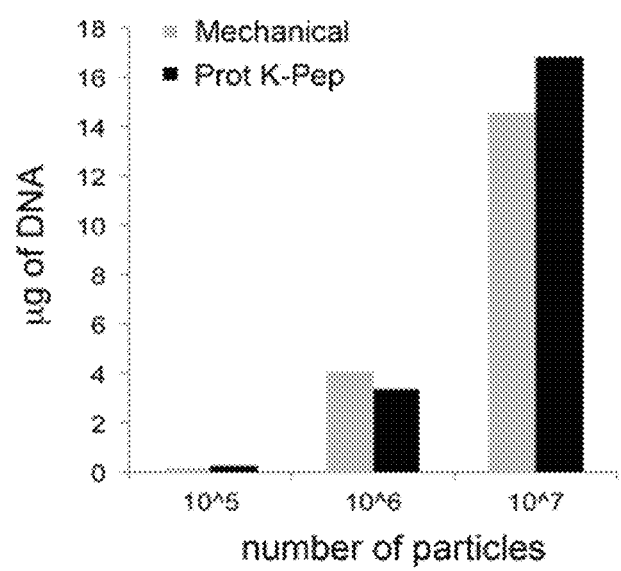

FIG. 52 illustrates a graph showing quantification of the DNA yield from nuclei isolated from representative samples.

Figure 53A:
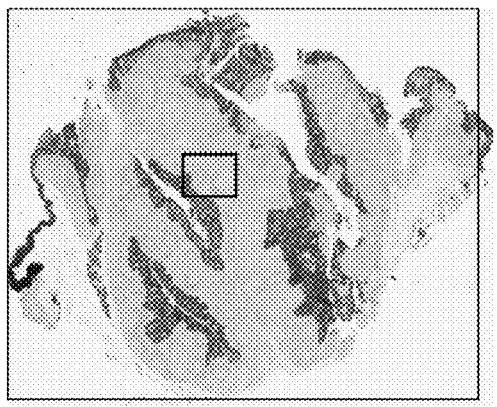
Figure 53B:
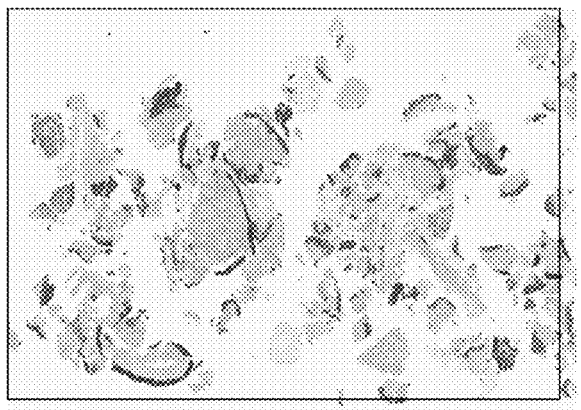

FIGS. 53A and 53B are whole slide images of a histological section taken from an intact tonsil stained with a pan-keratin antibody FIG. 53A depicts a traditional histological section of a normal tonsil detected by DAB for Pan-Keratin.

FIG. 53B is a section from a representative sample of tonsil detected by DAB for Pan-Keratin. The organization and structure of the tonsil is further highlighted in the box in figure FIG. 53A, where the epithelial tissue in brown is adjacent to multiple germinal centers containing the many different types of lymphocytes.

Figure 54A:
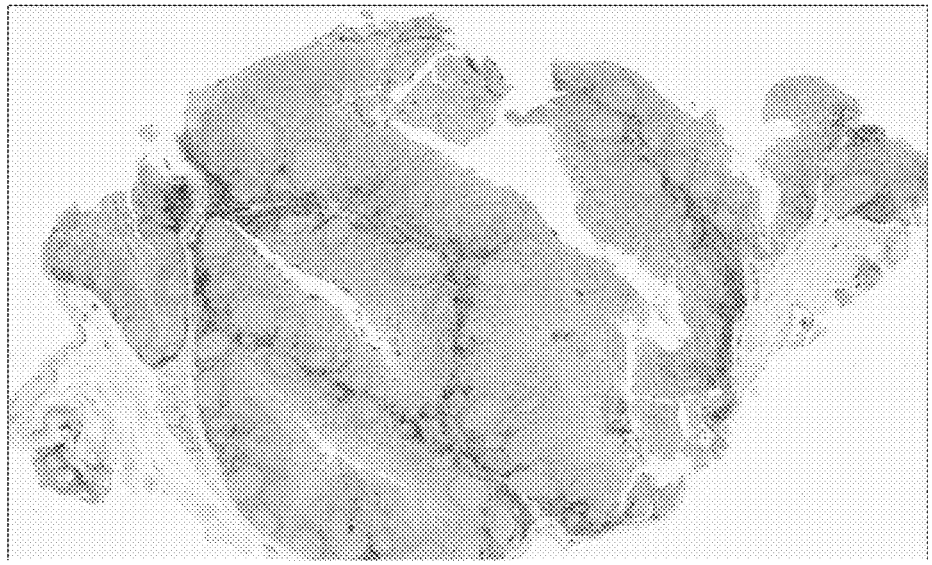

FIG. 54A is a whole slide image of a histological section taken from an intact tonsil stained with a pan-keratin antibody depicting a traditional histological section of a normal tonsil detected by DAB for Pan-Keratin.

Figure 54B:

FIG. 54B is a whole slide image of a histological section taken from an intact tonsil stained with a pan-keratin antibody depicting a section from a representative sample of tonsil detected by DAB for Pan-Keratin.

Figure 55:
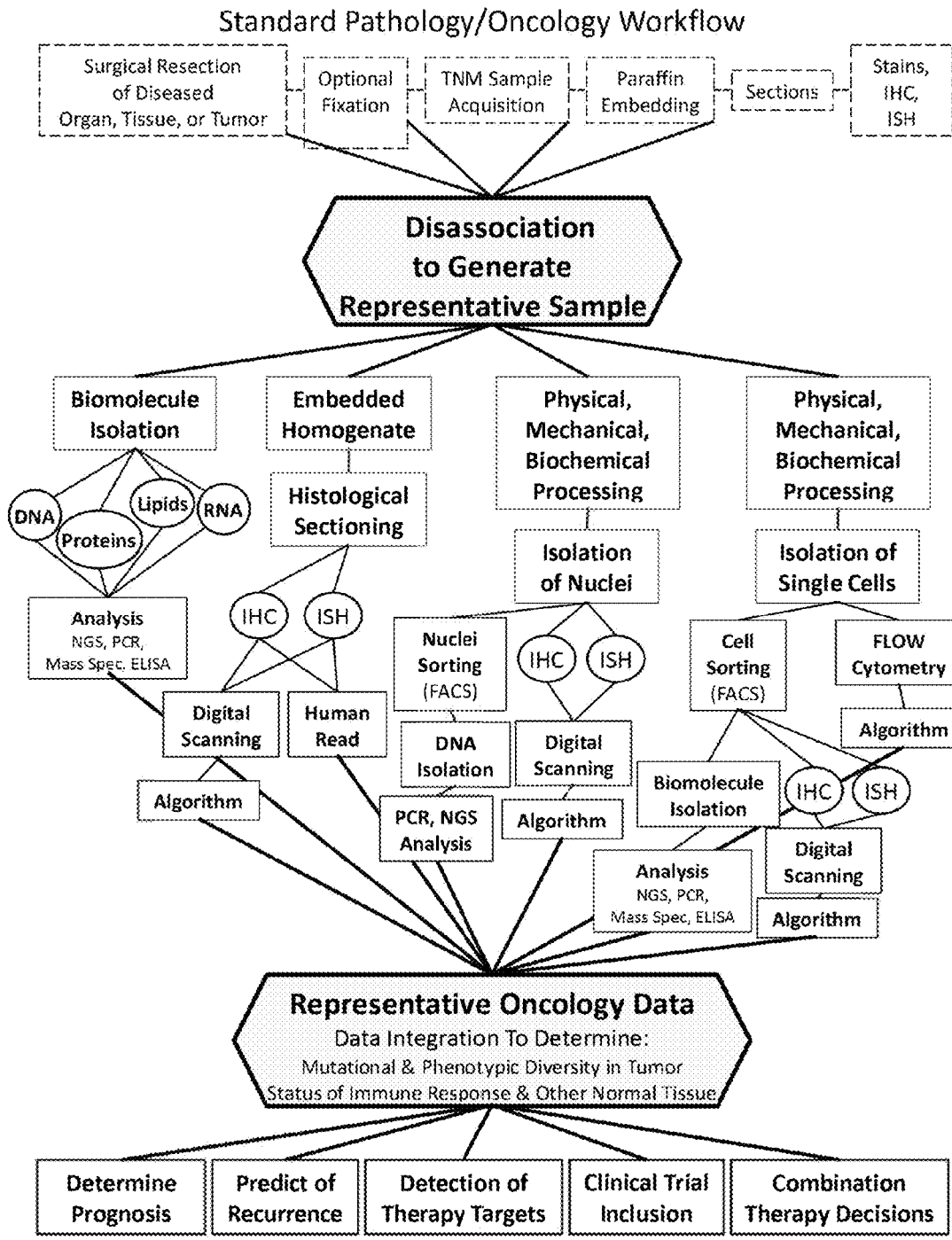

FIG. 55 is a diagram of the workflow of the current disclosure

DETAILED DESCRIPTION

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human.

A "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

Unless otherwise defined, all technical and scientific terms used herein have the same meaning as commonly understood to one of ordinary skill in the art to which this disclosure belongs.

The term "representative sample" in the disclosure refers to a sample (or a subset thereof) that accurately reflects the components of the entirety and, thus, the sample is an unbiased indication of entire population. Samples are derived from solid organs, tissues, and tumors ("OTT") that are originally composed of spatially segregated cellular structures, and further organized into spatially segregated cells types. Representative Sampling techniques and methods are those which sufficiently homogenize, mix, or otherwise disrupt the spatially stratified three dimensional structure of an OTT such that the components (cell structures, cells, peptides, nucleic acids, lipids, metabolites, etc.) of the original spatially stratified OTT are present in a sub-sample (a.k.a. —analytical sample) in the proportion that they existed in the original organ, tissue, or tumor. In some embodiments, the representative sample refers to a sample of the OTT that constitutes as much of the OTT as possible, approaching the entirety of the OTT or encompassing a significant enough portion of the OTT to approach the goal of representing the diversity of the OTT at the level of clusters of attached cells, individual cells, fragments of cells, organelles, peptides, nucleic acids, lipids, metabolites, etc. The representative sample may contain the minimum amount of the intact OTT required to encompass the diversity of the OTT. In an additional embodiment, the Representative sample may be comprise a plurality of segments or particles where at least a portion of those particles are embedded in paraffin and at least a portion of the remainder of the particles are homogenized.

Multiple representative samples may be made from a single OTT. In this embodiment, the surgically removed or resected OTT is first processed or otherwise manipulated into separate sub units, such that each sub unit is composed of spatially stratified cell structures, cells, peptides, nucleic acids, etc. Each sub unit is then sufficiently homogenized, mixed or otherwise disrupted to produce a representative sample of the OTT sub unit.

The representative sample may be homogenized or otherwise mixed or disrupted to the point that any analytical sample, or portion of the representative sample, contains a random sampling of the material present in the representative sample. The analytical sample is a large enough fraction of the representative sample so that it encompasses the diversity of the representative sample relative to the intended output of the analytical test being applied (i.e. cells v. clusters of attached cells). Any analytical sample used for a specific assay will produce data consistent with another analytical sample used for the same assay, within experimental error. In addition, any analytical sample chosen for a specific assay would provide information that could be cross-referenced to data generated with different assays using analytical samples taken from the same representative sample, or from other representative samples made from OTTs from the same patient, a different patient, or a combination of patients or subjects. Because the proportions of the original biological components are present in every analytical sample taken from a representative sample, data produced from analytical samples pertaining to the proportions of the biological components of OTTs can be compared between patients or combinations of patients.

Other samples containing less diversity than an analytical sample may be taken from a representative sample for analysis, for example a single cell. However, millions of single cells taken from a representative sample of an OTT would generate a "representative data set," which includes "representative oncology data."

In one embodiment, the cells or cell components are dissociated within the representative sample such that their relative proportion or percentages within the representative sample or a portion thereof accurately reflects or mimics the relative proportion or percentages of these cell types or components within the entire intact tissue specimen. The specimen may be, in one embodiment a solid tumor, lymph node, metastases, polyp, cyst, or portion thereof or combination of any of the foregoing.

In one embodiment, the representative samples disclosed herein are obtained by homogenization of large volumes of an intact tissue or tumor sample (such as a clinical tumor sample) or lymph node or metastases or combination thereof obtained from a subject. For example, the whole tumor or a substantial portion thereof may be used as the input material from which the representative sample is generated, e.g., at least 50%, at least 75%, or at least 95%, or preferably all of a tumor or lymph node. The representative sample may be generated from an intact tumor biopsy sample from a solid tumor. In one embodiment, the sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells, optionally from spatially distinct regions of the tumor. Generally, there are about 1 billion cells in a tumor or portion thereof having an about 1 cm diameter and, for the most part, this relationship proceeds on a linear scale. For example, an excisional sample such as a biopsy having about a 2 cm diameter can comprise 3-5 billion cells. In another embodiment, the representative samples disclosed herein are obtained by homogenization of one or more putative normal tissue specimens, e.g., derived from a subject at risk of developing cancer as the result of a genetic mutation or prior cancer, or adjacent normal tissue from a surgical resection for use as a control sample.

In an additional embodiment, the term "representative tumor sample" refers to a representative sample prepared from a tumor, e.g., a resected tumor, or from a sample potentially containing cancer cells, or from a sample to be tested for the potential presence of cancer cells, such as a lymph node. Likewise, the phrase "tumor sample" encompasses samples prepared from a tumor or from a sample potentially containing cancer cells, or a sample to be tested for the potential presence of cancer cells, such as a lymph node.

In an additional embodiment, the term "representative normal sample" refers to a representative sample prepared from a putative normal tissue, e.g., a biopsy, polyp, or cyst obtained from a patient, or a sample to be tested for the potential presence of cancer or precancerous cells or immune cells suggestive of an immune irregularity. Likewise, the phrase "normal sample" encompasses samples prepared from a putative normal tissue, e.g., a biopsy, polyp, or cyst potentially containing cancer cells, or to be tested for the potential presence of cancer cells, such as a lymph node. In an additional embodiment, a "normal sample" may also refer to a tissue that is likely disease free to which the tumor sample can be compared to identify phenotypic changes due to the disease state.

The term "representative data," as used herein, refers to any set of data, (e.g., expression of a gene, percentage of certain cell type (e.g., immune cells), protein expression, SNP expression or lack thereof, level, quantity of microRNA expression, or number of histological subtypes) or a relatively small quantity of data that that accurately reflects an entire data set, the source of which is derived from a representative sample of a tissue, organ, or tumor. In one embodiment, the representative data is the unbiased data indicating the diversity of the entire tissue, organ, or tumor. As used herein, a "dataset" is a collection of data. In one embodiment, the dataset is composed of separate elements but can be manipulated as a unit. In one embodiment, a dataset may include information regarding biomarker diversity or phenotypic diversity.

As used herein, the term "histological analysis" refers to the study of the microscopic anatomy of cells and tissues of plants and animals. This analysis is helpful in gathering information regarding the biological components of the sample, for instance nucleic acids (RNA, DNA), proteins lipids or metabolites. Histological techniques include those known to one of skill in the art, some non-limiting examples including PCR, mass spectrometry, next generation sequencing and ELISA. In addition, histological analysis can include the simultaneous detection of more than one biological component, i.e., multiplexing.

As used herein, "clinical decision making" refers to gathering information and integrating this information to draw diagnostic conclusions and determine which treatments to give to a patient. Such diagnostic conclusions may include the disease from which a patient suffers and what testing should be performed on the patient. In one embodiment, a clinical decision may also include determining disease prognosis, predicting recurrence of disease, predicting targets of therapy of disease, inclusion of subjects of clinical trials, or determination of a therapeutic treatment strategy for at least one subject.

As used herein, the term "homogenate" refers to the biomass obtained after an tissue is homogenized or processed. A homogenate can contain any cellular components from the tissue, including but not limited to cells, peptides, nucleic acids, lipids, metabolites, etc. In one aspect, the homogenate is the representative sample that accurately reflects the portion, ratio, or fraction of the components of the tissue from which it is derived. In some embodiments, the ratio of cellular structures, cellular components, or any constituents (cells, peptides, nucleic acids, lipids, metabolites, etc.) of the homogenate (or some or each subset of the homogenate) is the same, similar or substantially similar to the ratio of cellular structures, cellular components, or any constituents in the original intact tissue. Like a representative sample, the homogenate may contain the minimum amount of the intact organ, tissue, or tumor required to encompass the diversity of the organ, tissue, or tumor.

The tissue(s) from which the homogenate is derived may come from one tissue, two tissues, or multiple tissues. In some embodiments, the homogenate comes from one subject, two subjects, or more than two subjects. In one aspect, the two or more subjects are genetically homogenous subjects. In another aspect, the two or more subjects are phenotypically homogenous subjects. In some aspects, the two or more subjects are genetically diverse subjects. In one aspect, the two or more subjects are phenotypically diverse subjects. In another aspect, the two or more subjects are from the same gender. In a further aspect, the two or more subjects are from different genders. In yet another aspect, the two or more subjects are from different ethnicity groups. In one aspect, the two or more subjects are from the same ethnicity group. In another aspect, the subject is selected from the group consisting of an animal or a human subject.

As used herein, the term "substantially" means a high degree of identity in quality or quantity, e.g., at least about 60%, or alternatively at least about 70%, or alternatively about 80%, or alternatively about 85%, or alternatively about 90%, or alternatively about 95%, or alternatively about 98%.

"Similar" means less than 100% identical, or alternatively greater than 98% identical, or alternatively greater than 95% identical, or alternatively greater than 90% identical, or alternatively greater than 85% identical, or alternatively greater than 80% identical, or alternatively greater than 75% identical. The term "uniform" intends identity of at least 80%, or alternatively of at least 85%, or alternatively at least 90%, or alternatively at least 95%, or alternatively at least 98%, or alternatively at least 100%, identical. Non-uniform intends less than 80% identical.

As used herein, the term "processed" means that the homogenate composition has been subjected to, at a minimum, physical, mechanical, or chemical treatment. In one aspect, the resulting homogenate composition is subjected to more than two types of processing. In other aspects, the homogenate composition is subjected to three types of processing. In yet another aspect, the homogenate is subjected to four or more types of processing.

The term "derived from" means that the sample was obtained or received from a source.

The term "subset" means a part or component of a larger group. "Ratio" is a relative quantitative value of a part in relation to a larger group of components or parts.

As used herein, the terms "cellular structure," "cellular component," or "component" can be used interchangeably to refer to any substances or materials within the cells, tissues, or organisms, or any substances or materials that are produced during and after the cells, tissues, or organisms are processed. The substances or materials can be native or foreign to the cells, tissues, or organisms. In some aspects, the "cellular structure" and "cellular component" may also include any substances or materials that are modified or processed, e.g., the cells or nucleic acid with dye or radioactive materials. The cellular structures or cellular components include but are not limited to cells, receptors, proteins, lipids, cellular organelles, membranes, chemicals, nucleic acids, small molecules, bacteria, protozoa, viruses, parasites and/or portions or fractions thereof. As used herein, "cell fragments" include portions of a whole cell, such as nuclei, cellular membranes and cellular organelles.

As used herein, the term "spatially distinct" or "spatially segregated" refers to elements that are distributed in different regions of a three-dimensional space. In one embodiment, the representative sample captures all of the spatially distinct subpopulations of cancer cells within a tumor. In another embodiment, the tumor samples used to generate the representative sample are taken from different regions of the tumor sample. For example, proximal versus distal regions of the tumor, different faces of the tumor, different layers of the tumor, etc. in an effort to capture the diversity within the whole tumor.

The terms "homogenizing" or "homogenization" refer to a process (such as a mechanical process and/or a biochemical process) whereby a biological sample is brought to a state such that all fractions of the sample are equal in composition. Representative analytical samples may be prepared by removal of a portion of a sample that has been homogenized. In general, a tumor, lymph node, or other sample referred to as "liquefied" in the context of the present disclosure is understood to have been mixed or blended sufficiently as to be homogenized. A homogenized sample is mixed such that removing some of the sample (an aliquot) does not substantially alter the overall make-up of the sample remaining and the components of the aliquot removed are substantially identical to the components of the sample remaining. In the present disclosure the "homogenization" will in general preserve the integrity of the majority of the cells within the sample, e.g., at least 50, 80, 85, 90, 95, 96, 97, 98, 99, 99.9% or greater percentage of the cells in the sample will not be ruptured or lysed as a result of the homogenization process. The homogenates may be substantially dissociated into individual cells (or clusters of cells) and the resultant homogenate or homogenates are substantially homogeneous (consisting of or composed of similar elements or uniform throughout). In one embodiment, the term "homogenization" refers to a process in which a tissue or a biological sample is processed to the extent that any subsets, portions, or fractions of the tissue are similar, substantially similar or identical in some aspects.

In one embodiment, the term "mechanical homogenization" refers to the homogenization resulting from mechanical means.

As used herein, the term "biochemical disassociation" means disassociation using an enzyme, such as a protease. Biochemical dissociation may be affected by protease concentration, incubation time, and temperature.

As used herein, the term "physical separation" or "physical disassociation" of a tissue sample refers to homogenization or disassociation of the sample with a sharp object by mechanical means, for instance by cutting, mincing or dicing. "Cutting" generally results in tissue sections of approximately 1.0 mm-5.0 mm. in size. Mincing generally results in tissue sections of approximately 0.5-2.0 mm in size. Dicing generally results in tissue sections of approximately 0.1-1.0 mm in size.

As used herein, "mechanical separation" or "mechanical disassociation" of a tissue sample refers to homogenization or disassociation of the sample with a mechanical source, such as a traditional blender, a juicer or a bead beater, as is known to one of skill in the art.

As used herein, a "disassociated cell" is a cell that was once part of a tissue or organ, but that is separated from that tissue or organ.

Depending on the mechanical and/or biochemical dissociation process applied to the sample to generate the homogenate, the cell clusters may comprise more than one (1) cell to thousands of cells. The clusters can be dissociated (decreased in size and/or number of cells contained therein) by the application of further processing methods, e.g., by further mechanical and/or biochemical dissociation and/or by size exclusion, depending on the subsequent assay to be performed using the representative sample (for example, IHC requiring cell clusters containing tens to thousands of cells, or FACS or flow cytometry requiring single cells or fragments of cells).

The presently described methods are flexible with regard to the degree of sample dissociation. Target cell aggregate size may be controlled by further processing cell clusters obtained following application of a first mechanical means (such as blending or the equivalent) such that the clusters correspond with the dissociation goal of the sampling method. In one aspect, mechanical shearing and size exclusion, for instance sieving with a series of mesh, may be used to remove cell clusters at or below a certain size while retaining larger cell clusters for further processing to reach the target particle size. The resulting distribution of cell cluster particle sizes are determined by size exclusion techniques to remove certain particles from the dissociation process to reach a sizing plateau rather than a distribution.

After homogenization, the resultant clusters may contain at least 1-2, 2-100, 100-500, 500-1,000, 1,000-10,000, 10,000-50,000, or more cells. In one aspect, the clusters contain single cells, about 2-10 cells, about 10-20 cells, or about 20-40 cells. The size of the resultant clusters will vary. See, e.g., FIG. 20.

As a result of homogenizing the sample, the distribution of cells within the sample is substantially homogeneously distributed within the resultant homogenate or a portion or fraction thereof, such that the homogenate or any fraction thereof represents the heterogeneity of the original sample. A homogenized sample may be referred to as a liquid or liquefied sample based on its ability to flow, notwithstanding that many or most of the cells remain intact.

Other moieties may be added to these homogenates or representative samples, for example other cells, haptens or labels.

The term "heterogeneity" refers to diversity or incongruity, e.g., a composition of different or dissimilar parts, or variations in form, function, and behavior. The term "heterogeneous tissue sample" intends a sample that is not uniform in composition or character, for example, diverse in form, function or behavior. In the context of cancer, the term "tumor heterogeneity" describes the observation that different tumor cells may display distinct morphological, phenotypic, and genetic profiles, including cellular morphology, gene expression, gene mutations, metabolism, motility, proliferation, and metastatic potential. Heterogeneity can occur between tumors (inter-tumor heterogeneity) and within tumors (intra-tumor heterogeneity). Tumor heterogeneity has been observed in a variety of cancers including, but not limited to, lung cancer, leukemia's, breast cancer, kidney cancer, prostate cancer, colon cancer, brain cancer, esophageal cancer, cancers of the head and neck, bladder cancer, gynecological carcinomas, liposarcomas, and multiple myeloma. Two models are proposed to explain heterogeneity in tumor cells: the cancer stem cell model and the clonal evolution model. The cancer stem cell model provides that heterogeneity observed between tumor cells results from differences in the cancer stem cells from which tumor cells originate. The clonal evolution model provides that tumors arise from a single mutated cell but accumulate additional mutations (which give rise to additional subpopulations, each of which has the ability to divide and mutate further), which accounts for the observed diversity in cancer cells from the same tumor. These models are not believed to be mutually exclusive and, thus, both likely contribute to heterogeneity in varying amounts across different tumor types. Tumor heterogeneity comprises global variance (population variance) and the spatial structure of that variation (population spatial stratification) and, thus, both elements of variation should be considered in sample designs. Tumor heterogeneity can arise from genetic heterogeneity (e.g., resulting from exogenous factors, genomic instability, therapies, etc.), other heterogeneity (e.g., epigenetic), and/or the tumor microenvironment (e.g., regional difference in the tumor, such as oxygen availability or immune surveillance, impose different selective pressures on tumor cells).

The different tumor cell populations that arise as a result of the tumor heterogeneity are called "subclones", the progeny of a mutant cell arising in a clone.

The prevalence of subclones within a tumor may vary. Certain subclones comprise the majority of the tumor, but decrease over time and/or following certain treatments. Other subclones are initially undetectable, but later become abundant. Multiple subclones can exists simultaneously and vary in their prevalence over time it takes for the tumor to grow large enough to be detectable. The term "low prevalence events" or "low prevalence genetic events" within a tumor refers to rare events or rare genetic events (such as mutations) that occur at a rate of 10-1%, 1-0.1%, 0.1-0.01%, 0.01-0.001%, 0.001-0.0001%, 0.0001-0.00001%, 0.00001-0.000001%, or below 0.000001%. Because the sample generated by the disclosed methods is representative (or substantially representative) of the tumor as a whole, even low prevalence subclones (such as down to at least 0.000001%) in a tumor or biological sample can be detected, in addition to all other subclones that exist at higher prevalence rates.

The term "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein "normal tissue" refers to a tissue having no detectable lesion or abnormality that putatively correlates to an increased incidence of disease or in the context of cancer, malignancy. These normal samples may be derived from patients having genetic mutations or conditions that correlate with an increased incidence of disease (genetic or otherwise), cancer or malignancy. Normal tissue can be of the same type of tissue corresponding to the pathologic tissue from the same individual, or different individual; or normal tissue that is not related (e.g., either from a different location in the body or with a different histologic type) to the pathologic tissue either from the same individual or form other individuals.

As used herein "precancerous tissue" refers to a tissue containing some lesion or abnormality that putatively correlates to an increased incidence of cancer or malignancy.

The term "tumor" refers to a mass or a neoplasm, which itself is defined as an abnormal new growth of cells that usually grow more rapidly than normal cells and will continue to grow if not treated sometimes resulting in damage to adjacent structures. Tumor sizes can vary widely. A tumor may be solid or fluid-filled. A tumor can refer to benign (not malignant, generally harmless), or malignant (capable of metastasis) growths. Some tumors can contain neoplastic cells that are benign (such as carcinoma in situ) and, simultaneously, contain malignant cancer cells (such as adenocarcinoma). This should be understood to include neoplasms located in multiple locations throughout the body. Therefore, for purposes of the disclosure, tumors include primary tumors, lymph nodes, lymphatic tissue, and metastatic tumors. The dividing line between cancerous, pre-cancerous, and cancerous growths is not always clear, but there are general properties of each type of growth. Benign tumors are non-malignant tumors. A benign tumor is usually localized, and does not spread (metastasize) to other parts of the body. Most benign tumors respond well to treatment. However, if left untreated, some benign tumors can grow large and lead to serious injury or damage due to of their size. In this way, benign tumors can mimic malignant tumors and, thus, are sometimes treated. Malignant tumors are cancerous growths that are often resistant to treatment, may spread to other parts of the body, and sometimes recur after removal. "Cancer" is another term for a malignant growth (a malignant tumor or neoplasm).

The virulence of tumors may vary. Certain cancers can be relatively easy to treat and/or cure, whereas other cancers are more aggressive. Tumor virulence may be determined, at least in part, by differential gene expression or by the characterization of genomic alterations. In cancerous cells the mechanisms that allow a cell to activate or silence genes are damaged. As a result, there is often aberrant activation of genes specific to other tissues and/or to other stages of development. For example, in lung cancers, tumorous cells that express genes specific to the production of spermatozoids, which should be silent, are extremely virulent (a high-risk cancer that exhibits increased proliferative abilities and a facility to hide from the body's immune system). It has also been shown that in almost all cancers, tens of specific genes in the germline are aberrantly activated. See, e.g., Rousseaux et al., Ectopic Activation of Germline and Placental Genes Identifies Aggressive Metastasis-Prone Lung Cancers. *Science Translational Medicine* (2013) 5(186): 186. Accordingly, as the upregulation or downregulation of genes may be associated with a virulent form of a particular cancer, it is possible to be able to predict, following diagnostic tests, which cancers have a high risk of recurrence and a fatal prognosis, even in cases where the tumor is adequately treated, at an early stage of its development.

The term "lymph node" refers to an oval- or kidney-shaped organ of the lymphatic system, present widely throughout the body including the armpit and stomach and linked by lymphatic vessels. Lymph nodes contain a diverse number of immune cells, including but not limited to B cells and T cells. Lymph nodes are important for the proper functioning of the immune system and may act as filters for foreign particles and cancer cells.

The term "polyp" or "polyps" refers to an abnormal biological mass that is projecting from a mucous membrane. Polyps may be found in a number of tissues, including but not limited to colon, stomach, nose, ear, sinus(es), urinary bladder, and uterus.

The term "metastasis" or "metastatic tumor" refers to a tumor and/or its associated components, including but not limited to blood vessels, bones, meninges, that have developed or spread from one organ or part of the body to another.

The term "cyst" refers to a round or oval shaped closed sac that has a distinct membrane and division compared to the nearby tissue. In some aspects, a cyst is a cluster of cells that have grouped together to form a sac (not unlike the manner in which water molecules group together, forming a bubble). In some aspects, the cells forming the "shell" of such a sac or a cyst are distinctly abnormal when compared to all surrounding cells for that given location. A cyst may include but is not be limited to air, fluids, or any semi-solid materials. Some tumors may contain cysts, or be described as "cystic".

The term "resection" refers to all or part of an organ or other body structure that is removed from a subject.

The term "organ" or "organs" as used herein refers to any anatomical part or tissue having a specific function in an animal. The term includes a portion or all of an anatomical part or a tissue, e.g., a lobe of a lung. Such organs include, but are not limited to, adrenal gland, appendix, bladder, brain, ear, esophagus, eye, gall bladder, heart, kidney, intestine (e.g., large or small intestine), liver, lung, mouth, muscle, nose, pancreas, parathyroid gland, pineal gland, pituitary gland, skin, spleen, stomach, thymus, thyroid gland, trachea, uterus, vermiform appendix, or a portion thereof.

The term "cell cluster" (or "cell clusters") refers to an aggregation or aggregations of cells, for example of malignant cells, fibroblasts, immune cells, stem cells, or endothelial cells. In one aspect, the cell clusters include 1-10, 10-100, 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells. The term "plurality of cell clusters" means more than one cell cluster. The cell clusters are aggregated or exist separately. The cells within the cell clusters are adherent to each other by means of proteins such as cadherins, and are adherent to the surrounding extracellular matrix via integrins. Therefore, the cells within a cell cluster are most likely related to each other, and may be considered a subclone, or derived from a subclone.

As used herein, the term "organelle" refers to cellular membrane bound structures such as the chloroplast, mitochondrion, and nucleus. The term "organelle" includes natural and synthetic organelles.

The term "peptide," as used herein, is meant a short polymer of amino acids linked by peptide bonds. All of the amino acids may have an L- or D-configuration.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. In one aspect, the polynucleotide comprises modified nucleotides, such as methylated nucleotides and nucleotide analogs.

The term "lipid" is used in its conventional sense as a generic term encompassing fats, lipids, the alcohol-ether-soluble constituents of protoplasm, which are insoluble in water. Lipids compose the fats, fatty oils, essential oils, waxes, steroids, sterols, phospholipids, glycolipids, sulpholipids, aminolipids, chromolipids (lipochromes), and fatty acids. The term encompasses both naturally occurring and synthetically produced lipids. Preferred lipids in connection with the present disclosure are: phospholipids, including phophatidylcholines and phosphatidylethanolamines, and sphingomyelins.

The term "metabolite" refers to a compound, protein, or any substance, byproduct, or material resulting from enzymatic reactions, i.e., the compound synthesized by a process in which an enzyme takes part.

The term "liquid tissue" refers to any tissue that is or can be in the form of liquid, which includes but is not limited to blood, plasma, serum, saliva, semen, cervical secretions, saliva, urine, tears, sweat, breast milk, and amniotic fluids. The term "non-liquid tissue" refers to any tissue that is not liquid tissue.

The term "cytology needle aspirate" refers to the procedure of Fine-needle aspiration biopsy (FNAB, FNA or NAB), or fine-needle aspiration cytology (FNAC).

The term "effusion" refers to a procedure of collecting the fluid from a subject. In some aspects, the fluid collected by effusion can be described as having a pathological condition, disorder, sign or symptom of the abnormal. In another aspect, the fluid from an effusion can be an excessive accumulation of fluids in the body cavities, or peritoneal space.

The term "pap smear" refers to a screening procedure for cervical cancer. It tests for the presence of precancerous or cancerous cells on the cervix, the opening of the uterus.

As used herein the term "abnormal tissue" intends a tissue that displays a defined characteristic that is different from that characteristic in a normal tissue. For example, breast cancer tissue can in one aspect be "abnormal" as compared to breast tissue that is not phenotypically cancerous but can, nonetheless, be "normal" for another characteristic, such as gene expression of a specified biomarker.

The term "phenotypically normal tissue" refers to the tissue that has the physical characteristics, e.g., histological appearance, same with, similar or substantially similar to the characteristics that are regarded as normal. The term "phenotypically abnormal tissue" refers to the tissue that has the physical characteristics same with, similar or substantially similar to the characteristics that are regarded as abnormal.

The term "phenotypically homogeneous" intends that at least one or more physical characteristics, e.g., histological appearance, that is the same as, or similar or substantially similar to, the identified characteristic(s) as other members of the group or tissue type, e.g., breast, colon, lung.

The term "genotypically normal tissue" refers to the tissue that has the genomic, e.g., chromosomal, mitochondrial, RNA, microRNA, and/or non-coding RNA, characteristics, e.g., gene sequence, same with, similar or substantially similar to the characteristics that are regarded as normal. The term "genotypically abnormal tissue" refers to the tissue that has the genetic characteristics, e.g., gene sequence, same with, similar or substantially similar to the characteristics that are regarded as abnormal.

The term "genetically diverse" as it relates to cells, tissues or subjects, refers to a subject, tissue or cell population where at least two members of the group differ from each other or at least another individual, cell or tissue on the genomic level, e.g., chromosomal, mitochondrial, RNA, microRNA, and/or non-coding RNA. The term "genetically homogenous subject" as it relates to two or more individuals, refers to individuals who exhibit a substantially identical specified marker or characteristic at the genomic level, e.g., chromosomal, mitochondrial, RNA, microRNA, and/or non-coding RNA.

"Ethnicity group" refers to a social group that has a common national or cultural tradition. In one aspect, the term intends members of a group that derive from a common or closely related genetic origin.

The term "small molecule" refers to a low molecular weight organic material that can be used for regulating a biological process. In one aspect, the molecular weight ranges from 0-100 daltons, 100-200 daltons, 200-300 daltons, 300-400 daltons, 400-500 daltons, 500-600 daltons, 600-700 daltons, 700-800 daltons, 800-900 daltons, or 900-1000 daltons. In another aspect, the molecular weight is below 1000 daltons. The small molecules include but are not limited to organic compounds, peptides, metabolites, and lipids.

The term "dye" refers to a substance which can impart color to a subject by selective absorption of light. In some embodiment, a dye is soluble or solid. In another embodiment, the dye is retained in the substrate by absorption, solution, and mechanical retention, or by ionic or covalent chemical bonds. In a further embodiment, a dye is any organic or inorganic molecule or moiety that absorbs electromagnetic radiation, for example, at a selective wavelength.

As used herein, the term "quantitative data" means data expressing a certain quantity, amount or range which is associated with the measurement units. For example, the quantitative data for tumors include but are not limited to the sizes of tumors, or expression levels of biomarkers.

As used herein, the term "qualitative data" refers to information that describes the features, characteristics, or other natures of an object. For example, the qualitative data for cancer include but are not limited to the stages, appearance, and other physical characteristics of tumor.

As used herein, the term "normalized" as it relates to a measured value intends adjustment of a value measured on different scales to a notionally common scale.

Genes are just one type of cancer biomarkers. As used herein, the term "biomarker" or "marker" refers to a biological molecule found in blood, other body fluids, or tissues that is a sign of a normal or abnormal process, or of a condition or disease (such as cancer). A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology.

Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "clinically relevant marker" intends a marker or biomarker that is related to a clinical result or condition, e.g., the presence or absence of a disease or condition, e.g., cancer.

As used herein, the term "cancerous tissue" refers to any tissue bearing tumor cells. Cancerous tissues include but are not limited to muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, or connective tissue.

"Prognosis" intends prediction or likely outcome of a subject's current condition, including the possibility of recurring cancer and/or metastasis of the cancer in the patient.

As used herein, the term "preserve" or "fix" refers to a step in the preparation of biological samples, for example histological sections. Methods of preservation or fixation include but are not limited to chemical fixation, heat fixation, immersion, perfusion, and/or lyophilization. Accordingly, a "fixed sample" is a sample that has been processed as noted above.

The term "live cells" refers to any cells that have not been fixed or preserved. In some embodiments, the term "live cell" includes a functioning cell. Those of skill in the art can readily distinguish between a live cell and a dead cell for purposes of the present disclosure.

As used herein, the term "wax embedding" or "paraffin embedding" is used for a process in which the tissue specimen is infused with paraffin wax to preserve its cellular structures when sectioned using a microtome, and has the added benefit of being suitable for long term storage.

As used herein, the term "one or more tissues" refers to tissues from one or more subjects, or one or more tissue from the same subject. The term "two or more tissues" is used for tissue from two or more subjects, or two or more tissue from the same subject or patient.

As used herein, the term "premalignant or malignant cells" are used to describe any cells that have undergone malignant transformation or are poised to undergo malignant transformation. The characteristics of the premalignant or malignant cells include but are not limited to uncontrolled proliferation, metastasis, abnormal cellular metabolism, evading apoptosis, self-sufficiency with growth signals, and sustained angiogenesis. For example, a colon polyp may be premalignant for colon cancer.

As used herein, the term "circulating tumor cells" refers to tumor or cancer cells that are circulating within the vasculature, lymphatics, or other fluid. Circulating tumor cells include but are not limited to leukemia cells.

As used herein, the term "normal adjacent tissue" refers to the normal tissue adjacent to a tumor cell or a tumor tissue.

The term "reconstructing" as it relates to reconstructing the homogenized sample intends admixing or combining.

The term "extracting a constituent" as it relates to the homogenate intends isolating or purifying a component of a cellular structure As used herein, the term "FFPE sample" means formalin-fixed paraffin-embedded sample. The FFPE sample may be used for a number of medical studies, including but not limited to diagnosis, IHC, and profiling gene expression or origins of diseases.

The term "predetermined value" here generally represents a value that is used to compute the variation of data. In one aspect, a predetermined value is calculated based on historical data, or a different group of samples, or a group of samples that are similar with the data to study.

The term "risk value" refers to the quantitative or qualitative value that is associated with a risk. For example, the cancer risk value is the value that quantifies or qualifies the risk of incurring cancer.

The term "chromosome translocation" refers to a chromosome abnormality caused by rearrangement of parts between nonhomologous chromosomes.

The term "intra-chromosomal inversion" refers to a chromosome rearrangement in which a segment of a chromosome is reversed end to end. In one aspect, an inversion occurs when a single chromosome undergoes breakage and rearrangement within itself.

The term "therapeutic regimen" is used according to a meaning well known in the art. For example, the term refers to a treatment plan for an individual suffering from a pathological condition (e.g. chronic hepatitis C infection or cancer) that specifies factors including but not limited to the agent or agents to be administered to the patient, the dosages of such agent(s) and the schedule and duration of the treatment. A personalized dosage or treatment regimen is a therapy or dosage regimen based on concepts of precision medicine taking into account the individual characteristics of the patient or subject, e.g., genetic make-up, pharmacogenetics, ethnicity, treatment history, familial history, clinical chemistry or other relevant characteristics or measurements.

The term "chemotherapy" refers to treatment with a chemical agent. Chemotherapy can be defined as the utilization of pharmaceuticals specifically designed to target, combat and/or destroy diseased cells. Non-limiting examples of diseases that can be treated by chemotherapy include cancers, autoimmune diseases such as Systemic sclerosis, lupus erythematosus, rheumatoid arthritis, vasculitis, and viral infections. In one aspect, the chemotherapeutic agent destroys cancer cells by targeting rapidly dividing cells in the body. Due to lack of specificity to cancer cells, the toxic effects of chemotherapy are also seen in other rapidly dividing non-cancerous cells. Blood cells, cells in the mouth, intestinal tract, nose, nails and hair are some of the rapidly dividing cells in the body. Destruction of normal cells in the body gives rise to side effects like alopecia, cachexia, anemia, leucopenia and neutropenia. These side effects limit the effectiveness of chemotherapy and increase risk of dose reduction, directly impacting a patient survival.

The term "immunotherapy" refers to treatment involving activation or inactivation of a specific immune response and/or immune effector function(s). The term "radiation" or "radiation therapy" relates to a treatment involving use of high-energy particles or waves, including but not limited to x-rays, gamma rays, electron beams, or protons, to treating diseases (e.g., cancer) or a pathological condition. The term "surgery" relates to any methodical action, either with or without instruments, on a patient, to produce a curative or remedial effect.

The term "gene therapy" refers to the use of a gene transfer process or gene editing process (e.g. CRISPR), preferably, for the purpose of causing a therapeutic effect in a subject or a patient.

The term "hormone therapy" as used herein is defined as a treatment pertaining to modulating hormones. A hormone therapy may include but is not limited to removing the gland that synthesizes the hormone or the prohormone, blocking or inhibiting hormone synthesis, or preventing the hormone from binding to its receptor, or down-regulating or degrading the hormone receptor.

The term "stem cell therapy" as used herein is a treatment by using stem cells to treat or prevent a disease or pathological condition.

The term "transfusion" relates to a procedure of receiving blood via an intravenous line.

As used herein, the term "physical therapy" refers to the treatment of physical dysfunction or injury by the use of therapeutic exercise and the application of modalities, intended to restore or facilitate normal function or development.

As used herein, the term "photodynamic therapy" refers to a process whereby light of a specific wavelength is directed to tissues or cells undergoing treatment or investigation that have been rendered photosensitive through the administration of a photoreactive or photosensitizing agent. In one embodiment, the objective may be diagnostic, where the wavelength of light is selected to cause the photoreactive agent to fluoresce, thus yielding information about the tissue without damaging the tissue. The objective may also be therapeutic, where the wavelength of light delivered to the target tissue under treatment causes the photoreactive agent to undergo a photochemical interaction with oxygen that yields a high energy species, such as singlet oxygen, causing local tissue lysing or destruction, or the triggering of immunoresponse of the photosensitized tissue or cell.

As used herein, the term "differential expression" refers to the differences in gene or protein expression levels of two or more samples. In one aspect, the differential expression results may be used to identify the disease, a biomarker, or any patterns that may be associated with pathological conditions.

As used herein, the term "first profile" refers to the dataset of a subject or a group of subjects. In one aspect, the first profile can be used as a baseline to determine the changes in the subsequent profile(s). In another aspect, the data in the first profile may be incorporated in the subsequent analysis or in the process of generating the subsequent profiles.

As used herein, the term "predetermined profile" refers to a dataset or panels of datasets that are associated with physiological conditions. The predetermined profile can derive from a subject or a group of subjects. In one aspect, the predetermined profile can include the histological or known dataset of physiological conditions. In another aspect, the predetermined profile is used as a base line to determine the changes of physiological conditions (e.g., tumor progression).

As used herein, the term "quantitative score" refers to a numerical representation of the physiological conditions (e.g., disease risk).

As used herein, the term "proliferation" means growth and division of cells. In some embodiments, the term "proliferation" as used herein in reference to cells refers to a group of cells that can increase in number over a period of time.

The term "apoptosis" refers to the process of programmed cell death. In some aspect, the apoptosis is accompanied with cellular morphological changes and loss of cell viability.

The term "necrosis" encompasses cell necrosis states, as well as intermediate states, exhibiting necrotic and apoptotic characteristics.

The term "cell migration" as used herein means the migration of cells as induced by physiologically active substances or as caused by physiological changes (e.g., transformation).

The term "epithelial-mesenchymal transition" or "EMT" refers to a process in which epithelial cells that are normally non-proliferative and non-mobile undergo transition into mesenchymal cells characterized by a proliferative and mobile phenotype. EMT is a central mechanism for diversifying cells found in complex tissue, hence, is a process involved in organizing the formulation of the body plan (Kalluri and Nelson J Clin Invest 112(12):1776-1784, 2003). Although epithelial cells were once considered to be terminally differentiated, it is recognized that epithelia possess an element of plasticity enabling transition to mobile mesenchymal cells (Boyer et al. Biochem Pharmacol 60:1099, 2000; Nieto Nat Rev Mol Cell Biol 3:155-166, 2002). EMT is required, therefore, in adult tissue to enable formation of fibroblasts in injured tissues (Strutz et al. J Cell Biol 130:393-405, 1995; Iwano et al. J Clin Invest 110:341-350, 2002) and in initiating, metastases in epithelial cancer (Kiermer et al. Oncogene 20:6679-6688, 2001; Janda et al. J Cell Biol 156:299-313, 2002; Xue et al. Cancer Res 63:3386-3394, 2003).

In one aspect, EMT is a process of disaggregating epithelial units and re-shaping epithelia for movement in the formation of mesenchymal cells. The transition requires a molecular reprogramming of epithelium, generally considered to be by a variety of cytokines, metalloproteinases and membrane assembly inhibitors (Kalluri and Neilson 2003 supra; Yang and Liu Am J Pathol 159:1465-1475, 2001; Zeisberg et al. Am J Pathol 159:1313-1321, 2001; Fan Kindney Int 56:1455-1467, 1999).

As used herein, the term "mitosis" can be used interchangeably with the term "cell division." In some embodiments, mitosis refers to only one phase of the cell division process: the process in which the sister chromatids are partitioned equally between the two daughter cells. In eukaryotic cells, mitosis is followed by cytokinesis, which is the process by which the cell cytoplasm is cleaved into two distinct but genetically identical daughter cells.

At the onset of mitosis, small intracellular filamentous structures known as cytoplasmic microtubules, of which the major component is a protein called tubulin, disassemble into tubulin molecules. The tubulin then reassembles into microtubules forming an intracellular structure known as the "mitotic spindle." The mitotic spindle plays a critical role in distributing chromosomes within the dividing cell precisely between the two daughter nuclei. Cancer cells are characterized by more rapid cell division and proliferation than observed in most healthy cells, and many anti-cancer agents operate by inhibiting cell division. Since cancer cells divide more rapidly than do healthy cells, cancer cells are preferentially killed by anti-cancer agents which inhibit mitosis. Such compounds are called "antimitotic."

The term "cell cycle arrest" refers to a stopping point in the cell cycle in which the cells are not in the processes surrounding duplication and division. The natural cell cycle includes a number of checkpoints that allow the cell to determine whether to proceed with division or stop. These halts can also be induced by external factors like exposure to radiation or medications used to control cell growth.

The first phase of the cell cycle is G1, where a cell prepares to duplicate. The cells genetic material is duplicates during the S phase. Cell damage is repaired during the G2 phase before moving to M, mitosis. After mitosis, a cell may again enter G1, or move to G0, the resting stage. A checkpoint temporarily halts the cell cycle at each phase to allow the cell to decide if it should continue. Some cells are programmed to duplicate infrequently, while damaged cells may need time for repair or destruction.

In some embodiments, cell cycle arrest precedes apoptosis, or cell death. This occurs when a cell is no longer functional because of DNA damage. The cell is targeted for destruction. Cell cycle arrest allows cells for cell by checking periodically for signs of DNA destruction that might cause functional problems or lead to the development of a tumor.

The term "S-phase" refers to the period during the cell cycle in which DNA is replicated. The S-phase normally occurs between G1 phase and G2 phase. Precise and accurate DNA replication during the S-phase is necessary to prevent genetic abnormalities.

The term "senescence" as used herein refers to the permanent cessation of DNA replication and cell growth that is not reversible by growth factors. This phenomenon may occur at the end of the proliferative lifespan of normal cells or in normal or tumor cells in response to cytotoxic drugs, DNA damage. Senescence is characterized by certain morphological features including, but not limited to, increased cell size, flattened cell morphology, increased granularity, and the presence of senescence-associated β-galactosidase activity (SA-β-gal).

As used herein, the term "differentiation" refers to a process in which the structure or function of cells is specialized during the division, proliferation and growth thereof. Generally, differentiation refers to a phenomenon in which a relatively simple system is divided into two or more qualitatively different partial systems.

As used herein, the term "detection" refers to the action or process of identifying the presence of a specific molecule. In one embodiment, detection of a biomarker may refer to identifying the expression of a biomarker.

As used herein, the term "fixative agent" refers to an agent used for fixation of tissue for a number of purposes, including but not limited to delivery, storage, histological study, and processing.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide when in its native state or when manipulated by methods well known to those skilled in the art can be transcribed and/or translated to produce a mRNA. The antisense strand is the complement of such a nucleic acid, and the encoding sequence can be deduced therefrom.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

As used herein, the term "isolated cell" generally refers to a cell that is substantially separated from other cells of a tissue.

An "effective amount" or "efficacious amount" refers to the amount of an agent, or combined amounts of two or more agents, that, when administered for the treatment of a patient, mammal or other subject, is sufficient to effect such treatment for the disease. The "effective amount" will vary depending on the agent(s), the disease and its severity and the age, weight, etc., of the subject to be treated.

As used herein, the term "detectable marker or label" refers to at least one marker capable of directly or indirectly producing a detectable signal. A non-exhaustive list of markers include enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$ or $^{125}I$.

As used herein, the term "purification marker" refers to at least one marker useful for purification or identification. A non-exhaustive list of markers include His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa Fluor®, FITC, TRITC or any other fluorescent dye or hapten.

As used herein, the term "expression" refers to the process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "homology" or "identical", "percent identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical", "percent identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.govicgi-bin/BLAST.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

The term "isolated" as used herein refers to molecules, cells or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered.

The term "individual cell" or "single cell" means a structural and/or functional unit of an organism. In some aspect, the individual cell includes but is not limited to cytoplasm, nucleus, or cellular membrane.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "sonication" refers to the application of sound waves (acoustic energy) transmitted through a liquid medium. The sound waves may cause particles (e.g., cells or cell clusters) to oscillate about their mean position. In one aspect, the sonication leads to the dissociation of cell clusters to single cells suspension.

As used herein, "treating" or "treatment" of a disease in a subject refers to (1) preventing the symptoms or disease from occurring in a subject that is predisposed or does not yet display symptoms of the disease; and/or (2) inhibiting the disease or arresting its development; and/or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

Representative Substantially Homogenous Samples

The disclosure addresses the limitations of the prior art clinical sampling methods that fail to provide a representative sample. The characteristics of a representative sample parallel the key variables and characteristics of the larger entity or sample. The current practice of selective sampling is aimed at collecting tissue samples so as to meet the requirements of the TNM staging system. The samples for the TNM staging system are specifically taken so as to reflect the normal anatomy of the removed organ containing the tumor. While important for the prognostic staging of the TNM system, this selective sampling method produces biased tumor samples, or samples that do not contain the genetic and phenotypic diversity found throughout the tumor mass.

The present disclosure provides a processed homogenate composition derived from a heterogeneous tissue sample, comprising substantially homogeneously distributed cellular structures, wherein a ratio of cellular structures in each and/or any subset of the representative sample is substantially similar to the ratio of cellular structures in the sourced heterogeneous tissue sample. The homogenate composition is a new, unique tissue sample that also represents key characteristics of the original, sourced heterogeneous tissue sample. The compositions and methods to prepare the compositions as described herein overcome the failure of prior art methods to account for the issue of tissue heterogeneity in clinical samples, especially samples for use in clinical fields, e.g., clinical oncology.

Figures 2A, 2B:
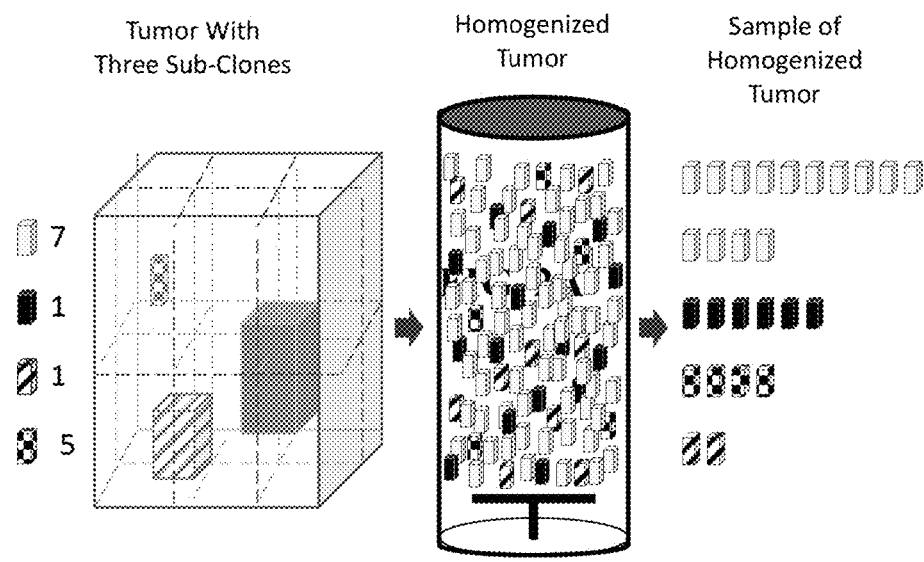
FIG. 2A is schematic representation of how the disclosed homogenization methods generate a representative sample that contains subclones at the proportion at which they existed within the solid tumor.
FIG. 2B is a schematic representation of how the homogenate facilities detection of low-prevalence subclones.

The representative sample of the present disclosure is illustrated in FIGS. 2A and 2B, which show a schematic representation of the homogenate of the disclosure. FIG. 2A shows a tumor with three subclones present in different proportions. The disclosed homogenization methods generate a representative sample that contains subclones at the proportion at which they existed within the solid tumor. Any sample taken from the homogenate will contain each subclone in the same proportion as present in the original tumor. FIG. 2B is an illustration of how the homogenate facilities detection of low-prevalence subclones.

The representative samples of the present disclosure overcome the sampling challenges imposed by the spatially stratified three dimensional structure of a tissue. In the representative sample the components (cell structures, cells, peptides, nucleic acids, lipids, metabolites, etc.) of the original spatially stratified organ, tumor, or tissue ("OTT") are present in a sub-sample or subset of the sample at the proportion that they existed in the original OTT. In some embodiments, the representative sample refers to a sample of the OTT that constitutes as much of the OTT as possible, approaching the entirety of the OTT or encompassing a significant enough portion of the OTT to approach the goal of representing the diversity of the OTT at the level of clusters of attached cells, individual cells, fragments of cells, organelles, peptides, nucleic acids, lipids, metabolites, etc. The representative sample may contain the minimum amount of the intact OTT required to encompass the diversity of the OTT.

Multiple representative samples may be made from a single OTT. In this embodiment, the surgically removed OTT is first processed or otherwise manipulated into separate sub units, such that each sub unit is composed of spatially stratified cell structures, cells, peptides, nucleic acids, etc. Each sub unit is then sufficiently homogenized, mixed or otherwise disrupted to produce a representative sample of the OTT sub unit.

The representative sample may be homogenized or otherwise mixed or disrupted to the point that any analytical sample, or portion of the representative sample, contains a random sampling of the material present in the representative sample. It is characteristic of the analytical sample that it is a large enough fraction of the representative sample that it encompasses the diversity of the representative sample, relative to the intended output of the analytical test being applied (i.e. cells v. chunks of cells). In the representative sample, any analytical sample used for a specific assay would produce data consistent with another analytical sample used for the same assay, within experimental error. Moreover, it is contemplated that any subset of the representative sample chosen for a specific assay would provide information that could be cross-referenced to data generated with different assays using analytical samples taken from the same representative sample, or from other representative samples made from OTTs from the same patient. It is also contemplated that, because the original proportions of the original biological components are present in every analytical sub-sample, data produced from analytical sub-samples pertaining to the proportions of the biological components of OTTs can be compared between patients.

In one embodiment, the representative sample is a processed homogenate composition derived from a heterogeneous tissue sample. The homogenate composition comprises, or alternatively consists essentially of, or yet further consists of, substantially homogeneously distributed cellular structures, wherein a ratio of cellular structures in each subset of the homogenate is substantially similar to the ratio of cellular structures in the tissue sample. In one embodiment, the tissue sample is selected from the group of: a tumor, a lymph node, a metastasis, a polyp, a cyst, a resection, an organ, or a fraction thereof. In another embodiment, the tissue sample comprises, or alternatively consists essentially of, or yet further consists of spatially segregated cellular structures. In another aspect, the cellular structures comprises, or alternatively consist essentially of, or yet further consist of a cell cluster, an individual cell, a fragment of a cell, an organelle, a peptide, a nucleic acid, a lipid, a metabolite, or a combination thereof. In one aspect, the homogenate comprises, or alternatively consists essentially of, or yet further consists of up to 25% of cellular structures from the tissue sample. In one aspect, the homogenate comprises, or alternatively consists essentially of, or yet further consists of up to 50% of cellular structures from the tissue sample. In another aspect, the homogenate comprises, or alternatively consists essentially of, or yet further consists of up to 75% of cellular structures from the tissue sample. In a different aspect, the homogenate comprises, or alternatively consists essentially of, or yet further consists of up to 100% of cellular structures from the tissue sample. In another aspect, the homogenate comprises, or alternatively consists essentially of, or yet further consists of 100% of cellular structures from the tissue sample.

In another embodiment, the homogenate comprises, or alternatively consists essentially of, or yet further consists of, 100% of cellular structures from the tissue sample. In one aspect, the tissue sample comprises, or alternatively consists essentially of, or yet further consists of, a non-liquid tissue sample. In another aspect, the tissue sample comprises, or alternatively consists essentially of, or yet further consists of a liquid tissue sample. In one aspect, the liquid tissue sample comprises, or alternatively consists essentially of, or yet further consists of a tissue isolated by one or more of a surgical resection, a cytology needle aspirate, an effusion sample, or a pap smear.

In yet another embodiment, the substantially homogenous cellular structures comprise, or alternatively consist essentially of, or yet further consist of a plurality of single cells or a plurality of cell clusters. In one aspect, the cellular structures are isolated from a normal tissue. In another aspect, the cellular structures are isolated from a phenotypically or genotypically normal tissue. In yet another aspect, the cellular structures are isolated from an abnormal tissue. In one aspect, the cellular structures are isolated from a phenotypically or genotypically abnormal tissue.

In one embodiment, the tissue sample comprises, or alternatively consists essentially of, or yet further consists of a stem cell, an epithelial cell, a blood cell, a fat cell, a skin cell, an endothelial cell, a tumor cell, or an immune cell. In one aspect, the tumor cell is derived from a cancerous tissue selected from the group of: lung cancer, leukemia, breast cancer, prostate cancer, colon cancer, brain cancer, esophageal cancer, cancers of the head and neck, bladder cancer, gynecological carcinomas, ovary cancer, cervical cancer, liposarcoma, melanoma, lymphoma, plasmacytoma, sarcoma, glioma, thymoma, hepatoma, and myeloma. In another aspect, the immune cells are cells selected from the group of: neutrophils, monocytes, dendritic cells, macrophages, lymphocytes, T-cells, B-cells, or natural killer cells.

In another embodiment, the tissue sample is not preserved or fixed. In one aspect, the tissue sample comprises a live cell or a cell recently isolated from the subject. In another embodiment, the tissue sample is preserved or fixed. In one aspect, the preserved or fixed tissue sample comprises a sample that has been frozen or fixed by a method of the group of:

freezing, freeze-drying and wax embedding.

In one embodiment, the heterogeneous tissue sample is isolated from one or more tissues from the same or different subjects. In one aspect, the tissue sample is isolated from one subject. In another aspect, the tissue sample comprises, or alternatively consists essentially of, or yet further consists of tissue isolated from two or more subjects and from the same or similar tissue types or different tissue types. In a further aspect, the two or more subjects are genetically homogenous subjects. In another aspect, the two or more subjects are phenotypically homogenous subjects. In a further aspect, the two or more subjects are genetically diverse subjects. In one aspect, the two or more subjects are phenotypically diverse subjects. In another aspect, the two or more subjects are from the same gender or different genders.

In a further aspect, the two or more subjects are from different genders. In yet another aspect, the two or more subjects are from different ethnicity groups. In one aspect, the two or more subjects are from the same ethnicity group. In another aspect, the subject is selected from the group consisting of an animal, a farm animal, a pet, a human subject.

In one embodiment, the homogenate further comprises, or alternatively consists essentially of, or yet further consists of, one or more of a non-human cell, a human cell, a detectable label, a purification label, a non-native protein, a nucleic acid or polynucleotide, a small molecule, a dye, a virus, a bacterium, a parasite, protozoan, or a chemical. In one aspect, the small molecule comprises, or alternatively consists essentially of, or yet further consists of a hapten, a peptide tag, a protein tag, a fluorescent tag, a nucleic acid tag, and combination thereof.

Method of Generating the Representative Data

This disclosure also relates to generating representative data from the representative sample or the homogenate composition herein described. In one aspect, the method for generating representative data comprises analyzing the homogenate composition as described herein. In a further aspect, the analyzing comprises generating quantitative and/or qualitative data for a marker in the homogenate composition. Any appropriate method to obtain data related to a marker can be used, non-limiting examples of such include measurement by single-cell sequencing, single-nucleus sequencing, flow cytometry, immunohistochemistry staining, hematoxylin and eosin staining, whole genome sequencing, high-throughput sequencing, mass spectrometry, DNA microarray, or a combination thereof.

The presently described method is a powerful tool for generating data sets in part because of the unique sampling techniques and composition of the disclosure. The cellular structures and/or discrete components of the representative sample essentially accurately reflects or mimics the relative proportion or percentages of these cell structure (including but not limited to types, makeup, and variations) within the entire tissue specimen, generally a solid tumor, lymph node, metastases, polyp, cyst, or portion thereof or combination of any of the foregoing. Therefore, the set of data from the analysis of the representative sample (or the homogenate composition) or the subset thereof would accurately reflect respective information of the entire tissue or biological sample from which the representative sample is derived. In some embodiments, the representative data is indicative of all of the features of the entire population of the original organ, tissue, or tumor from which the representative sample was derived.

As noted above, the method for generating representative data comprises, or alternatively consists essentially of, or yet further consists of, generating quantitative and/or qualitative data for a marker in the homogenate composition.

In the context of this method and composition, the marker comprises, or alternatively consists essentially of, or yet further consists of a polynucleotide, a DNA, a protein, an RNA, a lipid, a cell organelle, a metabolite, or a cell. In one aspect, the protein comprising a modification, said modification is selected from a group consisting of acetylation, ADP-ribosylation, acylation, ADP-ribosylation, amidation, covalent attachment of a flavin, covalent attachment of a heme, covalent attachment of a nucleotide or a nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, arginylation, and ubiquitination. In another aspect, the marker comprises, or alternatively consists essentially of, or yet further consists of a genomic polymorphism, a pharmacogenomics single nucleotide polymorphism (SNP), a genomic SNP, a somatic polymorphism, and differential expression of a protein, a lipid, and/or a cellular organelle. In a further aspect, the marker comprises, or alternatively consists essentially of, or yet further consists of a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion;

an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'-UTR, or a combination thereof. In a different aspect, the marker comprises, or alternatively consists essentially of, or yet further consists of an altered nucleotide sequence, encodes an altered amino acid sequence, a chromosomal translocation, an intra-chromosomal inversion, a change in copy number, a change in expression level, a change in protein level, a change in protein activity, or a change in methylation status, in a cancer tissue or cancer cell, as compared to a normal, healthy tissue or cell.

In another aspect, the marker is a tumor marker that is selected from the group consisting of: a protein, an antigen, an enzyme, a hormone, a DNA, an RNA, a microRNA, or a carbohydrate. In a further aspect, the marker is a tumor marker that is selected from the group consisting of: Her2, bRaf, ERBB2, P13KCA, FGFR2, p53, BRCA, CCND1, MAP2K4, ATR, AFP, ALK, BCR-ABL, BRCA1/BRCA2, BRAF, V600E, Ca-125, CA19.9, EGFR, Her-2, KIT, PSA, S100, KRAS, ER/Pr, UGT1A1, CD30, CD20, F1P1L1-PDGRFα, PDGFR, TMPT, TMPRSS2; ABCB5, AFP-L3, Alpha-fetoprotein, Alpha-methyl acyl-CoA racemase, BRCA1, BRCA2, CA 15-3, CA 242, Ca 27-29, CA-125, CA15-3, CA19-9, Calcitonin, Carcinoembryonic antigen, Carcinoembryonic antigen peptide-1, Des-gamma carboxy prothrombin, Desmin, Early prostate cancer antigen-2, Estrogen receptor, Fibrin degradation product, Glucose-6-phosphate isomerase, vE6, E7, L1, L2 or p16INK4a, Human chorionic gonadotropin, IL-6, Keratin 19, Lactate dehydrogenase, Leucyl aminopeptidase, Lipotropin, Metanephrines, Neprilysin, NMP22, Normetanephrine, PCA3, Prostate-specific antigen, Prostatic acid phosphatase, Synaptophysin, Thyroglobulin, TNF, a transcription factor selected from ERG, ETV1 (ER81), FLI1, EST1, EST2, ELK1, ETV6, ETV7, GABPα, ELF1, ETV4, ETV5, ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or FEV. XXX, Tumor associated glycoprotein 72, c-kit, SCF, pAKT, pc-kit, Vimentin, CTLA-4, PDL1, PDL2, PD1, B7-H3, B7-H4, BTLA, HVEM, KIR, TIM3, GAL9, GITR, LAG3, VISTA, KIR, 2B4, TRPO2, CD160, CGEN-15049, CHK 1, CHK2, A2aR, TL1A, CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 family, or the combination thereof. In one aspect, the marker is a tumor marker that comprises, or alternatively consists essentially of, or yet further consists of, one or more marker selected from the group of: a genomic polymorphism, a pharmacogenomics single nucleotide polymorphism (SNP), a genomic SNP, a somatic polymorphism, and differential expression of a protein, a lipid, and a cellular organelle. In another aspect, the tumor marker is selected from the group consisting of: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'-UTR, or a combination thereof. In a different aspect, the maker is a tumor marker that comprises, or alternatively consists essentially of, or yet further consists of a marker from the group of: an altered nucleotide sequence that encodes an altered amino acid sequence, a chromosomal translocation, an intra-chromosomal inversion, a change in copy number, a change in expression level, a change in protein level, a change in protein activity, and a change in methylation status, in a cancer tissue or cancer cell, each as "altered" as compared to a normal, healthy tissue or cell.

The data is generated from analyzing the homogenate composition as described herein. Non-liming examples of the tissue for analysis are samples selected from the group of: one or more premalignant or malignant cells, cells from a solid tumor, a soft tissue tumor or a metastatic lesion, tissue or cells from a surgical margin, a histologically normal tissue, one or more circulating tumor cells (CTC), a normal adjacent tissue (NAT), a blood sample from the same subject having or at risk of having the tumor, or an FFPE-sample.

In one embodiment, the representative data comprises the qualitative and quantitative data generated from a single marker. In one aspect, the representative data comprises the qualitative and/or quantitative data generated from two or more different markers. In a further aspect, the representative data is generated by measuring the same or multiple markers at different time points, e.g., before and after therapy and in one aspect, can be used to monitor therapy or a patient's condition over the course of treatment.

In one embodiment, the method for generating representative data further comprises, or alternatively consists essentially of, or yet further consists of assigning an internal value to the qualitative and/or quantitative data. In another embodiment, the method for generating representative data further comprises, or alternatively consists essentially of, or yet further consists of comparing the representative data to a predetermined value for the data. In a further aspect, the measured values of the marker are normalized and a composite score is obtained based on the normalized measured value of the marker. The composite score can further be compared to a predetermined score. In the context of cancer, in yet another embodiment, the method for generating representative data further comprises, or alternatively consists essentially of, or yet further consists of (a) measuring the tumor marker in the first biological sample, wherein the measured values of the tumor marker is normalized; (b) obtaining a composite score based on the normalized measured value; and (c) comparing the composite score to a predetermined score to determine a cancer risk value of the subject.

In another embodiment, the predetermined value is selected from clinical trial data, a data for a subject, data from scientific literature, and data for a biologic or small molecule under clinical development. In one aspect, the representative data comprises, or alternatively consists essentially of, or yet further consists of a representative oncology data, wherein the representative oncology data comprises, or alternatively consists essentially of, or yet further consists of quantitative and/or qualitative data of at least one tumor marker from a first biological sample, said tumor marker is associated with the presence of a tumor.

In one embodiment, the predetermined score is derived from the group of: a clinical trial data, a representative oncology data derived from a second biological sample, a representative oncology data derived from a group of biological samples, a data for clinical development a biologic or small molecule.

Methods for Determining Phenotypic Profiles

In one embodiment, the disclosure relates to a method of determining a phenotypic profile of a tissue sample, the method comprises, or alternatively consists essentially of, or yet further consists of analyzing the cellular structures of the homogenate composition. In one aspect, the cellular structures that can be analyzed for the phenotypic profile comprise, or alternatively consist essentially of, or yet further consist of a cell cluster, an individual cell, a fragment of a cell, an organelle, a peptide, a nucleic acid, a lipid, a metabolite, or a combination thereof. In another aspect, the cellular structures comprise a single cell or nucleus, wherein the single cell or nucleus is intact. In some embodiments, the analysis comprises, or alternatively consists essentially of, or yet further consists of analysis of numbers, types, states, percentages, and/or expressions of the cell structures. In another aspect, the analysis comprises, or alternatively consists essentially of, or yet further consists of single-cell analysis, single-nuclei analysis, single organelle analysis, or the combination thereof. In one aspect, the state of cellular structures comprises, or alternatively consists essentially of, or yet further consists of proliferation, apoptosis, necrosis, migration, epithelial-mesenchymal transition ("EMT"), mitosis, cell cycle arrest, S-phase, senescence, and/or differentiation. In another aspect, the analysis comprises, or alternatively consists essentially of, or yet further consists of analysis of a marker from the homogenate.

In one embodiment, the marker is selected from the group consisting of a DNA, a protein, an RNA, a lipid, a cell organelle, a metabolite, or a cell. In one aspect, the analysis of the marker comprises, or alternatively consists essentially of, or yet further consists of detection of the marker. In another aspect, the analysis of the marker comprises analysis of a marker from a single cell or a single nucleus.

Method of Treating a Disease

The disclosure, in another aspect, relates to a method of treating disease by selecting an effective therapeutic regime based on the representative data generated using the methods of the disclosure. With the right amount or type of information from the patient, the therapeutic regime can be tailored for the best response and highest safety margin to achieve the outcome for the patient. Moreover, the information can also enable the patient to receive many other benefits, e.g., earlier diagnoses, risk assessments, and effective treatments, thereby significantly improving the qualities of the healthcare.

Selection of an effective therapeutic regimen depends on several factors. First, a reliable diagnosis of the disease or the medical condition has to be achieved. In case of infectious diseases, cancer or other acute life-threatening diseases, this diagnosis has to be fast and efficient, since time plays a crucial role in the survival rate of patients suffering from those diseases. Second, a therapeutic treatment of an individual patient becomes more effective if the diagnosis is precise. For example, when cancer is sometimes treated with a standard "cocktail" of anti-cancer drugs, the cocktail often exhibits severe side effects for the patient. Unless the type of cancer (or other disease) is precisely determined, an individual treatment regime for this type of disease would not be extraordinarily effective than any other treatment regimen. Thus, the efficacy depends directly on the data or information acquired from the patient to be treated. A more effective treatment would be possible, if the treatment regimen would be cross-checked with regimens already successfully applied to this patient or other patients based on the physiological response to the early regime. Further, a precise diagnosis of the disease would lead to reduced costs for the individual treatment regimen, since unnecessary and ineffective medication is avoided. However, even those who are current on the latest treatment information require time to assimilate that information and understand how it relates to other treatment information in order to provide the best available treatment for a patient.

Therefore, the disclosure provides a method of treating a disease in a subject, comprising, or alternatively consisting essentially of, or yet further consisting of selecting an appropriate therapeutic regimen based on the representative data, wherein the representative data comprises a first profile of the subject.

In one aspect, non-limiting examples of the first profile comprise, or alternatively consist essentially of, or yet further consists of a profile from the group of: a marker profile, an antigen profile, a protein profile, a mutation profile, a lipid profile, an exosome profile, or a combination thereof. In another aspect, the marker comprises, or alternatively consists essentially of, or yet further consists of one or more from the group of: Her2, bRaf, ERBB2, P13KCA, FGFR2, p53, BRCA, CCND1, MAP2K4, ATR, AFP, ALK, BCR-ABL, BRCA1/BRCA2, BRAF, V600E, Ca-125, CA19.9, EGFR, Her-2, KIT, PSA, S100, KRAS, ER/Pr, UGT1A1, CD30, CD20, F1P1L1-PDGRFα, PDGFR, TMPT, TMPRSS2; ABCB5, AFP-L3, Alpha-fetoprotein, Alpha-methyl acyl-CoA racemase, BRCA1, BRCA2, CA 15-3, CA 242, Ca 27-29, CA-125, CA15-3, CA19-9, Calcitonin, Carcinoembryonic antigen, Carcinoembryonic antigen peptide-1, Des-gamma carboxy prothrombin, Desmin, Early prostate cancer antigen-2, Estrogen receptor, Fibrin degradation product, Glucose-6-phosphate isomerase, vE6, E7, L1, L2 or p16INK4a, Human chorionic gonadotropin, IL-6, Keratin 19, Lactate dehydrogenase, Leucyl aminopeptidase, Lipotropin, Metanephrines, Neprilysin, NMP22, Normetanephrine, PCA3, Prostate-specific antigen, Prostatic acid phosphatase, Synaptophysin, Thyroglobulin, TNF, a transcription factor selected from ERG, ETV1 (ER81), FLI1, EST1, EST2, ELK1, ETV6, ETV7, GABPα, ELF1, ETV4, ETV5, ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or FEV. XXX, Tumor associated glycoprotein 72, c-kit, SCF, pAKT, pc-kit, Vimentin, CTLA-4, PDL1, PDL2, PD1, B7-H3, B7-H4, BTLA, HVEM, KIR, TIM3, GAL9, GITR, LAG3, VISTA, KIR, 2B4, TRPO2, CD160, CGEN-15049, CHK 1, CHK2, A2aR, TL1A, CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 family, and the combination thereof. In some aspect, the first profile comprises a profile generated from the group of: one or more markers, one or more antigens, one or more proteins, one or more mutations, one or more lipids, one or more exosomes, or a combination thereof.

In some embodiments, the marker of the method is selected from the group consisting of: a genomic polymorphism, a pharmacogenomics single nucleotide polymorphism (SNP), a genomic SNP, a somatic polymorphism, and differential expression of a protein, a lipid, and a cellular organelle. In one aspect, the marker is selected from the group consisting of: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'-UTR, and a combination thereof.

The method can be used for determine the use of a therapeutic regimen that comprises, or alternatively consists essentially of, or yet further consists of a personalized dosage regimen. In one aspect, the therapeutic regimen is selected from the group consisting of: chemotherapy, an immunotherapy, radiation, surgery, a gene therapy, a hormone therapy, a stem cell therapy, a transfusion, a physical therapy, a photodynamic therapy, and a combination thereof.

In another embodiment, the method of treating a disease in a subject further comprises, or alternatively consists essentially of, or yet further consists of comparing the first profile of the subject to a predetermined profile to determine if the therapeutic regimen is appropriate for the subject. In one aspect, the predetermined profile is determined based on data selected from the group of: clinical trial data, a second profile of the subject, a profile of a different biological sample or a group of biological samples, a profile of a different subject or a group of subjects, a data for a biologic or small molecule, and a combination thereof.

In a further aspect, the treatment comprises the selection of one or more drugs and/or dosage (amount, length of administration, etc.) of such drugs administered to a patient to personalize the treatment based upon the patient's individual tissue or cancer profile. For instance, if two biomarkers in the representative sample predict response to a specified drug X and a different drug Y. are found within a single representative sample, both drugs might be given to the patient. If the biomarker for drug X is present within 75%, and the biomarker for drug Y is present at 25%, then drug X may be prioritized and delivered first, followed by drug Y. Alternatively, drug Y may precede drug X.

The method can be repeated at different time courses of the therapy and modified based on the changing marker expression of profile. In this aspect, the method is useful to monitor therapy and disease progression in patient or across different patients with the same or similar disease receiving the same or different therapies.

Method of Identifying a Clinically Relevant Marker

Data or information about clinically relevant markers or biomarkers can provide an indication of a likelihood of pathological conditions. The representative data in the disclosures may be used in to identify the clinical relevant markers, particularly those that have not been previously associated with any pathological conditions.

Thus, another aspect of this disclosure relates to a method of identifying a clinically relevant marker, comprising comparing the representative data with a predetermined data. Non-limiting examples of markers are noted above. In one aspect, the marker is selected from the group consisting of: a protein, an antigen, an enzyme, a hormone, a DNA, an RNA, a microRNA, or a carbohydrate. In another aspect, the marker comprises, or alternatively consists essentially of, or yet further consists of a genomic polymorphism, a pharmacogenomics single nucleotide polymorphism (SNP), a genomic SNP, a somatic polymorphism, and differential expression of a protein, a lipid, a protein modification, and a cellular organelle. In some aspect, the marker is selected from the group consisting of: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'-UTR, and a combination thereof. In one aspect, the marker is selected from the group of: an altered nucleotide sequence, encodes an altered amino acid sequence, a chromosomal translocation, an intra-chromosomal inversion, a change in copy number, a change in expression level, a change in protein level, a change in protein activity, and a change in methylation status, in a cancer tissue or cancer cell, each as compared to a normal, healthy tissue or cell.

In one embodiment, the predetermined data is generated from a data selected from the group of: clinical trial data, data of a subject or a group of subjects, data of a tissue sample or a group of tissue samples, data of a biologic or small molecule under clinical development, or a combination thereof.

In some aspect, a method of determining a prognosis of a cancer in a subject is provided, the method comprising assessing the representative data from a subject. In one embodiment, the method of determining a prognosis of a cancer further comprises, or alternatively consists essentially of, or yet further consists of calculating a quantitative score for the prognosis of the cancer, wherein the prognosis is classified based on the quantitative score.

In one embodiment, the representative data comprises information about number, types, states, and/or percentage of the cell structures in the homogenate. In another embodiment, the cell structures comprise, or alternatively consist essentially of, or yet further consist of stem cells, epithelial cells, blood cells, fat cells, skin cells, endothelial cells, cancer cells, or immune cells. In one embodiment, the immune cells comprise, or alternatively consist essentially of, or yet further consist of neutrophils, monocytes, macrophages, dendritic cells, natural killer cells, T-cells, and/or B-cells. In some embodiment, the T-cells comprise, or alternatively consist essentially of, or yet further consist of killer T cells, helper T cells, regulatory T cells, pan T cells, naïve T cells, activated T cells, and/or gamma delta T-cells.

In one embodiment, the states of cellular structures comprise, or alternatively consist essentially of, or yet further consist of proliferation, apoptosis, necrosis, migration, epithelial-mesenchymal transition ("EMT"), mitosis, cell cycle arrest, S-phase, senescence, and/or differentiation. In one embodiment, the representative data comprises information about a marker in the homogenate. In another embodiment, the marker is selected from the group of a DNA, a protein, an RNA, a lipid, a cell organelle, a metabolite, or a cell. In some embodiment, the marker comprises, or alternatively consists essentially of, or yet further consists of one or more of Her2, bRaf, ERBB2, PI3KCA, FGFR2, p53, BRCA, CCND1, MAP2K4, ATR, AFP, ALK, BCR-ABL, BRCA1/BRCA2, BRAF, V600E, Ca-125, CA19.9, EGFR, Her-2, KIT, PSA, S100, KRAS, ER/Pr, UGT1A1, CD30, CD20, F1P1L1-PDGRFα, PDGFR, TMPT, TMPRSS2; ABCB5, AFP-L3, Alpha-fetoprotein, Alpha-methyl acyl-CoA racemase, BRCA1, BRCA2, CA 15-3, CA 242, Ca 27-29, CA-125, CA15-3, CA19-9, Calcitonin, Carcinoembryonic antigen, Carcinoembryonic antigen peptide-1, Des-gamma carboxy prothrombin, Desmin, Early prostate cancer antigen-2, Estrogen receptor, Fibrin degradation product, Glucose-6-phosphate isomerase, vE6, E7, L1, L2 or p16INK4a, Human chorionic gonadotropin, IL-6, Keratin 19, Lactate dehydrogenase, Leucyl aminopeptidase, Lipotropin, Metanephrines, Neprilysin, NMP22, Normetanephrine, PCA3, Prostate-specific antigen, Prostatic acid phosphatase, Synaptophysin, Thyroglobulin, TNF, a transcription factor selected from ERG, ETV1 (ER81), FLI1, EST1, EST2, ELK1, ETV6, ETV7, GABPα, ELF1, ETV4, ETV5, ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or FEV. XXX, Tumor associated glycoprotein 72, c-kit, SCF, pAKT, pc-kit, Vimentin, CTLA-4, PDL1, PDL2, PD1, B7-H3, B7-H4, BTLA, HVEM, KIR, TIM3, GAL9, GITR, LAG3, VISTA, KIR, 2B4, TRPO2, CD160, CGEN-15049, CHK 1, CHK2, A2aR, TL1A, CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 family, and the combination thereof. In another embodiment, the marker is selected from the group consisting of: a protein modification, said modification is selected from a group consisting of is selected from a group consisting of acetylation, ADP-ribosylation, acylation, ADP-ribosylation, amidation, covalent attachment of a flavin, covalent attachment of a heme, covalent attachment of a nucleotide or a nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, arginylation, and ubiquitination. In some aspect, the marker is selected from the group consisting of: a genomic polymorphism, a pharmacogenomics single nucleotide polymorphism (SNP), a genomic SNP, a somatic polymorphism, and differential expression of a protein, a lipid, and/or a cellular organelle, a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'-UTR, an altered nucleotide sequence, encodes an altered amino acid sequence, a chromosomal translocation, an intra-chromosomal inversion, a change in copy number, a change in expression level, a change in protein level, a change in protein activity, or a change in methylation status, in a cancer tissue or cancer cell, as compared to a normal, healthy tissue or cell.

In another aspect, the disclosure is related to a method of monitoring a disease in a patient, comprising or alternatively consisting essentially of, or yet further consisting of analysis of the clinically relevant marker, wherein the clinically relevant marker is identified based on the representative data. In one aspect, the marker is selected from the group of: a protein, an antigen, an enzyme, a hormone, a DNA, an RNA, a microRNA, or a carbohydrate. In another aspect, the marker is DNA or RNA isolated from a sample selected from the group of: one or more premalignant or malignant cells, cells from a solid tumor, a soft tissue tumor or a metastatic lesion, tissue or cells from a surgical margin, a histologically normal tissue, one or more circulating tumor cells (CTC), a normal adjacent tissue (NAT), a blood sample from the same subject having or at risk of having the tumor, or an FFPE-sample. In one aspect, the disease is cancer.

Methods of Storing the Representative Sample (or the Homogenate Composition)

Once the representative sample is constructed, the sample may be transported for further processing and/or analysis. Therefore, the disclosure, in some embodiments, also relates to a method of storing the homogenate composition, comprising, or alternatively consisting essentially of, or yet further consisting of mixing the composition with an effective amount of a storage reagent, non-limiting examples of which are provided herein.

In one embodiment, the storage reagent comprises, or alternatively consists essentially of, or yet further consists of a preservative, a chaotrope, a detergent, a reducing agent, a chelator, a buffer, or a combination thereof. In one aspect, the mixed composition retains the phenotypic and genotypic characteristics of the composition before the mixture with the storage reagent. In another aspect, the mixed composition comprises, or alternatively consists essentially of, or yet further consists of a denatured proteins, an inactivated nuclease, an inactivated protease, an inactivate pathogen, a non-degraded nucleic acid, or a combination thereof. In some aspect, the chaotrope comprises, or alternatively consists essentially of, or yet further consists of guanidine thiocyanate, guanidine isocyanate, guanidine hydrochloride, or a combination thereof. In one aspect, the detergent comprises, or alternatively consists essentially of, or yet further consists of sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or a combination thereof. In another aspect, the reducing reagent comprises, or alternatively consists essentially of, or yet further consists of s mercaptoethanol, tris(2-carboxyethyl) phosphine, dithiothreitol, dimethylsulfoxide, tris(2-carboxyethyl)phosphine, or a combination thereof. In a further aspect, the chelator comprises, or alternatively consists essentially of, or yet further consists of ethylene glycol tetra acetic acid, hydroxyethylethylenediaminetriacetic acid, diethylene triamine penta acetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or a combination thereof. In a different aspect, the buffer comprises, or alternatively consists essentially of, or yet further consists of tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino) propane, 4-(2-hydroxyethyl)-1-piperazine ethanesulfonic acid, 3-(N-morpholine)propanesulfonic acid, bicarbonate, phosphate, or a combination thereof.

Method of Generating the Representative Sample

The disclosure generally relates to the development of a methodology for generating representative tissue samples of, e.g., whole organs, tumors, lymph nodes, metastases, or combinations thereof in order to address the issue of heterogeneity, e.g., tumor heterogeneity, in clinical specimens, especially clinical specimens for use in clinical oncology, and the use of such representative samples or portions thereof in various diagnostic and therapeutic methods as well as compositions comprising such representative samples for use in diagnosis and therapy, especially oncology.

The present application shows that the accepted sampling methods for cancer diagnostics, which utilize small samples of tumors for diagnostic testing, may result in a severe sampling bias in diagnostic pathology and oncology. Decisions concerning patient care, both prognostic (e.g., expectations of patient survival time) and predictive (e.g., whether the patient will respond to a specific therapy), are often made using single FFPE tissue sections in tumors that are considered "small", i.e., a two centimeter mass, using conventional methods all diagnostic data is typically taken from less than 0.03% of the tumor volume (i.e. a single section from an FFPE block). Further, these tissue samples from tumors are conventionally taken from very discrete regions of tumors, leaving diagnostic oncology blind to the heterogeneity present in the rest of the tumor. As a result, the data set is small (relative to the population) and consequently biased.

Likewise, similar to the low probability of detecting small sub-populations of genetically distinct cancer cells within solid tumors, small metastatic tumors within the lymph nodes surrounding the primary tumor site may not be detected using conventional histological examination. Lymph nodes range in size from a millimeter in diameter, to a few centimeters. The presence of tumor cells within a lymph node is dependent on the DNA mutations that result in tumor cell motility and invasion, as well as the mutations that confer the ability to survive in a new environment (i.e., breast vs. lymph node). The size of the metastatic tumor within the lymph node is dependent on the proliferation rate of the tumor and the length of time the metastatic tumor has been growing within the lymph node. The diagnostic test for presence of tumor cells within lymph nodes utilizes one or two thin sections of tissue (typically four microns in thickness) from an FFPE block. Using such methods, the critical factor for detection is the size of the tumor relative to the size of the lymph node. While a metastatic tumor that is 0.1 mm in diameter may fill 10% the volume of a small lymph node and have a reasonable probability of detection, the same size tumor would comprise only 0.005% of a lymph node that is two centimeters in diameter and have a very low probability of detection using current histological techniques. A significant number of patients that would be falsely labeled as node negative using conventional techniques could be detected and more appropriately treated using the methods disclosed herein. For example, more sensitive detection of node positive patients could better inform the decision whether to administer adjuvant chemotherapy.

IHC analysis of representative samples from lymph node tissue (e.g., prepared from surgically removed lymph nodes) can detect extremely small tumor micro-metastases through staining for epithelial markers combined with proliferation markers (for instance cytokeratin 8/18 dual IHC with Ki67). This may be accomplished by using markers that were positive in the primary tumor using other markers of metastatic cells, or other diagnostic markers. The metastatic tumor cells can also be detected by identifying nucleic acids for instance by utilizing a Next Generation Sequencing panel to identify cancer-associated mutations, including mutations present in the primary tumor. These methods will identify metastatic tumor cells In addition, the natural evolutionary course of the disease for each patient could be determined and correlated to specific mutations that may be targeted for therapy.

Current clinical practice for assessing tumors involves acquiring only a small portion of the tumor tissue for embedding and sectioning. In a basic scenario, the location of a region within the tumor containing a subclone of interest is assumed to be a random event. Therefore, while current practice carefully instructs as to which region to sample and to gain the most pertinent information for TNM staging, it is not necessarily informative for locating subclonal regions of the tumor. It is also not possible from gross inspection to determine if the subclone is present.

Embodiments of the present methods can address tumor heterogeneity in clinical oncology settings by providing methods for the efficient and reproducible production of cell samples that are representative of a patient's entire lymph node, tumor or tumors. As shown in FIG. 2A, a "representative" sample according to the disclosure comprises the different subpopulations of cancer cells comprised within a tumor, irrespective of its size. A "representative" sample according to the disclosure alternatively may comprise the different subpopulations within normal or control populations, or may comprise a mixed sample of tumor cells and normal cells.

Still alternatively, a representative sample according to the disclosure may comprise a representative or homogeneous biomolecules derived from a whole tumor, lymph nodes, or metastases, the fraction comprising a protein, lipid, nucleic acids or other moieties which are present in the starting tissue, e.g., a whole tumor, lymph nodes or metastases used to derive the sample or fraction thereof, wherein the relative proportions of such substituents are again representative of the starting tissue. For example, such biomolecules may be derived by the further dissociation or chemical or enzymatic treatment of the sample and/or by the use of methods that isolate or remove specific portions of the sample, such as by the use of size exclusion, e.g., sieving, to isolate or remove molecules of specific size or molecular weight, affinity purification methods which isolate or remove specific types of molecules from the representative sample, and the like. Accordingly, such methods essentially result in other types of representative samples according to the disclosure, e.g., homogeneous or representative samples comprising all of the proteins, nucleic acids, or lipids of the starting sample, e.g., a whole tumor, lymph nodes, metastases or organ, which representative sample may be used for protein, nucleic acid, and/or lipid analysis methods, and which is reflective of the entire tumor sample.

Therefore, irrespective of origin, in such representative samples the relative percentages cell subpopulations within a tumor or tumors, or other specific moieties present within the starting tissue, e.g., a tumor or lymph node metastases or organ are accurately reflected in the sample. Further, these representative samples, unlike samples obtained by conventional diagnostic methods, may be used in a plurality of assay methods, without compromising the ability to use the specimen in traditional diagnostic assays. Moreover, representative samples produced according to the disclosure can be used (and potentially reused) in several different assay formats separately or simultaneously in order to detect the presence of even minor sub-clone populations or other moieties such as tumor antigens or nucleic acids within a sample, e.g., a tumor, lymph node, or metastases.

Moreover, as discussed infra, representative samples from different patients or different tissues of single or different patients may each be labeled with unique identifying labels, e.g., a hapten, and the labeled samples of different patients or tissues combined and used in desired assay methods. Essentially, this provides for multiplexing of different patient samples.

Based thereon, representative samples derived by exemplary embodiments of the presently described methods should facilitate and substantially improve the accuracy of detecting, diagnosing, and/or staging of different types of tumors, i.e., different solid tumors, irrespective of tumor tissue type, location, size or volume. Also, the present methods may be used to produce representative samples from supposed normal tissue samples or putative precancerous tissues (e.g., obtained from subjects at higher risk of developing cancer because of a genetic risk or a prior cancer) so as identify rare cell types such as cancer stem lines that may be present therein even before any sign of the disease has manifested.

In a further embodiment, the disclosure relates to a method for preparing a tissue or biological samples containing heterogeneous cellular structures, comprising: (a) homogenizing the sample; (b) reconstructing the homogenized sample into a homogenate, said homogenate comprising substantially homogeneous cellular structures, wherein a ratio of the cellular structures in a subset of the homogenate is substantially similar to the ratio of the cellular structures in the tissue sample. In one aspect, the homogenate comprises, or alternatively consists essentially of, or yet further consists of a plurality of single cells or a plurality of cell clusters.

In one embodiment, the method for preparing a tissue sample further comprises, or alternatively consists essentially of, or yet further consists of fixing the homogenate with a fixative agent. In another aspect, the fixative agent comprises, or alternatively consists essentially of, or yet further consists of formalin, calcium, acetic acid, saline, alcohol, urea, bronopol, water, or a combination thereof. In a different aspect, the fixed homogenate is mounted to a slide.

In some embodiments, the method for preparing a tissue sample further comprises, or alternatively consists essentially of, or yet further consists of extracting a constituent from the homogenate. In one aspect, the constituent is DNA, RNA, protein, lipid, a cell organelle, an exosome, a cell, or a combination thereof. In another embodiment, the method for preparing a tissue sample further comprises, or alternatively consists essentially of, or yet further consists of isolating a cellular structure or a constituent from the homogenate. In one aspect, the cellular structure or the constituent comprises, or alternatively consists essentially of, or yet further consists of a single cell or single nucleus. In one aspect, the isolation comprises, or alternatively consists essentially of, or yet further consists of single-cell isolation or single-nucleus isolation. In another aspect, the single-cell isolation is performed by flow cytometry, laser microdissection, manual cell picking, random seeding and dilution, a microfluidics device, a lab-on-a-chip device, or the combination thereof. In one aspect, the single-nucleus isolation is performed by flow cytometry.

In one embodiment, the homogenization comprises, or alternatively consists essentially of, or yet further consists of chemical and/or biochemical dissociation, and/or optionally, mechanical homogenization. In one aspect, the homogenization process does not lyse the cells. In another aspect, the chemical treatment of the sample comprises, or alternatively consists essentially of, or yet further consists of enzymatic digestion of the sample, said enzymatic digestion comprising use of an enzyme selected from a group consisting of interstitial collagenase, Gelatinase-A, Stromelysin 1, Matrilysin, Neutrophil collagenase, Gelatinase-B, Stromelysin 2, Stromelysin 3, Macrophage metalloelastase, Collagenase 3, MT1-MMP, MT2-MMP, MT3-MMP, MT4-MMP, Collagenase 4, Enamelysin, X-MMP, CA-MMP, MT5-MMP, MT6-MMP, Matrilysin-2, MMP-22, endoproteinase, trypsin, chymotrypsin, endoproteinase Asp-N, endoproteinase Arg-C, endoproteinase Glu-C (V8 protease), endoproteinase Lys-C, pepsin, thermolysin, elastase, papain, proteinase K, subtilisin, clostripain, exopeptidase, carboxypeptidase A, carboxypeptidase B, carboxypeptidase P, carboxypeptidase Y, cathepsin C, acylamino-acid-releasing enzyme, and pyroglutamate aminopeptidase. In one aspect, the mechanical homogenization is performed by a device selected from a group consisting of a blender, a disassociator, an extractor, a mortar, a pestle, a dounce homogenizer, a tissue grinder, a rotary blade tissue homogenizer, and a bead beating homogenizer. In another aspect, the homogenate is created by manual dicing using a scalpel or knife. In one embodiment, the homogenization further comprises, or alternatively consists essentially of, or yet further consists of cell conditioning, said cell conditioning comprising adjusting pH and/heat, or treating the sample with a cell conditioning buffer.

In some aspects, before or after the sample is homogenized, the sample is treated with hormones, proteins, enzymes, lipids, detergents, sonication, physical agitation, or the combination thereof, before or after the homogenization.

In a further aspect, the homogenized sample comprises, or alternatively consists essentially of, or yet further consists of cells and/or cell clusters. In some aspect, the homogenized sample comprises, or alternatively consists essentially of, or yet further consists of cell clusters of uniform sizes. In another aspect, the homogenized sample comprises, or alternatively consists essentially of, or yet further consists of cell clusters of non-uniform sizes. In some aspect, the cell clusters comprise, or alternatively consist essentially of, or yet further consist of 1-100 cells, or 100-1,000 cells, 1,000-10,000 cells, or 10,000-100,000 cells. In an additional aspect, the cell clusters comprise, or alternatively consist essentially of, or yet further consist of more than 100,000 cells.

In one embodiment, the method for preparing a tissue sample further comprises, or alternatively consists essentially of, or yet further consists of passing the homogenized sample through a mesh, a filter, or a series of meshes or filters. In one aspect, the mesh or filter has a pore size ranging from about 1 micron to about 500 microns. In another aspect, the mesh or filter has a pore size less than 1 micron. In some aspect, the mesh or filter has a pore size ranging from about 1 micron to about 100 microns, from about 100 microns to about 200 microns, from about 200 microns to about 300 microns, from about 300 microns to about 400 microns, or from about 400 microns to about 500 microns. In an additional aspect, the mesh or filter has a pore size more than 500 microns.

In an additional embodiment, the tissue sample is collected from a tissue selected from the group consisting of a tumor, lymph node, a metastasis, polyp, cyst, biopsy, a whole organ, and combination thereof. In one aspect, the tissue sample is a solid sample or a liquid sample. In another aspect, the liquid sample comprises, or alternatively consists essentially of, or yet further consists of cytology needle aspirate, effusion sample, or pap smear. In one aspect, the cellular structures of the homogenate comprise, or alternatively consist essentially of, or yet further consist of at least one cell. In a different aspect, the cellular structures of the homogenate comprise, or alternatively consist essentially of, or yet further consist of at least 100 cells. In another aspect, the cellular structures of the homogenate comprise about 100-about 200 cells, about 200-about 1,000 cells, about 1,000-about 5,000 cells, or about 10,000-about 100,000 cells. In a different aspect, the cellular structures of the homogenate comprise, or alternatively consist essentially of, or yet further consist of about 100,000-about 1,000,000 cells; about 1,000,000-about 5,000,000 cells, about 5,000,000-about 1,000,000,000 cells, or about 1,000,000,000-about 5,000,000,000 cells. In a further aspect, the cellular structures of the homogenate comprise, or alternatively consist essentially of, or yet further consist of more than about 5,000,000,000 cells.

In one embodiment, the homogenate is not preserved or fixed. In one aspect, the homogenate comprises, or alternatively consists essentially of, or yet further consists of a live cell. In another aspect, the homogenate is preserved or fixed. In one aspect, the homogenate is frozen, freeze-dried, or embedded in an embedding medium. In a further aspect, the homogenate comprises cells from one or more tissues, and/or one or more subject.

In one embodiment, the tissue sample is isolated from a tumor, a lymph node, metastases, a polyp, a cyst, a resection, a whole organ, or a combination thereof. In one aspect, the homogenate further comprises, or alternatively consists essentially of, or yet further consists of a non-human cell, a human cell, a non-native protein, a nucleic acid, or a small molecule. In one embodiment, the small molecule is selected from a group consisting of a hapten, a peptide tag, a protein tag, a fluorescent tag, a nucleic acid tag, and combination thereof. In an additional aspect, the small molecule comprises, or alternatively consists essentially of, or yet further consists of a hapten, a peptide tag, a protein tag, a fluorescent tag, a nucleic acid tag, a luminescent tag, a biotin, and combination thereof.

In a an additional embodiment, the method for preparing a tissue sample further comprises, or alternatively consists essentially of, or yet further consists of assessing the substantially homogenous cellular structures within the homogenate. In one aspect, the substantially homogenous cellular structures are assessed by measuring distribution of an internal control within the homogenate. In another aspect, the internal control is selected from a group consisting of a non-human cell, a human cell, a non-native protein, a nucleic acid, a small molecule, a dye, a chemical, and combination thereof.

In another aspect, the disclosure provides a method for producing a biological sample suitable for assessing heterogeneity of cells within a sample (such as a tumor sample or lymph node or metastases or a combination thereof) and/or assessing the prognosis of a particular cancerous condition in a subject comprising (i) obtaining one or more intact biopsy samples from a solid tumor or a lymph node, preferably wherein each biopsy sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells, and optionally fixed or preserved (such as a formalin, paraffin, or ethanol fixed or preserved sample), and (ii) separately or in combination homogenizing the one or more biopsy samples, wherein the one or more homogenates each substantially homogeneously express the heterogeneity of the respective biopsy sample or samples.

As mentioned, these representative samples optionally may be further dissociated and/or treated to remove or isolate specific types of molecules such as specific cell types, proteins, nucleic acids, or lipids, and the like, thereby generating other representative samples which may be used in diagnostic and therapeutic methods.

In yet another aspect, the disclosure provides a method for producing a biological sample suitable for assessing heterogeneity of cells within a tumor or lymph node or metastases or combination thereof comprising (i) obtaining one or more biopsy samples from a solid tumor or a lymph node or metastases, preferably wherein each biopsy sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells, and optionally fixed or preserved (such as a formalin, paraffin, or ethanol fixed or preserved sample), and (ii) separately or in combination homogenizing the one or more biopsy samples, under conditions wherein the resultant homogenate or homogenates are substantially dissociated into individual cells and the resultant homogenate or homogenates are substantially homogeneous.

Again, these representative samples optionally may be further dissociated and/or treated to remove or isolate specific types of molecules such as specific cell types, proteins, nucleic acids, or lipids, and the like, thereby generating other representative samples which may be used in diagnostic and therapeutic methods.

In another aspect, the disclosure provides a method for producing a biological sample suitable for assessing whether a subject comprises or is at risk of developing a virulent form of a particular cancer and/or whether a subject with cancer comprises a virulent form of that particular cancer comprising (i) obtaining one or more intact biopsy samples from a solid tumor or a lymph node or metastases or precancerous cyst, preferably wherein each biopsy sample comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells, and optionally fixed or preserved (such as a formalin, paraffin, or ethanol fixed or preserved sample), and (ii) separately or in combination homogenizing the one or more biopsy samples, wherein the resultant one or more homogenates each substantially homogeneously express any heterogeneity of the respective biopsy sample or samples, and optionally isolating or detecting the expression of at least one biomarker. The upregulation or downregulation of the biomarker is associated with a virulent form of the particular cancer.

In yet another aspect, the disclosure provides a method for characterizing a phenotypic diversity within a heterogeneous tumor, lymph nodes or metastases or precancerous cyst and/or detecting genetically distinct subclones within a heterogeneous tumor lymph nodes or metastases or precancerous cyst and/or identifying low prevalence events within a tumor lymph nodes or metastases or precancerous cyst and/or determining the prevalence of targets within a tumor lymph nodes or metastases or precancerous cyst comprising (i) obtaining a sample or samples of the tumor lymph nodes or metastases or precancerous cyst that encompasses spatially distinct regions of the tumor lymph nodes or metastases or precancerous cyst, which is or are optionally fixed or preserved prior to homogenization e.g., with formalin, paraffin and/or ethanol, and (ii) homogenizing the tumor lymph nodes or metastases or precancerous cyst sample or samples, thereby producing a homogenate that is representative of the phenotypic diversity of the heterogeneous tumor lymph nodes or metastases or precancerous cyst and is suitable for characterizing the landscape of the tumor and/or detecting genetically distinct subclones within a heterogeneous tumor lymph nodes or metastases or precancerous cyst and/or identifying low prevalence events within a tumor lymph nodes or metastases or precancerous cyst and/or determining the prevalence of targets within a tumor lymph nodes or metastases or precancerous cyst.

In yet another aspect, the disclosure provides a method for detecting precancerous cells or cancerous cells in supposed normal tissues or putative precancerous tissues in a patient, e.g., one at risk of developing cancer because of a genetic mutation or previous cancer, or a patient with precancerous cysts or polyps comprising (i) obtaining a sample or samples of supposed normal tissues or putative precancerous tissues such as precancerous cysts or polyps that encompass spatially distinct regions of the supposed normal tissues or putative precancerous tissues of the patient, which is optionally fixed or preserved prior to homogenization e.g., with formalin, paraffin and/or ethanol, and (ii) homogenizing the sample or samples, thereby producing a homogenate that is representative of the supposed normal tissues or putative precancerous tissues and which is suitable for detecting rare cancerous cells or cancer stem cells, e.g., even before any sign of disease has manifested in the patient.

In another aspect, the disclosure provides methods of using representative samples and portions thereof produced by the any of the foregoing methods in different assay formats, wherein these assays may be effected in high throughput, performed simultaneously or at different times or different locations, and/or by automation (fully automated or semi-automated).

In another aspect, the disclosure representative samples or portions thereof produced by the any of the foregoing methods are stored for future use, e.g., frozen or freeze dried. In another aspect, the disclosure representative samples or portions thereof produced by the any of the foregoing methods are used to derive (and optionally purify) antibodies or antigens specific to a particular antigen from a cancer cell or cell types in a patient sample, which antibodies or antigens potentially may be used in personalized medicine, i.e., in the production of therapeutic or prophylactic cancer vaccines.

The homogenization step in all of the above-mentioned methods may be effected by a method which preserves the integrity of the cells within the sample, i.e., the bulk of the cells within the homogenized sample or samples are not lysed and whereby the resultant homogenate and portions thereof are "representative" of the sample or samples. Again this means that the cells within the sample or a portion thereof reflect the percentages of the different cell types within the entirety of the tissue sample or samples, e.g., a solid tumor or a lymph node. This may be effected, e.g., by mechanical dissociation of the tumor sample or a portion thereof (such as mechanical dissociation performed with or without the addition of liquid to the tumor sample or a portion thereof) and/or chemical or enzymatic dissociation of the tumor sample or a portion thereof (such as treatment with an enzyme that selectively or preferentially or primarily acts upon extracellular matrix proteins as compared to membrane-associated proteins). Alternatively, the homogenization methods may result in the dissociation of the cells while still generating a sample that is representative of the starting tissue, e.g., a whole tumor. Also, the homogenized representative samples optionally may be further dissociated and/or treated to remove or isolate specific types of molecules such as specific cell types, proteins, nucleic acids or lipids, and the like thereby generating other representative samples which may be used in diagnostic and therapeutic methods.

Any of the above methods may include detecting the expression of at least one biomarker, e.g., at least one lipid, protein, or nucleic acid biomarker, in the homogenate or a portion or fraction thereof. Additionally, the methods may further include detecting the percentage of tumor cells in the homogenate or a portion or fraction thereof that express a particular biomarker or combination of biomarkers. Optionally, tumor stem cells and/or the relative frequency or percentage of tumor subclones in the homogenate or a portion or fraction thereof are detected and/or isolated. Additionally, the methods may also include detecting a genetic target (such as a point mutation, a deletion, an addition, a translocation, a genetic fusion, or an amplification of a gene).

Any of the above methods may also be used to detect, isolate, and/or quantify specific immune cells (such as B lymphocytes, T lymphocytes, macrophages, NK cells, monocytes, or a combination thereof) present in the homogenate or a portion or fraction thereof, which provides valuable clinical information, e.g., immune status and disease state, and also in order to select suitable treatment protocols such as checkpoint inhibitors, cytokines, or other immune modulators.

The resultant homogenates or representative samples may comprise at least 1,000; 10,000; 100,000; 1,000,000; 5,000,000; 10,000,000; 50,000,000; 100,000,000; 500,000,000; 1,000,000,000; 5,000,000,000; 10,000,000,000; 50,000,000,000; 100,000,000,000, 1,000,000,000,000 or more cells.

The resultant homogenates or a fraction or portion thereof optionally may be frozen or freeze-dried or embedded in wax (such as paraffin) or, alternatively, used for further steps (some of which are discussed below) without such freezing or freeze-drying or wax. For example, a representative paraffin block, i.e., the resultant homogenate or a fraction or portion thereof embedded in paraffin, is suitable for use in the current anatomic pathology workflow, e.g., sectioning, preparing slides, staining, microscopy, antigen retrieval, etc.

The homogenates may be derived from two or more tumors taken from one or more subjects and the resultant homogenates or fractions thereof of each tumor are used to assess the similarities and/or differences of the two or more tumors or disease condition of different patients.

In addition, the homogenates may be derived from two or more putative normal or precancerous tissues, e.g., breast, cervical, colorectal, or precancerous cysts or polyps obtained from a subject, e.g., one with a BRCA mutation, and the resultant homogenates or fractions thereof used to assess whether any abnormal cells or disease biomarkers are present.

In addition, non-human cells (such as insect cells and/or mouse cells) or other foreign proteins, nucleic acids, or small molecules may be added to the homogenate to create an internal control for positive protein or nucleic acid detection.

Also, small molecules (such as haptens, peptide tags, protein tags, fluorescent tags, and/or nucleic acid tags) may be added to the sample and used to provide spatial information in the representative sample. For example, a sample (such a tumor or lymph node) may be sectioned, e.g., cut into quadrants, and a different hapten (or other suitable small molecule) may be "doped" into each section prior to homogenizing the sections to generate a representative sample. It should be understood that the number of sections that can be generated from each sample for "doping" prior to homogenization is not limited but, rather, likely selected in scale with the size of the sample, i.e., the larger the sample, the greater the number of sections that can be "tagged" with a small molecule prior to homogenization. In this way, spatial information can be maintained in the resultant homogenates or fractions thereof.

Small molecules can also be added to the sample prior to combining the sample with a different sample from another patient or the same patient and, thus, provides a means to differentiate samples when run in a multiplex assay format.

The samples which are homogenized are optionally formalin fixed or may be preserved in ethanol before or after homogenization. Because of safety concerns tissue samples are generally formalin or otherwise fixed prior to usage in pathology or diagnostic methods. Formalin or other fixation methods are generally known in the art. Exemplary methods are disclosed infra. In such case, the formalin fixed tumor sample may be soaked in water or buffered saline solution (such as PBS) prior to homogenization in step (ii).

Alternatively, or in addition, the tumor sample used in the disclosed methods may be preserved in ethanol prior to homogenization. However, it should be emphasized that formalin fixing or ethanol or other preservation procedure are not essential to the subject methods, and may be eliminated without compromising the suitability of the resultant homogenized representative sample.

The homogenization of unfixed tissue may be used to produce a representative live sample. A live representative sample may be cultured to create a representative tissue culture sample from individual patients. Such a representative sample can be divided numerous times to create multiple representative culture samples, which can be used to determine the efficacy of chemotherapy (such as an antibody, nucleic acid, small molecule, or polypeptide, which antagonizes, inhibits, or blocks the expression or functional activity of at least one known or unknown biomarker). Moreover, specific cell types (such as immune cells or tumor cells) can be selected using FACS analysis. For example, tumor infiltrated immune cells can be selected and cultured to determine the tumor specific antibodies being secreted by the immune system.

Also, as shown herein the disclosed methods for deriving representative samples and their use in diagnostic and therapeutic methods are suitable for both fixed and unfixed tissue samples.

Any of the disclosed methods for preparing a representative sample (such as a homogenate prepared from a tumor biopsy sample) may include the addition of at least one collagenase or other suitable enzyme or enzyme combination or other chemical such as a salt that itself breaks down or which facilitates the breakdown of the extracellular matrix before, during, or after homogenization; the use of elevated temperature and/or buffer conditions such as a cell conditioning buffer, e.g., CC1 or CC2, that disrupts cellular cross-links; and/or the use of a device for mechanical shearing (such as an IKA® blender, a gentleMACs™ Disassociator, or a functional equivalent). These methods may or may not be performed under conditions that maintain the viability and integrity of the cells within the sample, e.g., under some homogenization conditions the cells are substantially not lysed.

In one aspect, homogenization comprises the use of mortar & pestle, a dounce homogenizer or tissue grinder, a hand held electronic rotary blade tissue homogenizer (such as Omni-TH available from Thomas Scientific), a bead beating homogenizer (such as a bullet blender or a Burton Precellys® 24 Tissue Homogenizer or a Bead Ruptor available from OMNI), optionally at a speed of between about 100 and about 75,000 RPM for rotational homogenizers or a speed of about 0.5 m/s to about 2.5 m/s for bead beaters, and for a length of about 30 second to about 5 minutes, about 5 minutes to about 10 minutes, about 10 minutes to about 30 minutes, or about 30 minutes to about 60 minutes.

In another embodiment, homogenization comprises the use of interstitial collagenase, Gelatinase-A, Stromelysin 1, Matrilysin, Neutrophil collagenase, Gelatinase-B, Stromelysin 2, Stromelysin 3, Macrophage metalloelastase, Collagenase 3, MT1-MMP, MT2-MMP, MT3-MMP, MT4-MMP, Collagenase 4, Enamelysin, X-MMP, CA-MMP, MT5-MMP, MT6-MMP, Matrilysin-2, MMP-22, endoproteinase, trypsin, chymotrypsin, endoproteinase Asp-N, endoproteinase Arg-C, endoproteinase Glu-C (V8 protease), endoproteinase Lys-C, pepsin, thermolysin, elastase, papain, proteinase K, subtilisin, clostripain, exopeptidase, carboxypeptidase A, carboxypeptidase B, carboxypeptidase P, carboxypeptidase Y, cathepsin C, acylamino-acid-releasing enzyme, pyroglutamate aminopeptidase, or any combination thereof, optionally at a concentration of about 0.001 µg/ml to about 1000 mg/ml, and for a length of about 1 minute to about 120 minutes.

The tumor sample used in the disclosed methods that encompasses spatially distinct regions of the tumor or other tissue may comprise at least 10%, 20%, 30%, 40%, 50%, 60%, 70%, 75%, at least 85%, at least 95%, at least 96%, at least 97%, at least 98%, at least 99% or, preferably, the entirety of a tumor surgically removed from a patient. The tumor sample may be at least 1, 5, 10, 20, 50, 100 or more millimeters (mm) or centimeters (cm) in diameter.

The samples used in the subject methods generally will be derived from a solid tumor or tumors (including primary tumors and metastatic tumors), lymph nodes, metastases, or pre-cancerous tissues such as cysts or polyps. Alternatively, or in addition, the methods potentially also may also be effected with non-solid tumors, e.g., blood cancers. For example, the solid tumor samples which are homogenized optionally may be combined with liquid patient samples, e.g., blood, lymphatic fluid, effusion specimens, cerebrospinal fluid, bile, mucus, and/or urine samples from the patient. Homogenized samples may in addition or alternatively comprise biopsied "normal" or precancerous tissues, e.g., in order to detect diseased cells prior to disease manifestation.

Such tumor or other tissue sample or samples used in the disclosed methods may be from any source, e.g., derived from breast, colon, lung, pancreas, gall bladder, skin, bone, muscle, liver, kidney, cervix, ovarian, prostate, esophageal, stomach, or other organs, e.g., a breast cancer tumor, a lung cancer tumor, liver tumor, a prostate cancer tumor, a colon cancer tumor, a bladder cancer tumor, or a kidney cancer tumor. Generally, the tumor sample or other tissue used in the disclosed methods is of human origin.

The tumor or other tissue sample used in the disclosed methods may have a volume of at least 1 cm$^3$, at least 2 cm$^3$, at least 3 cm$^3$, at least 4 cm$^3$, at least 5 cm$^3$, at least 6 cm$^3$, at least 7 cm$^3$, at least 8 cm$^3$, at least 9 cm$^3$, at least 10 cm$^3$, at least 15 cm$^3$, at least 20 cm$^3$, at least 25 cm$^3$, at least 50 cm$^3$, at least 100 cm$^3$, at least 250 cm$^3$, at least 500 cm$^3$, at least 1,000 cm$^3$, at least 2,500 cm$^3$, at least 5,000 cm$^3$, at least 7,500 cm$^3$, at least 10,000 cm$^3$ or larger.

The tumor or other tissue sample used in the disclosed method may have a width at the widest point of at least 0.5 cm, at least 1 cm, at least 1.5 cm, at least 2 cm, at least 2.5 cm, at least 3 cm, at least 3.5 cm, at least 4 cm, at least 4.5 cm, at least 5 cm, at least 6 cm, at least 7 cm, at least 10 cm, at least 25 cm, at least 50 cm or larger.

Figure 24:
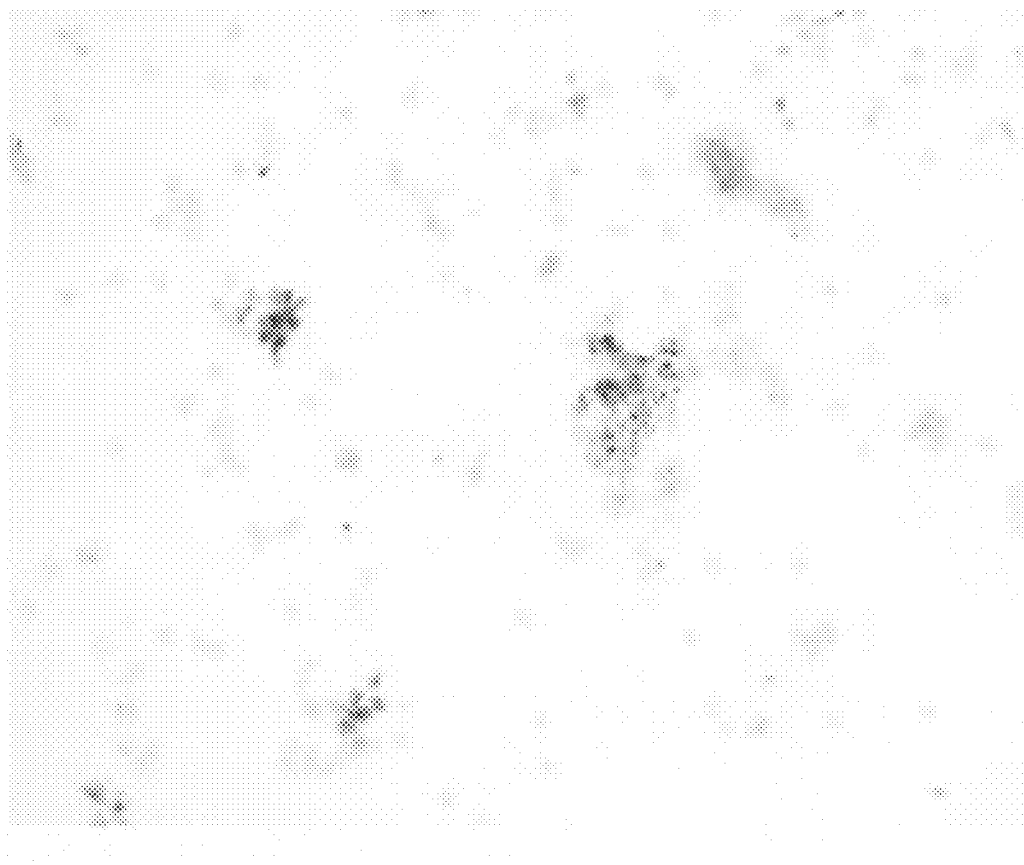
FIG. 24 shows staining of HPV16 ISH on Caski cells in a representative sample prepared from tissue recovered from a paraffin block. Tissue that was previously embedded in paraffin wax was recovered and homogenized in an IKA® to generate a representative sample.

Additionally, in some embodiments, representative samples can be made of tissue that has previously been formalin fixed and embedded in paraffin wax. In particular, the wax can be melted, the tissue recovered and hydrated, and then methods described herein, i.e., homogenization, applied to the sample, which is suitable for use in any number of assays (see, e.g., FIG. 24). FIG. 24 shows staining of HPV16 ISH on Caski cells in a representative sample prepared from tissue recovered from a paraffin block. Tissue that was previously embedded in paraffin wax was recovered and homogenized in an IKA® to generate a representative sample. In this way, the disclosed methods can be used to generate a representative sample using a sample or samples already prepared for TNM staging, by melting the wax, recovering the sample, rehydrating the tissue and homogenizing accordingly.

Any of the above methods may further comprise (iii) distributing the homogenate or a portion or fraction thereof onto one or more slides or other solid supports and, optionally, staining the one or more slides or other solid supports containing the homogenate or a portion or fraction thereof with hematoxylin and eosin stain; performing immunohistochemical staining on the slide or other solid support containing the homogenate or a portion or fraction thereof; or performing in situ hybridization on the slide or other solid support containing the homogenate or a portion or fraction thereof, i.e., any one of which would be considered step (iv) in the methods.

Moreover, any of the above methods may further comprise (iii) purifying nucleic acids (such as DNA or mRNA) from the homogenate or a portion or fraction thereof. The purified nucleic acids may be subject to Northern blot, DNA sequencing, PCR, RT-PCR, microarray profiling, differential display, or in situ hybridization. Instead, the purified nucleic acid may be conjugated to a nanoparticle (such as Quantum Dots™, paramagnetic nanoparticles, superparamagnetic nanoparticles, and metal nanoparticles, preferably alloyed quantum dots, including by way of example and without limitation, CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN, by way of example).

It is also contemplated that any of the above methods may further comprise purifying lipids or exosomes or other organelles from the homogenate or a portion or fraction thereof. The purified lipids may be subject to mass spectrometry or histochemistry.

Additionally, it is also contemplated that any of the above methods may further comprise purifying proteins from the homogenate or a portion or fraction thereof. The purified proteins may be subject to Western blot, ELISA, immuno-precipitation, chromatography, mass spectrometry, microarray profiling, interferometry, electrophoretic staining, or immuno-histochemical staining. Alternatively, or in addition to the foregoing, the purified proteins may be used to produce antisera specific to the tumor.

Moreover, it is contemplated that any of the above methods further comprise (iii) performing a genomic, transcriptomic, proteomic and/or metabolomic analysis on the homogenate or a portion or fraction thereof.

Furthermore, it is contemplated that any of the above methods further comprise (iii) affinity purifying specific cell types from the homogenate or a portion or fraction thereof.

The specific cell types may contain a biomarker of interest. Exemplary biomarkers of interest may include Her2, bRaf, an ERBB2 amplification, a P13KCA mutation, a FGFR2 amplification, a p53 mutation, a BRCA mutation, a CCND1 amplification, a MAP2K4 mutation, an ATR mutation, or any other biomarker the expression of which is correlated to a specific cancer; at least one of AFP, ALK, BCR-ABL, BRCA1/BRCA2, BRAF, V600E, Ca-125, CA19.9, EGFR, Her-2, KIT, PSA, S100, KRAS, ER/Pr, UGT1A1, CD30, CD20, F1P1L1-PDGRFα, PDGFR, TMPT, and TMPRSS2; or at least one biomarker selected from ABCB5, AFP-L3, Alpha-fetoprotein, Alpha-methyl acyl-CoA racemase, BRCA1, BRCA2, CA 15-3, CA 242, Ca 27-29, CA-125, CA15-3, CA19-9, Calcitonin, Carcinoembryonic antigen, Carcinoembryonic antigen peptide-1, Des-gamma carboxy prothrombin, Desmin, Early prostate cancer antigen-2, Estrogen receptor, Fibrin degradation product, Glucose-6-phosphate isomerase, an HPV antigen such as vE6, E7, L1, L2 or p16INK4a Human chorionic gonadotropin, IL-6, Keratin 19, Lactate dehydrogenase, Leucyl aminopeptidase, Lipotropin, Metanephrines, Neprilysin, NMP22, Normetanephrine, PCA3, Prostate-specific antigen, Prostatic acid phosphatase, Synaptophysin, Thyroglobulin, TNF, a transcription factor selected from ERG, ETV1 (ER81), FLI1, ETS1, ETS2, ELK1, ETV6 (TEL1), ETV7 (TEL2), GABPα, ELF1, ETV4 (E1AF; PEA3), ETV5 (ERM), ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or Tumor-associated glycoprotein 72, c-kit, SCF, pAKT, pc-kit, and Vimentin.

Alternatively, or in addition the biomarker of interest may be an immune checkpoint inhibitor such as, but not limited to, CTLA-4, PDL1, PDL2, PD1, B7-H3, B7-H4, BTLA, HVEM, KIR, TIM3, GAL9, GITR, LAG3, VISTA, KIR, 2B4, TRPO2, CD160, CGEN-15049, CHK 1, CHK2, A2aR, TL1A, and B-7 family ligands or a combination thereof or is a ligand of a checkpoint protein selected from the group consisting of CTLA-4, PDL1, PDL2, PD1, B7-H3, B7-H4, BTLA, HVEM, TIM3, GALS, LAG3, VISTA, KIR, 2B4, CD160, CGEN-15049, CHK1, CHK2, A2aR, B-7 family ligands, or a combination thereof.

The method of any of the foregoing claims which includes the detection of at least one biomarker associated with acute lymphoblastic leukemia (etv6, am11, cyclophilin b), B cell lymphoma (Ig-idiotype), glioma (E-cadherin, .alpha.-catenin, .beta.-catenin, .gamma.-catenin, p120 ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-C017-1A/GA733, APC), choriocarcinoma (CEA), epithelial cell cancer (cyclophilin b), gastric cancer (HER2/neu, c-erbB-2, ga733 glycoprotein), hepatocellular cancer (.alpha.-fetoprotein), Hodgkin's lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and/or T cell leukemia (HTLV-1 epitopes).

It is also contemplated that any of the above mentioned methods further comprise (iii) treating the homogenate or a portion or fraction thereof with collagenase or other enzyme or chemical or combination thereof that breaks down extracellular matrices, incubating the homogenate or a portion or fraction thereof under high temperature conditions, and/or mechanically agitating the homogenate or a portion or fraction thereof in order to dissociate the cells within the homogenate or a portion or fraction thereof. Generally, these methods will generate another representative sample that may be used in the disclosed analytic or therapeutic methods or a combination thereof.

Additionally, it is contemplated that any of the above described methods further comprise (iii) filtering or sizing the homogenate or a portion or fraction thereof, which may result in obtaining single cells or small cell clusters, such as doublets or triplets.

The cellular componentry of the representative sample may be separated by one or multiple filtration steps. For example, following homogenization and disassociation of the homogenate through physical and/or biochemical means, the disassociated sample may be filtered through a 1 micron filter to remove all intact cellular material. It is expected that the non-cellular representative sample will contain secreted factors from the tumor and normal stroma from within the tumor that will be of clinical utility, i.e., antibodies, growth factors, immunomodulators, and other unknown factors. The non-cellular representative sample may be analyzed by ELISA, mass spectrometry, next generation sequencing, and other diagnostic methods. To the extent that single cells derived from the representative sample are obtained following filtration, such cells may be analyzed using fluorescent activated cell sorting (FACS) and flow cytometry analysis.

Given the representative nature of the homogenate generated by the disclosed methods, the homogenate or a portion or fraction thereof can be used to detect a low prevalence genetic event (such as a genetic event that occurs at 20% prevalence, 15% prevalence, 10% prevalence, 5% prevalence, 2% prevalence, 1% prevalence, 0.5% prevalence, 0.1% prevalence, 0.001% prevalence, 0.0001% prevalence, 0.00001% prevalence, 0.000001% prevalence or less). Exemplary genetic events include a point mutation, a deletion, an addition, a translocation, a genetic fusion, or an amplification of a gene. Likewise, the methods can also involve detecting genetic or epigenetic heterogeneity of cells within the tumor sample or a portion thereof and/or detecting cells comprising rare genetic or epigenetic variations. Such cells may be present in the tumor sample at a frequency of less than 5%, less than 1%, less than 0.5%, less than 0.1%, less than 0.05%, or less than 0.01%.

The detected rare cells may comprise one or more genetic or epigenetic differences that confer resistance to an anti-cancer therapy and/or promote metastasis. Therefore, the detection of such cells will facilitate cancer prognosis as well as the selection of an appropriate therapeutic regimen such as surgery, chemotherapy and/or the use of biologics.

The foregoing methods may also include the use of at least one detectable label selected from fluorescent molecules or fluorochromes (such as sold by Invitrogen, e.g., see, The Handbook—A Guide to Fluorescent Probes and Labeling Technologies, Invitrogen Detection Technologies, Molecular Probes, Eugene, Oreg, or disclosed in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives, thiol-reactive europium chelates which emit at approximately 617 nm (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Invitrogen Detection Technologies, Molecular Probes (Eugene, Oreg.) and including the ALEXA FLUOR™ series of dyes (for example, as described in U.S. Pat. Nos. 5,696,157, 6,130,101 and 6,716, 979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912), a fluorescent nanoparticle, such as a semiconductor nanocrystal, e.g., a QUANTUM DOT™ (obtained, for example, from QuantumDot Corp, Invitrogen Nanocrystal Technologies, Eugene, Oreg.; see also, U.S. Pat. Nos. 6,815,064, 6,682,596 and 6,649,138). The semiconductor nanocrystals described in e.g., U.S. Pat. No. 6,602,671, Bruchez et. al. (1998) Science 281:2013-6, Chan et al. (1998) Science 281:2016-8, and U.S. Pat. Nos. 6,274,323, 6,927,069; 6,914, 256; 6,855,202; 6,709,929; 6,689,338; 6,500,622; 6,306, 736; 6,225,198; 6,207,392; 6,114,038; 6,048,616; 5,990, 479; 5,690,807; 5,571,018; 5,505,928; 5,262,357 and in U.S. Patent Publication No. 2003/0165951 as well as PCT Publication No. 99/26299 (published May 27, 1999), radioisotopes (such as $^3$H), metal chelates such as DOTA and DPTA chelates of radioactive or paramagnetic metal ions like $Gd^{3+}$, and liposomes, enzymes, for example horseradish peroxidase, alkaline phosphatase, acid phosphatase, glucose oxidase, β-galactosidase, β-glucuronidase or β lactamase, enzyme in combination with a chromogen, fluorogenic or luminogenic compound that generates a detectable signal, for example, those sold by Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate](ABTS), o-dianisidine, 4-chloronaphthol (4-CN), nitrophenyl-.beta.-D-galactopyranoside (ONPG), o-phenylenediamine (OPD), 5-bromo-4-chloro-3-indolyl-.beta.-galactopyranoside (X-Gal), methylumbelliferyl-.beta.-D-galactopyranoside (MU-Gal), p-nitrophenyl-.alpha.-D-galactopyranoside (PNP), 5-bromo-4-chloro-3-indolyl-.beta.-D-glucuronide (X-Gluc), 3-amino-9-ethyl carbazol (AEC), fuchsin, iodonitrotetrazolium (INT), tetrazolium blue and tetrazolium violet, among others.

The disclosed methods may be automated, in whole or in part. For example, steps (i) and (ii) may be automated, but any subsequent steps, e.g., steps (iii) and (iv), are manual. Alternatively, by way of example, steps (i) and (ii) may be manual, whereas subsequent steps, e.g., steps (iii) and (iv), are automated. Additionally, all steps encompassed by the methods may be automated.

The disclosed methods may be used, alone or in combination with other known methods (such as TNM), for tumor staging. In one aspect, the methods further comprise evaluating one or more of the morphological aspects of the tumor, the extent to which tumor cells have spread to the regional lymph nodes and/or lymphatic system, and whether or not the tumor has metastasized to distant organs based on the genomic, proteomic and/or lipidomic information contained in the representative sample.

The disclosed methods may further comprise employing an algorithm to calculate the percentage of tumor cells with or without a specific biomarker. The relative risk of metastatic (or virulent subclone) progression may be determined based on the percentage of cells within a representative tumor sample and/or representative lymph node sample with specific The disclosed methods may further comprise developing of a personalized dosage regimen based on the biomarker profile, the antigen profile, the mutational profile, the lipid profile, the protein profile, and/or the exosome profile contained in the representative sample. For example, based on the information contained in the representative sample (or such information in comparison to a representative lymph node sample and/or circulating DAN profile), the selection of drugs and/or dosage (amount, length of administration, etc.) of such drugs administered to a patient may be modified to personalize the treatment based upon the patient's individual cancer profile.

The disclosed methods may further comprise comparing the genomic profile of the representative sample to the genomic profile of a representative lymph node sample, and further optionally comparing these profiles to circulating tumor DNA from any distant metastases or a representative metastatic tumor sample.

The present disclosure also encompasses compositions produced by any of the methods in this disclosure.

Analysis of Representative Sample

Additionally, the disclosure contemplates using the results of the foregoing methods (such as the detection of rare genetic and/or epigenetic events, rare cells, etc.) or compositions produced by any of the foregoing methods, which involve homogenization of a tumor sample to prepare a representative sample suitable for further analysis using any number of standard diagnostic assays) in the selection of an appropriate therapeutic regimen for treating a subject. The therapeutic regimen can include any of chemotherapy, immunomodulator administration, radiation, cytokine administration, surgery, or a combination thereof.

Moreover, the disclosed method can be used to select at least one therapeutic agent (such as an antibody, nucleic acid, small molecule, or polypeptide, which antagonizes, inhibits, or blocks the expression or functional activity of at least one detected biomarker) suitable for use in a subject whose tumor was the source for the representative sample generated by the methods provided.

Recent advances in the field of cancer biology have undermined long held beliefs in regard to tumor physiology. Previously, the predominant thought was that all cells within a tumor were similar to one another, regardless of cancer stage. However, with the advent of new technologies, such as single cell sequencing, it is now understood that the cells within a tumor can be highly diverse. See Campbell et al. Subclonal phylogenetic structures in cancer revealed by ultra-deep sequencing. PNAS 2008; 105:13081-13086; and Navin et al. Tumor evolution inferred by single-cell sequencing. Nature. 2011; 472:90-94. The discovery of intra-tumor heterogeneity highlights new complexities that will need to be addressed in clinical oncology, including in cancer diagnostics.

Current pathological methods are based on cutting only a few small regions from a tumor, placing them into paraffin blocks, and cutting small sections from those blocks to be tested for cancer biomarkers. See Westra et al. Surgical Pathology Dissection: An Illustrated Guide. New York: Springer. 2003. This method may be useful in staging cancer, but the reliance upon sampling only a small fraction of the whole tumor makes the diagnostic results unlikely to be representative of the whole. As a result, the current methods: 1) fail to identify important disease characteristics, and 2) oversample a minor disease trait, which often does not determine or influence disease progression and/or outcome.

These problems are amplified as the size of the tumor increases and, as a result, the long term survival rates of cancer patients are often negatively impacted. For example, regardless of cancer stage, as tumor size increases, five year survival averages fall. See Lopez-Encuentra et al. Staging in lung cancer: is 3 cm a prognostic threshold in pathological stage 1 non-small cell lung cancer? A multicenter study of 1,020 patients. Chest. 2002; 121(5):1515-1520; Miller and Grigsby. Measurement of tumor volume by PET to evaluate prognosis in patients with advanced cervical cancer treated by radiation therapy. Int J Radiat Oncol Biol Phys. 2002; 53(2): 353-359; Elkin et al. The effect of changes in tumor size on breast carcinoma survival in the U.S.: 1975-1999. Cancer. 2005; 104(6): 1149-1157; Brookman-May et al. Difference between clinical and pathological renal tumor size, correlation with survival, and implications for patient counseling regarding nephron-sparing surgery. AJR. 2011; 197(5): 1137-1145; and Kornprat et al. Value of tumor size as a prognostic variable in colorectal cancer: a critical reappraisal. Am J Clin Oncol. 2011; 34(1): 43-49).

Accordingly, new technologies are needed to address the issue of tumor heterogeneity in clinical oncology, especially for those patients with large solid tumors. Also, improved methods are needed for identifying patient samples containing abnormal cells before disease manifestation in order to enhance the likelihood of a good therapeutic outcome.

In order to address the issue of tumor heterogeneity, some experts in the field of oncology have suggested testing multiple regions, thereby increasing the amount of tumor being sampled at one time. See, e.g., Alizadeh et al. Toward understanding and exploiting tumor heterogeneity. Nature Medicine. 2015; 21: 846-853. As demonstrated by the probabilistic model above, this technique cannot fully address the problems of tumor heterogeneity. The increase in workload for a pathology lab charged with processing this number of sample per patient makes this proposed method prohibitive.

In order for a sample to be representative, all the different fragments of the starting material must have an equal chance of ending up in the sample and this must be consistent across all samples. See Petersen et al. 2005. However, with current sectioning procedures, a large proportion of the tumor is incinerated after the paraffin blocks have been created. See Westra et al. 2003. Therefore, to date, not only are representative tumor samples not made, but current pathological practices discourage and even prohibit their creation.

In an additional aspect, the use of mechanical methods, e.g., shearing, and/or biochemical methods, e.g., heat and pH conditioning and enzymatic digestion of the extracellular matrix, may be used to create a representative sample from a tumor. The coupling of these approaches results in a representative sample of a tissue sample or samples, e.g., an entire tumor or substantial portion thereof without compromising the ability to use the specimen in traditional tissue based assays, e.g., hematoxylin and eosin staining, immunohistochemical analysis, and nucleic acid isolation. Indeed, each representative sample can be used in multiple different assays simultaneously. Additionally, homogenization of the organ, tissue, or tumor renders it suitable for use in additional diagnostic tests, such as whole genome sequencing, which may be important for future pharmacological and diagnostic discoveries and for personalized medicine. In addition, the homogenate is amenable to automation methods similar to those utilized for diagnostic tests from blood. Therefore, a representative sample can be used for a variety of diagnostic protocols in order to identify rare tumor sub-clones and by extension improve clinical diagnostics and personalized cancer treatment. Also, the resultant representative samples may be used to derive antibodies or antigens useful in the development of therapeutic or prophylactic tumor vaccines.

As exemplified herein, the inventors have demonstrated the ability to create a representative sample from clinical specimens, e.g., human tumor clinical specimens and have further shown that rare phenotypes, which would likely go unrecognized using traditional tumor sectioning, can be detected within the representative sample generated by the methods disclosed herein. Moreover, the inventors have shown that the disclosed methods can be used to generate a representative sample from a variety of different tissue types, fixed or unfixed tissues, and the resulting representative sample can be used for a variety of diagnostic tests including IHC and nucleic acid isolation.

Depending on the mechanical and/or biochemical dissociation process applied to the sample to generate the homogenate, the cell clusters may comprise more than one (1) cell to thousands of cells. The clumps can be dissociated (decreased in size and/or number of cells contained therein) by the application of further methods, e.g., by further mechanical and/or biochemical dissociation and/or by size exclusion, depending on the subsequent assay to be performed using the representative sample (for example, FACS and flow cytometry require single cells).

The method is flexible with regard to the degree of sample dissociation. Thus, it may be possible to control the mechanical process(es) to obtain a target cell aggregate size, e.g., by further processing cell clusters obtained following application of a first mechanical means (such as blending or the equivalent) until the clusters correspond with the dissociation goal of the sampling method (such as single cells). In one aspect, mechanical shearing and size exclusion, e.g., sieving with a series of mesh, are used to remove cell clusters at or below a certain size whilst retaining larger cell clusters to for further processing to reach the goal particle size. In this way, while the size range may look like a normal distribution, the resulting distribution of cell cluster particle size is manipulated by the usage of size exclusion, e.g., sieving size, to remove certain particles from the dissociation process and, thus, reach sizing plateau rather than a distribution.

Figure 17:
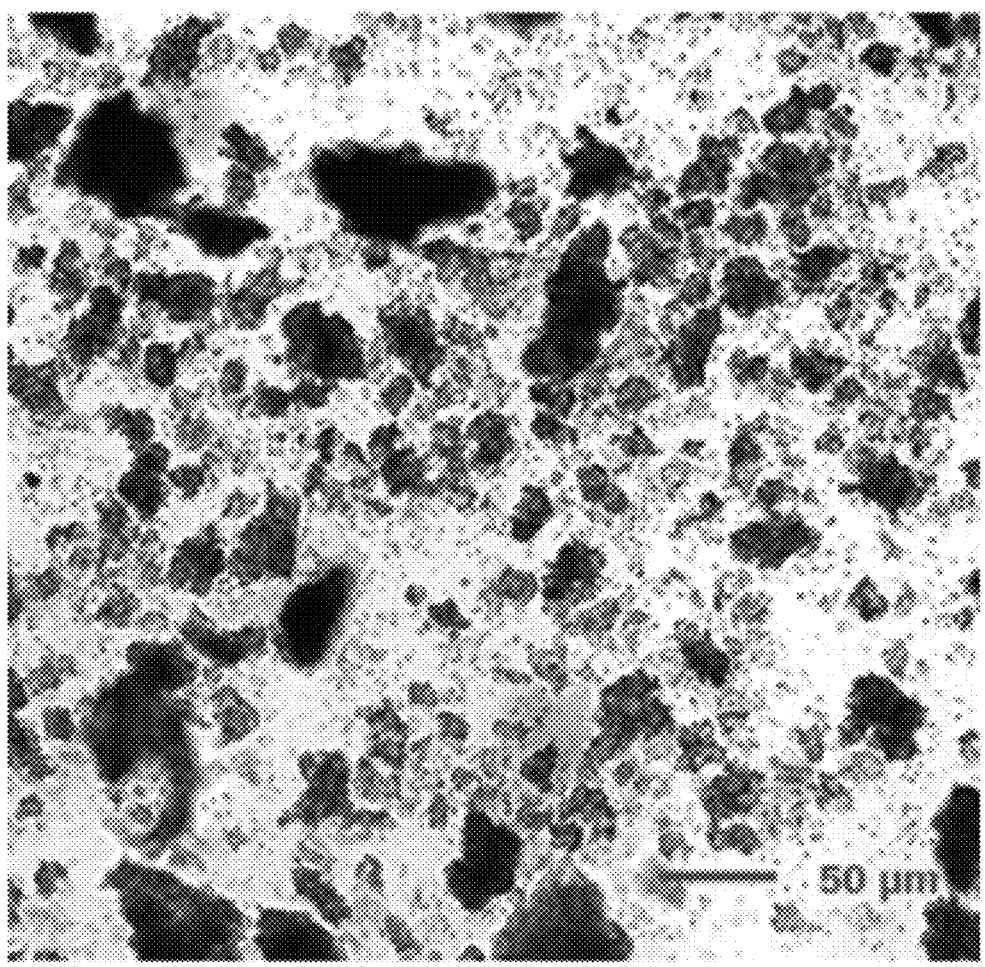
FIG. 17 shows a 5× magnification of homogenized tonsil tissue. Note the scale bar indicating 50 microns in length.

After homogenization, the resultant clusters may contain at least 1-2, 2-100, 100-500, 500-1,000, 1,000-10,000, 10,000-50,000, or more cells. In one aspect, the clusters contain single cells, about 2-10 cells, about 10-20 cells, or about 20-40 cells. The size of the resultant clusters will vary. See, e.g., FIG. 17.

As a result of homogenizing a tumor and/or lymph node sample (or homogenization of a tumor sample), any heterogeneity of cells within the sample, e.g., tumor or lymph node, is substantially homogeneously (uniformly) distributed within the resultant homogenate or a portion or fraction thereof, such that the homogenate (or any fraction thereof) substantially homogeneously expresses the heterogeneity of the tumor biopsy sample which was the input. By homogenizing tumors to generate a sample (or homogenate) that is representative of the tumor in its entirety, it is possible to characterize the phenotypic diversity (such as the percentage of cells with a specific gene mutation) of the tumor. A homogenized sample may be referred to as a liquid or liquefied sample based on its ability to flow or be poured, notwithstanding that many or most of the cells remain intact. In some instances, the representative sample may be a liquid sample (such as a cytology needle aspirate, effusion sample, or pap smear).

As mentioned, other moieties may be added to these homogenates or representative samples such as other cells, haptens or labels.

Sequencing the Representative Samples

With the ultimate goal of personalized medicine, oncologists rely on diagnosticians to detect key mutations from tumors so that they can link targeted therapies to specific changes within the tumor. Capturing sequence information via Next Generation Sequencing (NGS) from solid tumors is a critical component of the clinical oncology workflow, as tumor cells may invariably become resistant to therapy over time. One of the most significant obstacles inherent to all current clinical NGS workflows is that clinicians cannot detect the mutations that are driving tumor growth in all parts of the tumor, nor can clinicians detect mutations that confer pre-existing therapy resistance. Moreover, while some of the mutations may be in high prevalence within the tumor, other mutations (including driver mutations and resistance mutations) may be present in only a small fraction of the tumor. Typically, the root of this problem is the fact that clinicians utilize formalin fixed, paraffin embedded (FFPE) tissue sections from samples taken from the primary tumor. While the sampling issue can be thoroughly solved through the process of representative sampling, there are still some significant issues that must be resolved in clinical NGS workflows to fully realize personalized medicine.

Today, the NGS in the clinic can only be utilized to detect a targetable mutation (i.e. mutation linked to a targeted therapy) that is present within the majority of the tumor. Clinicians and researchers have focused on targetable mutations primarily due to the volume of data that is produced by NGS technologies. For instance, in a whole exome analysis of a tissue sample tens of thousands of genes will be examined, each gene being sequenced in tens to hundreds of small segments. Rather than use all of the data to make clinical decisions, many groups blind the vast majority of the data and report only the mutations that are known to be linked to a therapy.

The unmet technical and clinical need, however, is to detect all of the mutations present in a solid tumor whether they are "targetable" or not. Moreover, it is imperative for clinicians to determine the percentage of the tumor cells that contain a specific mutation. Only with data that captures the genomic diversity of the vast majority of the tumor can clinicians understand how to treat a patient with multiple "targetable, or druggable" mutations. For instance, if a solid tumor contains a mutation in the EGFR gene at 55% prevalence, a bRaf mutation at 20% prevalence, and a KIT mutation at 5% prevalence a clinician would want to target the bulk of the tumor with an EGFR inhibitor (e.g. Cetuximab, Panitumumab) until a clinical response is seen via imaging, or for a specified amount of time. The EGFR inhibitor would then be stopped, and the next most prevalent target of therapy would be administered, in this case a bRaf inhibitor (e.g. Vemurafenib). At this point the clinician may, or may not see a clinical response via imaging. The bRaf inhibitor would be stopped, and the least frequent target of therapy would be given, namely a KIT inhibitor (e.g. imatinib, Sunitinib). This three drug regimen can then be repeated. If the drugs can be tolerated together, then combination therapy would be another possibility. Alternatively, the drugs can be administered in reverse order; KIT inhibitor, bRaf inhibitor, followed by a EGFR inhibitor.

The critical component of this drug schedule is not the NGS technology or the inhibitors, but rather the determination of both the presence of all of the potential targets and their relative prevalence within the tumor using Representative Sampling techniques. In the above example, both the KIT mutation and the bRaf mutation would have been missed because they are present at a low prevalence. Had the area of the tumor that contained a high percentage of the bRaf mutant cells sampled, it would have appeared as if the bRaf mutation was driving the majority of the tumor and a bRaf inhibitor would have been given as a single agent. Targeting only one of the three mutations in the above example would have led to therapy resistance as the tumor cells that contained the other two mutations would not have responded to the single agent.

Other uses of NGS data from primary tumors attempt to determine whether the tumor cells can be targeted by the immune system, i.e. the use of immunotherapy. This includes the prediction of neo-antigens that may be targeted by the immune system. Exome sequencing of tumors can detect mutations that are predicted to result in changes to the expressed protein.

A critical factor in determining the prevalence of a mutation within a solid tumor is enriching/purifying the tumor cells away from the mixed population of tumor and normal cells. One technique that can be used to capture a high percentage of tumor cells is fluorescence activated cell sorting (FACS). Applying this technique to Representative Samples, the homogenized solid tumor must first be disassociated into single cells, or small multicellular tissue fragments. Single cells may be sorted based on cell and nuclear size, in addition to a fluorescent detection of a tumor marker. Negative selection of the normal cells away from the tumor cells will also result in a sample that is predominantly composed of tumor cells. Multicellular tissue fragment sorting (MTFS) can be enriched via fluorescent detection of a tumor marker, or in the case of negative selection a normal marker. Not only does this technique make interpretation of the NGS data easier, but it enables the detection of extremely low prevalence mutations in the tumor.

Additionally, FACS or MTFS can be used to discriminate multiple distinct populations of cells from tumors, each of which can be treated as a unique sample and analyzed independent of each other. Examples of this would be the differentiation of tumor cells, normal epithelial cells, endothelial cells, and immune cells.

Yet another application of NGS from a representative sample is the detection of neo-antigens that might be detectable by the immune system. To effectively utilize neo-antigens in an anti-tumor therapeutic regimen, clinicians must detect all potential antigenic mutations from the tumor. Similar to targeted therapy, it is critical to detect the majority of the neo-antigens for chimeric antigen receptor therapy (CAR-T).

Further, flow cytometry is an important component of a diagnostic workflow where clinicians may use the data from flow cytometry to determine the composition of the representative sample, relative to the percentage of the sample that is tumor, normal, diploid tumor, or various populations of tumor cells that are positive for a specific biomarker. An example of this workflow would be calculating the minimum number of cells needed to statistically power an IHC assay that requires 1,000 positive cells, by calculating the percentage of tumor in a representative sample.

Homogenization of Tumors or Portions Thereof

The present disclosure is directed to methods for homogenizing a tumor or other tissue sample, e.g., precancerous or putative normal tissues, which optionally may be preserved or fixed before or after homogenization, e.g., with formalin, paraffin and/or ethanol, to generate a "representative sample" that is an unbiased indication of the entirety of the tissue, e.g., a tumor, a lymph node, metastases, polyp, cyst, biopsy, whole organ, or combination of any of the foregoing. Again these methods may preserve the integrity and/or viability of the cells within the sample. Such representative samples may comprise majority clones (having a greater than 50% prevalence), primary sub-clones (having about a 20% to about a 50% prevalence), secondary subclones (having about a 10% to about a 20% prevalence), and minor subclones (having less than a 10% prevalence, preferably less than a 5% prevalence, more preferably less than a 1% prevalence, and most preferably less than a 0.1% prevalence). As discussed above, the representative samples facilitate the detection of low prevalence events, i.e., down to or below a 0.000001% occurrence. The representative samples because they reflect the entirety of the tissue sample, e.g., a solid tumor or lymph node, permit the detection of mutations in proportion to their occurrence in the tissue, generally a tumor or a lymph node/lymphatic tissue, which cannot reliably be done using current methods (such as FFPE slide staining).

The concept of homogenizing clinical specimens, e.g., human tumors, is counter to the historic sampling methods of pathology and oncology. There is no historical precedence for homogenizing whole human tumors, or even large portions of human tumors. Indeed, once the samples for TNM staging are taken the remaining tumor material is destroyed (since it is accepted that all medically relevant information is within the sections collected from TNM staging).

However, the inventors have identified that, rather than destroying residual tumor material, if all (or substantially all) of the available tumor is preserved and homogenized as a single sample, information from small subpopulations of cancer cells can be detected and analyzed.

In many cases, a sample (such as a tumor, lymph node, or metastases) is submitted entirely, either a single block or as multiple blocks depending on the size of the mass. For example, many breast tumors less than 2 cm in diameter are submitted entirely as are the majority of melanomas. Of the roughly 935,000 estimated cases of cancer in 2015, it is estimated that at least one-third of the tumor samples are amenable to homogenization. Tumors especially amenable to homogenization include colon tumors and kidney tumors.

The liquid nature of the homogenized tumor enables statistical analysis of the cellular population of the tumor. For instance, power analysis suggests that the probability of detecting a subclone at low prevalence increase with the analysis of an increased percentage of the sample. For example, a sample size of about 95 cells permits detection of a subclone with about 20% prevalence, a sample size of about 200 cells permits detection of a subclone with about 0.1% prevalence, a sample size of about 2,000 cells permits detection of a subclone with about 0.01% prevalence, and a sample size of about 20,000 cells permits detection of a subclone with about 0.001% prevalence. It is reasonable to anticipate that a tumor sample from the clinic comprises at least about 100-200; 200-1,000; 1,000-5,000; 10,000-100,000; 100,000-1,000,000; 1,000,000-5,000,000; 5,000,000-1,000,000,000; 1,000,000,000-5,000,000,0000, or more cells (i.e. trillions of cells), likely from spatially distinct regions of the tumor, and the representative samples generated from these tumors will have sufficient cell counts to permit adequate detection of subclones. Therefore, powering each diagnostic assay with a sufficient number of cells from the representative tumor samples obtained according to the disclosed methods, enables the detection of rare subclones within a tumor and, thus, facilitates the unbiased determination of the mutational landscape of cancers.

The disclosed methods for preparing representative sample do not require cell lysis, and in some embodiments maintain cell structure. As a result, the representative samples generated according to the disclosed methods wherein the integrity of the cells is maintained may be used in, e.g., ICC, IHC and flow cytometry. Alternatively, or in addition, the sample or representative sample or portions thereof optionally can be treated to disrupt (lyse) the cells and, thus, permit analysis of cellular components using, e.g., PCR, next-generation sequencing (NGS), and mass spectrometry.

The initial step in whole tumor sampling or identifying rare cell types in putative normal or precancerous tissues is acquiring sufficient amount of the tissue, e.g., tumor tissue. Generally, the more tumor tissue available for homogenization, the higher the probability of detecting rare tumor subpopulations. Realistically, the total amount of tumor material available for creating a representative sample will be less than 100% (as a result of the samples for the TNM staging system having already been removed from the tumor). Looking ahead, however, i.e., once the present methods become the standard of care, entire tumors (or at least more of the residual tumor) will be made available for homogenization in the clinic. The current practice is to fix the entire surgical resection in formalin prior to the gross inspection and sampling by the surgical pathologist; both fixed and un-fixed tissue is amenable to representative sampling. However, it is envisioned that formalin fixation may be eliminated or phased out, e.g., once the present methods become the standard of care. Although, it is also possible to use the existing TNM staging methods in combination with the representative sampling methods disclosed herein.

Once the tumor or other tissue has been acquired, as much tumor or other tissue as possible is placed into a blender (or other suitable device) and homogenized, generally as a result of mechanical shearing (although chemical and/or biochemical, e.g., enzymatic, dissociation may also contribute to the homogenization).

Homogenization by purely mechanical means, e.g., blending, produces a range of tissue fragments from thousands to hundreds of cells each, likely fitting to a normal distribution. However, the application of other homogenization methods alone or in combination with mechanical means, e.g., biochemical/chemical dissociation methods alone or in combination with mechanical means, may distort the distribution of tissue fragments from a normal distribution.

Additionally, a combination of mechanical means used in parallel or series that dissociate and homogenize the sample, e.g., a tumor or lymph node, into tissue fragments (such as single cells and cell clusters), can be used to generate a biomarker sample during or after the cellular sample being created. For example, a representative sample comprising intact cells may be generated by blending the sample, as discussed above, and the resulting "cell sample" may be used to analyze the intact cells; however, the cell sample may be further processed by another mechanical means, e.g., sonication, to produce a biomarker sample, i.e., disruption (lysis) of the intact cells permits analysis of the protein and/or DNA biomarkers in the sample.

The median of the tissue fragment size is inversely correlated to the energy of the blender (or other suitable device), such that at high energy the tissue fragments are very small. The component of the tissue that is most relevant to blender energy is collagen content, as the dermis requires significant energy for complete disassociation. The time of blending is also important; however, the most effective clinical application requires that the whole tumor be disassociated in a matter of minutes. Once the time of blending is fixed, the energy required to reach tumor disassociation under the desired time limit can readily be determined.

Following sufficient mechanical shearing (via blending or other suitable force) to disassociate the whole tumor, all of the subpopulations of tumor cells that were originally spatially segregated are distributed throughout the newly liquefied tumor sample. Test samples can be taken from the homogenized sample and tumor subpopulations (including rare or low prevalence or minor subpopulations) can be detected using different testing modalities.

For example, aliquots of the liquefied whole tumor sample can be taken, lysed to release the cellular components, and the nucleic acids purified for analysis by PCR or NGS. For example, cells may be lysed using a microfluidizer and/or by grinding, milling, chemical or enzymatic lysis and/or other techniques known in the art. Alternatively, or in addition, the protein components of the tumor cells can be purified for proteomic analysis methods such as mass spectrometry (MS). Moreover, the tissue fragments can be embedded in paraffin wax and sampled using the current pathology workflow. For long-term storage, the representative samples comprising the liquefied tumor can be stored in a suitable buffer and refrigerated or frozen or embedded in wax (such as paraffin) for storage.

Generally, assays such as those mentions above (such as PCR, NGS, MS, IHC, ICC, etc.) that can effectively utilize the initially-blended whole tumor sample (which contains clusters of cells) can be performed after the application of mechanical force (via a blender or sonicator or other suitable device to induce shearing) and without biochemical (enzymatic) processing. However, assays that require smaller groups of cells (such as 2-20 cells or even single cells) can also be used to analyze the representative sample, but additional processing of the sample is required to remove the protein-protein crosslinks induced during the formalin fixation of the surgically removed tissue. In particular, enzymatic digestion of blended tumor tissue is required to create a representative sample that consists of single cells and small cell clusters suitable for use in certain assays, e.g., cell sorting.

As discussed above, homogenization may be performed using only mechanical means (such as blending used alone or in series or parallel with other mechanical means), only biochemical/chemical means (such as enzymatic digestion), or a combination thereof. Combining both physical and biochemical (enzymatic) disruption of the tissue fragments can produce a sample that is suitable for a diagnostic assay requiring intact cells. The first physical method that initiates the breakdown of the protein crosslinks is incubating the tissue fragments in a low pH buffer at about 80 to about 85 degrees Celsius. The incubation step begins to non-specifically "open up" the tissue fragments, preparing them for the next steps in the process, which is the biochemical cleavage of cell-extracellular matrix connections holding the tissue fragments together. Incubation with an enzyme such as non-protein specific proteases, e.g., pepsin, trypsin, proteinase K, furin, endoproteinases (such as Asp-N and Glu-C, available from NEB, Sigma-Aldrich, Thermo Fisher, Promega, and the like), enterokinase, and subtilisins; protein specific proteases, e.g., collagenases (such as Collagenase types I-S, I-A, IA-S, II, II-S, IV, IV-S, VIII, V, V-S, XI, XI-S, III, VII, VII-S, S, F, H, and L (available from NEB, Sigma-Aldrich, Thermo Fisher, Promega, and the like), gelatinases, stromelysins, matrilysin, enamelysin, and admats (such as proteoglycan-degrading enzymes); and/or non-mammalian/non-bacterial enzyme replacements, e.g., fungal enzymes, e.g., Accutase® and Accumax® (Innovative Cell Technologies, San Diego, CA) or a combination of any of the foregoing, under suitable conditions may be effected in order to cleave these connections. Exemplary enzymes include, but are not limited to, Interstitial collagenase, Gelatinase-A, Stromelysin 1, Matrilysin, Neutrophil collagenase, Gelatinase-B, Stromelysin 2, Stromelysin 3, Macrophage metalloelastase, Collagenase 3, MT1-MMP, MT2-MMP, MT3-MMP, MT4-MMP, Collagenase 4, Enamelysin, X-MMP, CA-MMP, MT5-MMP, MT6-MMP, Matrilysin-2, MMP-22, endoproteinase, trypsin, chymotrypsin, endoproteinase Asp-N, endoproteinase Arg-C, endoproteinase Glu-C (V8 protease), endoproteinase Lys-C, pepsin, thermolysin, elastase, papain, proteinase K, subtilisin, clostripain, exopeptidase, carboxypeptidase A, carboxypeptidase B, carboxypeptidase P, carboxypeptidase Y, cathepsin C, acylamino-acid-releasing enzyme, pyroglutamate aminopeptidase under suitable conditions may be effected in order to cleave these connections. The enzymes may be used alone or in combination, e.g., a collagenase (such as Collagenase H) and another enzyme (such as AccuMax®), multiple collagenases, multiple other enzymes, etc.

Alternatively or in addition, the tissue fragments are sheared by applying mechanical force (such as a mortar and pestle, a grinding instrument similar to a meat grinder used in sausage production, or sonication), both before, and alternatively or in addition to, following biochemical digestion of the representative sample.

Figure 23:
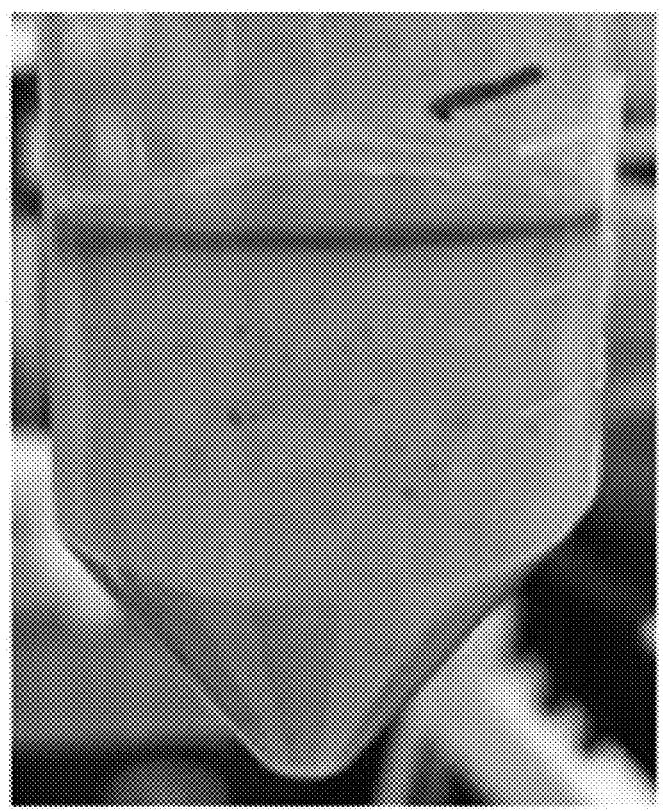
FIG. 23 is an image of tumor-educated platelets and other blood cells isolated from a biochemically digested representative sample by centrifugation. A human ovarian serous carcinoma tumor was blended and digested with Accumax® and Collagenase H followed by centrifugation resulting in the accumulation of platelets and red blood cells at the top of the centrifuged sample (red line).

Likewise, the biochemically-digested representative sample may be further processed by effecting centrifugation, which can be used to isolate certain cells or other material from the sample for additional analysis. For example, centrifugation of a representative sample prepared from a human ovarian serous carcinoma tumor that was blended and digested with AccuMax® and Collagenase H results in the isolation of tumor-educated platelets and other blood cells (FIG. 23). FIG. 23 is an image of tumor-educated platelets and other blood cells isolated from a biochemically digested representative sample by centrifugation. A human ovarian serous carcinoma tumor was blended and digested with Accumax® and Collagenase H followed by centrifugation resulting in the accumulation of platelets and red blood cells at the top of the centrifuged sample (red line).

The inventors show herein that coupling of cell conditioning using pH and heat with enzymatic digestion provides for an efficient dissociated representative sample creation. The process of improving accessibility of the stain (biological or chemical) to the molecular target is referred to herein as "cell conditioning." For example, cell conditioning in CC1 buffer or CC2 buffer (Ventana®) at high heat (70-100 degrees Celsius) aids in the enzymatic digestion of tumor tissue. Many alternatives to citrate buffer may be employed as cell conditioning solution.

One effective measure of the size of the tissue fragments following the additional processing comprises assessing how well the liquid sample passes through a mesh or filter (or a series of such meshes or filters) with a known pore size, e.g., less than 1 micron (e.g., about 0.5 microns), about 1-6 microns, about 6-10 microns, about 10-20 microns, about 20-30 microns, about 30-40 microns, about 40-100 microns, about 100-300 microns, about 300-500 microns, or greater than 500 microns. In one aspect, a series of filters ranging in size from about 1 micron to about 500 microns is used to separate cells within the homogenate. It is also possible to use a filter with a smaller pore size, e.g., less than 1 micron, e.g., about 0.45 um, to separate the subcellular portion of a biomarker sample from the cellular portion the sample after creating a representative cellular fraction. Therefore, size exclusion methods, e.g., sieving, following mechanical dissociation methods (such as blending or the equivalent) may be used as a quick method to separate a biomarker sample from a cellular sample.

Analysis of the Representative Sample or the Homogenate Composition

The representative samples, e.g., tumor samples generated by the disclosed methods provide several advantages over traditional tumor samples used in pathology and diagnosis, including (i) the ability to use the representative sample for several different diagnostic assays, some of which may be incompatible with solid tissue; (ii) the enhanced ability to detect low prevalence sub-clones, i.e., creation of a representative sample of a whole tumor removes under-sampling biases that inhibit low prevalence sub-clone discovery; and (iii) the elimination of sample proliferation within the diagnostic oncology lab, thereby creating a more efficient laboratory workflow, i.e., current practice dictates that as many as 3-10 blocks are made per tumor, although only 1 block is tested.

Therefore, the disclosure also relates to methods of analysis of the representative sample or the homogenate composition. In one aspect, the analysis comprises, or alternatively consists essentially of, or yet further consists of a nucleic acid analysis, a protein analysis, a lipid analysis, a cell analysis, a metabolite analysis, a genomic analysis, a transcriptomic analysis, a proteomic analysis, a metabolomic analysis, a lipidomic analysis, an immunological analysis, a cytochemical analysis, a genotypic analysis, a phenotypic analysis, or combination thereof. In one aspect, the nucleic acid analysis comprises, or alternatively consists essentially of, or yet further consists of a DNA analysis or a RNA analysis. In another aspect, the RNA analysis comprises, or alternatively consists essentially of, or yet further consists of a microRNA analysis. In a different aspect, the analysis of the homogenate comprises, or alternatively consists essentially of, or yet further consists of purifying a nucleic acid, a protein, an organelle, a metabolite, a chemical, a non-cellular component, or combination thereof.

In another embodiment, the analysis of the homogenate comprises, or alternatively consists essentially of, or yet further consists of binding a binding agent with a component of the homogenate. In some aspect, the binding agent comprises, or alternatively consists essentially of, or yet further consists of an antibody, a radioactive label, a fluorochrome, a hapten, an enzyme, a nucleic acid, a protein, a chemical, a primer, a ligand, a cell, a peptide, a probe, a fluorescent dye, a non-fluorescent dye, an enzyme, a biotin, or combination thereof. In one embodiment, the component of the homogenate comprises, or alternatively consists essentially of, or yet further consists of a nucleic acid, a protein, an organelle, a metabolite, a chemical, a non-cellular component, or combination thereof.

In one embodiment, the analysis of the homogenate further comprises, or alternatively consists essentially of, or yet further consists of detecting a signal from the binding agent or the component. In one aspect, the signal comprises, or alternatively consists essentially of, or yet further consists of a radioactive signal or a non-radioactive signal. In another aspect, the non-radioactive signal comprises, or alternatively consists essentially of, or yet further consists of a fluorescent signal, a chemifluorescent signal, or a luminescent signal. In a further aspect, the analysis of homogenate comprises, or alternatively consists essentially of, or yet further consists of sequencing analysis, histology analysis, or image analysis. In one aspect, the sequencing analysis comprises, or alternatively consists essentially of, or yet further consists of next-generation sequencing analysis, single-cell sequencing analysis, and/or single-nucleus sequencing. In another aspect, the histology analysis comprises, or alternatively consists essentially of, or yet further consists of next-generation histology analysis. In one aspect, the image analysis comprises, or alternatively consists essentially of, or yet further consists of next-generation analysis.

In one embodiment, the method for preparing a tissue sample further comprises, or alternatively consists essentially of, or yet further consists of detecting or quantifying a component of the homogenate, wherein the component comprises a cell, a nucleic acid, a protein, an organelle, a metabolite, a chemical, a non-cellular component, or combination thereof. In one aspect, the cell comprises, or alternatively consists essentially of, or yet further consists of an immune cell, a tumor cell, a stem cell, a progenitor cell, a blood cell, a germ cell, and a somatic cell. In another aspect, the analysis of the homogenate comprises, or alternatively consists essentially of, or yet further consists of analysis of the polarized light reflected from the homogenate. In one aspect, the analysis of the homogenate comprises, or alternatively consists essentially of, or yet further consists of analysis of an acoustic property, a mechanical property, or optical property of the homogenate. In a further aspect, the homogenate is analyzed with flow cytometry, hematoxylin and eosin staining, or immunohistochemistry.

In one embodiment, when the cells from the whole tumor have been disassociated to the desired degree, the representative sample can be deposited onto a glass slide in preparation for staining, e.g., ISH or ICC or IHC.

There are multiple ways to deposit cells onto glass slides, all of which involve drying cells onto slides. Buffers that enable the deposition of cells onto glass slides range from organic solvents (such as ethanol, methanol, limonene, formalin, and acetone), non-aqueous solvents (propylene glycol, polyethylene glycol, glycerol, vegetable oils such as olive oil, and injectable organic esters such as ethyl oleate), inorganic nonaqueous solvents (such as liquid ammonia, liquid sulfur dioxide, sulfuryl chloride and sulfuryl chloride fluoride, phosphoryl chloride, dinitrogen tetroxide, antimony trichloride, bromine pentafluoride, hydrogen fluoride, pure sulfuric acid and other inorganic acids), common buffers (such as PBS, HEPES, IVIES, PIPES, citric acid, TAPS, Bicine, Tris, Tricine, TAPSO, TES, MOPS, PIPES, CHES, cacodylate, carbonic acid, bicarbonate, or TE), to water. For example, cells may be diluted into methanol, which promotes uniform spreading over a glass slide and evaporates rapidly.

Additionally, other high volatility solvents (such as acetonitrile, Octanol, Chlorobutane, or other HPLC solvents) and refrigerant liquids (such as carbon tetrachloride, Trichlorofluoromethane, Dibromodifluoromethane, and others that have near room temperature boiling points (e.g., 25° C.)) may be used to obtain cellular-based representative cells on glass slides without the solvent effects of alcohols.

Typical H&E staining, ISH, In-Situ PCR, Immunohistochemical (IHC), Histochemical (HC), or Enzyme-histochemical (EHC) methods may be carried out using standard methods and, preferably, the methods set forth herein (see FIG. 10, FIG. 11 and FIG. 14). Applicable formats for the detection reaction according to the present disclosure may be, blotting techniques, such as Western-Blot, Southern-blot, Northern-blot, immuno-cytochemical or immuno-histochemical procedures. The blotting techniques are known to those of ordinary skill in the art and may be performed for example as electro-blots, semidry-blots, vacuum-blots or dot-blots. Immuno-cytochemical/histochemical staining procedures are known to those of skill in the art and may comprise binding agent mediated detection of polypeptides as well as in situ hybridization techniques. Both different techniques may even be applied simultaneously. In certain embodiment hybrid capture of nucleic acids may be used for the detection. Amplification reaction may also be applicable for the detection of e.g. nucleic acid molecules.

In-situ hybridization (ISH) is a technique that may be advantageously employed with the present disclosure, either alone or in combination with other techniques, since many of the steps in ISH must be carefully temperature controlled for a precise period of time. The precise amount of heat for a specific period of time is necessary to sufficiently denature the DNA so that subsequent hybridization may occur without over-heating to the point where cell morphology is degraded. Different specimens may be denatured using different temperatures depending on how the tissue was prepared and fixed. The steps of denaturation, hybridization, and post-hybridization washes may be effected at different temperatures that may depend on the particulars of the probe and tissue being tested. These temperatures can be controlled through the individualized control of the heaters, as discussed previously. DNA probes are typically hybridized at between 30 degrees-55 degrees Celsius, while RNA probes are typically hybridized at higher temperatures with the time for hybridization varying from 30 min. to 24 hours depending on target copy number, probe size and specimen type. Standard denaturation for cytogenetic preparations is performed at about 72 degrees Celsius for 2 min., while for tissue sections the conditions may vary from 55 degrees Celsius to 95 degrees Celsius from 2 to 30 min. Post-hybridization wash temperatures may vary from about 37 degrees Celsius to 72 degrees Celsius for 2 min. to 15 min. Salt concentration may vary from 0.1× to 2×SSC. Probe detection temperatures may vary from ambient to 42 degrees Celsius for 2 min. to 30 min.

ISH may be employed to detect DNA, cDNA, and high copy mRNA. It can be applied to smears, tissue, cell lines, and frozen sections and, in the context of the present disclosure, the representative samples generated according to the disclosed methods as well as compositions comprising the representative methods. Typically, the specimen is mounted on a 1"×3" glass slide.

Figure 16:
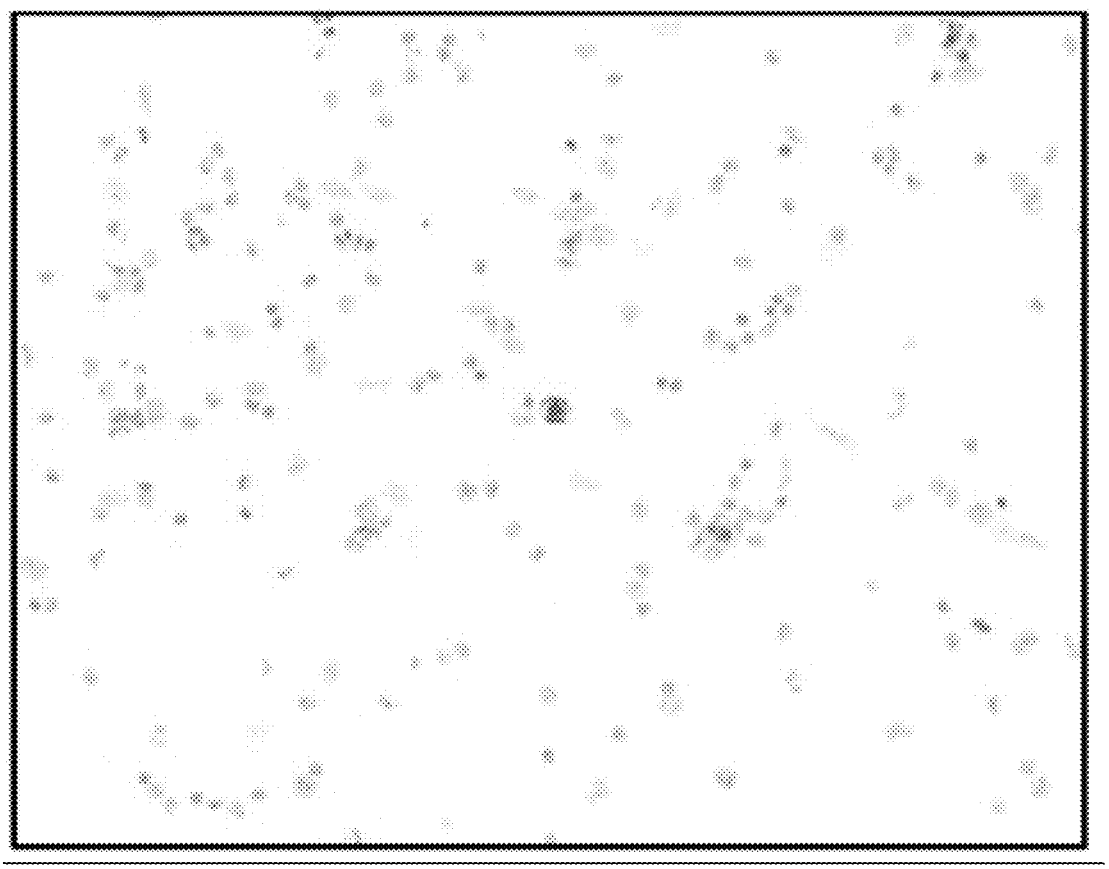
FIG. 16 shows the detection of b-Raf-positive cells, present at a prevalence of about 0.015% in a representative tonsil sample.

One advantage of IHC-based detection of biomarkers is the sensitivity of DAB detection. With this method, one can detect very rare events in a mixed population of cells. For example, the inventors have shown that a minor subclone that is a spatially distinct component of the whole sample (i.e., a Her-2 positive cell present at slightly more than 0.1% of the total tissue volume) was clearly visible in a representative sample generated according to the disclosed methods upon imaging at 20× magnification. See Example 1 and FIGS. 6A-6D. Moreover, the inventors have shown that a minor subclone (a bRaf mutant expressing xenograft tumor present in a bulk sample of disassociated tonsil tissue at a level of 0.015% of the total sample) was also clearly detected. See Example 4 and FIG. 16.

In addition to DAB-based IHC staining, all of the standard slide-based assays are suitable for use with homogenized tumor sample. For example, the inventors have shown that multiplexed IHC (using three antibodies detected in a single staining run), RNA-based ISH and DNA ISH can be used to analyze the representative samples generated according to the disclosed methods. See Example 3 and FIGS. 11 and 12.

The detection procedures according to the present disclosure may furthermore comprise a cytochemical staining procedure rendering a chromogenic or fluorescent staining of cells or cell compartments. Such staining procedures are known to those of skill in the art and may for example comprise e.g. staining for acidophilic or basophilic structures, of subcellular regions (e.g. the nucleus, the mitochondria, the golgi, the cytoplasm etc.), of specific molecules (of chromosomes, of lipids, of glycoproteins, of polysaccharids etc.) in the cytological specimens. Fluorescence dyes such as DAPI, Quinacrin, Chromomycin, etc. may be employed. Furthermore chromogenic dyes such as Azan, Acridin-orange, Hematoxylin, Eosin, Sudan-red, Thiazin-stains (Toluidin-blue, Thionin) may be applied. In other embodiments staining procedures such as Pap-staining, Giemsa-staining, Hematoxylin-Eosin staining, van-Gieson staining, Schiff-staining (using Schiff reagent), staining procedures employing precipitation of metals (such as e.g. of silver in staining procedures employing Silver Nitrate) or insoluble stains such as e.g. of Turnbulls-blue (or other insoluble metal cyanides), etc. may be used in the course of a method as disclosed herein. It must be understood, that the named dyes and staining methods shall be examples for the applicable methods and that any other method known in the art may be applied to a method as disclosed herein.

The staining procedures may produce chromogenic stains for light microscopic inspection or fluorescent stains for inspection under fluorescence microscopic conditions. In another embodiment of the present disclosure radiation emitting procedures, procedures employing substances impairing the transmission of radiation or other contrast media for imaging of the cytological conditions in a sample (e.g. the generation of optical impression by means such as (micro) autoradiographic or (micro-)radiographic picture generation) may be of use for a method according to the present disclosure.

All the staining and imaging procedures may be used for analysis not only in microscopic procedures but also in automated analysis procedures such flow cytometry, automated microscopic (computerized or computer aided, such as a whole slide scanner) analysis or any other method for analysis of stained cytological specimens. "Automated" or "Automatic" means activity substantially computer or machine driven and substantially free of human intervention.

Additional diagnostic methods may be applied to the representative samples and compositions comprising the representative sample, including, but not limited to, ELISA-based detection of proteins, affinity purification of specific cell types, etc. In order to further illustrate the numerous diagnostic and therapeutic applications of the present disclosure, the disclosure provide below an additional overview of various techniques that may be effected with the inventive representative samples and subsamples or components isolated therefrom, e.g., cells, nucleic acids, proteins, lipids et al.

Multiplexing and Batching Approaches Using the Representative Samples or the Homogenate Composition In one aspect, a representative sample prepared from a single sample obtained from a single patient may be used for subsequent diagnostic analysis using any of the methods disclosed herein and/or other comparable methods known in the art. The sample obtained from the patient may be labeled with a small molecule prior to homogenization and optional further processing, e.g., sieving. By introducing a small molecule label into the sample, the sample is now capable of being distinguished from other samples (including other tissue and/or tumor samples from the same patient as well as tissue and/or tumor samples obtained from different patients and, thus, using this labelling approach, different representative samples can be used in a multiplex assay format.

For example, a first tumor, a second tumor, and a third tumor may be obtained from a first patent. The first tumor may be labeled with a first small molecule, the second tumor labeled with a second small molecule, and the third tumor labeled with a third small molecule, such that each small molecule is distinguishable from the others. The labelled first tumor, second tumor, and third tumor can then be homogenized, alone or in combination, and the resulting "mixed" homogenate contains a representative sample of each tumor. The same "batching" approach may be used to perform a multiplex assay using multiple lymph node samples from the same patient and/or a combination of tumor and lymph node samples from the same patient.

In another aspect, a sample, e.g., tumor or lymph node, obtained from a patient is sectioned and each section is addressed with a small molecule prior to combining and collectively homogenizing the sections to generate a representative sample with spatial information. For example, a sample (such a tumor or lymph node) may be cut into quadrants and a different hapten (or other suitable small molecule) may be "doped" into each quadrant prior to collectively homogenizing the sections, e.g., each labeled section is placed into a blender and homogenized, to generate a representative sample with spatial information. It should be understood that the number of sections that can be generated from each sample for "doping" prior to homogenization is not limited but, rather, likely selected in scale with the size of the sample, i.e., the larger the sample, the greater the number of sections that can be "tagged" with a small molecule prior to homogenization. For example, a tumor and/or lymph node sample may be sectioned to form 2 sections, 3 sections, 4 sections, 5 sections, 6 sections, 7 sections, 8 sections, 10 sections, 15 sections, 20 sections, 25 sections, 30 sections, 35 sections, 40 sections, 45 sections, 50 sections, 55 sections, 60 sections, 65 sections, 70 sections, 75 sections, 80 sections, 85 sections, 90 sections, 95 sections, 100 sections, or more. Again, the number of sections prepared from each sample will vary with sample size. For example, a roughly 2 cm tumor sample may be sectioned into quadrants, each of which is labeled with a different small molecule, whereas a 50 cm tumor (such as a gastric tumor) may be sectioned into 100 sections, each of which is labelled with a different small molecule.

It should be noted that any number of different samples from the same patient or from different patients can be combined and multiplexed, permitted that each sample is addressed with a different label, e.g., at least 2 labels, at least 3 labels, at least 4 labels, at least 5 labels, at least 6 labels, at least 7 labels, at least 8 labels, at least 10 labels, at least 15 labels, at least 20 labels, at least 25 labels, at least 50 labels, at least 75 labels, at least 100 labels, etc.

Samples, such as tumor sample provided from whole tumors derived from either a single or multiple subjects, or sectioning of tumors derived from either a single or multiple subjects, may be conjugated to small molecule(s) (such as but not limited to haptens, peptide tags, protein tags, fluorescent tags, or nucleic acid tags, for example) in order to identify the origin of the tumor sample under investigation.

Conjugation may occur through use of various mechanisms, as detailed in Lemus and Karol (Methods Mol Med. 2008; 138:167-82) (which is hereby incorporated by reference in its entirety). Such conjugation methods can include but are not limited to spontaneous chemical reactions involving haptens characterized as isocyanates or anhydrides, activated chemical reactions involving haptens that bear a carboxyl group, crosslinking reactions involving haptens and carbodiimides or haptens and glutaraldehyde. Additional means of conjugation can occur through the use of diisocyanate and either of the following reactive groups: $\alpha$-NH$_2$, $\epsilon$-NH$_2$Lys, $\alpha$-COOH, SH-Cys; acid anhydride and either of the following reactive groups: $\alpha$-NH$_2$, $\epsilon$-NH$_2$Lys, $\alpha$-COOH, SH-Cys; 2,4,6 trinitrobenzene sulfonic acid (TNBS) and either of the following reactive groups: $\alpha$-NH$_2$ and $\epsilon$-NH$_2$Lys; an aromatic amino acid and tyrosine (wherein the aromatic amino acid is converted to a diazonium group); a carbohydrate and $\alpha$-NH$_2$ or $\epsilon$-NH$_2$Lys (wherein coupling can occur through either the reducing end, the carboxyl groups of acidic carbohydrates, or via hydroxyl groups); cyanogen bromide and $\alpha$-NH$_2$ or $\epsilon$-NH$_2$Lys (wherein carbohydrates activated by the cyanogen bromide spontaneously couple with amino groups); or a mixed anhydride and $\alpha$-NH$_2$ or $\epsilon$-NH$_2$Lys (wherein the R—COOH is converted into anhydride with isobutylchlorocarbonate).

Additional forms of conjugation of a small molecule to a tumor or tumor section sample may occur through but are not limited to such chemical reactions as an NHS-ester reaction (to form an amine bond), a maleimide reaction (to form a thioether bond), a hydrazide reaction (to form a hydrazone linkage), or an EDC coupling reaction (to form an amide bond). Additionally, conjugation of a small molecule to a tumor or tumor section sample or lymph node or lymph node section could occur through use of a homobifunctional or heterobifunctional crosslinkers (examples of which include, but are not limited to, sulfo-SMCC, DSS, or sulfo-SBED).

An example of small molecules that can be used as identifiers can include haptens. Examples of haptens that are typically used are digoxigenin, 2,4-dinitrophenyl, biotin, or avidin, or are haptens selected from azoles, nitroaryl compounds, benzofurazans, triterpenes, ureas, thioureas, rotenones, oxazoles, thiazoles, coumarins, cyclolignans, heterobiaryl compounds, azoaryl compounds or benzodiazepines. Further examples of haptens can include but are not limited to 2,4-dinitrophenyl, nitropyrazole and thiazole sulfonamide. See WO2014139979, which is hereby incorporated by reference in its entirety. Additional examples of haptens that could be used include but are not limited to being selected from an azole (e.g., an oxazole, a pyrazole, a thiazole), a benzofurazan, a triterpene, a urea, a thiourea other than a rhodamine thiourea, a nitroaryl other than dinitrophenyl or trinitrophenyl, a rotenoid, a cyclolignan, a heterobiaryl, an azoaryl, a benzodiazepine, or a coumarin (e.g., 2,3,6,7-tetrahydro-11-oxo-1H,5H,11H-[l]benzopyrano[6,7,8-ij]quinolizine-10-carboxylic acid or 7-diethylamino-3-carboxycoumarin). See WO2012003476 and WO2008063378, which are both hereby incorporated by reference in their entirety. Other examples of haptens that could be used include but are not limited to biotin, urushiol, hydralazine, fluorescein, digoxigenin, dinitrophenol, 2,4-dichlorophenoxyacetic acid, 2-chloro-4-(ethylamino)-6-(isopropylamino)-s-triazine, nicotine, morphine, structurally related s-triazines, SulcoFuron, FlucoFuron, agatharesinol, sequirin C, sugiresinol, hydroxysugiresinol, hinokiresinol, coniferyl alcohol, p-coumaric acid, hinokinin, guaiacylglycerol-beta-guaiacyl ether, morphine-3-glucuronide (M3G), codeine, nor-codeine, 6-monoacetylmorphine, (+) methamphetamine, ceftazidime, phenobarbital, p-hydroxyphenobarbital, aminophenobarbital, hexamethylene diisocyanate, cyclobarbital, 3'-ketocyclobarbital, 3'-hydroxycyclobarbital, secobarbital, barbital, metharbital, barbituric acid, thiopental, thiobarbituric acid, primidone, glutethimide, pentobarbital, diacetylmorphine, morphine-6-glucuronide (M6G), L-11-allyl-1,2,3,9,10,10a-hexahydro-4H-10,4a-iminoethano-phenanthren-6-ol, naloxone, pethidine, benzoylecgonine, 5-benzimidazolecarboxylic acid, dexamethasone, flumethasone, betamethasone, 9-alpha-fluoroprednisolone, desoxymethasone, triamcinolone, prednisolone, fluocortolone, cortisol, prednisone, cortisone, methylprednisolone, triamcinolone hexacetonide, carbofuran, BFNP (3-[[(2,3-dihydro-2,2-dimethyl-7-benzofuranyloxy)carbonyl]amino]propanoic acid), 2,3-dihydro-2,2-dimethyl-7-benzofuranol, bendiocarb, carbaryl, methiocarb, propoxur, aldicarb, methomyl, benalaxyl, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Bn-HG, furalaxyl, metalaxyl, acetochlor, dimetachlor, metolachlor, diethathyl-ethyl, benzoylprop-ethyl, propachlor, 2,4,5-trichlorophenoxyacetic acid, 2,4-dichlorophenoxybutyric acid (2,4-DB), MCPA, dichlorprop (2,4-DP), 1-[(2-chloro) phenylsulfonyl]monoamidosuccinic acid, chlorsulfuron, chlorbromuron, amidosulfuron, chlortoluron, isoproturon, diuron, linuron, O-methyl-O-(4-nitrophenyl)-N-(4-carboxybutyl)-phosphoramidothioate, parathion-methyl, parathion-ethyl, fenitrothion, fenthion, bromophos, chlorpyrifos-methyl, oxidized parathion-methyl, paraoxon, diazinon, azinphos-methyl, pirimiphos-methyl, methidathion, dimethylchlororothiophosphate, 4-nitrophenol, 2-nitrophenol, 2-chlorophenol, 4-chloro-3-methylphenol, fenitroxon, 3-methyl-4-nitrophenol, nonylphenol, HOM(3-[2-hydroxy-5nitro benzylthio]propionic acid, delor 103, 2,4,4'-trichlorobiphenyl, 2-(5-carboxypentanoylamino)-2,4,4'-dichlorobiphenyl, 4-chlorophenoxyacetic acid, 2-chlorophenoxyacetic acid, 1,1,1-trichloro-2, 2-bis-(p-chlorophenyl)ethane, 1,1-dichloro-2, 2-bis(p-chlorophenyl)ethylene, vitamin D2, vitamin D3, deethylhydroxyatrazine (DEHA), flourescein isothiocyanate, metanephrine, propazine, terbutylazine, ametryn (2-ethylamino-4-isopropylamino-6-methylthio-1,3, 5-triazine, cyanazine, OH-terbutylazine, hydroxytriazine (EQ-0027), atraton, atrazine mercapturic acid (AM), N4-acetyl-sulphamethazine, 2,4-dichlorophenol, 4-bromophenol, amoxicillin, 6-amino-penicillanic acid (6-APA), azlocillin, bacampicillin, carbenicillin, penicillin, 1-benzyl-3-(4-nitrophenyl)urea, 1-(3-chlorophenyl)-3-(2-methoxy-5-nitrophenyl)urea, 1-(3-chlorophenyl)-3-(4-methoxy-3-nitrophenyl)urea, 1-(4-chlorophenyl)-3-(4-nitrophenyl)urea, carbofuran-phenol, carbosulfan, benfuracarb, endrin, nendrin, heptachlor, chlordane, endosulfan, aldrin, dieldrin, fenvalerate isomers, thiabendazole, thiabendazole derivatives, albendazole, mebendazole, fenbendazole, cambendazole, fenvalerate haptens, pirimiphos-ethyl, 4-(methylthio)-m-cresol, chlorpyrifos-oxon, fenchlorphos, trichloronate, dichlofenthion, parathion, triadimefon, diflubenzuron, metolazone, furfuryl benzoate, paraquat, diethylcarbamazine, 2,4,6-triphenyl-N-(4-hydroxyphenyl)-pyridinium, o-DNCP, PCB congeners, 1-2-dichlorobenzene, retronecine, dicofol, tetraconazole, 2-(2,4-dichlorophenyl)-3-(1H-1,2,4-triazol-1-yl)propanol, imazalyl, fenarimol, and lupanine metabolites. For further examples, see Singh M. K., Srivastava S., Raghava G. P. S. and Varsheny G. C. (2004) HaptenDB. Nucleic Acids Research, and Singh M. et. al. HaptenDB: a comprehensive database of haptens, carrier proteins and anti-hapten antibodies. Bioinformatics. 2006, 22: 253-255, both of which are hereby included by reference in their entirety.

Additional small molecule identifiers can include but are not limited to fluorescent molecules or fluorochromes (such as sold by Invitrogen, e.g., see, The Handbook—A Guide to Fluorescent Probes and Labeling Technologies, Invitrogen Detection Technologies, Molecular Probes, Eugene, Oreg, or disclosed in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron®. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives, thiol-reactive europium chelates which emit at approximately 617 nm (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof, ALEXA FLUOR™ series of dyes (for example, as described in U.S. Pat. Nos. 5,696,157, 6,130,101 and 6,716,979), the BODIPY series of dyes (dipyrromethenboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912)), a fluorescent nanoparticle (such as a semiconductor nanocrystal, e.g., a QUANTUM DOT™ (obtained, for example, from QuantumDot Corp, Invitrogen Nanocrystal Technologies, Eugene, Oreg.; see also, U.S. Pat. Nos. 6,815,064, 6,682,596 and 6,649,138)), a nanoparticle (such as quantum dots, paramagnetic nanoparticles, superparamagnetic nanoparticles, and metal nanoparticles, preferably alloyed quantum dots, including by way of example and without limitation, CdSe, ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN, by way of example), the semiconductor nanocrystals described in e.g., U.S. Pat. No. 6,602,671, Bruchez et. al.

(1998) Science 281:2013-6, Chan et al. (1998) Science 281:2016-8, and U.S. Pat. Nos. 6,274,323, 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999), radioisotopes (such as $^3$H), metal chelates such as DOTA and DPTA chelates of radioactive or paramagnetic metal ions like $Gd^{3+}$, and liposomes, enzymes, for example horseradish peroxidase, alkaline phosphatase, acid phosphatase, glucose oxidase, β-galactosidase, β-glucuronidase or β lactamase, enzyme in combination with a chromogen, fluorogenic or luminogenic compound that generates a detectable signal, for example, those sold by Invitrogen Corporation, Eugene Oreg.), chromogenic compounds (including diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate](ABTS), o-dianisidine, 4-chloronaphthol (4-CN), nitrophenyl-.beta.-D-galactopyranoside (ONPG), o-phenylenediamine (OPD), 5-bromo-4-chloro-3-indolyl-.beta.-galactopyranoside (X-Gal), methylumbelliferyl-.beta.-D-galactopyranoside (MU-Gal), p-nitrophenyl-.alpha.-D-galactopyranoside (PNP), 5-bromo-4-chloro-3-indolyl-.beta.-D-glucuronide (X-Gluc), 3-amino-9-ethyl carbazol (AEC), fuchsin, iodonitrotetrazolium (INT), tetrazolium blue and tetrazolium violet, among others).

Small molecules may be directly detected or detected in combination with one another. For example, if a hapten is conjugated to a quantum dot, a quantum dot may be detected by its fluorescence at a characteristic wavelength. In other instances, detecting a hapten includes contacting a sample with an anti-hapten antibody and a detectable label, and detecting a label. In certain embodiments, a detectable label is conjugated to an anti-hapten antibody to form an anti-hapten antibody-label conjugate, and a conjugate binds to a hapten. In other instances, a sample is contacted with an anti-hapten antibody, which binds to a hapten. A sample then is contacted with an antibody conjugate capable of binding to an anti-hapten antibody, wherein an antibody conjugate includes a detectable label or a component of a detectable label system. In certain instances, a component of the detectable label system is an enzyme, such as horseradish peroxidase or alkaline phosphatase, which reacts with a chromogenic substrate or a substrate/chromogen complex thereby producing a detectable chromogenic deposition. In other examples, the label is a fluorescent label, such as a quantum dot. See WO2012003476, which is hereby incorporated in its entirety.

Additional means for identification of tumor sample origin within a mixed homogenate that comprises tumor samples derived from different subjects may include the use of DNA barcoding. DNA barcoding is a taxonomic method that uses a short genetic marker in an organism's DNA to identify it. In combination with next generation DNA sequencing methods, it may be possible to determine the identity of a sample with regard to its subject of origin through detection of DNA sequence that is specific to a subject of origin. Additionally, it is possible that a unique, artificial DNA sequence not derived directly from a subject could be conjugated to sample derived from a subject prior to combination with other tumor samples with differing origins, and that this unique artificial DNA barcode could be read later by DNA sequence analysis in order to identify the origin of a sample under investigation.

Likewise, additional means for subject identification within a mixed homogenate that comprises tumor samples derived from different subjects or different sample derived from the same subject may include the use affinity tags (such as those generally used during protein purification laboratory procedures which can include but are not limited to peptide tags and protein tags) that are conjugated to a tumor section sample. The affinity tag could be identified at the desired point of the sample analyses to determine the origin of the sample under investigation, similar to the principle of DNA barcoding. Such affinity tags include but are not limited to peptide tags or protein tags such as penta-histidine, tetra-histidine, glutathione sepharose transferase, CBP, CYD (covalent yet dissociable NorpD peptide), Strep II, FLAG, HPC (heavy chain of protein C), SUMO, AviTag, calmodulin-tag, polyglutamate tag, E-tag, HA-tag, Myc-tag, S-tag, SBP-tag, Softag 1, Softag 3, TC tag, V5 tag, VSV-tag, Xpress tag, Isopeptag, MBP, SpyTag, BCCP, green fluorescent protein tag, halo-tag, Nus-tag, thioredoxin-tag, Fc-tag, and Ty tag.

Any number of analytical assays, including, but not limited to, staining, immunohistochemical staining, flow cytometry, FACS, fluorescence-activated droplet sorting, image analysis, hybridization, DASH, molecular beacons, primer extension, microarrays, CISH, FISH, fiber FISH, quantitative FISH, flow FISH, comparative genomic hybridization, blotting, Western blotting, Southern blotting, Eastern blotting, Far-Western blotting, Southwestern blotting, Northwestern blotting, and Northern blotting, enzymatic assays, ELISA, ligand binding assays, immunoprecipitation, chromatin immunoprecipitation (ChIP), ChIP-seq, ChIP-ChIP, radioimmunoassays, fluorescence polarization, FRET, surface plasmon resonance, filter binding assays, affinity chromatography, immunocytochemistry, electrophoretic assays, nucleic acid electrophoresis, polyacrylamide gel electrophoresis, native gel methods, free-flow electrophoresis, isoelectric focusing, immunoelectrophoresis, electrophoretic mobility shift assays, restriction fragment length polymorphism analysis, zymography, gene expression profiling, DNA profiling with PCR, DNA microarrays, serial analysis of gene expression, real-time polymerase chain reaction, differential display PCR, RNA-seq, mass spectrometry, DNA methylation detection, acoustic energy, lipidomic-based analyses, quantification of immune cells, detection of cancer-associated markers, affinity purification of specific cell types, DNA sequencing, next-generation sequencing, detection of cancer-associated fusion proteins, and detection of chemotherapy resistance-associated markers can be effected using the "mixed" homogenate.

Multiplex assays are often, but not necessarily, used in high-throughput screening assays. Exemplary multiplex assay techniques include nucleic acid-based multiplex methods (such as DNA microarray used for gene expression or SNP detection assays; SAGE for gene expression; high-throughput sequencing (such as NGS); multiplex PCR; Multiplex Ligation-dependent Probe Amplification (MLPA); DNA sequencing by ligation; and bead-based multiplexing (such as Luminex/LAMP)) and protein-based multiplex methods (such as protein microarrays, antibody microarrays, antigen microarrays, antibody profiling, and bead-based multiplexing (such as Luminex/LAMP)) as well as other multiplex methods (such as tissue microarray, cellular microarray, chemical compound microarray, biomarker analysis, and ELISA).

Overview of Further Analytical Techniques

A sample of the present disclosure, e.g., produced by any of the methods described herein, may be subjected to further processing steps. These include, but are not limited to, further analytical techniques, such as those detailed in the present application, including further diagnostic assays are applicable to the analyses of the heterogeneous materials contained within a representative tumor sample. The following methodologies may be used in conjunction with the samples of the disclosure, which may result in information concerning the identities and biological properties of the cell contained within a heterogeneous tumor cell population. The combined analyses provided by the disclosure and the techniques described below can allows for identification, detection, or characterization of even minor sub-clone populations within the tumor. These results can be informative for diagnosis, the selection of treatment methods, and patient management.

In exemplary embodiments, a representative sample of the present disclosure may be subjected to one or more of the following methods or steps: staining, immunohistochemical staining, flow cytometry, FACS, fluorescence-activated droplet sorting, image analysis, hybridization, DASH, molecular beacons, primer extension, microarrays, CISH, FISH, fiber FISH, quantitative FISH, flow FISH, comparative genomic hybridization, blotting, Western blotting, Southern blotting, Eastern blotting, Far-Western blotting, Southwestern blotting, Northwestern blotting, and Northern blotting, enzymatic assays, ELISA, ligand binding assays, immunoprecipitation, ChIP, ChIP-seq, ChIP-ChIP, radioimmunoassays, fluorescence polarization, FRET, surface plasmon resonance, filter binding assays, affinity chromatography, immunocytochemistry, electrophoretic assays, nucleic acid electrophoresis, polyacrylamide gel electrophoresis, native gel methods, free-flow electrophoresis, isoelectric focusing, immunoelectrophoresis, electrophoretic mobility shift assays, restriction fragment length polymorphism analysis, zymography, gene expression profiling, DNA profiling with PCR, DNA microarrays, serial analysis of gene expression, real-time polymerase chain reaction, differential display PCR, RNA-seq, mass spectrometry, DNA methylation detection, acoustic energy, lipidomic-based analyses, quantification of immune cells, detection of cancer-associated markers, affinity purification of specific cell types, droplet-on-thermocouple silhouette quantitative PCR, DNA sequencing, next-generation sequencing, detection of cancer-associated fusion proteins, detection of chemotherapy resistance-associated markers, and Ki67, DNA ploidy, or other genotypic or phenotypic analysis. Exemplary embodiments of these methods are described below, which are intended to illustrate these techniques. However, it is to be understood that variants and alternatives of these methodologies, and other methodologies, may be utilized.

Staining Techniques

Fluids can be applied for pretreatment (e.g., protein-crosslinking, exposing nucleic acids, etc.), denaturation, hybridization, washing (e.g., stringency washing), detection (e.g., linking a visual or marker molecule to a probe), amplifying (e.g., amplifying proteins, genes, etc.), counter-staining, or the like. In various embodiments, the substances include, without limitation, stains (e.g., hematoxylin solutions, eosin solutions, or the like), wetting agents, probes, antibodies (e.g., monoclonal antibodies, polyclonal antibodies, etc.), antigen recovering fluids (e.g., aqueous- or non-aqueous-based antigen retrieval solutions, antigen recovering buffers, etc.), solvents (e.g., alcohol, limonene, or the like), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast. See WO2015197742 and WO2015150278, each of which is hereby incorporated by reference in its entirety.

The staining techniques may employ systems and methods for receiving a plurality of assay information along with a query for one or more features of interest, and projecting anatomical information from an anatomical assay onto an image of a staining assay, for example, an immunohistochemical (IHC) assay that is commonly registered with the anatomical assay, to locate or determine features appropriate for analysis. The anatomical information may be used to generate a mask that is projected on one or more commonly registered staining or IHC assays. A location of the feature of interest in the IHC assay may be correlated with the anatomical context provided by the mask, with any features of interest that match the anatomical mask being selected or indicated as appropriate for analysis. Furthermore, the anatomical mask may be partitioned into multiple regions, and multiple features of interest from multiple IHC assays may be correlated with each of these regions individually. Therefore, the disclosed systems and methods provide systematic, quantitative, and intuitive approaches for comprehensive multi-assay analysis, thereby overcoming the limiting ad-hoc or subjective visual analysis steps in the state of the art. See WO2015052128 which is hereby incorporated by reference in its entirety.

Typically, cancer samples are pathologically examined by fixing the cells onto microscopic slides and staining them using a variety of staining methods (e.g., morphological or cytogenetic stains). Stained specimens are then evaluated for the presence or absence of abnormal or cancerous cells and cell morphologies. Although providing only general information, histological staining methods are the most common methods currently practiced for the detection of cancerous cells in biological samples. Other staining methods often used for cancer detection include immunohistochemistry and activity stains. These methods are based on the presence or absence of specific antigens or enzymatic activities in cancerous cells. See WO2012152747 which is hereby incorporated by reference in its entirety.

Methods, kits, and systems for treating samples containing obfuscating pigments are disclosed. The method includes applying a clarifying reagent to the sample so that the obfuscating pigments within the sample are decolorized. Decolorizing the obfuscating pigments enhances pathologists' ability to examine the sample. In illustrative embodiments, an automated method of treating a sample mounted on a substrate to alleviate staining obfuscations associated with pigments within the sample is disclosed. The method includes placing the substrate upon which the sample is mounted on an automated instrument and applying a clarifying reagent so that the clarifying reagent contacts the sample and pigments within the sample are decolorized. The method further comprises applying a rinsing reagent so that the clarifying reagent is substantially removed from the sample and applying a chromogenic reagent so that the sample is specifically stained. Pigments within the sample are decolorized by the clarifying reagent so that the specifically stained sample is interpretable by a qualified reader. In other illustrative embodiments, disclosed is a kit for decolorizing obfuscating pigments in a sample. The kit includes a reagent bottle and a clarifying reagent deposited in the reagent bottle. The clarifying reagent comprises an aqueous solution of hydrogen peroxide and the reagent bottle is configured to be operably connected to an automated slide staining apparatus such that the automated slide staining apparatus controls the application of the clarifying reagent so that the clarifying reagent contacts the sample. In further illustrative embodiments, disclosed is a system for alleviating specific signal obfuscation for a histopathological sample containing pigments. The system includes an automated instrument, a clarifying reagent, and a chromogenic reagent. The automated instrument is configured to receive the histopathological sample adhered to a substrate, to deliver the clarifying reagent and the chromogenic reagent to the sample, and to provide heating and mixing to the clarifying reagent and the chromogenic reagent delivered to the sample. The clarifying reagent is configured to contact the histopathological sample and render the obfuscating pigments decolorized. The chromogenic reagent is configured to contact the histopathological sample and deposit a specific signal. See WO2014056812 which is hereby incorporated by reference in its entirety.

Immunostaining and in situ DNA analysis can be useful tools in histological diagnosis. Immunostaining can rely on the specific binding affinity of antibodies with epitopes in samples, and the increasing availability of antibodies which bind specifically with unique epitopes which are sometimes present only in certain types of diseased cells. Immunostaining may include a series of treatment steps conducted on a sample mounted on a glass slide to selectively highlight certain morphological indicators of disease states. In some instances, treatment steps can include pretreatment of the sample to reduce non-specific binding, antibody treatment and incubation, enzyme labeled secondary antibody treatment and incubation, substrate reaction with the enzyme and counterstain. The result can produce fluorescent or chromogenic highlighted areas of the sample having epitopes binding with the antibody. In some instances, in situ DNA analysis relies upon the specific binding affinity of probes with nucleotide sequences in cell or samples. Immunohistochemistry (IHC) or immunocytochemistry (ICC) can include the visualization of a cellular component in situ by detecting specific antibody-antigen interactions where the antibody has been tagged with a visible marker. IHC is sometimes referred to as the detection of antigens in tissues, while ICC is sometimes referred to as the detection of antigens in or on cultured cells (JAVOIS, Methods in Molecular Medicine, V. 115: Immunocytochemical Methods and Protocols, 2nd edition, (1999) Humana Press, Totowa, New Jersey, which is hereby incorporated by reference in its entirety), however, methods described as IHC or ICC may equally be applicable to the present disclosure. The visible marker may be a fluorescent dye, colloidal metal, hapten, radioactive marker or an enzyme. Regardless of the method of preparation, maximal signal strength with minimal background or non-specific staining can be desirable to give antigen visualization. See WO2013139555 which is hereby incorporated by reference in its entirety.

Based on early studies, miRNAs play a role in developmental regulation and cell differentiation in mammals, as well as cardiogenesis and lymphocyte development. In addition, miRNA are involved in other biological processes, such as hypoxia, apoptosis, stem cell differentiation, proliferation, inflammation, and response to infection. miRNA can be used to concurrently target multiple effectors of pathways involved in cell differentiation, proliferation and survival, key characteristics of oncogenesis. Several miRNAs have been linked to cancer. As a result, in-situ analysis of miRNA can be useful for cancer diagnosis and therapeutics, as miRNAs appear to act as oncogenes or tumor repressors. For example, many tumor cells have distinct miRNA expression patterns when compared with normal tissues. Studies using mice genetically altered to produce excess c-Myc—a protein with mutated forms implicated in several cancers—established that miRNA effects cancer development. Methods for detecting miRNA, as well as protein translated or otherwise regulated by miRNA, are highly desirable, particularly in automated methods for efficient and rapid detection. Prior methods for detecting miRNA do not detect both miRNA and its protein expression targets (potentially regulated by the miRNA) in the same sample. Exemplary methods typically use protease-based cell conditioning to digest cellular components to expose nucleic acid targets. Furthermore, exemplary methods correlate levels of miRNA and protein levels using northern and western blots. Further, molecular approaches that "grind and bind" the sample can be utilized. Tissue-based approaches have been previously demonstrated. These methods generally include an enzymatic step. See WO2013079606 which is hereby incorporated by reference in its entirety.

Disclosed embodiments may utilize an automated method particularly suited for multiplexed detection of miRNA and proteins. In illustrative embodiments, the expression of the one or more proteins may be regulated by the miRNA. In another embodiment, the method enables the cellular context between the miRNA and the protein to be identified. The method may comprise, for example, using an automated system to apply to a sample (a) reagents suitable for detecting a miRNA target, (b) reagents suitable for detecting a protein target, and (c) reagents suitable for staining the miRNA target and the protein target. One aspect of the present embodiments concerns using non-enzymatic cell conditioning, i.e. avoiding protease-based cell conditioning, to preserve the protein targets. A cell conditioning step can involve treating the sample with a cell conditioning solution, such as a buffer having a slightly basic pH, including a Tris-based buffer having a pH from about 7.7 to about 9, at a temperature greater than ambient, such as from about 80° C. to about 95° C. The automated method can detect the miRNA and protein targets simultaneously or sequentially, although better staining results typically are obtained by first detecting and staining the miRNA and then detecting and staining the protein target. A more particular disclosed embodiment first comprises performing non-enzymatic cell conditioning on the sample. The sample is then contacted with a nucleic acid specific binding moiety selected for a particular miRNA target, followed by detecting the miRNA specific binding moiety. The sample is then contacted with a protein specific binding moiety selected for a protein target, followed by detecting the protein specific binding moiety. In certain embodiments, the nucleic acid specific binding moiety is a locked nucleic acid (LNA) probe conjugated to a detectable moiety, such as an enzyme, a fluorophore, a luminophore, a hapten, a fluorescent nanoparticle, or combinations thereof. Certain suitable haptens are common in the art, such as digoxigenin, dinitrophenyl, biotin, fluorescein, rhodamine, bromodeoxyuridine, mouse immunoglobulin, or combinations thereof. Other suitable haptens were specifically developed by Ventana® Medical Systems, Inc., including haptens selected from oxazoles, pyrazoles, thiazoles, benzofurazans, triterpenes, ureas, thioureas, rotenoids, coumarins, cyclolignans, heterobiaryls, azoaryls, benzodiazepines, and combinations thereof. Haptens can be detected using an anti-hapten antibody. In certain disclosed embodiments, the anti-hapten antibody is detected by an anti-species antibody-enzyme conjugate, wherein the enzyme is any suitable enzyme, such as alkaline phosphatase or horseradish peroxidase. See WO2013079606 which is hereby incorporated by reference in its entirety.

Counterstaining is a method of post-treating samples after they have already been stained with agents to detect one or more targets, such that their structures can be more readily visualized under a microscope. For example, a counterstain is optionally used prior to coverslipping to render an immunohistochemical stain more distinct. Counterstains differ in color from a primary stain. Numerous counterstains are well known, such as hematoxylin, eosin, methyl green, methylene blue, Giemsa, Alcian blue, DAPI, and Nuclear Fast Red. In some examples, more than one stain can be mixed together to produce the counterstain. This provides flexibility and the ability to choose stains. For example, a first stain can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain. See WO2012116949 which is hereby incorporated by reference in its entirety.

Hematoxylin is a naturally-occurring compound found in the red heartwood of trees of the genus Hematoxylon. Hematoxylin itself is colorless in aqueous solution and is not the active ingredient that stains tissue components. Rather, an oxidation product of hematoxylin, hematein, becomes the active staining component of a hematoxylin dye solution, particularly upon complexation with a mordant. Hematein is produced naturally through exposure to air and sunlight. The natural process is termed "ripening," and can take 3 or more months to provide a solution suitable for staining cells. Automated staining procedures and systems use mechanical systems to deliver staining solutions to a biological sample. Standard hematein staining procedures utilized a premixed stock containing both the hematoxylin/hematein and a mordant. See WO2012096842 which is hereby incorporated by reference in its entirety.

Immunostaining typically utilizes a series of treatment steps conducted on a sample mounted on a glass slide to highlight by selective staining certain morphological indicators of disease states. Typical steps include pretreatment of the sample to reduce non-specific binding, antibody treatment and incubation, enzyme labeled secondary antibody treatment and incubation, substrate reaction with the enzyme to produce a fluorophore or chromophore highlighting areas of the sample having epitopes binding with the antibody, counterstaining, and the like. Each of these steps is separated by multiple rinse steps to remove unreacted residual reagent from the prior step. Incubations are conducted at elevated temperatures, usually around 40° C., and the samples typically are continuously protected from dehydration. In situ DNA analysis uses the specific binding affinity of probes with unique nucleotide sequences in samples and similarly involves a series of process steps, with a variety of reagents and process temperature. See WO2011139976 which is hereby incorporated by reference in its entirety.

Immunohistochemistry (IHC) Staining

Immunohistochemistry or IHC staining of a sample (or immunocytochemistry, which is the staining of cells), is perhaps the most commonly applied immunostaining technique. While the first cases of IHC staining used fluorescent dyes (see immunofluorescence), other non-fluorescent methods using enzymes such as peroxidase (see immunoperoxidase staining) and alkaline phosphatase are now used. These enzymes are capable of catalyzing reactions that give a colored product that is easily detectable by light microscopy. Alternatively, radioactive elements can be used as labels, and the immunoreaction can be visualized by autoradiography. Preparation or fixation can contribute to the preservation of cell morphology and architecture. Inappropriate or prolonged fixation may significantly diminish the antibody binding capability. Many antigens can be successfully demonstrated in formalin-fixed sample. The detection of many antigens can be improved by antigen retrieval methods that act by breaking some of the protein cross-links formed by fixation to uncover hidden antigenic sites. This can be accomplished by heating for varying lengths of times (heat induced epitope retrieval or HIER) or using enzyme digestion (proteolytic induced epitope retrieval or PIER).

Immunohistochemistry (IHC) refers to a method of determining the presence or distribution of an antigen (such as a protein) in a sample (such as a pancreatic cancer sample) by detecting interaction of the antigen with a specific binding agent, such as an antibody. A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Exemplary detectable labels that can be used for IHC include, but are not limited to, radioactive isotopes, fluorochromes (such as fluorescein, fluorescein isothiocyanate, and rhodamine), haptens, enzymes (such as horseradish peroxidase or alkaline phosphatase), and chromogens (such as 3,3'-diaminobenzidine or Fast Red). In some examples, IHC is utilized to detect the presence of or determine the amount of one or more proteins in a sample, for example, a pancreatic cancer sample. See WO2013019945, which is hereby incorporated by reference in its entirety.

Immunohistochemistry, or IHC, refers to the process of localizing antigens, such as a protein, in cells of a sample and using the antigens to promote specific binding of antibodies to the particular antigens. This detection technique has the advantage of being able to show exactly where a given protein is located within the sample. It is also an effective way to examine the samples themselves. The use of small molecules such as haptens, to detect antigens and nucleic acids has become a prominent method in IHC. Haptens, in combination with anti-hapten antibodies are useful for detecting particular molecular targets. For example, specific binding moieties such as primary antibodies and nucleic acid probes can be labeled with one or more hapten molecules, and once these specific binding moieties are bound to their molecular targets they can be detected using an anti-hapten antibody conjugate that includes an enzyme as part of a chromogenic based detection system or a detectable label such as a fluorescent label. Binding of the detectable anti-hapten antibody conjugate to a sample indicates the presence of the target in a sample. Digoxigenin, present exclusively in *Digitalis* plants as a secondary metabolite, is an example of a hapten that has been utilized in a variety of molecular assays. U.S. Pat. No. 4,469,797 discloses using immunoassays to determine digoxin concentrations in blood samples based upon the specific binding of anti-digoxin antibodies to the drug in the test sample. U.S. Pat. No. 5,198,537 describes a number of additional digoxigenin derivatives that have been used in immunological tests, such as immunoassays. For in situ assays such as immunohistochemical (IHC) assays and in situ hybridization (ISH) assays of samples, especially multiplexed assays of such samples, it is highly desirable to identify and develop methods which provide desirable results without background interference. One such method involves the use of Tyramide Signal Amplification (TSA), which is based on the patented catalyzed reporter deposition (CARD). U.S. Pat. No. 6,593,100, which is hereby incorporated by reference in its entirety, discloses enhancing the catalysis of an enzyme in a CARD or tyramide signal amplification (TSA) method by reacting a labeled phenol conjugate with an enzyme, wherein the reaction is carried out in the presence of an enhancing reagent. See WO2012003476, which is hereby incorporated by reference in its entirety, as are the foregoing publications.

Embodiments of methods for using the hapten conjugates may be utilized. In general the method may include the steps of a) immobilizing a peroxidase on a target in a sample, wherein the peroxidase is capable of reacting with a peroxidase-activatable aryl moiety, e.g., tyramine or a tyramine derivative, b) contacting the sample with a solution comprising a hapten conjugate, wherein the hapten conjugate comprises a hapten bound to a peroxidase-activatable aryl moiety as described above, and c) contacting the sample with a solution comprising peroxide, whereby the hapten conjugate reacts with the peroxidase and the peroxide, forming a covalent bond to the immobilized peroxidase or proximal to the immobilized peroxidase; and d) locating the target in the sample by detecting the hapten. See WO2012003476, which is hereby incorporated by reference in its entirety.

Expansion Microscopy

Expansion microscopy (ExM) provides a method for optical imaging of biological samples of interest, including but not limited to, cells, tissues, DNA, RNA, or lipids, with increased resolution compared to classical microscopy diffraction limit. ExM permits physical magnification of preserved biological samples, in which the biological samples of interest are infused with a composition (e.g., a polymer gel or a hydrogel) to the extent that the composition is embedded in the samples of interests. When the composition expands isotropically, the biological samples or a dye (or fluorophore) attached to the samples will expand, thus allowing optical imaging of the biological samples or fluorophore at a higher resolution. Under ExM, the biological sample is first stained with tag using standard techniques known to one of skill in the art, e.g., FISH, immunohistochemistry staining. The samples are then perfused with one or more gelatin solutions, for example a monomer, cross linker, or an initiator. In one embodiment, the gelatin solutions comprise swellable materials. Once the gelation process is completed, the biological samples are then optionally digested with proteases or other chemical treatments. The gel is expanded upon swelling, which may be accomplished through contact with outside factors, such as water or heat. The expansion of gel physically enlarges or expands the samples or tags embedded within the gel. The enlargement and/or expansion of the samples or tags permits optical imaging at much higher resolutions (e.g., at nanoscale). The ExM is applicable to a large number of biological samples, including but not limited to proteins, RNA, DNA, lipids, and those are not capable of identification and localization at a high resolution under classical microscopy. See U.S. application Ser. No. 14/627,310, which is incorporated by reference in its entirety.

The present disclosure provides a method of preparing the representative sample for microscopy, comprising, or alternatively consisting essentially of, or yet further consisting of embedding the representative sample (e.g., homogenate composition) or a portion thereof in a swellable material. The term "swellable material", as used herein, refers to a material that expands upon physical influence, including but not limited to contact with water, temperature (e.g., heat), physical stretch, and humidity. The swellable material may expand in one dimension, or two dimensions, or in three dimensions. In one embodiment, the swellable material is transparent such that upon expansion, light can pass through the sample. In one embodiment the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. In a preferred embodiment, the swellable polymer is polyacrylate and copolymers or crosslinked copolymers thereof. Alternatively or additionally, the swellable material can be formed in situ by chemically crosslinking water soluble oligomers or polymers.

The term "polymerizable material" refers to a material capable of polymerization, including but not limited to a monomer and oligomer. The term "crosslinker" refers to a molecule that contains two or more reactive ends capable of chemically attaching to specific functional groups (primary amines, sulfhydryls, etc.) on proteins or other molecules. In one embodiment, a crosslinker causes polymerization of oligomers or monomers. The term "polymerization initiator" refers to a compound, or anion thereof, which reacts with ethylene oxide in a manner which results in polymerization thereof. In certain embodiments, the polymerization initiator is the anion of a functional group which initiates the polymerization of ethylene oxide.

In one embodiment, the method further comprises, or alternatively consists essentially of, or yet further consists of enlarging the homogenate composition by swelling the swellable material. In another embodiment, the embedding process comprises, or alternatively consists essentially of, or yet further consists of permeating the homogenate with a composition comprising precursors of a swellable material and forming a swellable material in situ, and anchoring the homogenate composition to the swellable material. In one aspect, the swellable material is formed from a precursor of the swellable material, wherein the precursor comprises a polymerizable material, a polymerization initiator, or a crosslinker. In another aspect, the polymerizable material is a monomer or a oligomer. In a further embodiment, the monomer or the oligomer comprises substituted or unsubstituted methacrylate, acrylate, acrylamide, methacrylamide, vinylalcohol, vinylamine, allylamine, allylalcohol, or divinylic crosslinkers thereof (e.g., N,N-alkylene bisacrylamides).

Flow Cytometry

Flow cytometry is a laser-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second. Flow cytometry is routinely used in the diagnosis of health disorders, especially blood cancers, but has many other applications in basic research, clinical practice and clinical trials. A common variation is to physically sort particles based on their properties, so as to purify populations of interest.

Fluorescence-Activated Cell Sorting (FACS)

Fluorescence-activated cell sorting (FACS) is a specialized type of flow cytometry. It provides a method for sorting a heterogeneous mixture of cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest. The cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

Fluorescence-Activated Droplet Sorting of Single Cells

Compartmentalization of single cells in droplets enables the analysis of proteins released from or secreted by cells, thereby overcoming one of the major limitations of traditional flow cytometry and fluorescence-activated cell sorting. An example of this approach is a binding assay for detecting antibodies secreted from single mouse hybridoma cells. Secreted antibodies are detected after only 15 min by co-compartmentalizing single mouse hybridoma cells, a fluorescent probe and single beads coated with anti-mouse IgG antibodies in 50-pl droplets. The beads capture the secreted antibodies and, when the captured antibodies bind to the probe, the fluorescence becomes localized on the beads, generating a clearly distinguishable fluorescence signal that enables droplet sorting at ~200 Hz as well as cell enrichment. The microfluidic system described is easily adapted for screening other intracellular, cell-surface or secreted proteins and for quantifying catalytic or regulatory activities. In order to screen ~1 million cells, the microfluidic operations may be completed in 2-6 h; the entire process, including preparation of microfluidic devices and mammalian cells, may be completed in 5-7 d. See Mazutis et al. (2013). "Single-cell analysis and sorting using droplet-based microfluidics". Nat. Protoc. 8: 870-891, which is hereby incorporated by reference in its entirety.

Image Analysis

The samples may be analyzed by systems and computer-implemented methods for automatic immune cell detection that is of assistance in clinical immune profile studies. The automatic immune cell detection method involves retrieving a plurality of image channels from a multi-channel image such as an RGB image or biologically meaningful unmixed image. See WO2015177268, which is hereby incorporated by reference in its entirety.

An image analysis algorithm and/or system may be utilized that automatically computes an immune score from a set images of multiplex IHC slides and/or fluorescent stained slides. The image analysis algorithm involves a computer-implemented method for counting a number of types of cells in a single sample that has been stained with a multiplex assay, comprising: imaging the sample that has been stained with the multiplex assay that includes lymphocyte markers CD3, CD8, CD20, FoxP3, and tumor detection markers; un-mixing the image of single sample that has been stained with a multiplex assay into separate image channels for each marker of the multiplex assay; identifying regions of interest in each image channel based on intensity information in each channel, wherein regions of low intensity in each channel are removed, and regions of high intensity represent cell signals; generating a single surrogated image, wherein the surrogated image is a combination of the image channel information of all the lymphocyte markers; applying a cell detection algorithm, wherein the cell detection algorithm is a membrane finding algorithm or a nucleus finding algorithm; identifying features of the lymphocytes and combinations of lymphocytes in each image channel or image of combined channels, or a transformed image such as grayscale or absorbance image, or a surrogated image; training a classification algorithm based on features of known lymphocytes and lymphocyte combinations; applying the trained algorithm to features of the lymphocytes and combinations of lymphocytes in each image channel or in each image of combined channels, or in a transformed image such as grayscale or absorbance image, or in a surrogated image, that were identified to classify the detected cells as at least one of false positive cells, CD3 only T-cells, CD3 and CD8 T-cells, FP3 T-cells; and CD20 B-cells; counting a number of each different type of cell classified; generating a score of the sample, wherein the score is based on the number of each type of cell counted. See WO2015124737, which is hereby incorporated by reference in its entirety. Exemplary embodiments of the present disclosure may include utilizing systems and methods that include a two-step classification method. Operations disclosed herein include dividing a WS image into a plurality of patches, and first classifying each patch using a "soft" classification, such as SVM, and generating a confidence score and a label for each patch. The location of each patch, its features, and its type obtained as classification result, and its confidence score can be stored in a database. The second classification step includes comparing the low-confidence patches with the high-confidence patches in the database and using similar patches to augment the spatial coherence of the patches in the database. In other words, for each low-confidence patch, neighboring high-confidence patches make larger contributions towards refining the labels for each patch, which improves the segmentation accuracy in the low-confidence patches. In contrast to existing adaptive/active learning techniques for growing training databases, the disclosed operations are less concerned with growing a single training database and are instead focused on treating each test image independently while adaptively improving the classification accuracy based on the labeling confidence information for the image under analysis. In other words, a confident label patch database is generated for each image, and similarity retrieval operations are performed within the image to refine the classification results for low-confidence patches. See WO2015113895, which is hereby incorporated by reference in its entirety.

Exemplary embodiments of the present disclosure may include utilizing methods of detecting and scoring mesothelin (MSLN) expression, such as MSLN protein expression. In particular examples the methods include contacting a sample that includes tumor cells with a MSLN protein-specific binding agent (such as an antibody). Exemplary tumors that express MSLN include but are not limited to ovarian cancer, lung cancer (e.g., non-small cell lung carcinomas, NSCLCs), pancreatic cancer, and mesothelioma. Expression of MSLN protein in the tumor cells is detected or measured, for example using microscopy and immunohistochemistry (IHC). The sample is scored on a scale of 0 to 3+ for MSLN protein expression. For example, it is determined whether at least 10% of the tumor cells (such as at least about 10% of the tumor cells) in the sample are stained with the protein-specific binding agent (e.g., have detectable MSLN protein expression). The sample is assigned a score of zero for MSLN protein expression if less than 10%> (such as less than about 10%>) of the tumor cells are stained with the specific binding agent. The sample is assigned a score of 1+ for MSLN protein expression if at least 10% of the tumor cells (such as at least about 10% of the tumor cells) in the sample are stained with the protein-specific binding agent (e.g., have detectable MSLN protein expression), but less than 10%> of the tumor cells (such as less than about 10%) are stained with the specific binding agent at an intensity of 2+ or higher. The sample is assigned a score of 2+ for MSLN protein expression if at least 10% of the tumor cells (such as at least about 10% of the tumor cells) in the sample are stained with the protein-specific binding agent (e.g., have detectable MSLN protein expression) at an intensity of 2+ or higher and a majority of the stained tumor cells stain with 2+ intensity. The sample is assigned a score of 3+ for MSLN protein expression if at least 10% of the tumor cells (such as at least about 10% of the tumor cells) in the sample are stained with the protein-specific binding agent (e.g., have detectable MSLN protein expression) at an intensity of 2+ or higher and a majority of the stained tumor cells stain with 3+ intensity and at least 10% of the tumor cells (such as at least about 10% of the tumor cells) in the sample are stained with the protein-specific binding agent (e.g., have detectable MSLN protein expression) with 3+ intensity. An overview is provided in Table 13 and FIG. 20 of WO2015032695, which is hereby incorporated by reference in its entirety.

Hybridization

In situ hybridization (ISH) involves contacting a sample containing a target nucleic acid, a genomic target nucleic acid) in the context of a metaphase or interphase chromosome preparation (such as a sample mounted on a slide) with a labeled probe specifically hybridizable or specific for the target nucleic acid (for example, one or more of the probes disclosed herein). The slides are optionally pretreated, e.g., to remove materials that can interfere with uniform hybridization. The chromosome sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the target is performed using standard techniques. See WO2015124702, which is hereby incorporated by reference in its entirety.

Other methods of detecting cancerous cells utilize the presence of chromosomal aberrations in cancer cells. In particular, the deletion or multiplication of copies of whole chromosomes or chromosomal segments, and higher levels of amplifications of specific regions of the genome are common occurrences in cancer. Chromosomal aberrations are often detected using cytogenetic methods such as Giemsa-stained chromosomes (G-banding) or fluorescent in situ hybridization (FISH). See WO2012152747, which is hereby incorporated by reference in its entirety.

The presently disclosed technology provides improved methods for increased specificity in analyzing the molecular mechanisms of a cancer. Thus, in certain embodiments, the technology relates to a multivariate cancer diagnostic method wherein said method determines the presence of both molecular markers and phenotypic morphometric markers at the cellular level in a single cell or single sample containing cells, said method comprising: a) obtaining molecular marker data from a single sample from a subject comprising a single cell or cells; b) obtaining quantitative cell morphology data from the same single cell or cells as used in step (a) to provide a multivariable analysis of said single sample, the multivariable data set comprising both quantitative cell morphology data from step (b) and molecular marker data from step (a); and c) comparing the multivariable analysis data set obtained in step (b) with a reference multivariable analysis data set created by obtaining both molecular marker data and quantitative cell morphology data from cancer and non-cancer cell samples taken from individuals with known clinical outcome.

The comparison results of step (c) provide a prediction of a clinical outcome from the subject defined by specific combinations of features and markers statistically associated with cancer progression, occurrence, metastases or other feature of clinical outcome seen in the reference multivariable analysis data set. See WO2012152747, which is hereby incorporated by reference in its entirety.

Exemplary embodiments of the present disclosure may include utilizing technology provides information for determining pathological prognosis states of cancer by using fluorescent labeling of molecular markers in conjunction with specialized imaging approaches involving spectrally-resolved detection and data pre-processing. The technology provides an imaging approach that can acquire and analyze nuclear morphology on a sample that is prepared for detection of molecule-specific probes on a sample within a single data acquisition cycle. This imaging approach employs a combination of labeling, acquisition, pre-processing and analysis technologies. A multidimensional image is collected and analyzed to separate and distinguish different analyte channels of interest by emission wavelength. The subsequent analyte channels represent different aspects of the data that quantify the morphology and genetic rearrangement, genetic expression and/or protein expression of the cell. See WO2012152747, which is hereby incorporated by reference in its entirety.

Exemplary embodiments of the present disclosure may include utilizing a system, method, and kit for visualizing a nucleus. A sample can be pretreated with a protease to permeabilize the nucleus, and then incubated with a nanoparticle/DNA-binding moiety conjugate. The DNA-binding moiety includes at least one DNA-binding molecule. The conjugate binds to DNA within the nucleus, and the nanoparticle is visualized, thereby visualizing the nucleus. Computer and image analysis techniques are used to evaluate nuclear features such as chromosomal distribution, ploidy, shape, size, texture features, and/or contextual features. The method may be used in combination with other multiplexed tests on the sample, including fluorescence in situ hybridization. See WO2012116949, which is hereby incorporated by reference in its entirety.

Fluorescence in situ hybridization (FISH) is a technique that can be used to detect and localize the presence or absence of specific DNA sequences on chromosomes. FISH uses fluorescent probes that bind to only those parts of the chromosome with which they show a high degree of sequence similarity. FISH also can be used to detect particular mRNA sequences within a sample. See WO2012116949, which is hereby incorporated by reference in its entirety.

Numerous procedures for FISH, CISH, and SISH are known in the art. For example, procedures for performing FISH are described in U.S. Pat. Nos. 5,447,841; 5,472,842; and 5,427,932; CISH is described in U.S. Pat. No. 6,942,970, and additional detection methods are provided in U.S. Pat. No. 6,280,929, the disclosures of which are incorporated in their entirety herein by reference. Numerous reagents and detection schemes can be employed in conjunction with FISH, CISH, and SISH procedures to improve sensitivity, resolution, or other desirable properties. As discussed above, probes labeled with fluorophores (including fluorescent dyes and quantum dots) can be directly optically detected when performing FISH. Alternatively, the probe can be labeled with a non-fluorescent molecule, such as a hapten [such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell sample to which the probe is bound) with a labeled detection reagent, such as an antibody (or receptor, or other specific binding partner) specific for the chosen hapten or ligand. The detection reagent can be labeled with a fluorophore (e.g., quantum dot) or with another indirectly detectable moiety, or can be contacted with one or more additional specific binding agents (e.g., secondary or specific antibodies), which can in turn be labeled with a fluorophore. Optionally, the detectable label is attached directly to the antibody, receptor (or other specific binding agent). Alternatively, the detectable label is attached to the binding agent via a linker, such as a hydrazide thiol linker, a polyethylene glycol linker, or any other flexible attachment moiety with comparable reactivities. For example, a specific binding agent, such as an antibody, a receptor (or other anti-ligand), avidin, or the like can be covalently modified with a fluorophore (or other label) via a heterobifunctional polyalkyleneglycol linker such as a heterobifunctional polyethyleneglycol (PEG) linker. A heterobifunctional linker combines two different reactive groups selected, e.g., from a carbonyl-reactive group, an amine-reactive group, a thiol-reactive group and a photo-reactive group, the first of which attaches to the label and the second of which attaches to the specific binding agent. In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries [(e.g., linker and attachment chemistries) are described in U.S. Patent Application Publication Nos. 2006/0246524; 2006/0246523, and 2007/0117153, the disclosures of which are incorporated in their entirety herein by reference. See WO2015124702, which is hereby incorporated by reference in its entirety.

The methods of the present disclosure may allow for the detection of more than one (e.g., 2, 3, 4, etc.) different targets. In some embodiments, different detectable labels and/or detection systems may be used for each of the targets such that each can be individually detected in a single sample. Any appropriate detectable label and/or detection system may be used. More specifically, the present disclosure features systems for bright field in situ hybridization. In some embodiments, the system comprises a probe set comprising X unique 2'-O-methyl RNA probes specific to a target RNA, wherein X>2 (e.g., X=2, X=3, X=4, X=5, etc.), the probes target X distinct portions within the target RNA. Each 2'-O-methyl RNA probe may be conjugated with at least one detectable moiety. The detectable moiety may be adapted to bind a reactive chromogen conjugate system (e.g. tyramide chromogen conjugate system) for signal amplification. In some embodiments, the 2'-O-methyl RNA probes each comprise between 15 to 30 nucleotides, between 20 to 50 nucleotides, between 40 to 80 nucleotides, between 20 to 100 nucleotides, or between 20 to 200 nucleotides in length. See WO2015124738, which is hereby incorporated by reference in its entirety.

The specimen can be a breast cell sample processed according to an in situ hybridization (ISH) protocol. The ISH protocol can provide visualization of specific nucleic acid sequences (e.g., DNA, mRNA, etc.) in cell preparations by hybridizing complementary strands of nucleotides (e.g., probes) to the sequence of interest. The ISH protocol can include, without limitation, a dual SISH and Red ISH protocol, single Red ISH protocol, single SISH protocol, or the like. See WO2013113707, which is hereby incorporated by reference in its entirety.

Dynamic Allele-Specific Hybridization (DASH)

Dynamic allele-specific hybridization (DASH) genotyping takes advantage of the differences in the melting temperature in DNA that results from the instability of mismatched base pairs. The process can be vastly automated and encompasses a few simple principles. In the first step, a genomic segment is amplified and attached to a bead through a PCR reaction with a biotinylated primer. In the second step, the amplified product is attached to a streptavidin column and washed with NaOH to remove the un-biotinylated strand. An allele-specific oligonucleotide is then added in the presence of a molecule that fluoresces when bound to double-stranded DNA. The intensity is then measured as temperature is increased until the melting temperature (Tm) can be determined. A SNP will result in a lower than expected Tm. Because DASH genotyping is measuring a quantifiable change in Tm, it is capable of measuring all types of mutations, not just SNPs. Other benefits of DASH include its ability to work with label free probes and its simple design and performance conditions.

Molecular Beacons

Molecular beacons make use of a specifically engineered single-stranded oligonucleotide probe. The oligonucleotide is designed such that there are complementary regions at each end and a probe sequence located in between. This design allows the probe to take on a hairpin, or stem-loop, structure in its natural, isolated state. Attached to one end of the probe is a fluorophore and to the other end a fluorescence quencher. Because of the stem-loop structure of the probe, the fluorophore is in close proximity to the quencher, thus preventing the molecule from emitting any fluorescence. The molecule is also engineered such that only the probe sequence is complementary to the genomic DNA that will be used in the assay (Abravaya et al. (April 2003). "Molecular beacons as diagnostic tools: technology and applications". Clin. Chem. Lab. Med. 41 (4): 468-74). If the probe sequence of the molecular beacon encounters its target genomic DNA during the assay, it will anneal and hybridize. Because of the length of the probe sequence, the hairpin segment of the probe will be denatured in favor of forming a longer, more stable probe-target hybrid. This conformational change permits the fluorophore and quencher to be free of their tight proximity due to the hairpin association, allowing the molecule to fluoresce. If on the other hand, the probe sequence encounters a target sequence with as little as one non-complementary nucleotide, the molecular beacon will preferentially stay in its natural hairpin state and no fluorescence will be observed, as the fluorophore remains quenched.

Primer Extension

Primer extension is a two-step process that first involves the hybridization of a probe to the bases immediately upstream of the SNP nucleotide followed by a 'mini-sequencing' reaction, in which DNA polymerase extends the hybridized primer by adding a base that is complementary to the SNP nucleotide. This incorporated base is detected and determines the SNP allele (Syvanen, Nat Rev Genet. 2001 December; 2(12):930-42). Because primer extension is based on the highly accurate DNA polymerase enzyme, the method is generally very reliable. Primer extension is able to genotype most SNPs under very similar reaction conditions making it also highly flexible. The primer extension method is used in a number of assay formats. These formats use a wide range of detection techniques that include MALDI-TOF Mass spectrometry (see Sequenom) and ELISA-like methods. Generally, there are two main approaches which use the incorporation of either fluorescently labeled dideoxynucleotides (ddNTP) or fluorescently labeled deoxynucleotides (dNTP). With ddNTPs, probes hybridize to the target DNA immediately upstream of SNP nucleotide, and a single, ddNTP complementary to the SNP allele is added to the 3' end of the probe (the missing 3'-hydroxyl in didioxynucleotide prevents further nucleotides from being added). Each ddNTP is labeled with a different fluorescent signal allowing for the detection of all four alleles in the same reaction. With dNTPs, allele-specific probes have 3' bases which are complementary to each of the SNP alleles being interrogated. If the target DNA contains an allele complementary to the probe's 3' base, the target DNA will completely hybridize to the probe, allowing DNA polymerase to extend from the 3' end of the probe. This is detected by the incorporation of the fluorescently labeled dNTPs onto the end of the probe. If the target DNA does not contain an allele complementary to the probe's 3' base, the target DNA will produce a mismatch at the 3' end of the probe and DNA polymerase will not be able to extend from the 3' end of the probe. The benefit of the second approach is that several labeled dNTPs may get incorporated into the growing strand, allowing for increased signal.

Microarrays

The core principle behind microarrays is hybridization between two DNA strands, the property of complementary nucleic acid sequences to specifically pair with each other by forming hydrogen bonds between complementary nucleotide base pairs. A high number of complementary base pairs in a nucleotide sequence results in tighter non-covalent bonding between the two strands. After washing off non-specific bonding sequences, only strongly paired strands will remain hybridized. Fluorescently labeled target sequences that bind to a probe sequence generate a signal that depends on the hybridization conditions (such as temperature), and washing after hybridization. Total strength of the signal, from a spot (feature), depends upon the amount of target sample binding to the probes present on that spot. Microarrays use relative quantitation in which the intensity of a feature is compared to the intensity of the same feature under a different condition, and the identity of the feature is known by its position.

Nucleic acid arrays (also known as oligonucleotide arrays, DNA microarrays, DNA chips, gene chips, or biochips) have become powerful analytical tools. A nucleic acid array is essentially a systematic distribution of oligonucleotides on a surface, for example, in rows and columns. Oligonucleotides can be either physically or covalently adhered to a surface. One approach for physically adhering oligonucleotides to a surface involves drying oligonucleotide solutions as they contact the surface. After drying or otherwise fixing, the oligonucleotides are confined in a "spot" on the surface. The drying approach began with the production of very low density arrays called "dot blots." Dot blots can be made by manually depositing drops of oligonucleotides on a solid surface and drying. Most dot blots involve fewer than about 20 different oligonucleotides spots arranged in rows and columns. Advancing past dot blots, micro-spotting approaches used mechanical or robotic systems to create a multiplicity of microscopic spots. The small size of the spots enabled much higher dot densities. For example, micro-spotting was used to deposit tens of thousands of spots onto a microscope slide. According to a different approach, oligonucleotides have been directly synthesized on a substrate or support. Mask-less photolithography and digital optical chemistry techniques are techniques for directly synthesizing nucleic acids on a support; these approaches have been used to generate very high density arrays (for example, U.S. Pat. No. 7,785,863, which is hereby incorporated by reference in its entirety). Similarly, mask-less photolithography has been used to manufacture peptide arrays (see, for example, Singh-Gasson et al. Maskless fabrication of light-directed oligonucleotide microarrays using a digital micromirror array. Nat Biotechnol 1999, 17:974-978, which is hereby incorporated by reference in its entirety). Digital optical chemistry has been used that create arrays with millions of discrete areas each containing a population of unique oligonucleotides. Nucleic acid and peptide arrays include an array of areas (referred to as "dots" herein) on a substrate surface, each area designated for a particular oligonucleotide or peptide. The "array density" is essentially the number of rows and columns of dots distributed in a given area. A high density array has a larger number of rows and columns in a given area. As the nucleic acid and peptide array industries have developed, the availability of high density arrays has also increased. As the number of dots in a given area increases, the size of each dot is reduced. For example, one dot in an array having millions of unique oligonucleotides or peptides distributed across the area of a microscope slide would be approximately 100 pm2. The small size of this dot creates technical challenges in reading and understanding the results of using the array. For example, while a 100 pm2 dot may be visually observed in isolation, humans cannot visually resolve two or more 100 pm2 dots in close proximity without magnification. Thus, the manufacture and use of high density arrays has advanced to the stage that users can no longer read the array visually. Because the arrays include vast numbers (millions) of closely arrayed dots in a small area, sophisticated imaging devices detect signals from the array and software is used to interpret the data. Furthermore, highly sensitive detection methods may be utilized. Fluorescence imaging, being a highly sensitive technique, has become the standard approach for detecting hybridization events. Fluorescence imaging of these arrays generally uses microscopes equipped with filters and cameras. Fluorescence generally cannot be visually resolved without the aid of these devices. The highly complex fluorescence images are processed using software because the volume of data is high and its presentation is not cognizable. For example, U.S. Pat. No. 6,090,555 to Fiekowsky, et al. describes a complex process involving computer assisted alignment and deconvolution of fluorescence images acquired from a nucleic acid array. While the ability to perform massively parallel genomic or proteomic investigations is of great value, nucleic acid and peptide arrays have been limited in applicability by the difficulty in detecting and deciphering binding events. Furthermore, the use of fluorescence creates many hurdles to the general applicability of arrays due to fluorescence signals degrading over time and the complexity of the accompanying fluorescence detection hardware. The present disclosure relates to a device and a method of using the device to detect target molecules, the device including an oligonucleotide or peptide array. The device includes a plurality of binding molecules bound to a substrate surface. The binding molecules are designed to bind to a target molecule. Binding of the target and the binding molecules can be identified through examination of the device. In some embodiments, the device enables the detection of a hybridization event between a target nucleic acid and an immobilized oligonucleotide. In other embodiments, the device enables the detection of a binding event between a target polypeptide and an immobilized peptide. In illustrative embodiments, a device comprises a substrate with at least one substrate surface, and a plurality of immobilized oligonucleotides or peptides bound to the substrate surface, wherein the plurality of immobilized oligonucleotides or peptides are patterned on the substrate surface to form at least one optically decipherable pattern. See WO2013110574, which is hereby incorporated by reference in its entirety.

Exemplary embodiments of the present disclosure may include utilizing a device for the detection of one or more target compounds. One type of target compound of particular interest is target nucleic acids or target oligonucleotides. Another type of target compound of particular interest is target polypeptides. For embodiments of the present disclosure including immobilized oligonucleotides, target nucleic acids would commonly be understood to be the target molecule type. However, those of ordinary skill in the art appreciate that immobilized oligonucleotides provide a binding partner for oligonucleotide-binding moiety conjugates that are capable of detecting a variety of other target compounds. For example, using the immobilized oligonucleotide, an antibody-oligonucleotide conjugate could be immobilized on the device to transform the device into an antibody microarray. An antibody microarray could be used to detect a protein target of interest. Similarly, embodiments that include immobilized peptides, the target molecule type could include antibodies, proteins, or enzymes. However, the underlying peptides could also be modified by using conjugates of the peptide binding moiety and a molecular targeting moiety. Furthermore, while the present disclosure specifically discloses immobilized oligonucleotides and peptides, those are merely exemplary immobilized detection moieties. There are many other useful immobilized detection moieties that may be incorporated into a device as described herein, without departing from the concept as disclosed herein. For example, the detection moieties may include aptamers, ligands, chelators, carbohydrates, and man-made equivalents thereof. See WO2013110574, which is hereby incorporated by reference in its entirety.

Methods of isolating CTCs can include the use of antibodies specific for EpCAM, ERG, PSMA, or combinations thereof. The isolated CTCs are applied to a glass slide or other substrate and fixed (for example using methods known in the art). Novel spreading methods using prostate-specific antibodies as discussed herein may also be used to isolate CTCs and apply them to a substrate, such as a glass slide, before fixation. The mounted and fixed CTCs are then contacted with one or more nucleic acid probes specific for ERG, PTEN, and CEN-10, for example under conditions sufficient for the nucleic acid probes to hybridize to their complementary sequence in the CTCs. The nucleic acid probes are labeled, for example with one or more quantum dots. For example, the nucleic acid probe(s) specific for ERG, PTEN, and CEN-10 can each labeled with a different quantum dot, to permit one to distinguish the probes from one another. After allowing the nucleic acid probes to hybridize to ERG, PTEN, and CEN-10, signals from the one or more quantum dots on the one or more nucleic acid probes are detected, for example by using spectral imaging. The signals are then analyzed, to determine whether in the isolated CTCs, one or more ERGs are rearranged, whether one or more PTEN genes are deleted, and whether CEN-10 is detected. Based on whether one or more ERGs is rearranged, whether one or more PTEN genes is deleted, and whether CEN-10 is detected, the prostate cancer is characterized. See WO2013101989, which is hereby incorporated by reference in its entirety.

Chromogenic In Situ Hybridization (CISH)

Chromogenic in situ hybridization (CISH) is a cytogenetic technique that combines the chromogenic signal detection method of immunohistochemistry (IHC) techniques with in situ hybridization. It was developed around the year 2000 as an alternative to fluorescence in situ hybridization (FISH) for detection of HER-2/neu oncogene amplification. CISH is similar to FISH in that they are both in situ hybridization techniques used to detect the presence or absence of specific regions of DNA. However, CISH is much more practical in diagnostic laboratories because it uses bright-field microscopes rather than the more expensive and complicated fluorescence microscopes used in FISH. Probe design for CISH may be very similar to that for FISH with differences in labelling and detection. FISH probes are generally labelled with a variety of different fluorescent tags and can only be detected under a fluorescence microscope, whereas CISH probes are labelled with biotin or digoxigenin and can be detected using a bright-field microscope after other treatment steps have been applied. CISH probes are approximately 20 nucleotides in length and are designed for DNA targets. They are complementary to the targeted sequence and bind to it after a denaturation and hybridization step. Only a few CISH probes are available commercially, so for most applications they have to be extracted, amplified, sequenced, labelled and mapped from bacterial artificial chromosomes (BACs). BACs were developed during the Human Genome Project as it was necessary to isolate and amplify short fragments of human DNA for sequencing purposes. Nowadays, BACs can be selected and positioned on the human genome using public databases such as the UCSC Genome Browser. This ensures the complementarity and sequence specificity. DNA is extracted from the BAC clones and amplified using a polymerase-based technique, such as degenerate oligonucleotide primed (DOP)-PCR. Next, the clones are sequenced and their position on the genome is verified. Probe labelling can be carried out by using either random priming or nick translation to incorporate biotin or digoxigenin.

Preparation of samples, hybridization of probes, and detection: The sample may include chromosomes in interphase or metaphase. Samples are securely attached to a surface, such as a glass slide. The sample may undergo pepsin digestion to ensure the target is accessible. 10-20 µL of probe is added, the sample is covered with a coverslip which is sealed with rubber cement, and the slide is heated to 97° C. for 5-10 minutes to denature the DNA. The slide is then placed in a 37° C. oven overnight so that the probe can hybridize. On the next day, the sample is washed and a blocker for nonspecific protein binding sites is applied. If horseradish peroxidase (HRP) is going to be used, the sample must be incubated in hydrogen peroxide to suppress endogenous peroxidase activity. If digoxigenin was used as a probe label, an anti-digoxigenin fluorescein primary antibody followed by a HRP-conjugated anti-fluorescein secondary antibody is then applied. If biotin was used as a probe label, non-specific binding sites must first be blocked using bovine serum albumin (BSA). Then, HRP-conjugated streptavidin is used for detection. HRP then converts diaminobenzidine (DAB) into an insoluble brown product, which can be detected in a bright-field microscope under 40- to 60-fold magnification. A counterstain such as hematoxylin and eosin can be used to make the product more visible.

Molecular cytogenetic techniques, such as chromogenic in situ hybridization (CISH) combine visual evaluation of chromosomes (karyotypic analysis) with molecular techniques. Molecular cytogenetics methods are based on hybridization of a nucleic acid probe to its complementary nucleic acid within a cell. A probe for a specific chromosomal region will recognize and hybridize to its complementary sequence on a metaphase chromosome or within an interphase nucleus (for example in a sample). Probes have been developed for a variety of diagnostic and research purposes. Sequence probes hybridize to single copy DNA sequences in a specific chromosomal region or gene. These are the probes used to identify the chromosomal critical region or gene associated with a syndrome or condition of interest. On metaphase chromosomes, such probes hybridize to each chromatid, usually giving two small, discrete signals per chromosome. Hybridization of sequence probes, such as repeat depleted probes or unique sequence probes, has made possible detection of chromosomal abnormalities associated with numerous diseases and syndromes, including constitutive genetic anomalies, such as microdeletion syndromes, chromosome translocations, gene amplification and aneuploidy syndromes, neoplastic diseases as well as pathogen infections. Most commonly these techniques are applied to standard cytogenetic preparations on microscope slides. In addition, these procedures can be used on slides of fixed cells or other nuclear isolates. For example, these techniques are frequently used to characterize tumor cells for both diagnosis and prognosis of cancer. Numerous chromosomal abnormalities have been associated with the development of cancer (for example, aneuploidies such as trisomy 8 associated with certain myeloid disorders; translocations such as the BCR/ABL rearrangement in chronic myelogenous leukemia; and amplifications of specific nucleic acid sequences associated with neoplastic transformation). Molecular techniques can augment standard cytogenetic testing in the detection and characterization of such acquired chromosomal anomalies. Systems for dual color CISH have been introduced. These include the Dako DuoCISH™ system and the Zyto Vision ZytoDot® 2C system. Both of these systems use separate enzymes (alkaline phosphatase and horseradish peroxidase) for the two color detection steps.

The present disclosure relates to systems and processes for chromogenic in situ hybridization (CISH), and in particular to methods which prevent interference between two or more color detection systems in a single assay, and further relates to processes for scoring assays utilizing break-apart probes. See WO2011133625, which is hereby incorporated in its entirety.

Fluorescence In Situ Hybridization (FISH)

Fluorescence in situ hybridization (FISH) is a cytogenetic technique that uses fluorescent probes that bind to only those parts of the chromosome with a high degree of sequence complementarity. It was developed by biomedical researchers in the early 1980s and is used to detect and localize the presence or absence of specific DNA sequences on chromosomes. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (such as mRNA, lncRNA and miRNA) in cells, circulating tumor cells, and samples. In this context, it can help define the spatial-temporal patterns of gene expression within cells.

Probes: RNA and DNA: RNA probes can be designed for any gene or any sequence within a gene for visualization of mRNA, lncRNA and miRNA in cells. FISH is used by examining the cellular reproduction cycle, specifically interphase of the nuclei for any chromosomal abnormalities. This technique [FISH] allows the analysis of a large series of archival cases much easier to identify the pinpointed chromosome by creating a probe with an artificial chromosomal foundation that will attract similar chromosomes. The hybridization signals for each probe when a nucleic abnormality is detected. Each probe for the detection of mRNA and lncRNA is composed of 20 oligonucleotide pairs, each pair covering a space of 40-50 bp. For miRNA detection, the probes use proprietary chemistry for specific detection of miRNA and cover the entire miRNA sequence. Probes are often derived from fragments of DNA that were isolated, purified, and amplified for use in the Human Genome Project. The size of the human genome is so large, compared to the length that could be sequenced directly, that it was necessary to divide the genome into fragments. (In the eventual analysis, these fragments were put into order by digesting a copy of each fragment into still smaller fragments using sequence-specific endonucleases, measuring the size of each small fragment using size-exclusion chromatography, and using that information to determine where the large fragments overlapped one another.) To preserve the fragments with their individual DNA sequences, the fragments were added into a system of continually replicating bacteria populations. Clonal populations of bacteria, each population maintaining a single artificial chromosome, are stored in various laboratories around the world. The artificial chromosomes (BAC) can be grown, extracted, and labeled, in any lab. These fragments are on the order of 100 thousand base-pairs, and are the basis for most FISH probes.

Preparation and hybridization process—RNA: Cells can be permeabilized to allow target accessibility. FISH has also been successfully done on unfixed cells. A target-specific probe, composed of 20 oligonucleotide pairs, hybridizes to the target RNA(s). Separate but compatible signal amplification systems enable the multiplex assay (up to two targets per assay). Signal amplification is achieved via a series of sequential hybridization steps. At the end of the assay the samples are visualized under a fluorescence microscope.

Preparation and hybridization process—DNA: First, a probe is constructed. The probe must be large enough to hybridize specifically with its target but not so large as to impede the hybridization process. The probe is tagged directly with fluorophores, with targets for antibodies or with biotin. Tagging can be done in various ways, such as nick translation, or PCR using tagged nucleotides. Then, an interphase or metaphase chromosome preparation is produced. The chromosomes are firmly attached to a substrate, usually glass. Repetitive DNA sequences must be blocked by adding short fragments of DNA to the sample. The probe is then applied to the chromosome DNA and incubated for approximately 12 hours while hybridizing. Several wash steps remove all un-hybridized or partially hybridized probes. The results are then visualized and quantified using a microscope that is capable of exciting the dye and recording images. If the fluorescent signal is weak, amplification of the signal may be necessary in order to exceed the detection threshold of the microscope. Fluorescent signal strength depends on many factors such as probe labeling efficiency, the type of probe, and the type of dye. Fluorescently tagged antibodies or streptavidin are bound to the dye molecule. These secondary components are selected so that they have a strong signal.

Fiber FISH

In an alternative technique to interphase or metaphase preparations, fiber FISH, interphase chromosomes are attached to a slide in such a way that they are stretched out in a straight line, rather than being tightly coiled, as in conventional FISH, or adopting a chromosome territory conformation, as in interphase FISH. This is accomplished by applying mechanical shear along the length of the slide, either to cells that have been fixed to the slide and then lysed, or to a solution of purified DNA. A technique known as chromosome combing is increasingly used for this purpose. The extended conformation of the chromosomes allows dramatically higher resolution—even down to a few kilobases.

Quantitative FISH (Q-FISH)

Quantitative Fluorescent in situ hybridization (Q-FISH) is a cytogenetic technique based on the traditional FISH methodology. In Q-FISH, the technique uses labelled (Cy3 or FITC) synthetic DNA mimics called peptide nucleic acid (PNA) oligonucleotides to quantify target sequences in chromosomal DNA using fluorescent microscopy and analysis software.

Flow FISH

Flow-FISH is a cytogenetic technique to quantify the copy number of specific repetitive elements in genomic DNA of whole cell populations via the combination of flow cytometry with cytogenetic fluorescent in situ hybridization staining protocols. Flow-FISH was first published in 1998 by Rufer et al. as a modification of another technique for analyzing telomere length, Q-FISH, that employs peptide nucleic acid probes of a 5'-CCCTAACCCTAACCCTAA-3' (SEQ ID NO: 1) sequence labeled with a fluorescein fluorophore to stain telomeric repeats on prepared metaphase spreads of cells that have been treated with colcemid, hypotonic shock, and fixation to slides via methanol/acetic acid treatment (protocol available online). Images of the resultant fluorescent spots could then be analyzed via a specialized computer program (method and software available from the Flintbox Network) to yield quantitative fluorescence values that can then be used to estimate actual telomere length. The fluorescence yielded by probe staining is considered to be quantitative because PNA binds preferentially to DNA at low ionic salt concentrations and in the presence of formamide, thus the DNA duplex may not reform once it has been melted and annealed to PNA probe, allowing the probe to saturate its target repeat sequence (as it is not displaced from the target DNA by competing anti sense DNA on the complementary strand), thus yielding a reliable and quantifiable readout of the frequency of PNA probe target at a given chromosomal site after washing away of unbound probe.

Comparative Genomic Hybridization

Comparative genomic hybridization is a molecular cytogenetic method for analyzing copy number variations (CNVs) relative to ploidy level in the DNA of a test sample compared to a reference sample, without the need for culturing cells. The aim of this technique is to quickly and efficiently compare two genomic DNA samples arising from two sources, which are most often closely related, because it is suspected that they contain differences in terms of either gains or losses of either whole chromosomes or sub-chromosomal regions (a portion of a whole chromosome). This technique was originally developed for the evaluation of the differences between the chromosomal complements of solid tumor and normal tissue samples, and has an improved resolution of 5-10 megabases compared to the more traditional cytogenetic analysis techniques of giemsa banding (g-banding) and fluorescence in situ hybridization (FISH) which are limited by the resolution of the microscope utilized.

Blotting

Exemplary blotting techniques that may be utilized include Western, Southern, Eastern, Far-western, Southwestern, Northwestern, and Northern blotting, as further described in the following sections and as known in the art.

Western Blotting

The western blot (sometimes called the protein immunoblot) is a widely used analytical technique used to detect specific proteins in a sample homogenate or extract. It uses gel electrophoresis to separate native proteins by 3-D structure or denatured proteins by the length of the polypeptide. The proteins are then transferred to a membrane (typically nitrocellulose or PVDF), where they are stained with antibodies specific to the target protein. The gel electrophoresis step is included in western blot analysis to resolve the issue of the cross-reactivity of antibodies.

Southern Blotting

Southern blotting combines transfer of electrophoresis-separated DNA fragments to a filter membrane and subsequent fragment detection by probe hybridization. Hybridization of the probe to a specific DNA fragment on the filter membrane indicates that this fragment contains DNA sequence that is complementary to the probe. The transfer step of the DNA from the electrophoresis gel to a membrane permits easy binding of the labeled hybridization probe to the size-fractionated DNA. It also allows for the fixation of the target-probe hybrids, which may be utilized for analysis by autoradiography or other detection methods. Southern blots performed with restriction enzyme-digested genomic DNA may be used to determine the number of sequences (e.g., gene copies) in a genome. A probe that hybridizes only to a single DNA segment that has not been cut by the restriction enzyme will produce a single band on a Southern blot, whereas multiple bands will likely be observed when the probe hybridizes to several highly similar sequences (e.g., those that may be the result of sequence duplication). Modification of the hybridization conditions (for example, increasing the hybridization temperature or decreasing salt concentration) may be used to increase specificity and decrease hybridization of the probe to sequences that are less than 100% similar.

Eastern Blotting

The eastern blot is a biochemical technique used to analyze protein post translational modifications (PTM) such as lipids, phospho-moieties, and glycoconjugates. It is most often used to detect carbohydrate epitopes. Thus, eastern blotting can be considered an extension of the biochemical technique of western blotting. Multiple techniques have been described by the term eastern blotting, most use proteins blotted from SDS-PAGE gel on to a PVDF or nitrocellulose membrane. Transferred proteins are analyzed for post-translational modifications using probes that may detect lipids, carbohydrate, phosphorylation or any other protein modification. Eastern blotting should be used to refer to methods that detect their targets through specific interaction of the PTM and the probe, distinguishing them from a standard Far-western blot. In principle, eastern blotting is similar to lectin blotting (i.e. detection of carbohydrate epitopes on proteins or lipids).

Far-Western Blotting

Far-western blotting employs non-antibody proteins to probe the protein(s) of interest on the blot. In this way, binding partners of the probe (or the blotted) protein may be identified. The probe protein is often produced in E. coli using an expression cloning vector. Proteins in a cell lysate containing prey proteins are firstly separated by SDS or native PAGE, and transferred to a membrane, as in a standard WB. The proteins in the membrane are then denatured and renatured. The membrane is then blocked and probed, usually with purified bait protein(s). The bait proteins are detected on spots in the membrane where a prey protein is located, if the bait proteins and the prey protein together form a complex. The probe protein can then be visualized through the usual methods—it may be radiolabelled; it may bear a specific affinity tag like His or FLAG for which antibodies exist; or there may be a protein specific antibody (to the probe protein).

Southwestern Blotting

Southwestern blotting, based along the lines of Southern blotting (which was created by Edwin Southern) and first described by B. Bowen, J. Steinberg and colleagues in 1980, is a lab technique which involves identifying and characterizing DNA-binding proteins (proteins that bind to DNA) by their ability to bind to specific oligonucleotide probes. The proteins are separated by gel electrophoresis and are subsequently transferred to nitrocellulose membranes similar to other types of blotting. "Southwestern blot mapping" is performed for rapid characterization of both DNA-binding proteins and their specific sites on genomic DNA. Proteins are separated on a polyacrylamide gel (PAGE) containing sodium dodecyl sulfate (SDS), renatured by removing SDS in the presence of urea, and blotted onto nitrocellulose by diffusion. The genomic DNA region of interest is digested by restriction enzymes selected to produce fragments of appropriate but different sizes, which are subsequently end-labeled and allowed to bind to the separated proteins. The specifically bound DNA is eluted from each individual protein-DNA complex and analyzed by polyacrylamide gel electrophoresis. Evidence that specific DNA binding proteins may be detected by this technique has been presented. Moreover, their sequence-specific binding allows the purification of the corresponding selectively bound DNA fragments and may improve protein-mediated cloning of DNA regulatory sequences.

Northwestern Blotting

Running a Northwestern blot involves separating the RNA binding proteins by gel electrophoresis, which will separate the RNA binding proteins based upon their size and charge. Individual samples can be loaded in to the agarose or polyacrylamide gel (usually an SDS-PAGE) in order to analyze multiple samples at the same time. Once the gel electrophoresis is complete, the gel and associated RNA binding proteins are transferred to a nitrocellulose transfer paper. The newly transferred blots are then soaked in a blocking solution; non-fat milk and bovine serum albumin are common blocking buffers. This blocking solution assists with preventing non-specific binding of the primary and/or secondary antibodies to the nitrocellulose membrane. Once the blocking solution has adequate contact time with the blot, a specific competitor RNA is applied and given time to incubate at room temperature. During this time, the competitor RNA binds to the RNA binding proteins in the samples that are on the blot. The incubation time during this process can vary depending on the concentration of the competitor RNA applied; though incubation time is typically one hour. After the incubation is complete, the blot is usually washed at least 3 times for 5 minutes each wash, in order to dilute out the RNA in the solution. Common wash buffers include Phosphate buffered saline (PBS) or a 10% Tween™ 20 solution. Improper or inadequate washing will affect the clarity of the development of the blot. Once washing is complete the blot is then typically developed by x-ray or similar autoradiography methods.

Northern Blotting

A general Northern blotting procedure starts with extraction of total RNA from a homogenized sample or from cells. Eukaryotic mRNA can then be isolated through the use of oligo (dT) cellulose chromatography to isolate only those RNAs with a poly(A) tail. RNA samples are then separated by gel electrophoresis. Since the gels are fragile and the probes are unable to enter the matrix, the RNA samples, now separated by size, are transferred to a nylon membrane through a capillary or vacuum blotting system. A nylon membrane with a positive charge is the most effective for use in northern blotting since the negatively charged nucleic acids have a high affinity for them. The transfer buffer used for the blotting usually contains formamide because it lowers the annealing temperature of the probe-RNA interaction, thus eliminating the need for high temperatures, which could cause RNA degradation. Once the RNA has been transferred to the membrane, it is immobilized through covalent linkage to the membrane by UV light or heat. After a probe has been labeled, it is hybridized to the RNA on the membrane. Experimental conditions that can affect the efficiency and specificity of hybridization include ionic strength, viscosity, duplex length, mismatched base pairs, and base composition. The membrane is washed to ensure that the probe has bound specifically and to prevent background signals from arising. The hybrid signals are then detected by X-ray film and can be quantified by densitometry. To create controls for comparison in a northern blot sample, not displaying the gene product of interest can be used after determination by microarrays or RT-PCR.

Enzymatic

A proximity detection method is described that utilizes enzymatic biotinylation to detect targets in a sample potentially using automated staining platforms. One disclosed embodiment comprises contacting the sample with a first conjugate comprising a biotin ligase and a first specific binding moiety that binds proximally to the first target; contacting the sample with a second conjugate comprising a biotin ligase substrate and a second specific binding moiety that binds proximally to the second target; subjecting the sample to conditions that allow biotinylation of the biotin ligase substrate by the biotin ligase when the first target and the second target have a proximal arrangement; and detecting biotinylation of the biotin ligase substrate. The conditions that allow biotinylation of the substrate include addition of biotin and ATP. The method also may comprise contacting the sample with a streptavidin-enzyme conjugate. Signal amplification also can be used. See WO2014139980, which is hereby incorporated by reference in its entirety.

Enzyme-Linked Immunosorbent Assay (ELISA)

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bio-conjugation. Between each step, the plate is typically washed with a mild detergent solution to remove any proteins or antibodies that are non-specifically bound. After the final wash step, the plate is developed by adding an enzymatic substrate to produce a visible signal, which indicates the quantity of antigen in the sample.

Ligand Binding Assays

The method of analyzing a sample known or suspected of containing circulating CTCs can include an imaging step. In one example, imaging includes imaging immunofluorescence of the CTC identification reagents (for example by detecting the label associated with each antibody used). In another example, imaging includes using multi-spectral bandpass filters. The immunofluorescence can emanate from antibodies labeled directly or indirectly with fluorophores or the immunofluorescence can result from exciting the fluorophores with spectrally filtered visible light. In one embodiment, the spectrally filtered visible light includes a first selected range to excite a first fluorophore and a second selected range to excite a second fluorophore, wherein the first selected range does not significantly excite the second fluorophore and the second selected range does not significantly excite the first fluorophore. Imaging the sample can include acquiring a first immunofluorescence image of the sample excited by the first selected range and acquiring a second immunofluorescence image of the sample excited by the second selected range (and acquiring additional immunofluorescence images for each label if more than two CTC identification reagents were used) and locating or identifying the CTCs by locating or visualizing the CTC identification reagents, which can include comparing or overlaying the first immunofluorescence image and the second immunofluorescence image (and additional images if so obtained). For example, imaging the first immunofluorescence image can identify CK+ cells, and the second immunofluorescence image can identify CD45+ cells, wherein comparing or overlaying includes identifying cells that are CK+ and CD45−. In another embodiment, locating the CTCs by locating the CTC identification reagents includes algorithmically analyzing the first immunofluorescence image and the second immunofluorescence image (and additional immunofluorescence image s if obtained) using a computer. In one embodiment, algorithmically analyzing includes digitally interrogating the images to measure cell size, cell compartment localization of markers, and/or intensity of marker expression. See WO2013101989, which is hereby incorporated by reference in its entirety.

Immunoprecipitation (IP)

The liquid phase ligand binding assay of Immunoprecipitation (IP) is a method that is used to purify or enrich a specific protein, or a group of proteins, using an antibody from a complex mixture. The extract of disrupted cells or samples can be mixed with an antibody against the antigen of interest, which produces the antigen-antibody complex. When antigen concentration is low, the antigen-antibody complex precipitation can take hours or even days and becomes hard to isolate the small amount of precipitate formed. The enzyme-linked immunosorbent assay (ELISA) or Western blotting are two different ways that the purified antigen (or multiple antigens) can be obtained and analyzed. This method involves purifying an antigen through the aid of an attached antibody on a solid (beaded) support, such as agarose resin. The immobilized protein complex can be accomplished either in a single step or successively. IP can also be used in conjunction with biosynthetic radioisotope labeling. Using this technique combination, one can determine if a specific antigen is synthesized by a sample or by a cell.

Chromatin Immunoprecipitation (ChIP)

Chromatin Immunoprecipitation (ChIP) is a type of immunoprecipitation experimental technique used to investigate the interaction between proteins and DNA in the cell. It aims to determine whether specific proteins are associated with specific genomic regions, such as transcription factors on promoters or other DNA binding sites, and possibly defining cistromes. ChIP also aims to determine the specific location in the genome that various histone modifications are associated with, indicating the target of the histone modifiers.

Chromatin Immunoprecipitation Sequencing (ChIP-Seq)

ChIP-sequencing, also known as ChIP-seq, is a method used to analyze protein interactions with DNA. ChIP-seq combines chromatin immunoprecipitation (ChIP) with massively parallel DNA sequencing to identify the binding sites of DNA-associated proteins. It can be used to map global binding sites precisely for any protein of interest. ChIP-seq is used primarily to determine how transcription factors and other chromatin-associated proteins influence phenotype-affecting mechanisms. Determining how proteins interact with DNA to regulate gene expression is essential for fully understanding many biological processes and disease states. This epigenetic information is complementary to genotype and expression analysis. ChIP-seq technology is currently seen primarily as an alternative to ChIP-chip which can utilize a hybridization array. This necessarily introduces some bias, as an array is restricted to a fixed number of probes. Sequencing, by contrast, is thought to have less bias, although the sequencing bias of different sequencing technologies is not yet fully understood. Specific DNA sites in direct physical interaction with transcription factors and other proteins can be isolated by chromatin immunoprecipitation. ChIP produces a library of target DNA sites bound to a protein of interest in vivo. Massively parallel sequence analyses are used in conjunction with whole-genome sequence databases to analyze the interaction pattern of any protein with DNA, or the pattern of any epigenetic chromatin modifications. This can be applied to the set of ChIP-able proteins and modifications, such as transcription factors, polymerases and transcriptional machinery, structural proteins, protein modifications, and DNA modifications. As an alternative to the dependence on specific antibodies, different methods have been developed to find the superset of all nucleosome-depleted or nucleosome-disrupted active regulatory regions in the genome, like DNase-Seq and FAIRE-Seq.

ChIP-On-Chip (ChIP-ChIP)

ChIP-on-chip (also known as ChIP-chip) is a technology that combines chromatin immunoprecipitation ('ChIP') with DNA microarray ("chip"). Like regular ChIP, ChIP-on-chip is used to investigate interactions between proteins and DNA in vivo. Specifically, it allows the identification of the cistrome, sum of binding sites, for DNA-binding proteins on a genome-wide basis. Whole-genome analysis can be performed to determine the locations of binding sites for almost any protein of interest. As the name of the technique suggests, such proteins are generally those operating in the context of chromatin. The most prominent representatives of this class are transcription factors, replication-related proteins, like Origin Recognition Complex Protein (ORC), histones, their variants, and histone modifications. The goal of ChIP-on-chip is to locate protein binding sites that may help identify functional elements in the genome. For example, in the case of a transcription factor as a protein of interest, one can determine its transcription factor binding sites throughout the genome. Other proteins allow the identification of promoter regions, enhancers, repressors and silencing elements, insulators, boundary elements, and sequences that control DNA replication. If histones are subject of interest, it is believed that the distribution of modifications and their localizations may offer new insights into the mechanisms of regulation. One of the long-term goals ChIP-on-chip was designed for is to establish a catalogue of (selected) organisms that lists all protein-DNA interactions under various physiological conditions. This knowledge would ultimately help in the understanding of the machinery behind gene regulation, cell proliferation, and disease progression. Hence, ChIP-on-chip offers not only huge potential to complement our knowledge about the orchestration of the genome on the nucleotide level, but also on higher levels of information and regulation as it is propagated by research on epigenetics.

Radioimmunoassay

Radioimmunoassay (MA) is a very sensitive in vitro assay technique used to measure concentrations of antigens (for example, hormone levels in blood) by use of antibodies. As such, it can be seen as the inverse of a radiobinding assay, which quantifies an antibody by use of corresponding antigens. Classically, to perform a radioimmunoassay, a known quantity of an antigen is made radioactive, frequently by labeling it with gamma-radioactive isotopes of iodine, such as 125-I, attached to tyrosine. This radiolabeled antigen is then mixed with a known amount of antibody for that antigen, and as a result, the two specifically bind to one another. Then, a sample of serum from a patient containing an unknown quantity of that same antigen is added. This causes the unlabeled (or "cold") antigen from the serum to compete with the radiolabeled antigen ("hot") for antibody binding sites. As the concentration of "cold" antigen is increased, more of it binds to the antibody, displacing the radiolabeled variant, and reducing the ratio of antibody-bound radiolabeled antigen to free radiolabeled antigen. The bound antigens are then separated from the unbound ones, and the radioactivity of the bound antigen remaining in the supernatant is measured using a gamma counter.

This method can be used for any biological molecule in principle and is not restricted to serum antigens, nor is it required to use the indirect method of measuring the free antigen instead of directly measuring the captured antigen. For example, if it is undesirable or not possible to radiolabel the antigen or target molecule of interest, an RIA can done if two different antibodies that recognize the target are available and the target is large enough (e.g., a protein) to present multiple epitopes to the antibodies. One antibody would be radiolabeled as above while the other would remain unmodified. The RIA would begin with the "cold" unlabeled antibody being allowed to interact and bind to the target molecule in solution. Preferably, this unlabeled antibody is immobilized in some way, such as coupled to an agarose bead, coated to a surface, etc. Next, the "hot" radiolabeled antibody is allowed to interact with the first antibody-target molecule complex. After extensive washing, the direct amount of radioactive antibody bound is measured and the amount of target molecule quantified by comparing it to a reference amount assayed at the same time. This method is similar in principle to the non-radioactive sandwich ELISA method.

Fluorescence Polarization

Fluorescence polarization is synonymous with fluorescence anisotropy. This method measures the change in the rotational speed of a fluorescent-labeled ligand once it is bound to the receptor. Polarized light is used in order to excite the ligand, and the amount of light emitted is measured. Depolarization of the emitted light depends on the size of the present ligand. If a small ligand is used, it will have a large depolarization, which will rapidly rotate the light. If the ligand utilized is of a larger size, the resulting depolarization will be reduced. An advantage of this method is that it may only include one labeling step. However, if this method is used at low nanomolar concentrations, results may be precise.

Förster Resonance Energy Transfer (FRET)

Forster Resonance Energy Transfer (also referred to as fluorescence resonance energy transfer) utilizes energy transferred between the donor and the acceptor molecules that are in close proximity, e.g., a donor- and acceptor-fluorophore, or a fluorophore and a quencher. FRET uses a fluorescence labeled ligand like FP. Energy transfer within FRET begins by exciting the donor. The dipole-dipole interaction between the donor and the acceptor molecule transfers the energy from the donor to the acceptor molecule. Interactions between or among molecules to which the donor and acceptors can be monitored by detecting the fluorescence spectra associated with the entry transfer, or absence thereof. For example, if a ligand is bound to a receptor-antibody complex, then the acceptor will emit light. The energy transfer depends on the distance between the donor and acceptor, such that the presence or absence of the transfer indicates the molecular distance. Typically, a distance smaller than 10 nm allows efficient energy transfer between the acceptor and donor, though greater or lesser distances may be used depending on the particular molecules involved.

Surface Plasmon Resonance (SPR)

Surface Plasmon Resonance (SPR) does not require labeling of the ligand. Instead, it works by measuring the change in the angle at which the polarized light is reflected from a surface (refractive index). The angle is related to the change in mass or layer of thickness, such as immobilization of a ligand changing the resonance angle, which increases the reflected light. The device for which SPR is derived includes a sensor chip, a flow cell, a light source, a prism, and a fixed angle position detector.

Filter-Binding Assays

Filter assays are solid phase ligand binding assays that use filters to measure the affinity between two molecules. In a filter binding assay, the filters are used to trap cell membranes by sucking the medium through them. This rapid method occurs at a fast speed in which filtration and a recovery can be achieved for the found fraction. Washing filters with a buffer removes residual unbound ligands and any other ligands present that are capable of being washed away from the binding sites. The receptor-ligand complexes present while the filter is being washed will not dissociate significantly because they will be completely trapped by the filters. Characteristics of the filter are important for each job being done. A thicker filter is useful to get a more complete recovery of small membrane pieces, but may require a longer wash time. It is recommended to pretreat the filters to help trap negatively charged membrane pieces. Soaking the filter in a solution that would give the filter a positive surface charge would attract the negatively charged membrane fragments.

Affinity Chromatography

Affinity chromatography is a method of separating biochemical mixtures based on a highly specific interaction such as that between antigen and antibody, enzyme and substrate, or receptor and ligand. The stationary phase is typically a gel matrix, often of agarose; a linear sugar molecule derived from algae. Usually the starting point is an undefined heterogeneous group of molecules in solution, such as a cell lysate, growth medium or blood serum. The molecule of interest will have a well-known and defined property, and can be exploited during the affinity purification process. The process itself can be thought of as an entrapment, with the target molecule becoming trapped on a solid or stationary phase or medium. The other molecules in the mobile phase will not become trapped as they do not possess this property. The stationary phase can then be removed from the mixture, washed and the target molecule released from the entrapment in a process known as elution. Possibly the most common use of affinity chromatography is for the purification of recombinant proteins.

Immunoaffinity: Another use for the procedure is the affinity purification of antibodies from blood serum. If serum is known to contain antibodies against a specific antigen (for example if the serum comes from an organism immunized against the antigen concerned) then it can be used for the affinity purification of that antigen. This is also known as Immunoaffinity Chromatography. For example if an organism is immunized against a GST-fusion protein it will produce antibodies against the fusion-protein, and possibly antibodies against the GST tag as well. The protein can then be covalently coupled to a solid support such as agarose and used as an affinity ligand in purifications of antibody from immune serum. For thoroughness the GST protein and the GST-fusion protein can each be coupled separately. The serum is initially allowed to bind to the GST affinity matrix. This will remove antibodies against the GST part of the fusion protein. The serum is then separated from the solid support and allowed to bind to the GST-fusion protein matrix. This allows any antibodies that recognize the antigen to be captured on the solid support. Elution of the antibodies of interest is most often achieved using a low pH buffer such as glycine pH 2.8. The eluate is collected into a neutral tris or phosphate buffer, to neutralize the low pH elution buffer and halt any degradation of the antibody's activity. This is a nice example as affinity purification is used to purify the initial GST-fusion protein, to remove the undesirable anti-GST antibodies from the serum and to purify the target antibody. A simplified strategy is often employed to purify antibodies generated against peptide antigens. When the peptide antigens are produced synthetically, a terminal cysteine residue is added at either the N- or C-terminus of the peptide. This cysteine residue contains a sulfhydryl functional group which allows the peptide to be easily conjugated to a carrier protein (e.g. Keyhole Limpet Hemocyanin (KLH)). The same cysteine-containing peptide is also immobilized onto an agarose resin through the cysteine residue and is then used to purify the antibody. Most monoclonal antibodies have been purified using affinity chromatography based on immunoglobulin-specific Protein A or Protein G, derived from bacteria.

Immunocytochemistry (ICC)

Immunocytochemistry (ICC) is a common laboratory technique that is used to anatomically visualize the localization of a specific protein or antigen in cells by use of a specific primary antibody that binds to it. The primary antibody allows visualization of the protein under a fluorescence microscope when it is bound by a secondary antibody that has a conjugated fluorophore. ICC allows researchers to evaluate whether or not cells in a particular sample express the antigen in question. In cases where an immunopositive signal is found, ICC also allows researchers to determine which sub-cellular compartments are expressing the antigen. There are many methods to obtain immunological detection on samples, including those tied directly to primary antibodies or antisera. A direct method involves the use of a detectable tag (e.g., fluorescent molecule, gold particles, etc.) directly to the antibody that is then allowed to bind to the antigen (e.g., protein) in a cell. Alternatively, there are many indirect methods. In one such method, the antigen is bound by a primary antibody which is then amplified by use of a secondary antibody which binds to the primary antibody. Next, a tertiary reagent containing an enzymatic moiety is applied and binds to the secondary antibody. When the quaternary reagent, or substrate, is applied, the enzymatic end of the tertiary reagent converts the substrate into a pigment reaction product, which produces a color (many colors are possible; brown, black, red, etc.,) in the same location that the original primary antibody recognized that antigen of interest. Some examples of substrates used (also known as chromogens) are AEC (3-Amino-9-EthylCarbazole), or DAB (3,3'-Diaminobenzidine). Use of one of these reagents after exposure to the necessary enzyme (e.g., horseradish peroxidase conjugated to an antibody reagent) produces a positive immunoreaction product. Immunocytochemical visualization of specific antigens of interest can be used when a less specific stain like H&E (Hematoxylin and Eosin) cannot be used for a diagnosis to be made or to provide additional predictive information regarding treatment (in some cancers, for example). Alternatively the secondary antibody may be covalently linked to a fluorophore (FITC and Rhodamine are the most common) which is detected in a fluorescence or confocal microscope. The location of fluorescence will vary according to the target molecule, external for membrane proteins, and internal for cytoplasmic proteins. In this way immunofluorescence is a powerful technique when combined with confocal microscopy for studying the location of proteins and dynamic processes (exocytosis, endocytosis, etc.).

Electrophoretic Assays

Exemplary electrophoretic assays that may be utilized include nucleic acid electrophoresis, PAGE, native gel methods, free-flow electrophoresis, IEF, EMSA, RFLP analysis, and zymography, as are known in the art and as further described below, Nucleic Acid Electrophoresis Nucleic acid electrophoresis is an analytical technique used to separate DNA or RNA fragments by size and reactivity. Nucleic acid molecules which are to be analyzed are set upon a viscous medium, the gel, where an electric field induces the nucleic acids to migrate toward the anode, due to the net negative charge of the sugar-phosphate backbone of the nucleic acid chain. The separation of these fragments is accomplished by exploiting the mobilities with which different sized molecules are able to pass through the gel. Longer molecules migrate more slowly because they experience more resistance within the gel. Because the size of the molecule affects its mobility, smaller fragments end up nearer to the anode than longer ones in a given period. After some time, the voltage is removed and the fragmentation gradient is analyzed. For larger separations between similar sized fragments, either the voltage or run time can be increased. Extended runs across a low voltage gel yield the most accurate resolution. Voltage is, however, not the sole factor in determining electrophoresis of nucleic acids.

Polyacrylamide Gel Electrophoresis (PAGE)

Polyacrylamide gel electrophoresis (PAGE), describes a technique widely used in biochemistry, forensics, genetics, molecular biology and biotechnology to separate biological macromolecules, usually proteins or nucleic acids, according to their electrophoretic mobility. Mobility is a function of the length, conformation and charge of the molecule.

SDS-PAGE: sodium dodecyl sulfate (SDS) is an anionic detergent applied to protein samples to linearize proteins and to impart a negative charge to linearized proteins. This procedure is called SDS-PAGE. In most proteins, the binding of SDS to the polypeptide chain imparts an even distribution of charge per unit mass, thereby resulting in a fractionation by approximate size during electrophoresis. Proteins that have a greater hydrophobic content, for instance many membrane proteins, and those that interact with surfactants in their native environment, are intrinsically harder to treat accurately using this method, due to the greater variability in the ratio of bound SDS.

Two-dimensional gel electrophoresis: 2-D electrophoresis begins with 1-D electrophoresis but then separates the molecules by a second property in a direction 90 degrees from the first. In 1-D electrophoresis, proteins (or other molecules) are separated in one dimension, so that all the proteins/molecules will lie along a lane but that the molecules are spread out across a 2-D gel. Because it is unlikely that two molecules will be similar in two distinct properties, molecules are more effectively separated in 2-D electrophoresis than in 1-D electrophoresis. The two dimensions that proteins are separated into using this technique can be isoelectric point, protein complex mass in the native state, and protein mass. The result of this is a gel with proteins spread out on its surface. These proteins can then be detected by a variety of means, but the most commonly used stains are silver and Coomassie Brilliant Blue staining.

Native Gel Methods

Native gels, also known as non-denaturing gels, analyze proteins that are still in their folded state. Thus, the electrophoretic mobility depends not only on the charge-to-mass ratio, but also to the physical shape and size of the protein. Below are examples of different forms of native gel methods.

Clear native gel electrophoresis: CN-PAGE (commonly referred to as Native PAGE) separates acidic water-soluble and membrane proteins in a polyacrylamide gradient gel. It uses no charged dye so the electrophoretic mobility of proteins in CN-PAGE (in contrast to the charge shift technique BN-PAGE) is related to the intrinsic charge of the proteins. The migration distance depends on the protein charge, its size and the pore size of the gel. In many cases this method has lower resolution than BN-PAGE, but CN-PAGE offers advantages whenever Coomassie dye would interfere with further analytical techniques, for example it has been described as a very efficient microscale separation technique for FRET analyses. Also CN-PAGE is milder than BN-PAGE so it can retain labile supramolecular assemblies of membrane protein complexes that are dissociated under the conditions of BN-PAGE.

Blue native PAGE: BN-PAGE is a native PAGE technique, where the Coomassie Brilliant Blue dye provides the necessary charges to the protein complexes for the electrophoretic separation. The disadvantage of Coomassie is that in binding to proteins it can act like a detergent causing complexes to dissociate. Another drawback is the potential quenching of chemoluminescence (e.g. in subsequent western blot detection or activity assays) or fluorescence of proteins with prosthetic groups (e.g. heme or chlorophyll) or labelled with fluorescent dyes.

Quantitative preparative native continuous polyacrylamide gel electrophoresis: QPNC-PAGE, or quantitative preparative native continuous polyacrylamide gel electrophoresis, is a high-resolution technique applied in biochemistry and bioinorganic chemistry to separate proteins by isoelectric point. This standardized variant of native gel electrophoresis is used by biologists to isolate active or native metalloproteins in biological samples and to resolve properly and improperly folded metal cofactor-containing proteins or protein isoforms in complex protein mixtures. As omics platform for biomedical approaches QPNC-PAGE contributes to the development of metal-based drugs for protein-misfolding diseases, and as such, to the biobased economy.

Free-Flow Electrophoresis

Free-flow electrophoresis (FFE), also known as carrier-free electrophoresis, is a continuous electrophoretic and liquid-based separation technique. It is typically used for quantitative and semiquantitative separations of proteins, peptides, organelles, cells, DNA origami and particles. The advantage of FFE is that the separation is conducted in a fast and gentle liquid-based manner, without any interaction of a solid matrix, like polyacrylamide in gel electrophoresis. This ensures a very high recovery rate because no analytes can get lost. FFE separations are continuous, which ensures a high throughput of analytes for preparative applications. Furthermore, the separations can be conducted under native or denaturing conditions. An even and laminar liquid film is conducted between two plates, split up in parallel fractionation tubes, and collected in microtiter plates. A high voltage electric field is applied perpendicular to the laminar flow. Analytes in the laminar flow are separated by charge density and isoelectric point.

Isoelectric Focusing

Isoelectric focusing (IEF), also known as electrofocusing, is a technique for separating different molecules by differences in their isoelectric point (pI). IEF involves adding an ampholyte solution into immobilized pH gradient (IPG) gels. IPGs are the acrylamide gel matrix co-polymerized with the pH gradient, which result in completely stable gradients except the most alkaline (>12) pH values. The immobilized pH gradient is obtained by the continuous change in the ratio of Immobilines. An Immobiline is a weak acid or base defined by its pK value. A protein that is in a pH region below its isoelectric point (pI) will be positively charged and so will migrate towards the cathode (negatively charged electrode). As it migrates through a gradient of increasing pH, however, the protein's overall charge will decrease until the protein reaches the pH region that corresponds to its pI. At this point it has no net charge and so migration ceases (as there is no electrical attraction towards either electrode). As a result, the proteins become focused into sharp stationary bands with each protein positioned at a point in the pH gradient corresponding to its pI. The technique is capable of extremely high resolution with proteins differing by a single charge being fractionated into separate bands. Molecules to be focused are distributed over a medium that has a pH gradient (usually created by aliphatic ampholytes). An electric current is passed through the medium, creating a "positive" anode and "negative" cathode end. Negatively charged molecules migrate through the pH gradient in the medium toward the "positive" end while positively charged molecules move toward the "negative" end. As a particle moves towards the pole opposite of its charge it moves through the changing pH gradient until it reaches a point in which the pH of that molecules isoelectric point is reached. At this point the molecule no longer has a net electric charge (due to the protonation or deprotonation of the associated functional groups) and as such will not proceed any further within the gel. The gradient is established before adding the particles of interest by first subjecting a solution of small molecules such as polyampholytes with varying pI values to electrophoresis.

Immunoelectrophoresis

Immunoelectrophoresis is a general name for a number of biochemical methods for separation and characterization of proteins based on electrophoresis and reaction with antibodies. Variants of immunoelectrophoresis typically utilize immunoglobulins, also known as antibodies, reacting with the proteins to be separated or characterized. Agarose as 1% gel slabs of about 1 mm thickness buffered at high pH (around 8.6) is traditionally preferred for the electrophoresis as well as the reaction with antibodies. The agarose was chosen as the gel matrix because it has large pores allowing free passage and separation of proteins, but provides an anchor for the immunoprecipitates of protein and specific antibodies. The high pH was chosen because antibodies are practically immobile at high pH. Electrophoresis equipment with a horizontal cooling plate was normally recommended for the electrophoresis. Immunoprecipitates may be seen in the wet agarose gel, but are stained with protein stains like Coomassie Brilliant Blue in the dried gel. In contrast to SDS-gel electrophoresis, the electrophoresis in agarose allows native conditions, preserving the native structure and activities of the proteins under investigation, therefore immunoelectrophoresis allows characterization of enzyme activities and ligand binding etc. in addition to electrophoretic separation.

Affinity immunoelectrophoresis is based on changes in the electrophoretic pattern of proteins through specific interaction or complex formation with other macromolecules or ligands. Affinity immunoelectrophoresis has been used for estimation of binding constants, as for instance with lectins or for characterization of proteins with specific features like glycan content or ligand binding. Some variants of affinity immunoelectrophoresis are similar to affinity chromatography by use of immobilized ligands. The open structure of the immunoprecipitate in the agarose gel will allow additional binding of radioactively labeled antibodies to reveal specific proteins. This variation has been used for identification of allergens through reaction with IgE.

Electrophoretic Mobility Shift Assay (EMSA)

An electrophoretic mobility shift assay (EMSA) or mobility shift electrophoresis, also referred as a gel shift assay, gel mobility shift assay, band shift assay, or gel retardation assay, is a common affinity electrophoresis technique used to study protein—DNA or protein—RNA interactions. This procedure can determine if a protein or mixture of proteins is capable of binding to a given DNA or RNA sequence, and can sometimes indicate if more than one protein molecule is involved in the binding complex. Gel shift assays are often performed in vitro concurrently with DNase footprinting, primer extension, and promoter-probe experiments when studying transcription initiation, DNA replication, DNA repair or RNA processing and maturation. Although precursors can be found in earlier literature, most current assays are based on methods described by Garner and Revzin and Fried and Crothers.

Restriction Fragment Length Polymorphism Analysis

RFLP analysis. DNA is collected from cells, such as a blood sample, and cut into small pieces using a restriction enzyme. This generates thousands of DNA fragments of differing sizes as a consequence of variations between DNA sequences of different individuals. The fragments are then separated on the basis of size using gel electrophoresis. The separated fragments are then transferred to a nitrocellulose or nylon filter; this procedure is called a Southern blot. The DNA fragments within the blot are permanently fixed to the filter, and the DNA strands are denatured. Radiolabeled probe molecules are then added that are complementary to sequences in the genome that contain repeat sequences. These repeat sequences tend to vary in length among different individuals and are called variable number tandem repeat sequences or VNTRs. The probe molecules hybridize to DNA fragments containing the repeat sequences and excess probe molecules are washed away. The blot is then exposed to an X-ray film. Fragments of DNA that have bound to the probe molecules appear as dark bands on the film.

Zymography

Zymography is an electrophoretic technique for the detection of hydrolytic enzymes, based on the substrate repertoire of the enzyme. In gel zymography, samples are prepared in a standard, non-reducing loading buffer for SDS-PAGE. No reducing agent or boiling are necessary since these would interfere with refolding of the enzyme. A suitable substrate (commonly gelatin or casein) is embedded in the resolving gel during preparation of the acrylamide gel. Following electrophoresis, the SDS is removed from the gel (or zymogram) by incubation in unbuffered Triton X-100, followed by incubation in an appropriate digestion buffer, for a length of time at 37° C. The zymogram is subsequently stained (commonly with Amido Black or Coomassie Brilliant Blue), and areas of digestion appear as clear bands against a darkly stained background where the substrate has been degraded by the enzyme.

Gene Expression Profiling

Exemplary gene expression profiling techniques that may be utilized include DNA profiling with PCR, DNA microarrays, SAGE, real-time PCR, differential display PCR, and RNA-seq, as further described in the following sections and as known in the art.

DNA Profiling with PCR

The polymerase chain reaction (PCR) process mimics the biological process of DNA replication, but confines it to specific DNA sequences of interest. With the disclosure of the PCR technique, DNA profiling took huge strides forward in both discriminating power and the ability to recover information from very small (or degraded) starting samples. PCR greatly amplifies the amounts of a specific region of DNA. In the PCR process, the DNA sample is denatured into the separate individual polynucleotide strands through heating. Two oligonucleotide DNA primers are used to hybridize to two corresponding nearby sites on opposite DNA strands in such a fashion that the normal enzymatic extension of the active terminal of each primer (that is, the 3' end) leads toward the other primer. PCR uses replication enzymes that are tolerant of high temperatures, such as the thermostable Taq polymerase. In this fashion, two new copies of the sequence of interest are generated. Repeated denaturation, hybridization, and extension in this fashion produce an exponentially growing number of copies of the DNA of interest. Instruments that perform thermal cycling are now readily available from commercial sources. This process can produce a million-fold or greater amplification of the desired region in 2 hours or less.

DNA Microarray

The core principle behind microarrays is hybridization between two DNA strands, the property of complementary nucleic acid sequences to specifically pair with each other by forming hydrogen bonds between complementary nucleotide base pairs. A high number of complementary base pairs in a nucleotide sequence means tighter non-covalent bonding between the two strands. After washing off non-specific bonding sequences, only strongly paired strands will remain hybridized. Fluorescently labeled target sequences that bind to a probe sequence generate a signal that depends on the hybridization conditions (such as temperature), and washing after hybridization. Total strength of the signal, from a spot (feature), depends upon the amount of target sample binding to the probes present on that spot. Microarrays use relative quantitation in which the intensity of a feature is compared to the intensity of the same feature under a different condition, and the identity of the feature is known by its position.

Serial Analysis of Gene Expression (SAGE)

Serial analysis of gene expression (SAGE) is a technique used by molecular biologists to produce a snapshot of the messenger RNA population in a sample of interest in the form of small tags that correspond to fragments of those transcripts. Briefly, SAGE experiments proceed as follows:

The mRNA of an input sample (e.g., a tumour) is isolated and a reverse transcriptase and biotinylated primers are used to synthesize cDNA from mRNA.

The cDNA is bound to Streptavidin beads via interaction with the biotin attached to the primers, and is then cleaved using a restriction endonuclease called an anchoring enzyme (AE). The location of the cleavage site and thus the length of the remaining cDNA bound to the bead will vary for each individual cDNA (mRNA).

The cleaved cDNA downstream from the cleavage site is then discarded, and the remaining immobile cDNA fragments upstream from cleavage sites are divided in half and exposed to one of two adapter oligonucleotides (A or B) containing several components in the following order upstream from the attachment site: 1) Sticky ends with the AE cut site to allow for attachment to cleaved cDNA; 2) A recognition site for a restriction endonuclease known as the tagging enzyme (TE), which cuts about 15 nucleotides downstream of its recognition site (within the original cDNA/mRNA sequence); 3) A short primer sequence unique to either adapter A or B, which will later be used for further amplification via PCR.

After adapter ligation, cDNA are cleaved using TE to remove them from the beads, leaving only a short "tag" of about 11 nucleotides of original cDNA (15 nucleotides minus the 4 corresponding to the AE recognition site).

The cleaved cDNA tags are then repaired with DNA polymerase to produce blunt end cDNA fragments.

These cDNA tag fragments (with adapter primers and AE and TE recognition sites attached) are ligated, sandwiching the two tag sequences together, and flanking adapters A and B at either end. These new constructs, called ditags, are then PCR amplified using anchor A and B specific primers.

The ditags are then cleaved using the original AE, and allowed to link together with other ditags, which will be ligated to create a cDNA concatemer with each ditag being separated by the AE recognition site.

These concatemers are then transformed into bacteria for amplification through bacterial replication.

The cDNA concatemers can then be isolated and sequenced using modern high-throughput DNA sequencers, and these sequences can be analyzed with computer programs which quantify the recurrence of individual tags.

Real-Time Polymerase Chain Reaction

A real-time polymerase chain reaction is a laboratory technique of molecular biology based on the polymerase chain reaction (PCR). It monitors the amplification of a targeted DNA molecule during the PCR, i.e. in real-time, and not at its end, as in conventional PCR. Real-time PCR can be used quantitatively (Quantitative real-time PCR), semi-quantitatively, i.e. above/below a certain amount of DNA molecules (Semi quantitative real-time PCR) or qualitatively (Qualitative real-time PCR). Two common methods for the detection of PCR products in real-time PCR are: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. Real-time PCR is carried out in a thermal cycler with the capacity to illuminate each sample with a beam of light of at least one specified wavelength and detect the fluorescence emitted by the excited fluorophore. The thermal cycler is also able to rapidly heat and chill samples, thereby taking advantage of the physicochemical properties of the nucleic acids and DNA polymerase. The PCR process generally consists of a series of temperature changes that are repeated 25-50 times. These cycles normally consist of three stages: the first, at around 95° C., allows the separation of the double chain; the second, at a temperature of around 50-60° C., allows the binding of the primers with the DNA template; the third, at between 68-72° C., facilitates the polymerization carried out by the DNA polymerase. Due to the small size of the fragments the last step is usually omitted in this type of PCR as the enzyme is able to increase their number during the change between the alignment stage and the denaturing stage. In addition, in four steps PCR the fluorescence is measured during short temperature phase lasting only a few seconds in each cycle, with a temperature of, for example, 80° C., in order to reduce the signal caused by the presence of primer dimers when a non-specific dye is used. The temperatures and the timings used for each cycle depend on a wide variety of parameters, such as: the enzyme used to synthesize the DNA, the concentration of divalent ions and deoxyribonucleotides (dNTPs) in the reaction and the bonding temperature of the primers.

Differential Display PCR

Differential display (also referred to as DDRT-PCR or DD-PCR) is the technique where a researcher can compare and identify changes in gene expression at the mRNA level between any pair of eukaryotic cell samples. The assay may be extended to more than one pair, if needed. The paired samples will have morphological, genetic or other experimental differences for which the researcher wishes to study the gene expression patterns, hoping to elucidate the root cause of the particular difference or specific genes that are affected by the experiment. The concept of differential display is to use a limited number of short arbitrary primers in combination with the anchored oligo-dT primers to systematically amplify and visualize most of the mRNA in a cell. After its disclosure in the early 1990s, differential display became a common technique for identifying differentially expressed genes at the mRNA level. Different streamlined DD-PCR protocols have been proposed including fluorescent DD process as well as radioactive labeling, which offers high accuracy and readout.

RNA-Sequencing (RNA-Seq)

RNA sequencing (RNA-seq), also called whole transcriptome shotgun sequencing (WTSS), is a technology that uses the capabilities of next-generation sequencing to reveal a snapshot of RNA presence and quantity from a genome at a given moment in time.

RNA 'Poly(A)' Library RNA-seq: Creation of a sequence library can change from platform to platform in high throughput sequencing, where each has several kits designed to build different types of libraries and adapting the resulting sequences to the specific requirements of their instruments. However, due to the nature of the template being analyzed, there are commonalities within each technology. Frequently, in mRNA analysis the 3' polyadenylated (poly(A)) tail is targeted in order to ensure that coding RNA is separated from noncoding RNA. This can be accomplished simply with poly (T) oligos covalently attached to a given substrate. Presently many studies utilize magnetic beads for this step. Studies including portions of the transcriptome outside poly(A) RNAs have shown that when using poly(T) magnetic beads, the flow-through RNA (non-poly(A) RNA) can yield important noncoding RNA gene discovery which would have otherwise gone unnoticed. Also, since ribosomal RNA represents over 90% of the RNA within a given cell, studies have shown that its removal via probe hybridization increases the capacity to retrieve data from the remaining portion of the transcriptome. The next step is reverse transcription. Due to the 5' bias of randomly primed-reverse transcription as well as secondary structures influencing primer binding sites, hydrolysis of RNA into 200-300 nucleotides prior to reverse transcription reduces both problems simultaneously. However, there are trade-offs with this method where although the overall body of the transcripts are efficiently converted to DNA, the 5' and 3' ends are less so. Depending on the aim of the study, researchers may choose to apply or ignore this step.

Small RNA/non-coding RNA sequencing: When sequencing RNA other than mRNA, the library preparation is modified. The cellular RNA is selected based on the desired size range. For small RNA targets, such as miRNA, the RNA is isolated through size selection. This can be performed with a size exclusion gel, through size selection magnetic beads, or with a commercially developed kit. Once isolated, linkers are added to the 3' and 5' end then purified. The final step is cDNA generation through reverse transcription.

Direct RNA Sequencing: As converting RNA into cDNA using reverse transcriptase has been shown to introduce biases and artifacts that may interfere with both the proper characterization and quantification of transcripts, single molecule Direct RNA Sequencing (DRS™) technology was under development by Helicos™ (now bankrupt). DRS™ sequences RNA molecules directly in a massively-parallel manner without RNA conversion to cDNA or other biasing sample manipulations such as ligation and amplification. Once the cDNA is synthesized it can be further fragmented to reach the desired fragment length of the sequencing system.

(Protein) Mass Spectrometry

Protein mass spectrometry refers to the application of mass spectrometry to the study of proteins. Mass spectrometry is an important emerging method for the characterization of proteins. The two primary methods for ionization of whole proteins are electrospray ionization (ESI) and matrix-assisted laser desorption/ionization (MALDI). In keeping with the performance and mass range of available mass spectrometers, two approaches are used for characterizing proteins. In the first, intact proteins are ionized by either of the two techniques described above, and then introduced to a mass analyzer. This approach is referred to as "top-down" strategy of protein analysis. In the second, proteins are enzymatically digested into smaller peptides using a protease such as trypsin. Subsequently these peptides are introduced into the mass spectrometer and identified by peptide mass fingerprinting or tandem mass spectrometry. Hence, this latter approach (also called "bottom-up" proteomics) uses identification at the peptide level to infer the existence of proteins. Whole protein mass analysis is primarily conducted using either time-of-flight (TOF) MS, or Fourier transform ion cyclotron resonance (FT-ICR). These two types of instrument are preferable here because of their wide mass range, and in the case of FT-ICR, its high mass accuracy. Mass analysis of proteolytic peptides is a much more popular method of protein characterization, as cheaper instrument designs can be used for characterization. Additionally, sample preparation is easier once whole proteins have been digested into smaller peptide fragments. The most widely used instrument for peptide mass analysis are the MALDI time-of-flight instruments as they permit the acquisition of peptide mass fingerprints (PMFs) at high pace (1 PMF can be analyzed in approx. 10 sec). Multiple stage quadrupole-time-of-flight and the quadrupole ion trap also find use in this application.

Mass spectrometry CMS has been increasingly used for bioanalytical analyses. Mass spectrometry is well suited for multiplexing because mass differentiation allows many simultaneous detection channels. However, complex biomolecules, such as DNA, have complex mass spectra and may be difficult to detect in a matrix due to relatively poor sensitivity. MS is an analytical technique that measures the mass-to-charge ratio of charged species. It can be used for determining the chemical composition of a sample or molecule. Samples analyzed by mass spectrometry are ionized to generate charged molecules or atoms, separated according to their mass-to-charge ratios, and detected. The technique is used both qualitatively and quantitatively according to various applications. Inductively coupled plasmas OCP) are a type of plasma source in which the energy is supplied by electric currents which are produced by electromagnetic induction, that is, by time-varying magnetic fields. ICP can be used as an ionization source for mass spectrometry. The combination of inductively-coupled plasma and mass spectrometry is referred to as ICP-MS. Mass spectral imaging (MSI) is an application of mass spectrometry that involves analyzing chemical information with spatial information such that the chemical information can be visualized as a chemical image or map. By generating a chemical map, compositional differences across the sample surface can be elucidated. Laser ablation is the process of removing material from a solid surface by irradiating it with a laser beam. Laser ablation has been used as a means of sampling materials for mass spectrometry, in particular for mass spectral imaging. According to one embodiment, a system for sample mass spectral imaging includes a laser ablation sampler, an inductively-coupled plasma ionizer, a mass spectrometer, and a computer. Illustratively, the laser ablation sampler comprises a laser, a laser ablation chamber, and a sample platform configured such that the laser can irradiate a sample positioned on the sample platform to form an ablated sample, wherein the laser and the sample platform are coordinated by the computer. The laser ablation sampler and inductively-coupled plasma ionizer are operably connected so that the ablated sample can be transferred from the laser ablation sampler into the inductively-coupled plasma ionizer, thereby evaporating, vaporizing, atomizing, and ionizing the ablated sample to form an atomic ion population having a mass-to-charge ratio distribution. The mass spectrometer is operably connected to the inductively-coupled plasma ionizer so that the ion population can be transferred from the inductively-coupled plasma ionizer to the mass spectrometer, wherein the mass spectrometer separates the ion population according to the mass-to-charge ratio distribution, thereby generating mass-to-charge ratio data. The computer is configured to accept location inputs and communicate with the laser ablation sampler so as to ablate the sample according to the location inputs and it is configured to relate the mass-to-charge ratio data to a location on the sample according to the location inputs. In further illustrative embodiments, the system further comprises a registration system configured to determine the position of the sample, thereby enabling automatic relation of the location inputs to the location on the sample upon which the laser is configured to irradiate. In illustrative embodiments, a composition for multiplexed sample LA-ICP-MS assays includes a mass tag and a specific binding moiety conjugated to the mass tag. The mass tag includes a population of atoms of a first kind that is detectably distinct from elements endogenous to a sample. In one embodiment, the population of atoms of the first kind is a non-endogenous stable isotope of an element. In another embodiment, the population of atoms is configured as a colloidal particle. See WO2014079802, which is hereby incorporated by reference in its entirety.

A method for detecting a target in a sample concerns contacting a sample with an enzyme-specific binding moiety conjugate selected to recognize the target. The sample then is contacted with a mass tag precursor conjugate, comprising a mass tag precursor and an enzyme substrate, a tyramine moiety, or a tyramine derivative, and an optional linker. The mass tag precursor conjugate undergoes reaction with the enzyme or with the product of the enzymatic reaction to produce precipitated mass tags, covalently bound mass tags, or non-covalently bound mass tags. The sample is exposed to an energy source, which provides sufficient energy to produce a mass code from the mass tag. After ionization, the mass code can be detected using a detection method, such as mass spectrometry. In some embodiments, the sample is exposed to a first solution comprising the enzyme-specific binding moiety conjugate and a second solution comprising the mass tag precursor conjugate. Enzyme moieties of the enzyme-specific binding moiety can be selected from oxidoreductase enzymes (e.g. peroxidases), phosphatases (e.g. alkaline phosphatase), lactamases (e.g. (3-lactamase), and galactosidases (e.g. β-D-galactosidase, (3-galactosidase). Specific binding moieties can be selected from a protein, a polypeptide, an oligopeptide, a peptide, a nucleic acid, DNA, RNA, an oligosaccharide, a polysaccharide, and monomers thereof. Particular disclosed embodiments concern using alkaline phosphatase-antibody conjugates and horseradish peroxidase-antibody conjugates. In some disclosed embodiments, a specific binding moiety recognizes the target. In other disclosed embodiments, the specific binding moiety recognizes a primary antibody bound to the target. In some embodiments, depositing a mass tag includes immobilizing an enzyme at a target, and contacting the sample with an enzyme substrate moiety and a mass tag precursor. The enzyme substrate moiety reacts with the enzyme and the mass tag precursor to produce and deposit a mass tag at the target. When two or more targets are present in the sample, mass tags are deposited sequentially at each target as described above. After a mass tag is deposited, the corresponding enzyme is deactivated prior to depositing a subsequent mass tag at a subsequent target. In other disclosed embodiments, the enzyme reacts with a mass tag precursor-tyramine conjugate or a mass tag precursor-tyramine derivative conjugate to deposit, typically covalently, the mass tag proximal to the target. In some embodiments, immobilizing an enzyme at a target includes contacting the sample with a conjugate comprising a specific binding moiety and an enzyme. In certain embodiments, the specific binding moiety is an antibody. The specific binding moiety is capable of recognizing and binding directly to the target or to another specific binding moiety previously bound to the target. In particular embodiments, the first enzyme, the second enzyme, and any additional enzyme are the same. See WO2012003478, which is hereby incorporated by reference in its entirety.

DNA Methylation Detection

Recently, methods of diagnosing cancer through the measurement of DNA methylation have been suggested. DNA methylation occurs mainly on the cytosine of CpG islands in the promoter region of a specific gene to interfere with the binding of transcription factors, thus silencing the expression of the gene. Thus, detecting the methylation of CpG islands in the promoter of tumor inhibitory genes greatly assists in cancer research. Recently, an attempt has been actively made to determine promoter methylation, by methods such as methylation-specific PCR (hereinafter referred to as MSP) or automatic DNA sequencing, for the diagnosis and screening of cancer. See WO2009069984A2, which is hereby incorporated by reference in its entirety.

Acoustic Energy

At least some embodiments are directed to methods and systems for analyzing a specimen. The specimen can be analyzed based on its properties. These properties include acoustic properties, mechanical properties, optical properties, or the like that may be static or dynamic during processing. In some embodiments, the properties of the specimen are continuously or periodically monitored during processing to evaluate the state and condition of the specimen. Based on obtained information, processing can be controlled to enhance processing consistency, reduce processing times, improve processing quality, or the like. Acoustics can be used to analyze soft objects, such as samples. When an acoustical signal interacts with a sample, the transmitted signal depends on several mechanical properties of the sample, such as elasticity and firmness. As samples that have been placed into fixative (e.g., formalin) become more heavily cross-linked, the speed of transmission will change according to the properties of the sample. In some embodiments, a status of a biological sample can be monitored based on a time of flight of acoustic waves. The status can be a density status, fixation status, staining status, or the like. Monitoring can include, without limitation, measuring changes in sample density, cross-linking, decalcification, stain coloration, or the like. The biological sample can be non-fluidic samples, such as bone, or other type of sample. In some embodiments, methods and systems are directed to using acoustic energy to monitor a specimen. Based on interaction between the acoustic energy in reflected and/or transmission modes, information about the specimen may be obtained. Acoustic measurements can be taken. Examples of measurements include acoustic signal amplitude, attenuation, scatter, absorption, time of flight (TOF) in the specimen, phase shifts of acoustic waves, or combinations thereof. The specimen, in some embodiments, has properties that change during processing. In some embodiments, a fixative is applied to the specimen. As the specimen becomes more fixed, mechanical properties (e.g., elasticity, stiffness, etc.) change due to molecular crosslinking. These changes can be monitored using sound speed measurements via TOF. Based on the measurements, a fixative state or other histological state of the specimen can be determined. To avoid under-fixation or over-fixation, the static characteristics of the sample, dynamic characteristics of the sample, or both can be monitored. Characteristics of the sample include transmission characteristics, reflectance characteristics, absorption characteristics, attenuation characteristics, or the like. In certain embodiments, a method for evaluating a sample includes analyzing acoustic wave speed before, during and/or after sample processing. This is accomplished by first establishing a baseline measurement for a fresh, unfixed sample by delivering an acoustic wave from a transmitter to the sample taken from a subject. The baseline TOF acoustic wave is detected using a receiver. After or during processing the sample, a second acoustic wave is delivered from the transmitter to the sample. The second TOF acoustic wave is detected using the receiver after the second acoustic wave has traveled through the sample. Sound speeds in the sample are compared based on the first TOF and the second TOF to determine a change in speed. These measurements can be unique for each sample analyzed and therefore used to establish a baseline for each sample. Additional TOF measurements can be used to determine TOF contributions attributable to the media, measurement channel, or the like. In some embodiments, the TOF of the media is measured when no specimen is present to determine a baseline TOF of the media. See WO2011109769, which is hereby incorporated by reference in its entirety.

Lipidomics

Lipidomics research involves the identification and quantification of the thousands of cellular lipid molecular species and their interactions with other lipids, proteins, and other metabolites. Investigators in lipidomics examine the structures, functions, interactions, and dynamics of cellular lipids and the changes that occur during perturbation of the system. Lipidomic analysis techniques can include mass spectrometry (MS), nuclear magnetic resonance (NMR) spectroscopy, fluorescence spectroscopy, dual polarization interferometry and computational methods. In lipidomic research, data quantitatively describing the spatial and temporal alterations in the content and composition of different lipid molecular species is accrued after perturbation of cells through changes in its physiological or pathological state. Information obtained from these studies facilitates mechanistic insights into changes in cellular function.

Quantification of Immune Cells

Immune cell quantification in samples can occur through using epigenetic-based, quantitative real-time PCR assisted cell counting (qPACC). The methylation status of the chromatin structure of either actively expressed or silenced genes is the basis of the epigenetic-based cell identification and quantification technology. Discovery of cell type specific removal of methyl groups (demethylation) from the 5'-carbon of the cytosine base in the dinucleotide cytosine phosphate guanine permits precise and robust quantification of immune cells from only small amounts of human blood or tissue samples. These epigenetic biomarkers located on genomic DNA are stably associated with cells of interest. Kleen and Yuan (November 2015). "Quantitative real-time PCR assisted cell counting (qPACC) for epigenetic-based immune cell quantification in blood and tissue". J. Immunother. Cancer 46 (3).

Detection of Cancer-Associated Markers

Detection of "tumor markers", including but not limited to proteins, antigens, enzymes, hormones, DNA mutations, and carbohydrates associated with the presence of a cancer, using techniques such as but not limited to RNA, DNA, or protein sequencing, is of importance for the correct diagnosis of a cancer-type, and for selection of the appropriate method of treatment. Such markers include but are not limited to alpha fetoprotein (often associated with but not limited to germ cell tumors and hepatocellular carcinomas), CA 15-3 (often associated with but not limited to breast cancer), CA27-29 (often associated with but not limited to breast cancer), CA19-9 (often associated with but not limited to pancreatic cancer, colorectal cancer and other types of gastrointestinal cancer), CA-125 (often associated with but not limited to ovarian cancer, endometrial cancer, fallopian tube cancer, lung cancer, breast cancer and gastrointestinal cancer), calcitonin (often associated with but not limited to medullary thyroid carcinoma), calretinin (often associated with but not limited to mesothelioma, sex cord-gonadal stromal tumour, adrenocortical carcinoma, synovial sarcoma), carcinoembryonic antigen (often associated with but not limited to gastrointestinal cancer, cervix cancer, lung cancer, ovarian cancer, breast cancer, urinary tract cancer), CD34 (often associated with but not limited to hemangiopericytoma/solitary fibrous tumor, pleomorphic lipoma, gastrointestinal stromal tumor, dermatofibrosarcoma protuberans), CD99MIC 2 (often associated with but not limited to Ewing sarcoma, primitive neuroectodermal tumor, hemangiopericytoma/solitary fibrous tumor, synovial sarcoma, lymphoma, leukemia, sex cord-gonadal stromal tumor), CD117 (often associated with but not limited to gastrointestinal stromal tumor, mastocytosis, seminoma), chromogranin (often associated with but not limited to neuroendocrine tumor), chromosomes 3, 7, 17, and 9p21 (often associated with but not limited to bladder cancer), various types of cytokeratin (often associated with but not limited to many types of carcinoma and some types of sarcoma), desmin (often associated with but not limited to smooth muscle sarcoma, skeletal muscle sarcoma, and endometrial stromal sarcoma), epithelial membrane antigen (often associated with but not limited to various types of carcinoma, meningioma, and some types of sarcoma), Factor VIII/CD31 FL1 (often associated with but not limited to vascular sarcoma), glial fibrillary acidic protein (often associated with but not limited to glioma (astrocytoma, ependymoma)), gross cystic disease fluid protein (often associated with but not limited to breast cancer, ovarian cancer, and salivary gland cancer), HMB-45 (often associated with but not limited to melanoma, PEComa (for example angiomyolipoma), clear cell carcinoma, adrenocortical carcinoma), human chorionic gonadotropin (often associated with but not limited to gestational trophoblastic disease, germ cell tumor, and choriocarcinoma), immunoglobulin (often associated with but not limited to lymphoma, leukemia), inhibin (often associated with but not limited to sex cord-gonadal stromal tumour, adrenocortical carcinoma, hemangioblastoma), various types of keratin (often associated with but not limited to carcinoma, some types of sarcoma), various types of lymphocyte markers (often associated with but not limited to lymphoma, leukemia), MART-1 (Melan-A) (often associated with but not limited to melanoma, steroid-producing tumors (adrenocortical carcinoma, gonadal tumor)), Myo D1 (often associated with but not limited to rhabdomyosarcoma, small, round, blue cell tumor), muscle-specific actin (MSA) (often associated with but not limited to myosarcoma (leiomyosarcoma, rhabdomyosarcoma)), neurofilament (often associated with but not limited to neuroendocrine tumor, small-cell carcinoma of the lung), neuron-specific enolase (often associated with but not limited to neuroendocrine tumor, small-cell carcinoma of the lung, breast cancer), placental alkaline phosphatase (PLAP) (often associated with but not limited to seminoma, dysgerminoma, embryonal carcinoma), prostate-specific antigen (often associated with but not limited to prostate cancer), PTPRC (CD45) (often associated with but not limited to lymphoma, leukemia, histiocytic tumor), S100 protein (often associated with but not limited to melanoma, sarcoma (neurosarcoma, lipoma, chondrosarcoma), astrocytoma, gastrointestinal stromal tumor, salivary gland cancer, some types of adenocarcinoma, histiocytic tumor (dendritic cell, macrophage)), smooth muscle actin (SMA) (often associated with but not limited to gastrointestinal stromal tumor, leiomyosarcoma, PEComa), synaptophysin (often associated with but not limited to neuroendocrine tumor), thyroglobulin (often associated with but not limited to a postoperative marker of thyroid cancer), thyroid transcription factor-1 (often associated with but not limited to all types of thyroid cancer, lung cancer), Tumor M2-PK (often associated with but not limited to colorectal cancer, breast cancer, renal cell carcinoma, lung cancer, pancreatic cancer, esophageal cancer, stomach cancer, cervical cancer, ovarian cancer), vimentin (often associated with but not limited to sarcoma, renal cell carcinoma, endometrial cancer, lung carcinoma, lymphoma, leukemia, melanoma), ALK gene rearrangements (often associated with but not limited to non-small-cell lung cancer and anaplastic large cell lymphoma), Beta-2-microglobulin (B2M) (often associated with but not limited to Multiple myeloma, chronic lymphocytic leukemia, and some lymphomas), Beta-human chorionic gonadotropin (Beta-hCG) (often associated with but not limited to choriocarcinoma and germ cell tumors), BRCA1 and BRCA2 gene mutations (often associated with but not limited to ovarian cancer), BCR-ABL fusion gene (Philadelphia chromosome) (often associated with but not limited to chronic myeloid leukemia, acute lymphoblastic leukemia, and acute myelogenous leukemia), BRAF V600 mutations (often associated with but not limited to Cutaneous melanoma and colorectal cancer), CD20 (often associated with but not limited to Non-Hodgkin lymphoma), Chromogranin A (CgA) (often associated with but not limited to Neuroendocrine tumors), Circulating tumor cells of epithelial origin (CELLSEARCH®) (often associated with but not limited to Metastatic breast, prostate, and colorectal cancers), Cytokeratin fragment 21-1 (often associated with but not limited to lunch cancer), EGFR gene mutation analysis (often associated with but not limited to non-small-cell lung cancer), Estrogen receptor (ER)/progesterone receptor (PR) (often associated with but not limited to breast cancer), HE4 (often associated with but not limited to ovarian cancer), KRAS gene mutation analysis (often associated with but not limited to Colorectal cancer and non-small cell lung cancer), Lactate dehydrogenase (often associated with but not limited to Germ cell tumors, lymphoma, leukemia, melanoma, and neuroblastoma), Neuron-specific enolase (NSE) (often associated with but limited to Small cell lung cancer and neuroblastoma), Nuclear matrix protein 22 (often associated with but not limited to bladder cancer), Programmed death ligand 1 (PD-L1) (often associated with but not limited to non-small-cell lung cancer), Urokinase plasminogen activator (uPA) and plasminogen activator inhibitor (PAI-1) (often associated with but not limited to breast cancer), 5-Protein signature (OVAL®) (often associated with but not limited to ovarian cancer), 21-Gene signature (Oncotype DX®) (often associated with breast cancer), 70-Gene signature (Mammaprint®) (often associated with but not limited to breast cancer), and HER2/neu gene amplification or overexpression (often associated with but not limited to breast cancer, ovarian cancer, gastroesophageal junction adenocarcinoma, stomach cancer, non-small-cell lung cancers and uterine cancer). Additional biomarkers associated with tumors may include but are not limited to a P13KCA mutation, a FGFR2 amplification, a p53 mutation, a BRCA mutation, a CCND1 amplification, a MAP2K4 mutation, an ATR mutation, or any other biomarker the expression of which is correlated to a specific cancer; at least one of AFP, ALK, BCR-ABL, BRCA1/BRCA2, BRAF, V600E, Ca-125, CA19.9, EGFR, Her-2, KIT, PSA, S100, KRAS, ER/Pr, UGT1A1, CD30, CD20, F1P1L1-PDGRFα, PDGFR, TMPT, and TMPRSS2; or at least one biomarker selected from ABCB5, AFP-L3, Alpha-fetoprotein, Alpha-methyl acyl-CoA racemase, BRCA1, BRCA2, CA 15-3, CA 242, Ca 27-29, CA-125, CA15-3, CA19-9, Calcitonin, Carcinoembryonic antigen, Carcinoembryonic antigen peptide-1, Des-gamma carboxy prothrombin, Desmin, Early prostate cancer antigen-2, Estrogen receptor, Fibrin degradation product, Glucose-6-phosphate isomerase, an HPV antigen such as vE6, E7, L1, L2 or p16INK4a Human chorionic gonadotropin, IL-6, Keratin 19, Lactate dehydrogenase, Leucyl aminopeptidase, Lipotropin, Metanephrines, Neprilysin, NMP22, Normetanephrine, PCA3, Prostate-specific antigen, Prostatic acid phosphatase, Synaptophysin, Thyroglobulin, TNF, a transcription factor selected from ERG, ETV1 (ER81), FLI1, ETS1, ETS2, ELK1, ETV6 (TEL1), ETV7 (TEL2), GABPα, ELF1, ETV4 (E1AF; PEA3), ETV5 (ERM), ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or FEV, Tumor-associated glycoprotein 72, c-kit, SCF, pAKT, pc-kit, and Vimentin. Alternatively, or in addition the biomarker of interest may be an immune checkpoint inhibitor such as, but not limited to, CTLA-4, PDL1, PDL2, PD1, B7-H3, B7-H4, BTLA, HVEM, KIR, TIM3, GAL9, GITR, LAG3, VISTA, KIR, 2B4, TRPO2, CD160, CGEN-15049, CHK 1, CHK2, A2aR, TL1A, and B-7 family ligands or a combination thereof or is a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 family ligands, or a combination thereof. Additional markers may include but is not limited to the detection of at least one biomarker associated with acute lymphoblastic leukemia (etv6, am11, cyclophilin b), B cell lymphoma (Ig-idiotype), glioma (E-cadherin, .alpha.-catenin, .beta.-catenin, .gamma.-catenin, p120 ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-C017-1A/GA733, APC), choriocarcinoma (CEA), epithelial cell cancer (cyclophilin b), gastric cancer (HER2/neu, c-erbB-2, ga733 glycoprotein), hepatocellular cancer (.alpha.-fetoprotein), Hodgkin's lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and/or T cell leukemia (HTLV-1 epitopes).

Precise targeting of specific aspects of kinase cascades is now known to provide previously unattainable breakthroughs for disease therapies. The importance of the protein kinase family is underscored by the numerous disease states that arise due to dysregulation of kinase activity. Aberrant cell signaling by many of these protein and lipid kinases can lead to diseases, such as cancer. Several protein serine/threonine and tyrosine kinases are known to be activated in cancer cells and to drive tumour growth and progression. The technology described herein provides methods for enriching (or isolating) kinases, for example ATP-dependent kinases, utilizing one or more kinase capture agents. Examples of kinase capture agents include, but are not limited to, relatively non-selective protein kinase inhibitors, substrates or pseudosubstrates. The methods are useful, for example, for profiling of kinomes by tandem mass spectrometry. Although many highly selective and potent small molecule kinase inhibitors have been previously identified, as is described herein above, a large number of relatively non-selective small molecule kinase inhibitors have also been identified. For the methods described herein, use of relatively non-selective small molecule kinase inhibitors reduces the need for tailoring purification procedures for individual kinases, and amplifies the analytical signal obtained by enriching enzymes normally present in cells, tissues and bodily fluids at only catalytic concentrations. However, it will be recognized that selective small molecule kinase inhibitors also can be useful in these kinase analysis methods. In addition, a combination of a non-selective and a selective small molecule kinase inhibitor can be useful in these methods. Furthermore, a kinase capture agent (or more than one kinase capture agent) can also be combined with a phosphatase capture agent to enrich (or isolate) kinases and phosphatases concurrently. The methods described herein also can be applied to multiplexed analysis of protein kinases and/or phosphatases by tandem mass spectrometry from a single or multiple specimens. The technology described herein provides a method for analyzing a population of kinases, such as a kinome. The method involves separating kinases from a sample using one or more kinase capture agents, proteolytically digesting a protein sample to constituent peptides (for example with a protease such as trypsin), supplementing the obtained peptides with rationally designed calibrator peptides relating to particular protein kinase peptide sequences that contain scissile aspartate-proline (DP) bonds, and quantifying the native peptides derived from the kinase population by tandem mass spectrometry. Strategies for profiling the relative abundance of protein and lipid kinases in multiple samples using isobaric peptide tags containing scissile DP bonds are also described. One of skill in the art will recognize that similar methodology can be applied to analyze phosphatases or a combination of kinases and phosphatases. See WO2007131191, which is hereby incorporated by reference in its entirety.

Affinity Purification of Specific Cell Types

Putative circulating tumor cells have now been reported in multiple human tumors including AML, CIVIL, multiple myeloma, brain tumors, breast tumors, melanoma, and prostate cancer, colon cancer, and gastric cancer. In principle, circulating tumor cells can be identified by several experimental strategies. Many circulating tumor cells appear to express the cell surface markers that identify their normal counterparts. This observation provides a relatively simple enrichment procedure utilizing either flow cytometry-based cell sorting or microbeads-based affinity purification of the cells. See Schawb, M. Encyclopedia of Cancer, $3^{rd}$ edition, Springer-Verlag Berlin Heidelberg, 2011.

DNA Sequencing

In further exemplary embodiments, the sample, or one or more cells thereof, may be subjected to DNA sequencing. DNA sequencing may be targeted, e.g., to particular genes, regions, regulatory sequences, introns, exons, SNPs, potential fusions, etc., e.g., to detect sequences associated with cancer or pertinent to the diagnosis thereof. DNA sequencing may also be conducted on the entire genome or a significant portion thereof. Exemplary sequencing methods that may be utilized include, without limitation thereto, Sanger sequencing and dye-terminator sequencing, as well as next-generation sequencing (NGS) technologies such as pyrosequencing, nanopore sequencing, micropore-based sequencing, nanoball sequencing, MPSS, SOLiD™, Solexa®, Ion Torrent™, Starlite, SMRT, tSMS, sequencing by synthesis, sequencing by ligation, mass spectrometry sequencing, polymerase sequencing, RNA polymerase (RNAP) sequencing, microscopy-based sequencing, microfluidic Sanger sequencing, microscopy-based sequencing, RNAP sequencing, tunnelling currents DNA sequencing, and in vitro virus sequencing. See WO2014144478, WO2015058093, WO2014106076 and WO2013068528, each of which is hereby incorporated by reference in its entirety.

DNA sequencing technologies have advanced exponentially. Most recently, high-throughput sequencing (or next-generation sequencing) technologies parallelize the sequencing process, producing thousands or millions of sequences at once. In ultra-high-throughput sequencing as many as 500,000 sequencing-by-synthesis operations may be run in parallel. Next-generation sequencing lowers the costs and greatly increases the speed over the industry standard dye-terminator methods.

Pyrosequencing amplifies DNA inside water droplets in an oil solution (emulsion PCR), with each droplet containing a single DNA template attached to a single primer-coated bead that then forms a clonal colony. The sequencing machine contains many pico liter-volume wells each containing a single bead and sequencing enzymes. Pyrosequencing uses luciferase to generate light for detection of the individual nucleotides added to the nascent DNA, and the combined data are used to generate sequence read-outs. See Margulies, M et al. 2005, Nature, 437, 376-380, which is hereby incorporated by reference in its entirety. Pyrosequencing sequencing is a sequencing-by-synthesis technology that utilizes also utilizes pyrosequencing. Pyrosequencing sequencing of DNA involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed. In another embodiment, pyrosequencing is used to measure gene expression. Pyrosequecing of RNA applies similar to pyrosequencing of DNA, and is accomplished by attaching applications of partial rRNA gene sequencings to microscopic beads and then placing the attachments into individual wells. The attached partial rRNA sequence is then amplified in order to determine the gene expression profile. Sharon Marsh, Pyrosequencing® Protocols in Methods in Molecular Biology, Vol. 373, 15-23 (2007).

Another example of a sequencing technique that can be used in the methods of the provided disclosure is nanopore sequencing (Soni G V and Meller, AClin Chem 53: 1996-2001, 2007, which is hereby incorporated by reference in its entirety). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence. See Bayley, Clin Chem. 2015 January; 61(1):25-31, which is hereby incorporated by reference in its entirety.

Another example of a DNA and RNA detection techniques that may be used in the methods of the provided disclosure is SOLiD™ technology (Applied Biosystems). SOLiD™ technology systems is a ligation based sequencing technology that may utilized to run massively parallel next generation sequencing of both DNA and RNA. In DNA SOLiD™ sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in micro-reactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In other embodiments, SOLiD™ Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997, the contents of each of which are incorporated by reference herein in their entirety).

Another sequencing technique that can be used in the methods of the provided disclosure includes, for example, Helicos™ True Single Molecule Sequencing (tSMS) (Harris T. D. et al. (2008) Science 320: 106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm. The flow cell is then loaded into an instrument, e.g., HeliScope® sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), each of which is incorporated by reference herein in its entirety.

Another example of a sequencing technology that may be used in the methods of the provided disclosure includes the single molecule, real-time (SMRT) technology of Pacific Biosciences to sequence both DNA and RNA. In SMRT, each of the four DNA bases is attached to one of four different fluorescent dyes. These dyes are phospho-linked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated. In order to sequence RNA, the DNA polymerase is replaced with a reverse transcriptase in the ZMW, and the process is followed accordingly.

Another example of a sequencing technique that can be used in the methods of the provided disclosure involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced. Another example of a sequencing technique that can be used in the methods of the provided disclosure involves using an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

DNA nanoball sequencing is a type of high throughput sequencing technology used to determine the entire genomic sequence of an organism. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run. See WO2014122548 and Drmanac et al., Science. 2010 Jan. 1; 327(5961):78-81; Porreca, Nat Biotechnol. 2010 January; 28(1):43-4, each of which is hereby incorporated by reference in its entirety.

Massively Parallel Signature Sequencing (MPSS) was one of the earlier next-generation sequencing technologies. MPSS uses a complex approach of adapter ligation followed by adapter decoding, reading the sequence in increments of four nucleotides.

Polony sequencing combines an in vitro paired-tag library with emulsion PCR, an automated microscope, and ligation-based sequencing chemistry to sequence an *E. coli* genome. The technology was also incorporated into the Applied Biosystems SOLiD™ platform.

In Solexa® sequencing, DNA molecules and primers are first attached on a slide and amplified with polymerase so that local clonal colonies, initially coined "DNA colonies", are formed. To determine the sequence, four types of reversible terminator bases (RT-bases) are added and non-incorporated nucleotides are washed away. Unlike pyrosequencing, the DNA chains are extended one nucleotide at a time and image acquisition can be performed at a delayed moment, allowing for large arrays of DNA colonies to be captured by sequential images taken from a single camera. SOLiD™ technology employs sequencing by ligation. Here, a pool of all possible oligonucleotides of a fixed length are labeled according to the sequenced position.

Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Solexa® sequencing.

In Ion Torrent™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H+), which signal detected and recorded in a sequencing instrument. The signal strength is proportional to the number of nucleotides incorporated. Ion Torrent™ data may also be output as a FASTQ file. See U.S. publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each of which is hereby incorporated by reference in its entirety.

Detection of Cancer Associated Fusion Proteins

Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulate the prostate cancer. Most fusion genes are found from hematological cancers, sarcomas, and prostate cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Presence of certain chromosomal aberrations and their resulting fusion genes is commonly used within cancer diagnostics in order to set a precise diagnosis. Chromosome banding analysis, fluorescence in situ hybridization (FISH), reverse transcription polymerase chain reaction (RT-PCR), and next generation sequencing (exome and/or transcriptome) are common methods employed at diagnostic laboratories for identification of cancer-associated fusion proteins.

Detection of Chemotherapy Resistance Markers

Drug resistance is a cause of the failure of chemotherapy of malignant tumors, resistance being either preexisting (intrinsic resistance) or induced by the drugs (acquired resistance). The detection of resistant markers are based on but not limited to the identification of carcinoma-associated fibroblasts through immunohistochemistry and flow cytometry, aldehyde dehydrogenase 1, cleaved caspase 3, cyclooxygenase 2, phosphorylated Akt, Ki-67, and H2AX proteins using immunohistochemical staining, P-glycoprotein expression, hyaluronan, (the major glycosaminoglycan component of the extracellular matrix), gain in 3q26.2, and losses in 6q11.2-12, 9p22.3, 9p22.2-22.1, 9p22.1-21.3, Xp22.2-22.12, Xp22.11-11.3, and Xp11.23-11.1 as identified through whole genome array comparative genomic hybridization, LRP overexpression as identified through immunostaining, HGF and c-MET which are gene products related to the microRNA MiR-193a-5p using RNA sequencing, CD44 overexpression identified through cell sorting, and trichostatin A, a potent inhibitor of histone deactylases. Chemotherapy resistance markers may often take the form of overexpression of a protein, identification of this overexpression at either/or the DNA, RNA, or protein level using techniques such as but not limited to DNA sequencing, RNA sequencing, and protein sequencing. Some chemotherapy resistance markers take the form of epigenetic changes, and the identification of these alterations through DNA pyrosequencing can be of particular use to identification of chemotherapy resistance markers. Additionally, mutations to genes may directly affect the expression of the gene product, potentially leading to the formation of cancerous cells, and the identification of gene mutations through DNA sequencing is of high utility. At present, resistance is usually diagnosed during treatment after a long period of drug administration. Over time, specific mutations can be found that confer resistance to tyrosine kinase inhibitors, for instance inhibitors of the Epithelial Growth Factor Receptor (EGFR). Detection of mutations such as the T790M in the EGFR gene using PCR or DNA sequencing indicate resistance to EGFR tyrosine kinase inhibition and would eliminate the possibility of treating patients with such inhibitors, especially in the case of non-small cell lung cancer. Methods for a rapid assessment of drug resistance exist currently. Three classes of test procedures are generally used: fresh tumor cell culture tests, cancer biomarker tests and positron emission tomography (PET) tests. Drug resistance can be diagnosed before treatment in-vitro with fresh tumor cell culture tests, and after a short time of treatment in-vivo with PET tests. See Lippert, T. et al. (2011). "Current status of methods to assess cancer drug resistance". Int. J. Med. Sci. 8 (3): 245-253.

Moreover, as the presence of tumor cells within draining lymph nodes is indicative of the metastatic potential of cancer, determining the resistance profile of tumor cells that have already escaped the primary tumor is of utmost importance. Representative sampling of excised lymph nodes (or other lymphatic tissues) followed by the above methods for assessing therapeutic resistance will be of high utility. The lymphatic system include lymph nodes (such as cervical lymph nodes, lumbar lymph nodes, pelvic lymph nodes, inguinal lymph nodes, and auxiliary lymph nodes) as well as other organs composed of lymphatic tissue (such as the spleen and the thymus), and should be understood to also include lymphatics of the mammary gland, cisterna chyli, lymphatics of the lower limb, thoracic duct, and lymphatics of the upper limb). Currently, the analysis of resistance markers in lymph nodes and lymphatic tissue is not practical because of the limited amount of sample. However, the representative sampling methods disclosed herein provide a way to characterize the genomic profile of this tissue.

Use of Representative Samples for the Production of Tumor Specific Antigens or Tumor Specific Antibodies and Antitumor Vaccines As mentioned supra, another application of the subject samples is for the isolation of tumor cells and antigens derived therefrom which may be used in the production of tumor specific antibodies or in the manufacture of cancer or tumor vaccines.

One approach to cancer vaccination is to separate proteins from cancer cells and immunize cancer patients against those proteins, in the hope of stimulating an immune reaction that could kill the cancer cells. Therapeutic cancer vaccines are being developed for the treatment of breast, lung, colon, skin, kidney, prostate, and other cancers. In fact, one such vaccine developed by Dendreon Corporation for treating prostate cancer received U.S. Food and Drug Administration (FDA) approval for use in the treatment of advanced prostate cancer patients on Apr. 29, 2010. The approval of this vaccine Provenge® has stimulated renewed interest in this type of therapy.

For example, tumor cells or proteolytically-cleaved cell surface antigens derived from tumor cells identified in homogenized tumor samples according to the disclosure may be used in developing effective therapeutic or prophylactic tumor vaccines. These antigens may be naked or multimerized or conjugated to other moieties, e.g., other proteins, adjuvants or loaded onto cells, e.g., dendritic cells. It has been shown that the proteolytic treatment of live cancer cells can release antigenic targets that are sufficient to induce an anti-cancer immune response that exceeds that of untreated cancer cells in vitro. (Lokhov et al., J Cancer 2010 1:230-241).

In particular the disclosure contemplates tumor vaccines containing one or a cocktail of different antigens derived from tumor cells isolated from a particular patient sample, essentially the production of a "personalized cancer vaccine" so that a patient may be treated with immune stimulating moieties specific to their particular tumor type. In general these vaccines will comprise an effective amount of such antigens to generate an effective immune response, e.g., an antigen specific CTL response against tumor cells expressing the particular antigens. As mentioned, in some instances these antigens may be loaded onto other moieties, e.g., dendritic cells. Generally such vaccines will also comprise other immune adjuvants, e.g., cytokines, TLR agonists, TNF/R agonists or antagonists, agents that modulate checkpoint inhibitors and the like. Although, at the most basic level, the representative sample itself may be used directly as a therapeutic. For example, a primary tumor removed from a patient may be homogenized according to the methods disclosed herein and the representative sample reinjected into the patient to generate an immune response against the tumor antigens contained in the sample. The representative sample itself would be expected to contain the most diverse tumor antigen profile as it comprises all subclones (e.g., majority, primary, secondary, low prevalence, etc.).

Also, the disclosure further contemplates the use of such antigens for the production of antisera and monoclonal antibodies. These antibodies may be used for diagnostic purposes, i.e., for the detection of tumor cells or antigens in samples. Alternatively such antibodies, particularly human or humanized antibodies specific to such tumor antigens may be used therapeutically in the treatment of cancers that express these antigens. Methods of making antibodies for potential use in therapy are well known in the art.

Moreover, the disclosure further contemplates the use of the subject representative samples to identify the B cell receptor and/or T cell receptor population which, in turn, can be used to inform strategic vaccine generation.

Furthermore, representative samples generated by the subject methods may also be used to develop CAR-T systems.

Use of Representative Samples for the Detection of Neoantigens

Identifying neoantigens from isolated tumor cells is of paramount importance for treatment of a subject with cancer(s). As such, samples generated using the disclosure may be subject to any relevant diagnostic methods, such as but not limited to those discussed in the present application, for identification of a neoantigen biomarker with a tumor sample.

Neoantigens result from mutations occurring during tumor growth and differ from native antigens to which the immune system is tolerant. Mounting evidence suggests that immune rejection of tumors, for example that which is seen with checkpoint modulators, may be mediated by recognition of neoantigens. Neoantigens have the potential to: (1) uniquely mark a tumor (relative to non-tumor cells) for recognition and destruction by for example the immune system (See Lennerz et al., 2005, Proc Natl Acad Sci USA. 102(44):16013-8, which is hereby incorporated by reference in its entirety); and (2) avoid central and sometimes peripheral tolerance, and thus be recognized for targeted cancer treatment (See Gotter et al. "Medullary Epithelial Cells of the Human Thymus Express a Highly Diverse Selection of Tissue-specific Genes Colocalized in Chromosomal Clusters." J. Exp. Med. 199.2 (2004):155-166, which is hereby incorporated by reference in its entirety). See US 20110293637 A1, which is hereby incorporated by reference in its entirety.

Recent technological innovations have made it possible to dissect the immune response to patient-specific neoantigens that arise as a consequence of tumor-specific mutations, and emerging data suggest that recognition of such neoantigens is a major factor in the activity of clinical immunotherapies. These observations indicate that neoantigen load may form a biomarker in cancer immunotherapy and provide an incentive for the development of novel therapeutic approaches. See Schumacher, T. N. and Schreiber, R. D. (2015) Neoantigens in cancer immunotherapy. Science 348:6230. 69-74, which is hereby incorporated by reference in its entirety.

Based on data obtained over the past few years, it is plausible that neoantigen-specific reactivity forms a major "active ingredient" of successful cancer immunotherapies. In other words, the genetic damage that on the one hand leads to oncogenic outgrowth can also be targeted by the immune system to control malignancies. Based on this finding, it will be important to engineer therapeutic interventions by which neoantigen-specific reactivity is selectively enhanced. Because of the tumor-restricted expression of antigens that are being targeted, these personalized cancer immunotherapies offer the promise of high specificity and safety. Conceivably, the boosting of neoantigen-specific reactivity that can be achieved with such personalized immunotherapies will further increase the spectrum of human malignancies that respond to cancer immunotherapy. See Schumacher, T. N. and Schreiber, R. D. (2015) Neoantigens in cancer immunotherapy. Science 348:6230. 69-74, which is hereby incorporated by reference in its entirety.

Neoantigens may comprise personal mutations unique to each patient and that dramatically out-number mutations to oncogenes. The subset of those mutations that alter protein coding sequences also creates personal, novel antigens—neoantigens—which may provide the "foreign" signal needed for cancer immunotherapy. See Hacohen et al. Getting Personal with Neoantigen-based Therapeutic Cancer Vaccines. Cancer Immunol Res; 1(1); 11-15. ©2013 AACR.

As discussed above, cancer peptide vaccines constitute another approach to eliciting and boosting anti-tumor immune responses. An approach that targets tumor-specific antigens generated from gene mutations occurring in tumor cells during neoplastic transformation would aide in personalized patient treatment. Immune responses to these so-called "cancer neoantigens" may not be attenuated by host central tolerance in the thymus and do not trigger autoimmune reactions. Recent developments in genomics and bioinformatics, including massively parallel sequencing (MPS) and epitope prediction algorithms, have provided a major breakthrough, enabling more comprehensive and efficient identification of target antigens. See Kitano, I. A. et al. (2015) Cancer Neoantigens: A Promising Source of Immunogens for Cancer Immunotherapy. J Clin Cell Immunol 6:322, which is hereby included by reference in its entirety.

There is a growing interest in cancer therapies that seek to target cancerous cells with a patient's own immune system (e.g., cancer vaccines) because such therapies may mitigate/eliminate some of the herein-described disadvantages. Cancer vaccines are typically composed of tumor antigens and immunostimulatory molecules (e.g., cytokines or TLR ligands) that work together to induce antigen-specific cytotoxic T cells that target and destroy tumor cells. Current cancer vaccines typically contain shared tumor antigens, which are native proteins (i.e. —proteins encoded by the DNA of all the normal cells in the individual) that are selectively expressed or over-expressed in tumors found in many individuals. Vaccines containing tumor-specific and patient-specific neoantigens are a potentially useful therapeutic avenue for treating a subject suffering from a cancer. See WO 2015095811 A2, which is hereby incorporated by reference in its entirety.

Accordingly, representative samples prepared from tissue, e.g., tumors or lymph nodes, obtained from cancer patients can be used to identify the neoantigen load that forms a biomarker in cancer immunotherapy and, thus, provide for the development of novel therapeutic approaches that selectively enhance T cell reactivity against the identified class or classes of antigen.

Current sampling techniques in the diagnostic pathology lab focus on taking prescribed samples from specific anatomical locations on surgically resected tissues. As indicated in the dashed boxes in FIG. 56, the historical standard practice is to acquire 5-7 small areas of a resected tumor to fulfill the requirements of the TNM staging system. The dissected samples are further processed into paraffin embedded tissue blocks, histological sections are taken, and the tumor is staged and optionally analyzed for biomarkers using common staining techniques. Once all the diagnostic information has been gathered and reviewed by an anatomic pathologist, the residual surgical tissue including any remaining tumor tissue is destroyed by incineration.

The inventive aspect of this work involves utilization of the residual surgically resected material, a source of tissue that has been universally destroyed since the world-wide acceptance of the TNM staging system in the mid-1950s. At multiple points within the current workflow, surgically resected tissue can be processed for disruption via multiple tissue disassociation methods (including, but not limited to, blending, mincing/dicing, and juicing). As shown in FIG. Z, tissue can be disassociated immediately following surgical removal (fresh tissue), following fixation of the tissue, after TNM sample acquisition, or after tissue samples have been embedded in paraffin wax. Once sufficiently homogenized, the disassociated tissue is referred to as a "Representative Sample". The unique and unanticipated attribute of the Representative Sample is that it contains all of the diversity that existed within the original surgically resected tissue, such as the diversity of tissue, cells, and all biomolecules.

Other inventive aspects of this application include all further processing of fresh and fixed representative samples, as such high quantities of human residual surgical material have never been sampled in diagnostic oncology as this material has been destroyed since the 1950s. As indicated in FIG. 56, in some embodiments, biomolecules can be isolated directly from a representative sample using novel techniques, and further analyzed using current, and future, analysis tools. Biomolecules such as DNA can be isolated and sequenced using NGS, and the resulting data can be used to calculate the percentage of the tumor that contains a specific targeted mutation. Moreover, the mutation rates can be further used to determine the diversity of tumor subclones contained within a resected tumor. Protein analysis using ELISA, immuno-precipitation, or mass-spectrophotometry can be used to determine the presence of a targetable protein complex, or of the activation states of tyrosine kinases within a tumor.

In another embodiment, a portion of the representative sample, in the form of a homogenate, can be uniquely processed and embedded in paraffin wax to be analyzed using current histological methodology. Staining of embedded representative samples can be read and interpreted by an anatomic pathologist, or imaged using a digital imaging system. Once digitally imaged, the heterogeneity in the staining result can be quantified and used to mathematically represent the spatial heterogeneity of protein expression, gene copy number alterations, or mRNA expression.

In another embodiment, a portion of a representative sample can be further processed using novel mechanical and enzymatic disassociation methods to generate a suspension of individual nuclei. Nuclei isolated from representative samples can be stained using novel staining methods for further analysis using FLOW cytometry to determine the percentage of cells expressing certain nuclear transcription factors and other indicators of phenotypic changes. Alternatively, the stained nuclei can be isolated using FACS (fluorescently activated cell sorting) or magnetic bead affinity subtraction, followed by DNA isolation and NGS or PCR analysis. Isolated nuclei can alternatively be plated onto glass slides and subjected to histological techniques such as IHC and ISH.

In yet another embodiment, a portion of a representative sample can be further processed using novel mechanical and enzymatic disassociation methods to generate a population of individual cells. Cells generated from representative samples of resected tissues can be further analyzed by FLOW cytometry to interrogate the diversity of cell types, phenotypes, and other biomarkers such as targetable oncogenes and immuno-modulators in tumor cells, and immunophenotyping of immune cells removed from a tumor. The cells could be further processed for FACS to isolate cells expressing specific biomarkers. Biomolecules from FACS sorted cells could be isolated for further analytical testing, or the cells can be plated onto glass slides for histological detection methods including IHC and ISH.

As residual surgical tissue, especially in solid tumor oncology, has been destroyed for the past ~50 years, data derived from novel representative sampling and analysis techniques will generate unprecedented clinical oncology data. Such "Representative Oncology Data" (FIG. 56) will enable, for the first time, the ability to calculate the mutational and phenotypic diversity in tumor cells as well as the status of the anti-tumor immune response and other normal tissues. Novel "Representative Oncology Data" will be used to improve the prognosis of cancer patients, predict the recurrence at the site of surgery or distant metastases, detect all available "targetable" alterations, select for inclusion in a clinical trial, and determine combination therapy targets, dosage, and timing.

The present disclosure has been described in detail. In order to further illustrate the present disclosure and its intrinsic benefits the following examples discussing experiments conducted by the inventors are provided.

The following examples are offered to illustrate, but not to limit, the claimed disclosure.

EXAMPLES

Example 1: Preparation of Representative Tissue Samples

Figure 3:
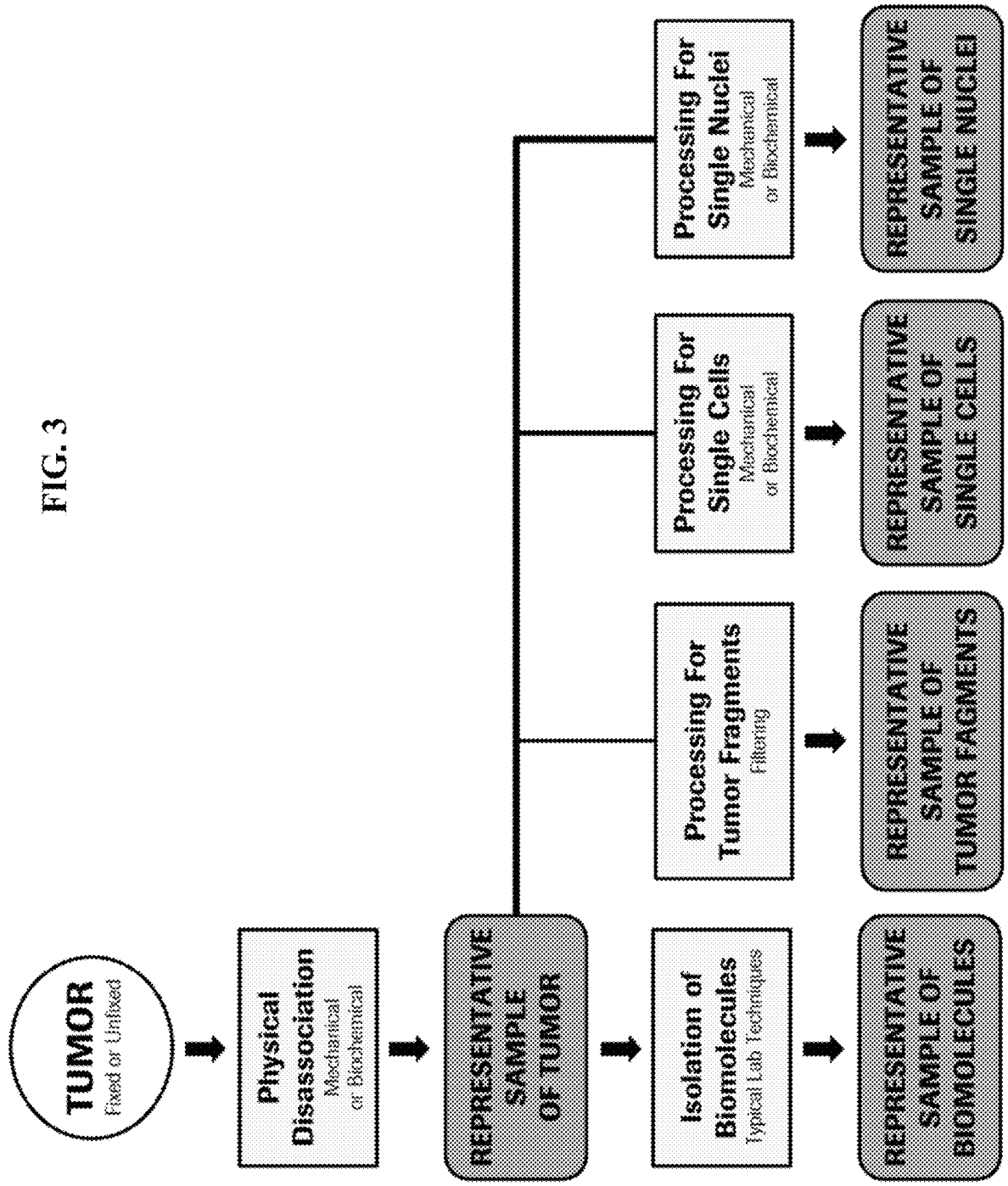
FIG. 3 is a flow chart depicting schematically the disclosed protocol using physical, mechanical, biochemical methods for generating representative tumor samples that are representative of heterogeneity within a tumor.

Representative tissue samples were derived from formalin-fixed tumor samples using the homogenization methodology described herein and depicted schematically in FIG. 3. In general, tumor samples, i.e., formalin-fixed tumor samples were optionally removed from the surrounding adjacent normal tissue and mechanically disassociated, producing a representative sample containing all of the components of the original resected tumor. The representative sample can then be further processed for downstream analysis. Such processing included preconditioning in CC1 buffer at 85° C., before being transferred to buffer (e.g., PBS) containing 60 mg/mL Collagenase H and 1 mM $CaCl_2$. The resultant enzyme treated homogenized tissue was then incubated with Collagenase H for at least about 30 minutes at 40° C. before being returned to CC1 buffer and heated at 85° C. for about 10 minutes to inactivate any remaining collagenase enzyme. The representative sample was then used to derive subsamples which were then used for a variety of diagnostic assays.

Methods

Figure 15:
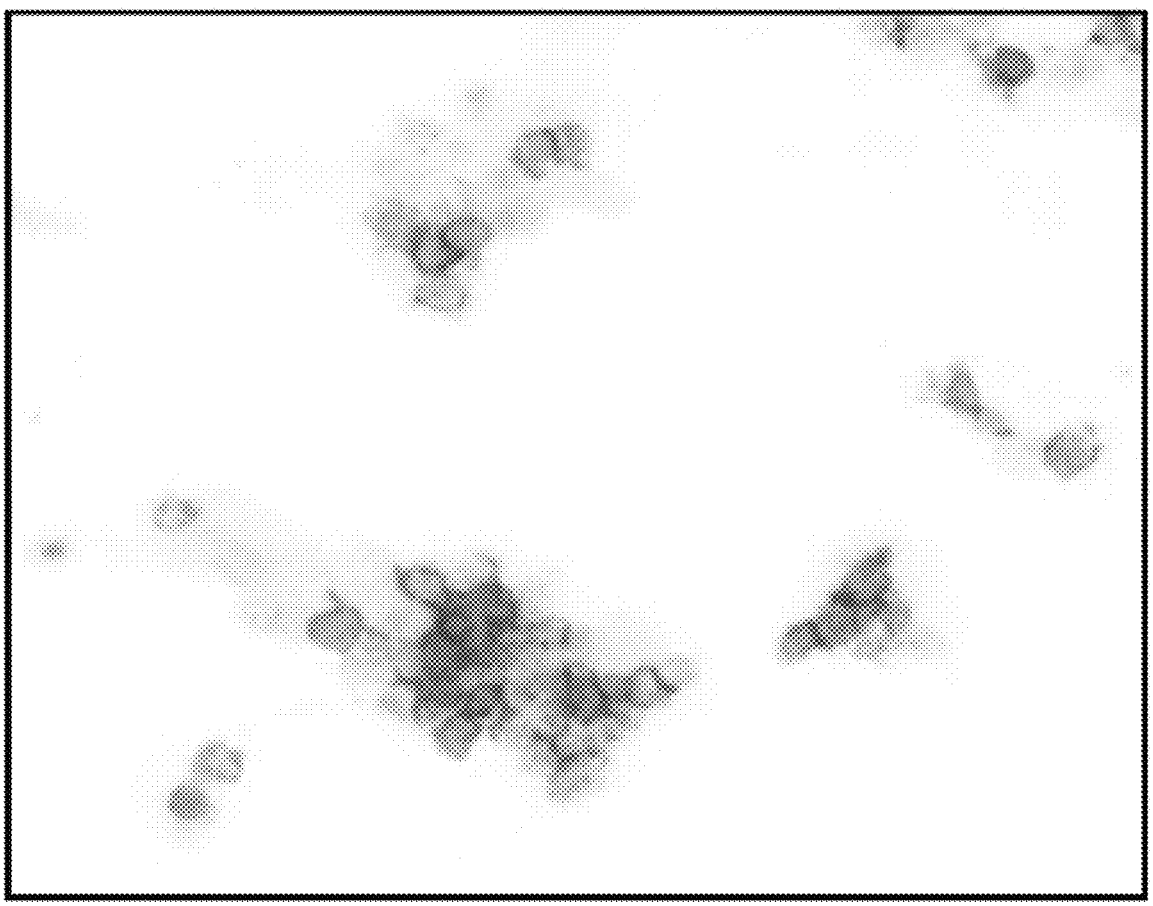
FIG. 15 shows the detection of Ki-67, CD20, and CD3 using multiplex chromogenic IHC in the representative sample generated from human tonsil specimens.

Materials: Mechanical shearing of tissue was performed using a Hamilton Beach® Single Serve Blender (Walmart, Tucson, AZ) or an IKA® Works Tube Mill Control System (0004180001) from IKA-Works® (Staufen in Breisgau, Germany) and using a gentleMACs™ Dissociator from Miltenyi Biotec (Teterow, Germany). Note the various size of tissue fragments following homogenization, ranging from a few cells to clusters containing tens of thousands of cells (FIG. 15). Heat and pH cell conditioning was performed in Cell Conditioning 1 (CC1) buffer from Ventana® Medical Systems (Tucson, AZ; catalog #950-124). AccuMax® was obtained from Innovative Cell Technologies (San Diego, CA). Collagenase H (11074032001) was obtained from Roche (Basel, Switzerland). The following antibodies from Ventana® Medical Systems (Tucson, AZ) were used: anti PD-L1 (SP263) rabbit, monoclonal primary antibody (790-4905); anti Ber-EP4 mouse, monoclonal antibody (760-4383); anti CD8 (SP57) rabbit, monoclonal primary antibody (790-4460); anti HER-2/neu (4B5) rabbit, monoclonal primary antibody (790-2991).

Tissue Samples: All tissue samples and meat were fixed in 10% neutral buffered formalin for 24 hours at Ventana® Medical Systems. HER2-positive xenograft was generated at Ventana® Medical Systems. Chicken and fish meat were obtained from Walmart (Tucson, AZ). Human tonsils were obtained from Northwest Medical Center (Tucson, AZ).

Digestion and Analysis: Sample was preconditioned in CC1 buffer at 85° C., and subsequently treated with AccuMax® containing 1 mg/ml Collagenase H for 1 hour at room temperature, then incubated for 1 hour at 40° C. Biochemical digestion of the tissues was analyzed by running the digested sample through the following micron meshes in sequential order: 500, 300, 100, 40, 20, 10, 6, and 1 micron. The flow through and retained fractions were weighed for each mesh.

Hematoxylin and Eosin Staining: Representative samples were plated in 70 μL methanol on VWR plus slides. Hematoxylin and Eosin (H&E) staining was performed using a Ventana® Medical Systems Symphony platform (Ventana® Medical Systems, Tucson, AZ) and the corresponding H&E Symphony Reagents (Ventana® Medical Systems, Tucson, AZ).

Immunohistochemistry: Representative samples were plated in 70 μL methanol on VWR plus slides. Brightfield DAB-based immunohistochemistry (IHC) was performed using a Ventana® Medical Systems Benchmark® XT platform (Ventana® Medical Systems, Tucson, AZ). Visualization of biomarkers was performed using the OptiView® DAB Detection Kit from Ventana (760-700). Antibodies were incubated for 4 minutes.

RNA Isolation: RNA was isolated from representative samples of human tonsil using an acid phenol method described previously in Chen et al. 2007.

Results and Discussion

Using the above-described methods, representative samples from different sample types, including clinical tissue specimens of human tumors and fixed animal tissues, were created.

Cell preconditioning in CC1 buffer at 85° C. was coupled with enzymatic digestion of the extracellular matrix to create a sample ranging in size from single cells to small cell clumps.

An enzyme specific to extracellular matrix proteins, i.e., Collagenase H, was used instead of a general protease, e.g., trypsin, to minimize the loss of membrane associated biomarkers during biochemical digestion of the tissue.

Figure 4:
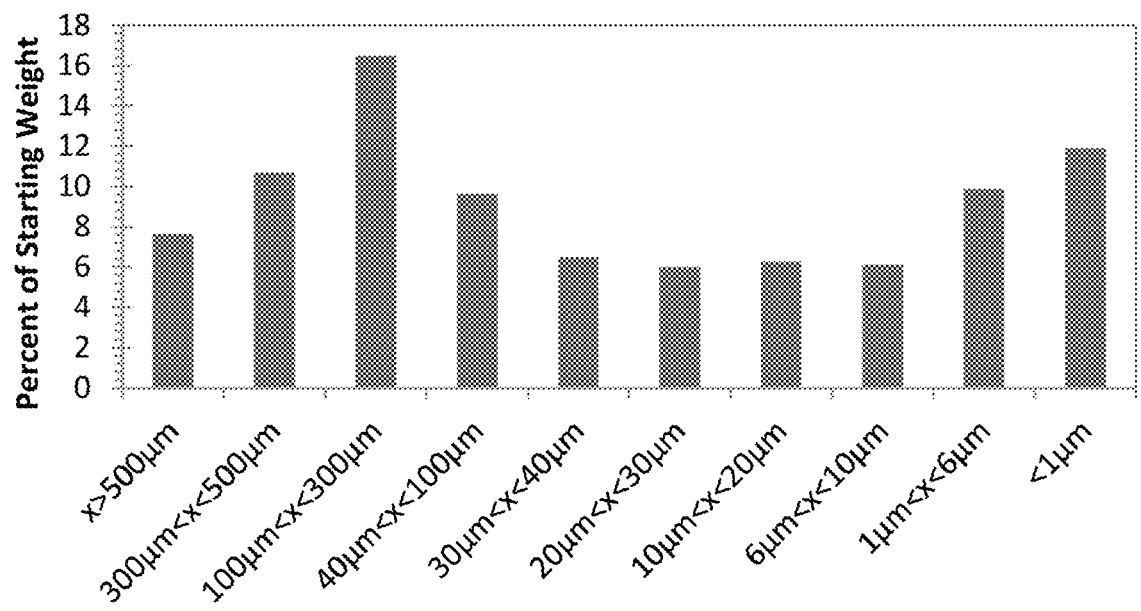
FIG. 4 is a graph showing the results from size fractionation of the representative sample.

The majority of the sample was digested into 100 micron sized fragments and smaller (FIG. 4). Here, percent weight of the digested sample was used to characterize the different size fragments in the biochemically digested representative sample following filtration through a series of micron meshes.

Figure 5A:
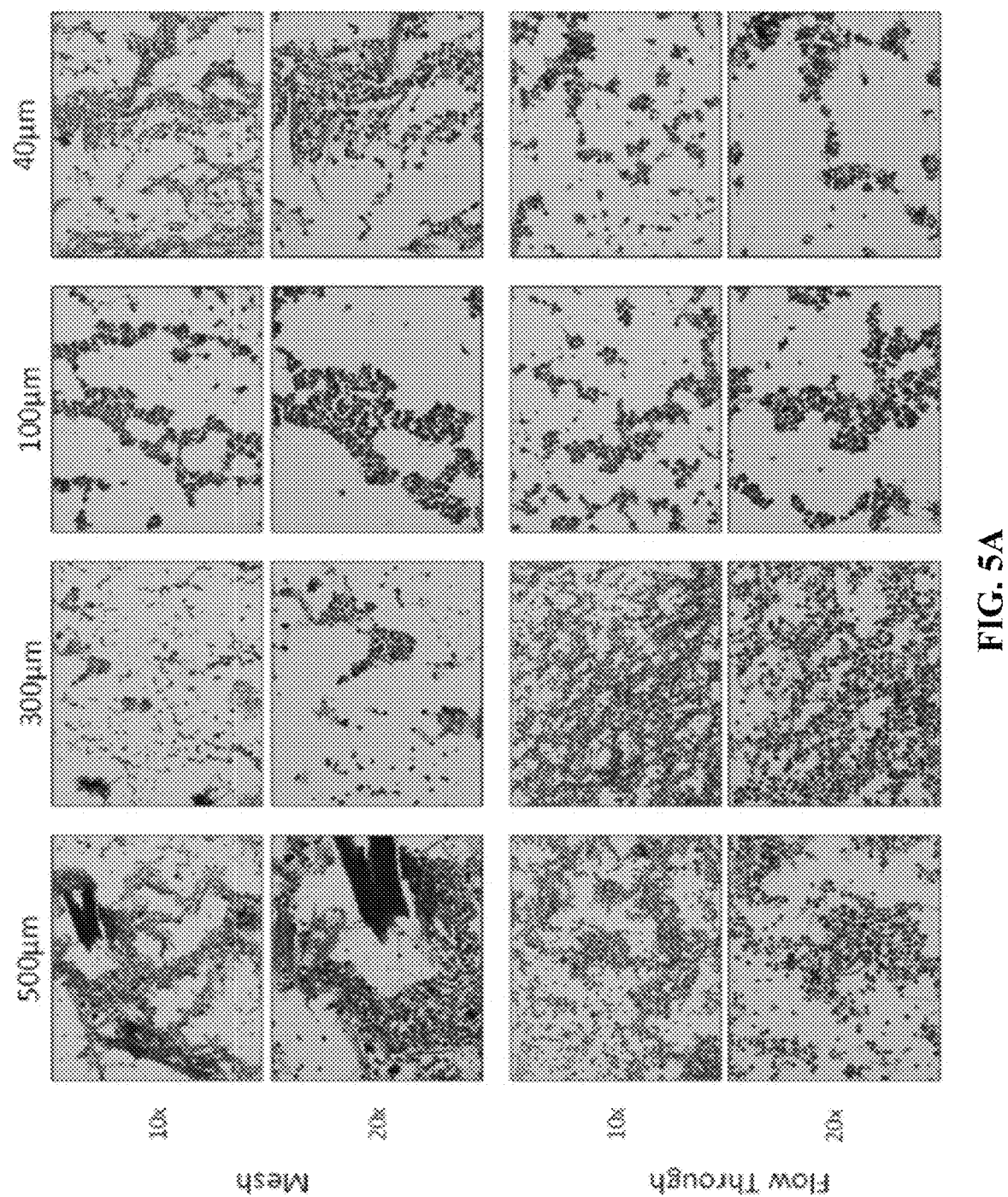
FIG. 5A illustrates the comparative H&E staining of a fraction retained in the mesh (top) and the flow through (bottom) of the micron mesh following a series filtrations of the biochemically-digested representative sample. Different mesh sizes and magnifications are comparatively illustrated.
Figure 5B:
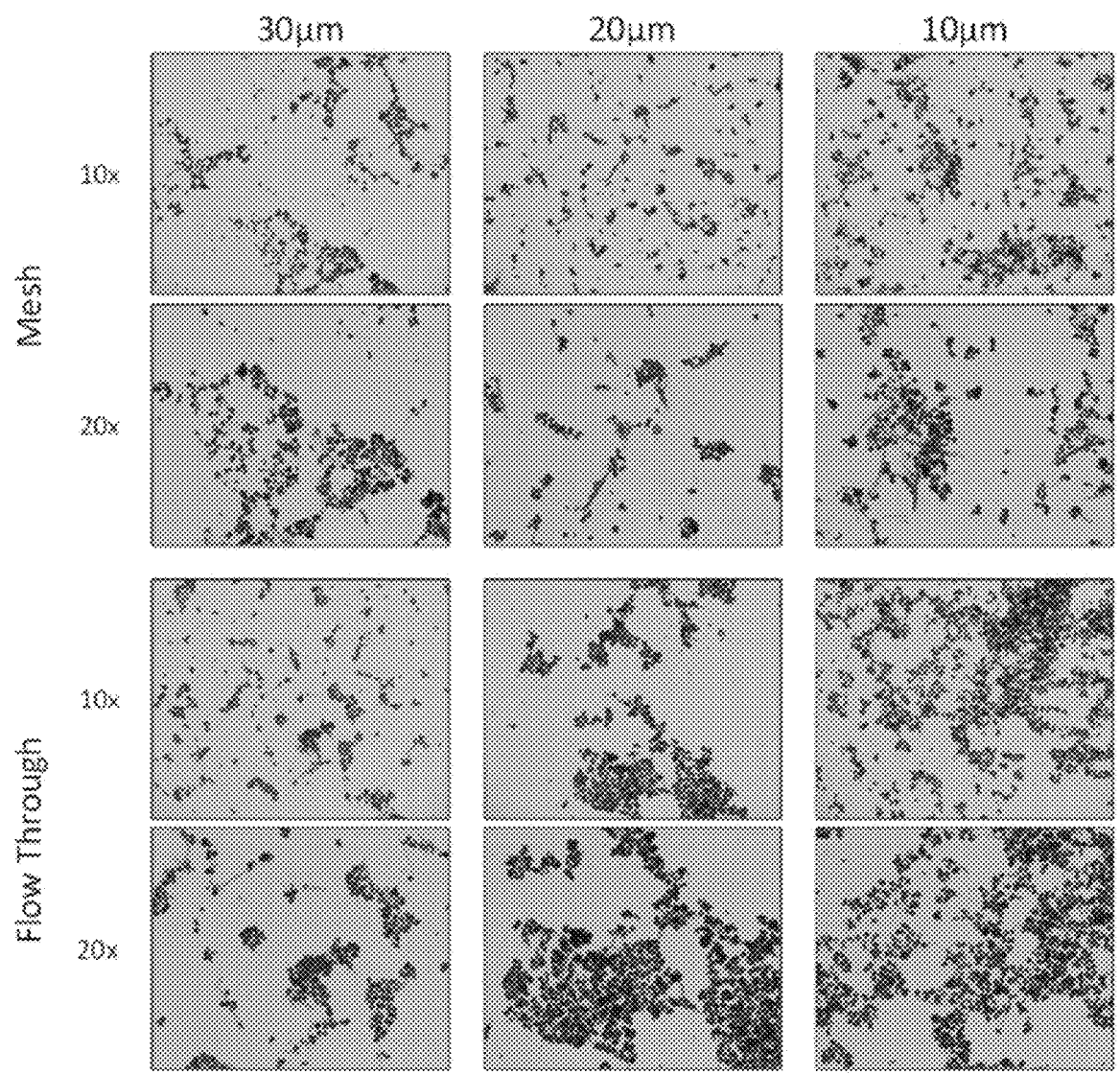
FIG. 5B illustrates the comparative H&E staining of the fraction retained in the mesh (top) and the flow through (bottom) of the micron mesh following a series filtrations of the biochemically-digested representative sample. Different mesh sizes and magnifications are comparatively illustrated.
Figure 5C:
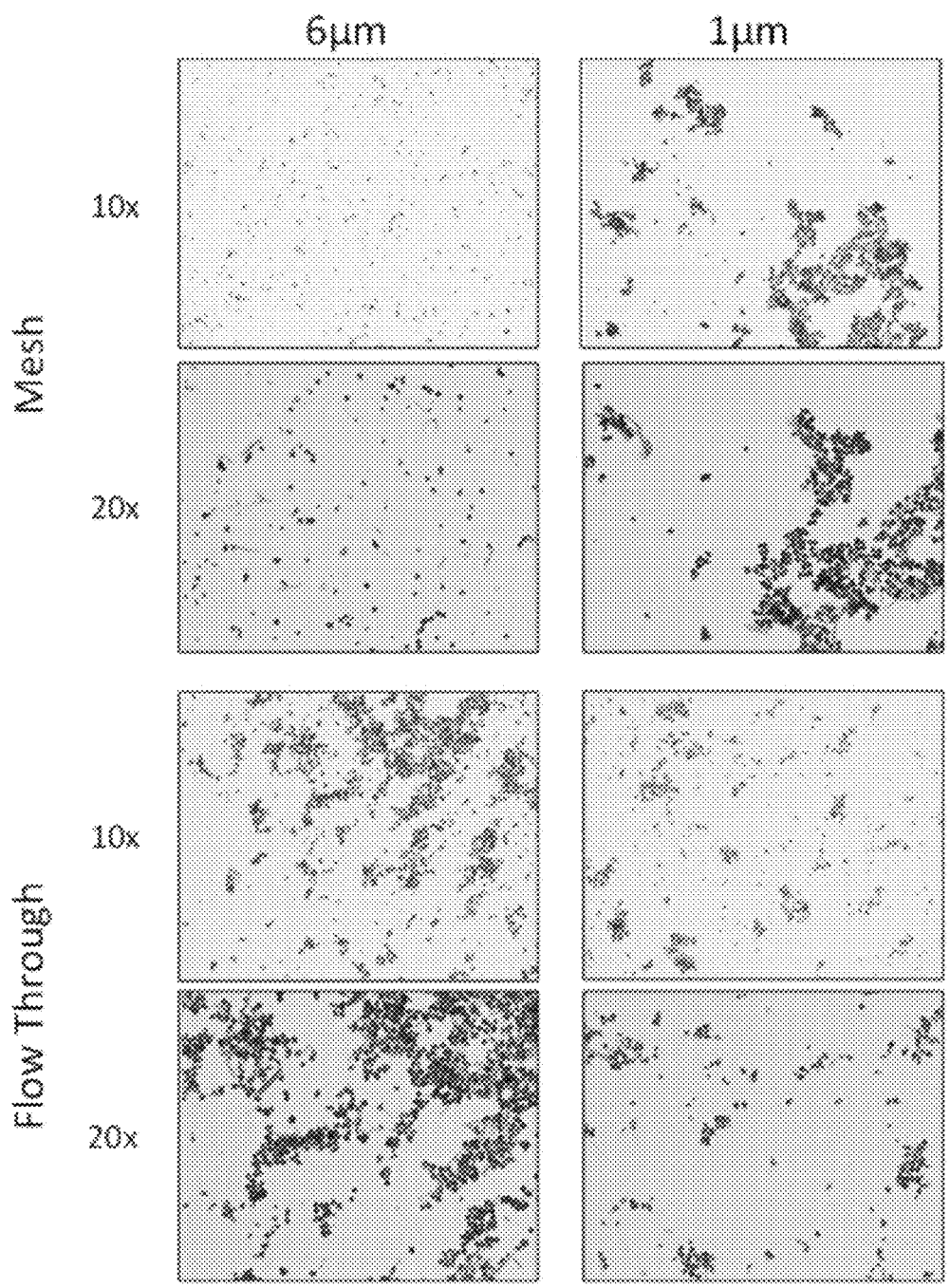
FIG. 5C illustrates the comparative H&E staining of the fraction retained in the mesh (top) and the flow through (bottom) of the micron mesh following a series filtrations of the biochemically-digested representative sample. Different mesh sizes and magnifications are comparatively illustrated.
Figure 7A:
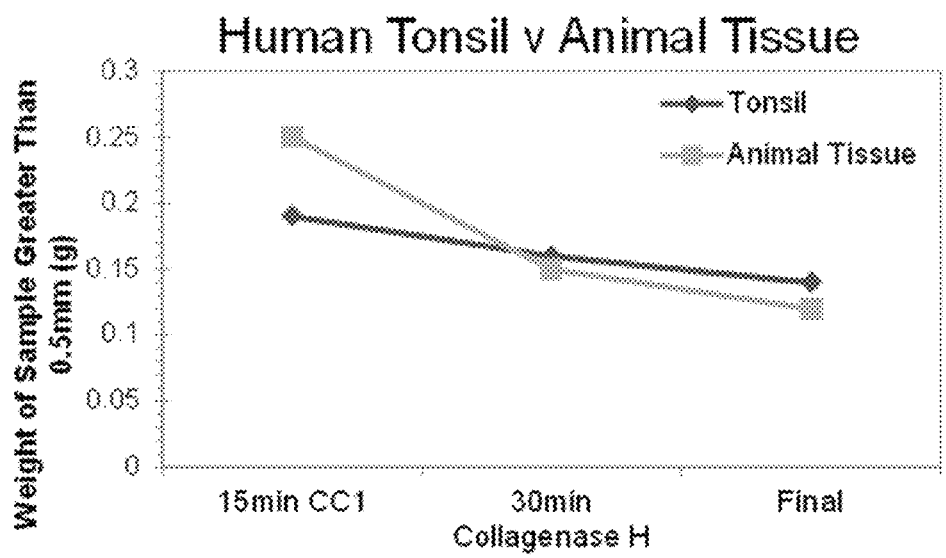
FIG. 7A illustrates a representative sample generated from human tissue using biochemical digestion and heat preconditioning with CC1 followed by a 30 minute digestion with Collagenase H.
Figure 7B:
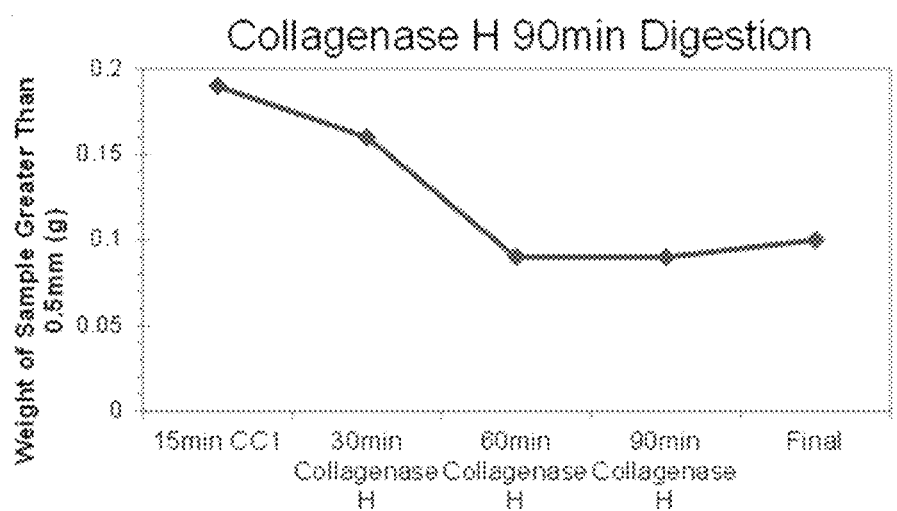
FIG. 7B illustrates a representative sample generated from human tissue using biochemical digestion and heat preconditioning with CC1 followed by duration of the Collagenase H digestion.

Non-tumor cells were filtered by running the sample through mesh filters 6 microns and smaller as is seen in the H&E staining. FIGS. 5A-C show H&E staining of the flow through and retained fractions collected following series filtration of the biochemically-digested representative sample. FIG. 7A illustrates H&E staining of the fraction retained in the mesh (top) and the flow through (bottom) of 500, 300, 100, and 40 micron mesh. FIG. 7B illustrates H&E staining of the fraction retained in the mesh (top) and the flow through (bottom) of 30, 20, and 10 micron mesh. FIG. 7C illustrates H&E staining of the fraction retained in the mesh (top) and the flow through (bottom) of 6 and 1 micron mesh.

The H&E staining of the flow through from the 6 micron and 1 micron filter (FIG. 5C, in particular) showed no enlarged nuclei indicative of tumor cells. Accordingly, this approach may be used for enriching tumor cells in the representative sample as well as isolating tumor-educated platelets and other blood cells from the sample.

Figure 6A:
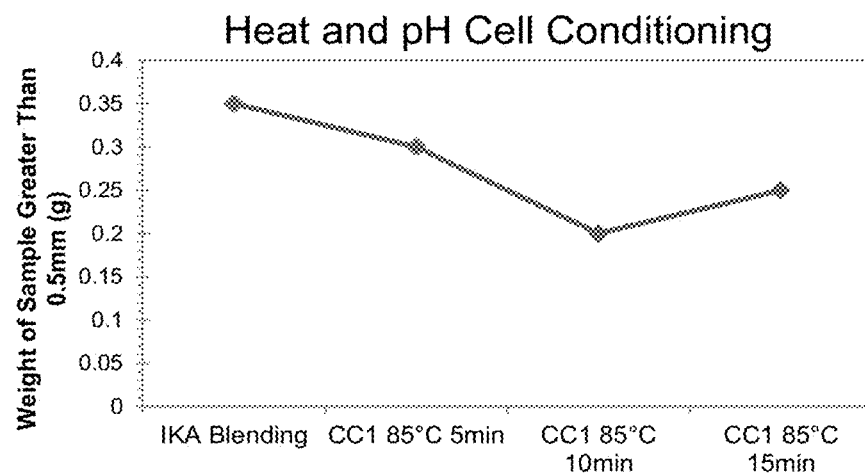
FIG. 6A shows protein detection in a representative sample generated from a Her2 positive xenograft derived from human breast cancer cells mixed with animal tissue via homogenization followed by biochemical digestion with heat and preconditioning in CC1 buffer at 85° C.
Figure 6B:
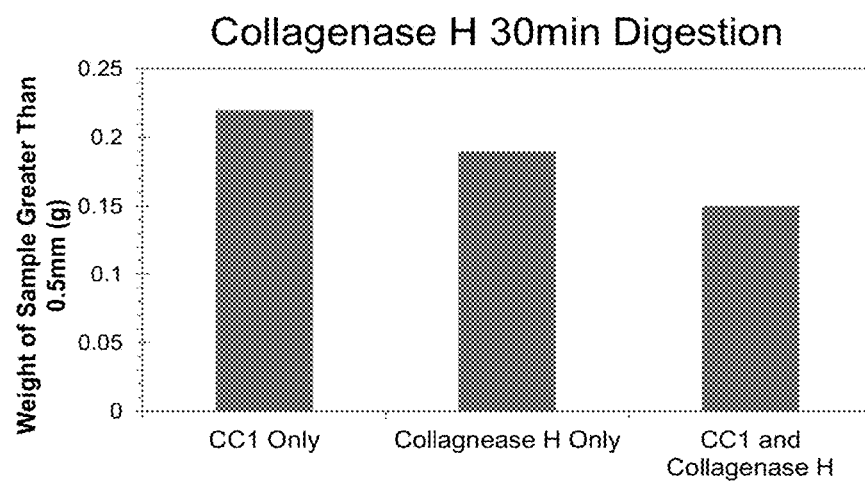
FIG. 6B shows protein detection in a representative sample generated from a Her2 positive xenograft derived from human breast cancer cells mixed with animal tissue via homogenization followed by biochemical digestion with heat and preconditioning in CC1 buffer at 85° C. followed by Collagenase H digestion for at least 30 minutes.
Figure 6C:
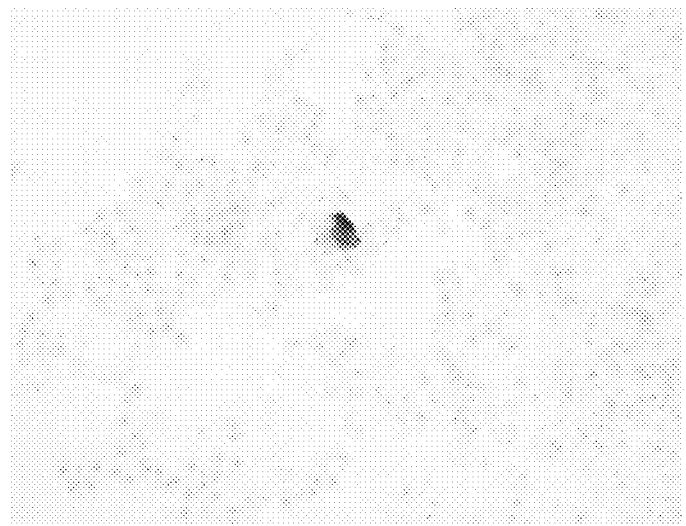
FIG. 6C shows protein detection in a representative sample generated from a Her2 positive xenograft derived from human breast cancer cells mixed with animal tissue via homogenization followed by biochemical digestion with heat and illustrates a mechanically disassociated, CC1 preconditioned, and Collagenase H digested sample.
Figure 6D:
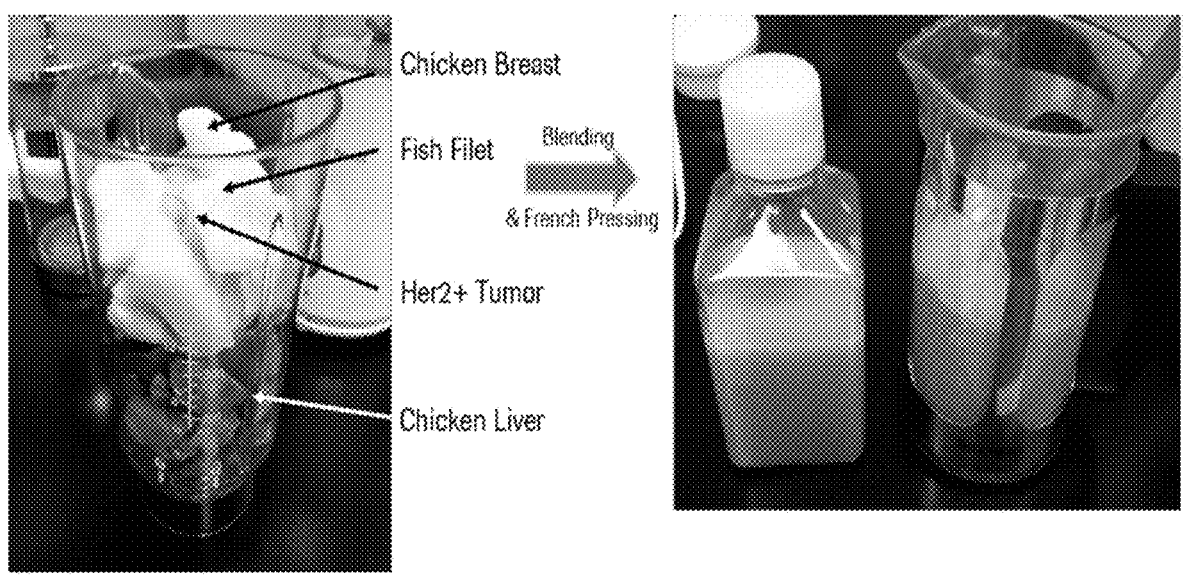
FIG. 6D is an image of the animal tissue, i.e., chicken breast, fish fillet, and chicken liver, with the Her2 positive xenograft blended to generate the representative sample analyzed as shown in FIGS. 6A-6C.

The above-described method was first tested in a tissue sample comprised of 300 grams of various fixed animal tissues including chicken breast, chicken liver, and fish filet. In order to model a rare tumor sub-clone, a small (0.4 gram) HER-2 positive xenograft was added to the tissue sample. The tissue was mechanically disassociated and filtered using a french press prior to being used in this experiment. The tissue sample was then pre-conditioned in CC1 buffer for 15 minutes at 85° C. The pre-conditioned tissue sample was homogenized using the gentleMACs™ Dissociator (FIG. 6D) and a 1 mL sample was collected every 5 minutes. Each sample collected was run through a 600 pcs mesh to measure disassociation of the tissue. Preconditioning alone was able to promote some digestion, but the reaction hit a plateau after 10 minutes (FIG. 6A). By comparing the ability of Collagenase H alone versus Collagenase H in combination with CC1 preconditioning to dissociate the sample, it was determined that CC1 preconditioning was able to promote Collagenase H digestion. In particular, CC1 preconditioning followed by Collagenase H digestion for at least 30 minutes gave the best reduction in particle size as measured by the 600 pcs strainer (FIG. 6B). The representativeness of the sample was tested by plating several aliquots and analyzing each for HER-2 positive cells using DAB-IHC. HER-2 positive cells were detected on every slide created (FIG. 6C). Considering the weight ratios (0.4 gram HER-2 positive xenograft to 300 grams of meat), the above-described method generated a representative sample that permitted the detection of sub-clones at a prevalence of at least 0.1%.

Next, the protocol was tested on human lymph node (tonsil) tissues. A resected tonsil was mechanically disassociated in an IKA® tube mill to create a representative lymph node sample. Preconditioning with CC1 followed by a 30 minute digestion with Collagenase H disassociated the tonsil tissue (FIG. 7A). The time course of the Collagenase H digestion was extended to 90 minutes, and it was observed that the enzymatic reaction plateaued around 60 minutes (FIG. 7B). Accordingly, it is expected that most human tissue need only be digested with Collagenase H for about 30 to about 60 minutes, but no more than about 90 minutes.

Next, four 500 μL aliquots of the dissociated human tonsil tissue sample were used to isolate nucleic acids. Two 500 μL aliquots were stored as cell pellets at −20° C., while the other two 500 μL aliquots were paraffin embedded. RNA was isolated from all of the aliquots, but the yield was much higher in the non-paraffin embedded aliquots (Table 1).

TABLE 1

Total RNA isolated from dissociated human tonsil tissue samples, formalin fixed (FF) and formalin fixed paraffin embedded (FFPE).

|   | FF | FFPE |
|---|---|---|
| 1 | 578 μg | 198 μg |
| 2 | 569 μg | 127 μg |

These results indicate that the representative samples are suitable for diagnostic tests, such as genomic and transcriptomic sequencing, and, moreover, that the representative samples generated using the methods described herein are a better source of material than traditional paraffin embedded tissue samples.

Example 2: Preparation of Representative Tumor Samples

Representative tumor samples were generated from a kidney sample and a lung sample.

Methods

Materials: Mechanical shearing of tissue was performed using an IKA® Works Tube Mill Control System (0004180001) from IKA-Works® (Staufen im Breisgau, Germany) and using a gentleMACs™ Dissociator from Miltenyi Biotec (Teterow, Germany). Heat and pH cell conditioning was performed in Cell Conditioning 1 (CC1) buffer from Ventana® Medical Systems (Tucson, AZ; catalog #950-124). Collagenase H (11074032001) was obtained from Roche (Basel, Switzerland). The following antibodies from Ventana® Medical Systems (Tucson, AZ) were used: anti PD-L1 (SP263) rabbit, monoclonal primary antibody (790-4905); anti Ber-EP4 mouse, monoclonal antibody (760-4383); anti CD8 (SP57) rabbit, monoclonal primary antibody (790-4460); anti HER-2/neu (4B5) rabbit, monoclonal primary antibody (790-2991).

Clinical Samples: Tissue samples were fixed in 10% neutral buffered formalin for between 24 and 72 hours at Tucson Medical Center, and Vanderbilt Medical Center. Lung tumor biopsy was obtained from Tucson Medical Center (Tucson, AZ). Kidney tumor biopsy fragments were obtained from Vanderbilt University (Nashville, TN).

Digestion Analysis: Biochemical digestion of the tissues was analyzed by running a 1 mL sample through a 600 pcs strainer and weighing the material that collected on the mesh.

Hematoxylin and Eosin Staining: Representative samples were plated in 70 µL methanol on VWR plus slides. Hematoxylin and Eosin (H&E) staining was performed using a Ventana® Medical Systems Symphony platform (Ventana® Medical Systems, Tucson, AZ) and the corresponding H&E Symphony Reagents (Ventana® Medical Systems, Tucson, AZ).

Immunohistochemistry: Representative samples were plated in 70 µL methanol on VWR plus slides. Brightfield DAB-based immunohistochemistry (IHC) was performed using a Ventana® Medical Systems Benchmark® XT platform (Ventana® Medical Systems, Tucson, AZ). Visualization of biomarkers was performed using the OptiView® DAB Detection Kit from Ventana® (760-700). Antibodies were incubated for 4 minutes.

RNA Isolation: RNA was isolated from representative samples of human tonsil using an acid phenol method described previously in Chen et al. 2007.

Results and Discussion

Figure 8A:
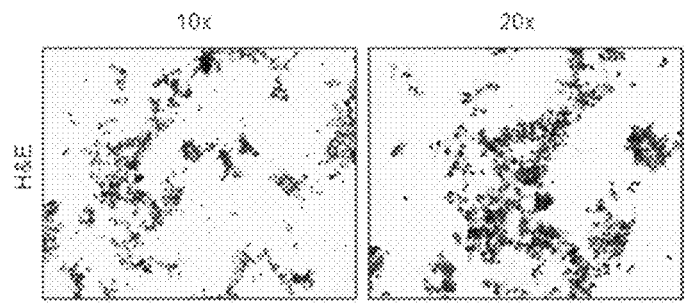
FIG. 8A illustrates H&E staining of a representative human kidney sample following mechanical disassociation, preconditioning, and enzymatic digestion.
Figure 8B:
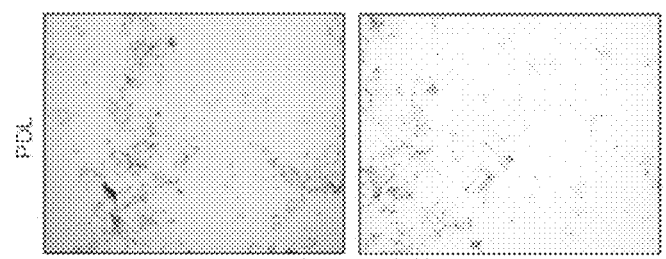
FIG. 8B illustrates DAB-IHC analysis of the representative human kidney sample to detect PD-L1.
Figure 8C:
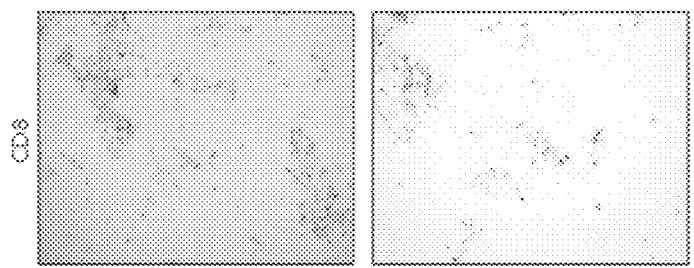
FIG. 8C illustrates DAB-IHC analysis of the representative human kidney sample to detect CD8.
Figure 8D:
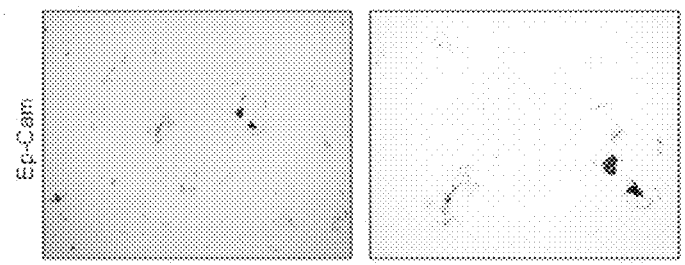
FIG. 8D illustrates DAB-IHC analysis of the representative human kidney sample to detect Ep-Cam. The left hand column shows a 10× magnification of the slides containing the representative sample, whereas the right hand column shows a 20× magnification of the slides containing the representative sample.

In particular, a representative sample was generated from a baseball sized kidney tumor from a 61 year old male according to the methodology described herein and shown in FIG. 3. Standard H&E staining was used to visualize the tissue fragment sizes in the kidney sample following mechanical disassociation, preconditioning, and enzymatic digestion (FIG. 8A). The sample was then subjected to DAB-IHC analysis for three different biomarkers: PD-L1 (FIG. 8B), CD8 (FIG. 8C), and Ep-Cam (FIG. 8D). All three proteins were detected in the representative kidney tumor clinical sample.

Figure 1A:
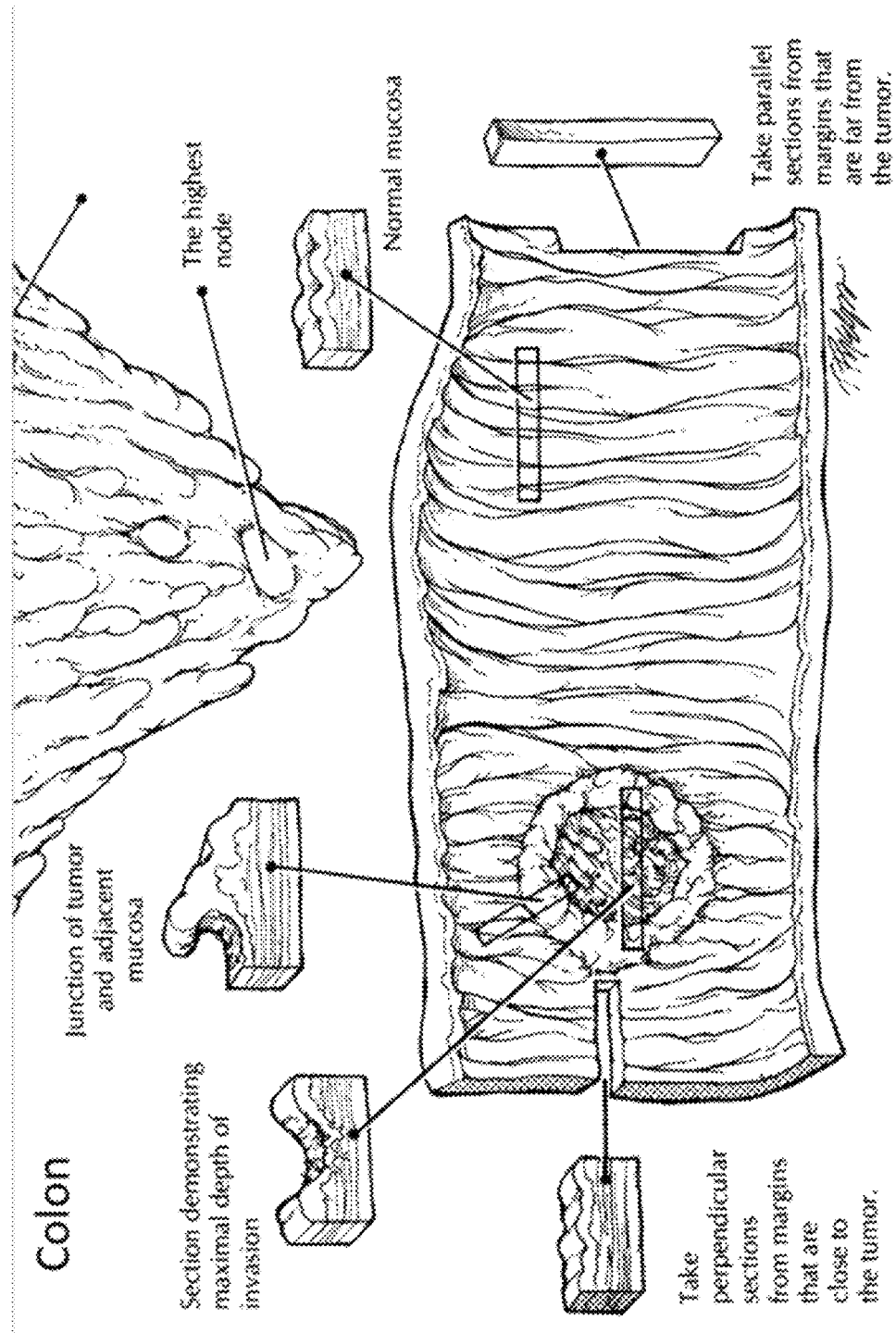
FIG. 1A is a schematic representation of the disclosed method for sample acquisition of a colon.
Figure 1B:
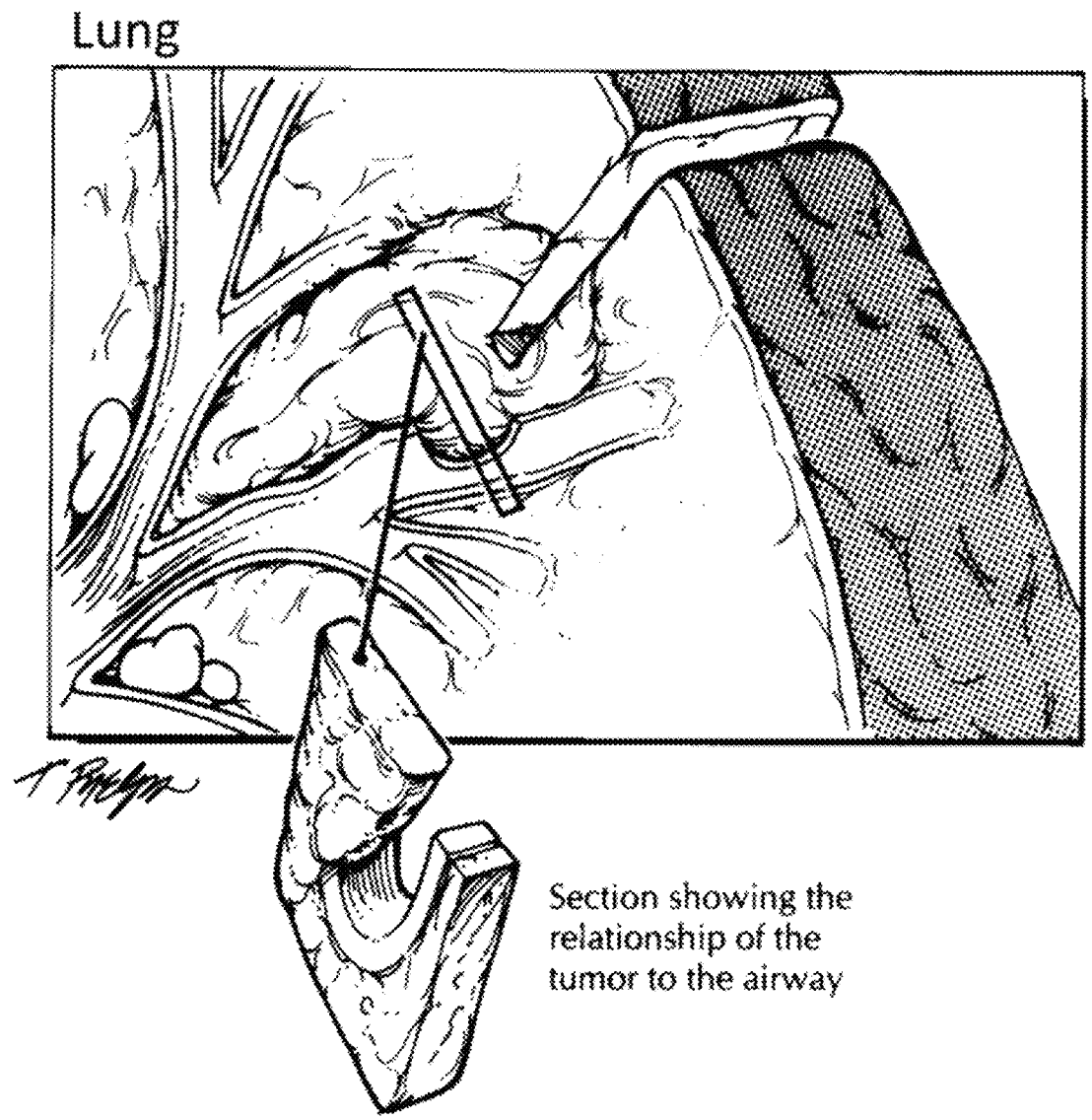
FIG. 1B is a schematic representation of the disclosed method for sample acquisition of lung tissue.
Figure 1C:
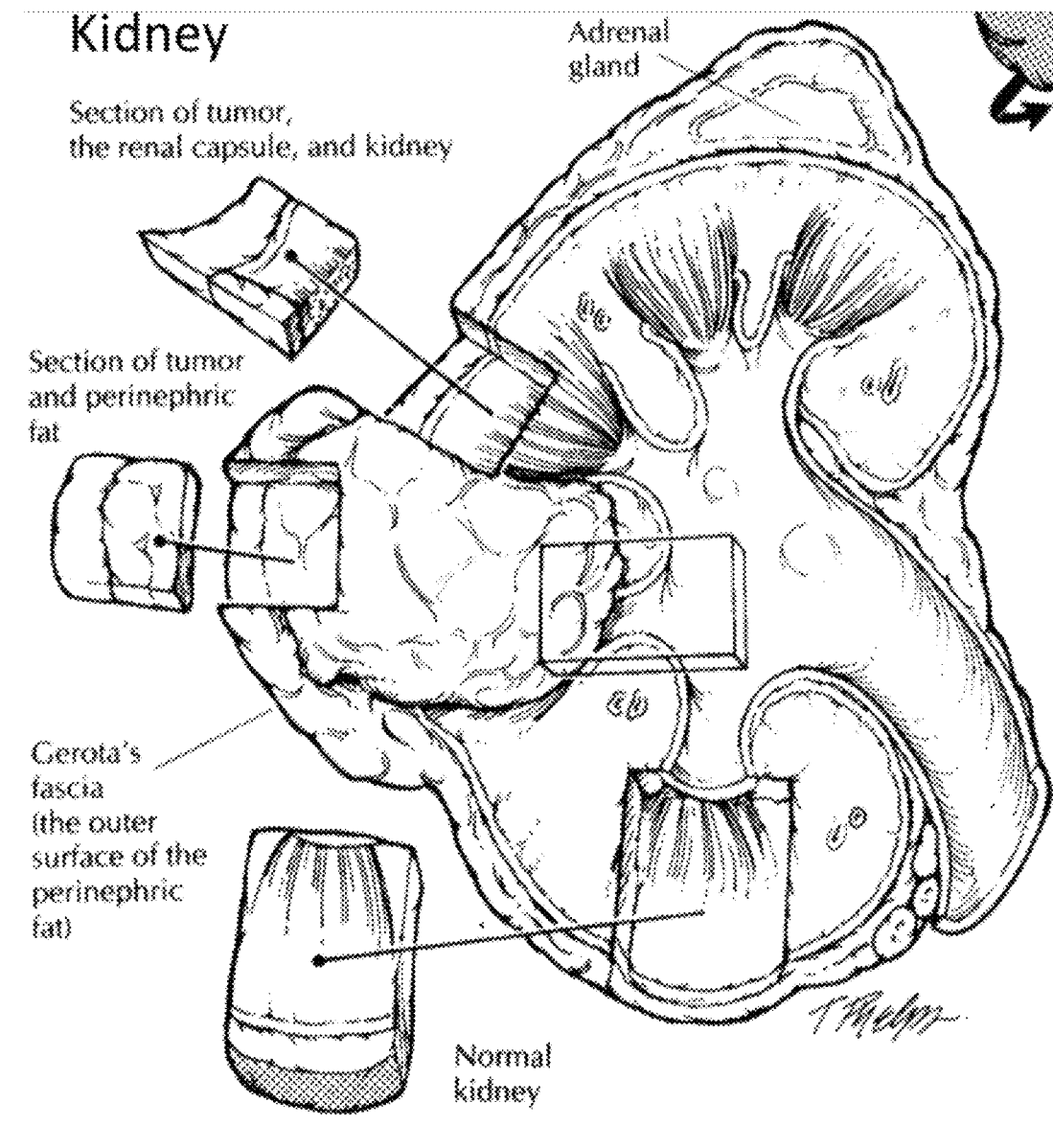
FIG. 1C is a schematic representation of the disclosed method for sample acquisition of a colon of kidney tissue.
Figure 9A:
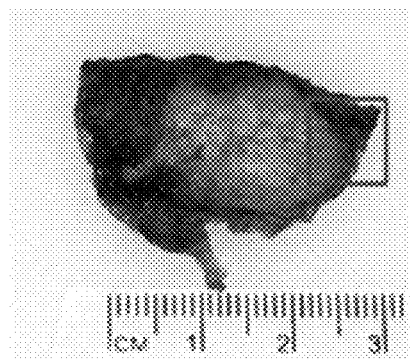
FIG. 9A is an image of protein detection in an approximately 3 cm lung tumor sample used as the source material for generating the representative sample.
Figure 9B:
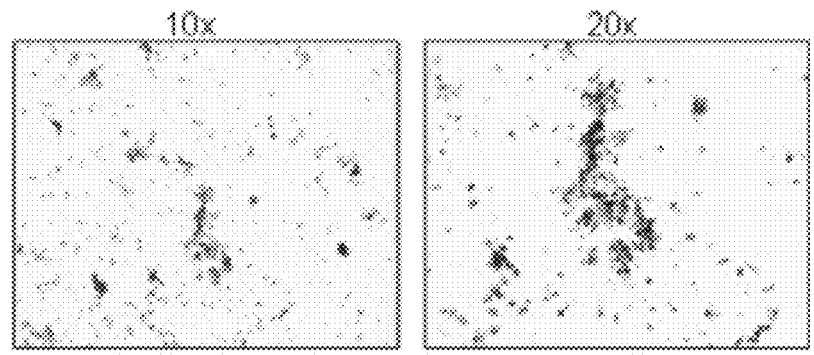
FIG. 9B illustrates H&E staining of a representative human lung sample following mechanical disassociation, preconditioning, and enzymatic digestion; images are compared at 10× and 20× magnification levels.

Additionally, a representative sample was generated from a portion of a half-dollar sized lung tumor from an 87 year old female (FIG. 9A). A small section was cut from the clinical tissue sample (FIG. 9A) and processed according to standard pathology practices. The remaining tissue was used to create a representative sample according to the methodology described herein and shown in FIG. 1. Standard H&E staining was used to visualize the tissue fragment sizes in the lung sample following mechanical disassociation, preconditioning, and enzymatic digestion (FIG. 9B).

Figure 9C:
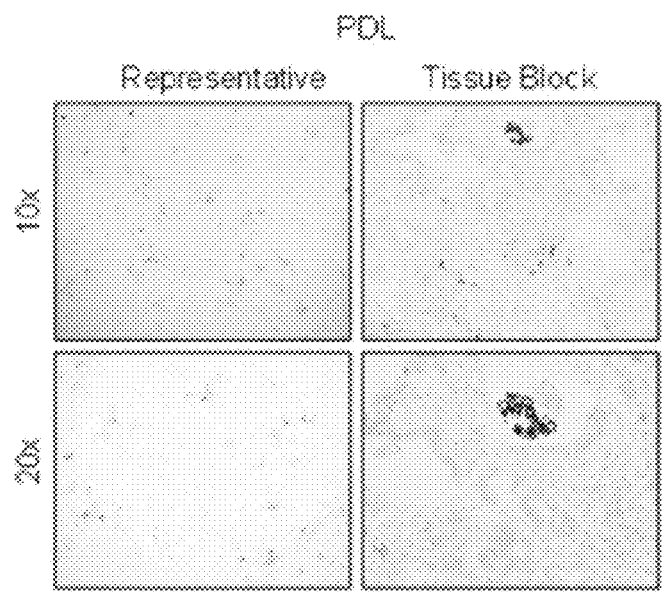
FIG. 9C illustrates DAB-IHC analysis of the representative human lung sample to detect PD-L1; images are compared at 10× and 20× magnification levels; samples from a tissue block are compared to those from representative sampling.
Figure 9D:
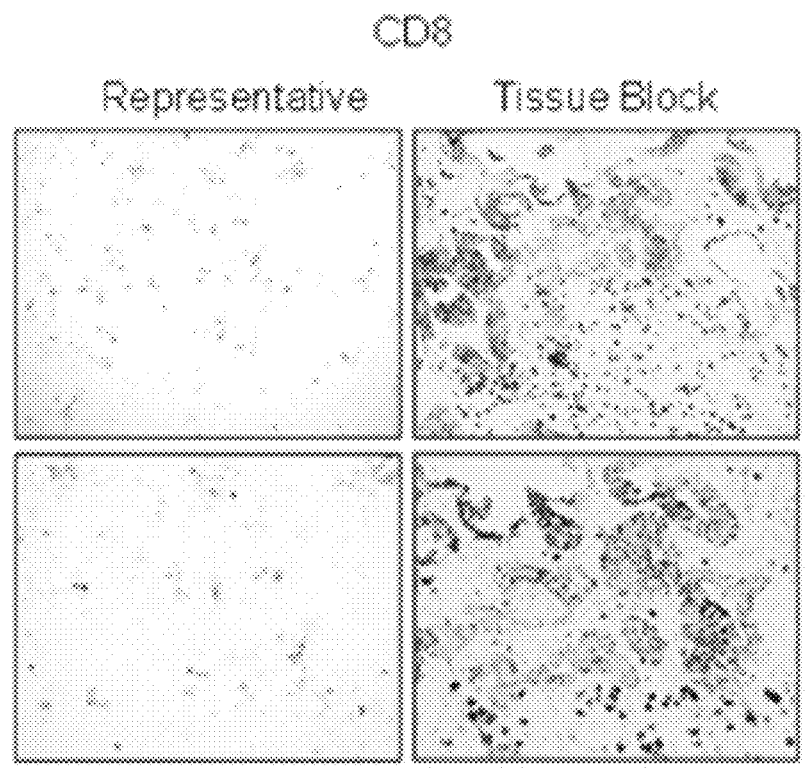
FIG. 9D illustrates DAB-IHC analysis of the representative human lung sample to detect CD8; images are compared at 10× and 20× magnification levels; samples from a tissue block are compared to those from representative sampling
Figure 9E:
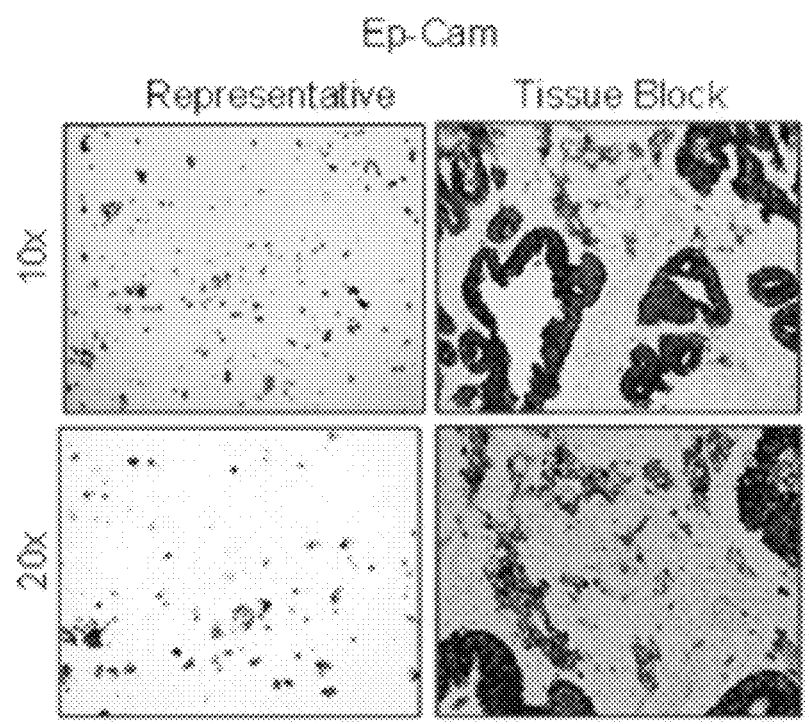
FIG. 9E illustrates DAB-IHC analysis of the representative human lung sample to detect Ep-Cam; images are compared at 10× and 20× magnification levels; samples from a tissue block are compared to those from representative sampling

The representative sample and the traditional tissue sections ("tissue block") were then subjected to DAB-IHC analysis for three different biomarkers: PD-L1 (FIG. 9C), CD8 (FIG. 9D), and Ep-Cam (FIG. 9E). Similar amounts of staining were observed in the representative sample and the traditional tissue sections, indicating that there was no loss of signal for large prevalence sub-clones using the inventive methods.

These results demonstrate that coupling mechanical manipulation of tissue with biochemical digestion can create a sample representative of the heterogeneity and diversity in a variety of tumor types. Moreover, the representative samples are suitable for use in various diagnostic tests, such as hematoxylin and eosin staining, immunohistochemical analysis, nucleic acid isolation and sequencing, and facilitate the detection of rare tumor sub-clones, thereby improving clinical diagnostics and personalized cancer treatment.

Example 3: Immunocytochemical Detection of Proteins in Representative Samples Derived from Intact Formalin Fixed Specimens Representative tissue and tumor samples were generated from a fixed tissue or tumor specimens using the homogenization methodology described herein and depicted schematically in FIG. 3, and proteins of interest, e.g., biologically and/or medically prognostic or predictive markers, were detected in the representative sample using immunocytochemistry (ICC).

Immunohistochemical (IHC) detection of proteins from histological sections of fixed biological samples is a common practice in anatomic pathology that impacts medical decisions, particularly in the context of solid tumor oncology. Immunocytochemical (ICC) detection of proteins from fixed specimens also impacts medical decisions, e.g. in cytological examination of pleural effusions from metastatic carcinoma, and differs from IHC in that the sample originally lacks histological architecture. ICC is reserved for cytological specimens, e.g. cervical cytology via Pap smear or thin layer prep. Histological sections, while maintaining many features important for today's practice of solid tumor pathology, such as stromal versus tumor architecture, represent a fraction of the cellular content of the tumor, and by extension bio-informational content, of an entire fixed biological specimen. The reformatting of intact fixed tumor specimens to yield a sample representative of the entirety of the tumor, and one that can provide statistically powered information having potential medical value is critical for the future of strategic personalized medicine.

Methods

Antibodies: Table 2 lists the antibodies and the fixed specimens used in this study. The antibodies are sold by Ventana® Medical Systems, Inc.

TABLE 2

Antibodies used in ICC analysis of representative sample.

| Antibody | Ventana Catalog Number |
|---|---|
| CD3 | 790-4467 |
| CD8 | 760-4437 |
| CD20 | 760-4383 |
| Ki-67 | 790-4286 |
| Ep-CAM (Ber-EP4) | 760-4383 |
| PDL-1 | 790-4905 |
| Her2 | 790-2991 |

Tissue Samples: All tissue samples were fixed in 10% neutral buffered formalin for 24 hours at Ventana® Medical Systems. Human tonsils were obtained from Northwest Medical Center (Tucson, AZ). Animal tissues were procured from commercial sources, e.g., chicken liver was obtained from the store.

Materials: Mechanical shearing of tissue was performed using an IKA® Works Tube Mill Control System (0004180001) from IKA-Works® (Staufen in Breisgau, Germany) and using a gentleMACs™ Dissociator from Miltenyi Biotec (Teterow, Germany). Heat and pH cell conditioning was performed in Cell Conditioning 1 (CC1) buffer from Ventana® Medical Systems (Tucson, AZ; catalog #950-124).

Blending. 200 µl mineral oil was added to an IKA® tube mill (Part #MT 40.100) blending gasket to prevent leakage during homogenization. 5 grams of tissue was added to the mill along with 1× tissue volume PBS. The sample was spun at 15000 rpm for 2 minutes (10 seconds spin, 2 seconds pause between spins). The homogenized sample was removed from the mill and added to a gentleMACs™ dissociator (Part #30-093-237) along with double the volume of PBS. The sample was blended using program h_tumor_01 (36 seconds of rotation), which was repeated a total of three times before the sample was poured over into 50 mL conical tube and centrifuged at 300×g for 3 minutes. The PBS aqueous layer was removed for conditioning.

Cell Conditioning: 1 volume pre-warmed Cell Conditioning Solution (CC1) was added. The sample was then placed on a heat block set to 85 degrees C. for 5 minutes. Following this, the sample was blended using the gentleMACs™ dissociator (3×program h_tumor_02). The heating step and blending step was performed two additional times each, prior to centrifuging the sample at 300×g for 3 minutes.

Plating: A 100 ul aliquot of the sample was relocated to an epitube, and 1 volume equivalent of 100% methanol was added. 70 µL of methanol/sample per VWR superfrost slide was used for plating and paraffin embedding Automated Immunocytochemistry: Brightfield DAB-based immunocytochemistry (ICC) was performed on representative samples deposited onto positively-charged glass slides using a Ventana® Medical Systems, Inc. Benchmark® XT platform (Ventana® Medical Systems, Inc, Tucson, AZ) with research software. DAB detection of each antibody was performed using the OptiView® DAB Detection Kit (VMSI Cat #760-700) with and without the OptiView® AMP Kit (VMSI Cat #760-099). Amplification was used to yield a low level of background within specimens and to allow reduced primary antibody incubation times. All detections were fully automated and performed on a Benchmark® XT autostainer (VMSI) after cell conditioning of specimens in CC1 buffer (VMSI Cat #950-124) for two rounds of 4 minutes. All primary antibody incubations were performed at 37° C. for 4 minutes (see Results and Discussion), allowing the total run time to remain under 2 hours and 20 minutes. Single DAB ICC was accomplished using the protocol shown in FIG. 10. FIG. 10 provides an exemplary DAB ICC protocol, set forth in steps 1-102, for protein detection in representative samples. In this particular example, the protocol was used to detect Her2.

Chromogenic multiplexed detection was accomplished as described in FIG. 11, in the following order: Ki-67→CD20→CD3. Heat denaturation of enzymes and primary antibody melt-offs were performed between Ki-67 and CD20 and CD20 and CD3 via 90° C. incubation in Cell Conditioning 2 (CC2) buffer (VMSI Cat #950-123) for 12 minutes to prevent cross-reactivity.

Results and Discussion

Figure 12:
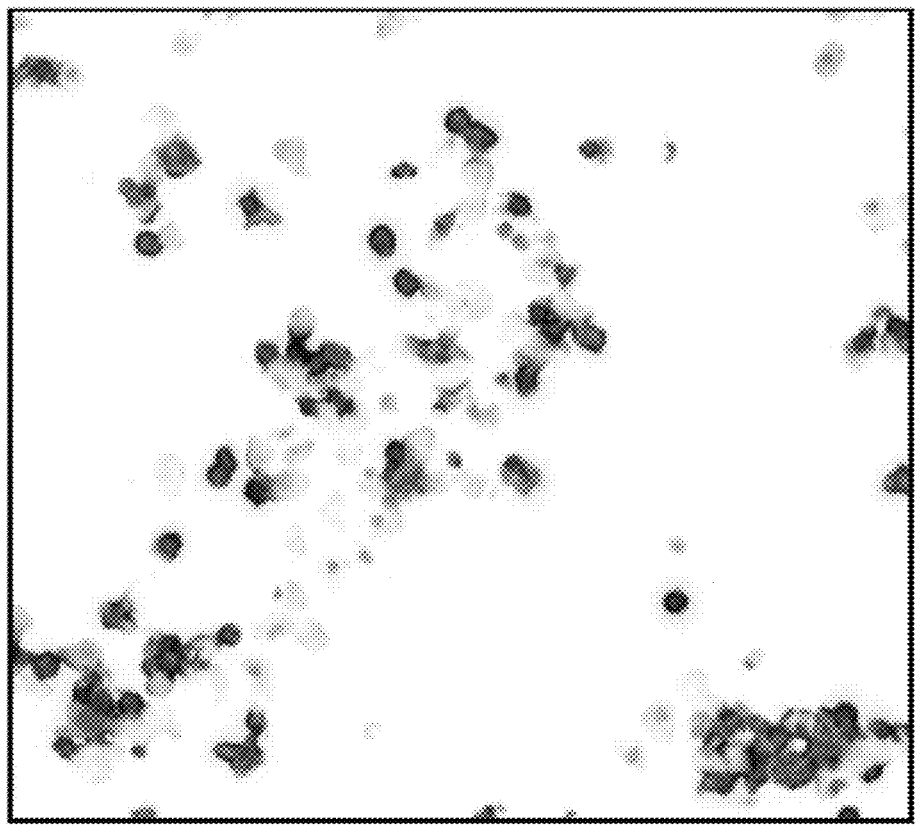
FIG. 12 shows the detection of CD20, which demarcates B-cells, using automated DAB ICC in a representative sample prepared from a mixture of animal tissue and human tonsil specimens. CD20 was detected in cells from the human tonsil tissue contained in the representative sample.

To determine whether representative samples deposited onto glass slides could be stained using automated ICC, samples from a prepared mixture of animal tissue and tonsil specimens were stained for single biomarker DAB ICC (FIG. 12). FIG. 12 shows the detection of CD20, which demarcates B-cells, using automated DAB ICC in a representative sample prepared from a mixture of animal tissue and human tonsil specimens. CD20 was detected in cells from the human tonsil tissue contained in the representative sample.

A four minute primary antibody incubation with amplification was selected to minimize background and run time (e.g., Rep Dia-Her2 DAB Protocol, FIG. 10). All antibodies tested (see Table 2) were determined to be compatible with this protocol.

Figure 13A:
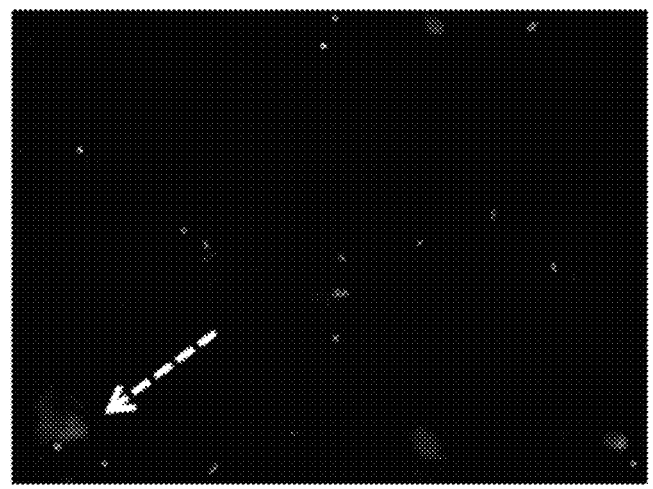
FIG. 13A shows the detection of Her2-positive Calu-3 cells present in a representative sample prepared from tonsil tissue and a Her-2 positive xenograft tumor using fluorescence ICC. Illustrated is a representative sample containing Calu-3 cells incubated with secondary antibody only (negative control). The background signal in Calu-3 cells generated by the secondary antibody is designated by the dashed line arrow.
Figure 13B:
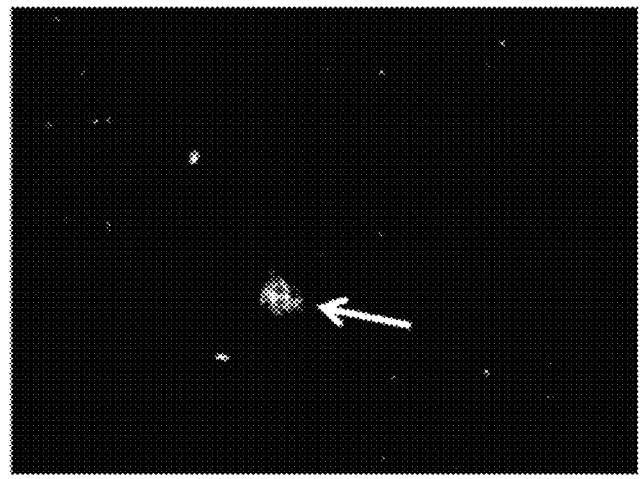
FIG. 13B illustrates the detection of Her2-positive Calu-3 cells present in a representative sample prepared from tonsil tissue and a Her-2 positive xenograft tumor using fluorescence ICC. Illustrated is a representative sample containing Calu-3 cells incubated with a Her2 antibody (4B5) prior to addition of the secondary antibody FIG. 14 provides an exemplary multiplex chromogenic ICC protocol (set forth in steps 1-225) for detection of multiple proteins in a representative sample.

A protocol to test the feasibility of detecting single markers using fluorescence ICC was also developed (see FIG. 11). For example, Her2 was detected using fluorescence ICC (FIGS. 13A and 13B). Here, FIGS. 13A and 13B show the detection of Her2-positive Calu-3 cells present in a representative sample prepared from tonsil tissue and a Her-2 positive xenograft tumor using fluorescence ICC. FIG. 13A illustrates a representative sample containing Calu-3 cells incubated with secondary antibody only (negative control). The background signal in Calu-3 cells generated by the secondary antibody is designated by the dashed line arrow. FIG. 13B illustrates a representative sample containing Calu-3 cells was incubated with a Her2 antibody (4B5) prior to addition of the secondary antibody. Her-2 signal in Calu-3 cells is designated by the solid line arrow. Signal from smaller non-specific cells derived from tonsil is seen without Her2 antibody (4B5) addition (FIG. 13A) and with Her2 antibody (4B5) addition (FIG. 13B).

Next, a representative sample prepared from a tonsil specimen was prepared and placed on a glass slide to test analysis with multiplex chromogenic ICC. The representative tonsil specimens were stained for three immune markers, each detected using a separate color according to the protocol shown in FIG. 14. FIG. 14 provides an exemplary multiplex chromogenic ICC protocol (set forth in steps 1-225) for detection of multiple proteins in a representative sample. In this particular example, species-specific antibodies to Ki-67, CD20, and CD3 and anti-species-enzyme conjugate-driven deposition of chromogen was used to detect the three immune markers.

For example, chromogenic multiplexing was performed on the representative tonsil specimens to detect Ki-67, CD20, and CD3 using species-specific secondary antibodies followed by anti-species-enzyme conjugate-driven deposition of chromogen with heat denaturation steps to eliminate enzyme activity, as previously described in Wenjun Zang et al., "Quantum dot in situ hybridization", WO2014139979. Biologically appropriate detections and overlays of color were observed in the representative tonsil specimens subjected to chromogenic multiplex (FIG. 15).

Next, ICC was performed on representative samples prepared from clinical specimens. In particular, representative samples prepared from formalin fixed lung tumor or formalin fixed kidney tumor were prepared and tested for PDL-1 (a marker produced by tumors for blocking anti-tumor immunity and a target for dictating immunotherapy), CD8 (a crucial T-cell marker for understanding anti-tumor immunity level), and Ep-Cam (a marker indicative of epithelial cancers). Each of the tested biomarkers tested (PDL-1, CD8, and Ep-Cam) were detected, at varying levels, in the representative samples prepared from the clinical tumor specimens (see FIGS. 8A-8D and FIGS. 9A-9D).

These results demonstrate fully automated single and multiplexed ICC detection of markers in representative samples derived from an intact formalin fixed tissue specimen and, moreover, shows that a sample representative of the intact fixed tissue specimen offers the capability to detect rare subpopulations of cells within the sample.

Example 4: Preparation of Representative Samples from Lymph Nodes and the Use Thereof to Detect Rare Subclones This example describes the generation of a representative sample from lymph node tissue, which permitted sensitive detection of cancer cells that may result from tumor metastasis. Representative tissue samples were derived from formalin-fixed tumor samples using the homogenization methodology described herein and depicted schematically in FIG. 3. In general, tumor samples, i.e., formalin-fixed tumor samples were initially mechanically disassociated, and then preconditioned in CC1 buffer at 85° C., before being transferred to buffer 1×PBS buffer.

Methods

Antibodies: Anti-BRAFV600E mouse monoclonal antibody (Catalog No. 790-4855, Ventana® Medical Systems, Inc.) was used to detect b-Raf.

Tissue Samples: All tissue samples were fixed in 10% neutral buffered formalin for 24 hours at Ventana® Medical Systems. HER2-positive or BRAF xenograft was generated at Ventana® Medical Systems. Human tonsils were obtained from Northwest Medical Center (Tucson, AZ).

Materials: Mechanical shearing of tissue was performed using an IKA® Works Tube Mill Control System (0004180001) from IKA-Works® (Staufen in Breisgau, Germany) and using a gentleMACs™ Dissociator from Miltenyi Biotec (Teterow, Germany). Heat and pH cell conditioning was performed in Cell Conditioning 1 (CC1) buffer from Ventana® Medical Systems (Tucson, AZ; catalog #950-124).

Blending: 200 μl mineral oil was added to an IKA® tube mill (Part #MT 40.100) blending gasket to prevent leakage during homogenization. 5 grams of tissue was added to the mill along with 1× tissue volume PBS. The sample was spun at 15000 rpm for 2 minutes (10 seconds spin, 2 seconds pause between spins). The homogenized sample was removed from the mill and added to a gentleMACs™ dissociator (Part #30-093-237) along with double the volume of PBS. The sample was blended using program h_tumor_01 (36 seconds of rotation), which was repeated a total of three times before the sample was poured over into 50 mL conical tube and centrifuged at 300×g for 3 minutes. The PBS aqueous layer was removed for conditioning.

Cell Conditioning: 1 volume pre-warmed Cell Conditioning Solution (CC1) was added. The sample was then placed on a heat block set to 85 degrees C. for 5 minutes. Following this, the sample was blended using the gentleMACs™ dissociator (3×program h_tumor_02). The heating step and blending step was performed two additional times each, prior to centrifuging the sample at 300×g for 3 minutes.

Plating: A 100 ul aliquot of the sample was relocated to an epitube, and 1 volume equivalent of 100% methanol was added. 70 μL of methanol/sample per VWR superfrost slide was used for plating.

Automated Immunocytochemistry: Brightfield DAB-based immunocytochemistry (ICC) was performed on representative samples deposited onto positively-charged glass slides using a Ventana® Medical Systems, Inc. Benchmark® XT platform (Ventana® Medical Systems, Inc, Tucson, AZ) with research software. DAB detection of the antibody was performed using the OptiView® DAB Detection Kit (VMSI Cat #760-700) with and without the OptiView® AMP Kit (VMSI Cat #760-099). Amplification was used to yield a low level of background within specimens and to allow reduced primary antibody incubation times. All detections were fully automated and performed on a Benchmark® XT autostainer (VMSI) after cell conditioning of specimens in CC1 buffer (VMSI Cat #950-124) for two rounds of 4 minutes.

Results and Discussion

To determine whether low prevalence events within a representative samples from a lymph node (such as a tonsil) could be detected, the representative lymph node sample was deposited onto glass slides and stained using automated ICC as set forth in FIG. 10.

To test the sensitivity of the detection of a tumor cell within a representative sample of a lymph node, a decreasing amount of a representative sample of a bRaf V600E positive human xenograft was spiked into a lymph node homogenate. The following cell percentages (the prevalence of the BRAFV600E-positive cells in the total volume of the sample) were used: 50%, 25%, 12.5%, 6.25%, 3.12%, 1.5%, 0.15%, 0,015%, 0.0015%, and 0.00015%. bRaf-positive cells were detected at a prevalence as low as 0.015% (FIG. 16), demonstrating that ICC can be used on representative tissue samples prepared from lymph nodes to find extremely rare cell subpopulations that may be therapeutically actionable (e.g., vemurafinib for BRAFV600E+).

An analogous dilution series experiment was also performed with Her2-positive cell, which were added at decreasing ratios to the representative tonsil sample to yield the following cell percentages: 50%, 25%, 12.5%, 6.25%, 3.12%, 1.5%, 0.15%, 0,015%, 0.0015%, and 0.00015%. Similar to b-Raf-positive cells, Her2-positive cells could also be detected at very low levels, i.e., about 0.015% (data not shown), again suggesting that ICC analysis of representative samples can be used to find extremely rare cell subpopulations that may be therapeutically actionable (e.g. Herceptin for Her2+).

Example 5: Preparation of Representative Samples from Whole Tumors

This example describes representative samples created from surgically resected primary tumors.

Methods

Figure 18A:
FIG. 18A illustrates residual surgical material from a colon resection that still contains an eight (8) cm colon adenocarcinoma.
Figure 18B:
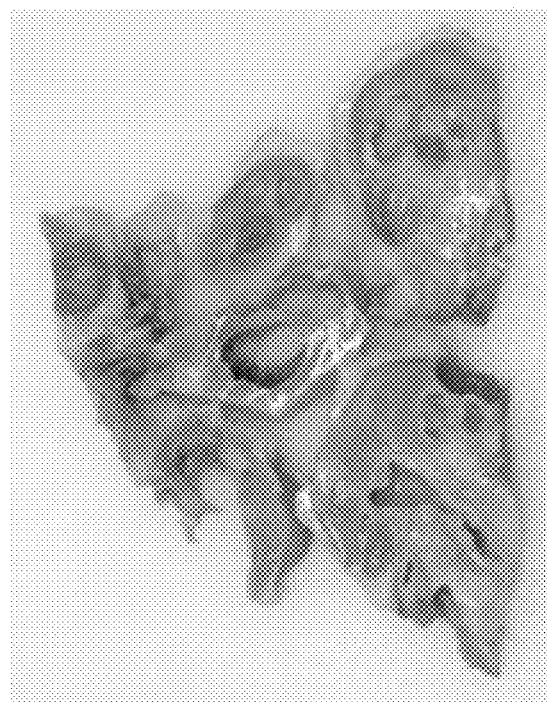
FIG. 18B illustrates residual surgical tissue from a partial nephrectomy of a kidney containing a papillary urothelial kidney tumor.

Representative tissue samples were derived from a formalin-fixed surgically resected colon around eight cm in diameter, and a partial resection of a kidney (procured from GLAS Tissue Consultants, Winston-Salem, NC) (FIGS. 18A and 18B). Here. FIG. 18A illustrates material from a colon resection that still contains an eight (8) cm colon adenocarcinoma while FIG. 18B illustrates residual tissue from a partial nephrectomy of a kidney containing a papillary urothelial kidney tumor.

Samples of the tumor were acquired and processed for histological examination (i.e., paraffin embedding, histological sectioning) to mimic the TNM sampling process. The residual tumor tissue was dissected by a pathologist using a scalpel, and the tumor tissue was homogenized using the IKA Works® Tube Mill Control System (0004180001) from IKA-Works® (Staufen im Breisgau, Germany) or a Hamilton Beach® Single Serve Blender. Samples of the homogenates were then mechanically disassociated, and then preconditioned in CC1 buffer at 85° C., before being transferred to buffer (e.g., PBS) containing AccuMax® with 1 mg/mL Collagenase H in AccuMax® buffer. The resultant enzyme treated homogenated tissue was then incubated with Collagenase H for at least about 30 minutes at 40° C. before being returned to CC1 buffer and heated at 85° C. for about 10 minutes to inactivate any remaining collagenase enzyme. The representative sample was then used to derive sub-samples which were then used for a variety of diagnostic assays.

Samples were stained with H&E as well as ALK IHC on a Ventana® staining platform.

Results and Discussion

Figure 19A:
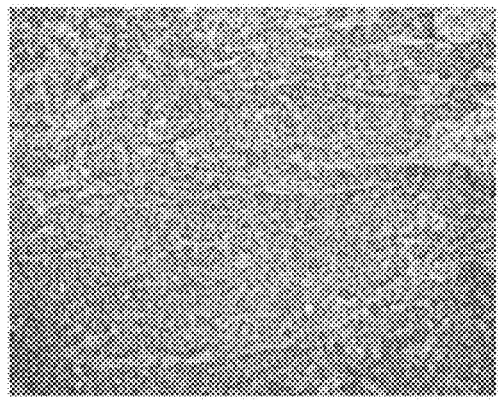
FIG. 19A illustrates H&E staining of a first histological section obtained from the adenocarcinoma of the colon.
Figure 19B:
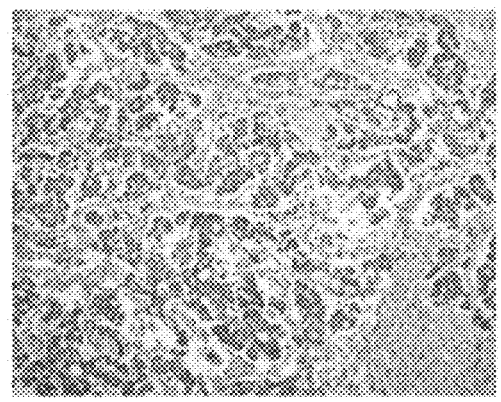
FIG. 19B illustrates H&E staining of a second and different section from the adenocarcinoma of the colon. The difference in H&E staining as compared to FIG. 19A shows variation within the same tumor.
Figure 19C:
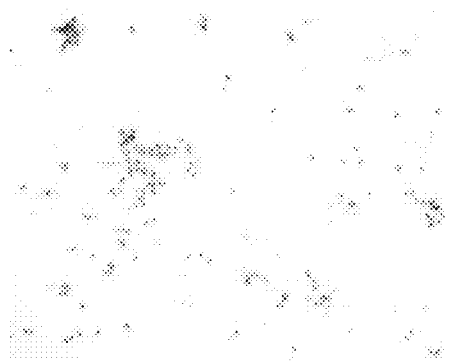
FIG. 19C illustrates H&E staining of a representative sample prepared from the adenocarcinoma of the colon.
Figure 20A:
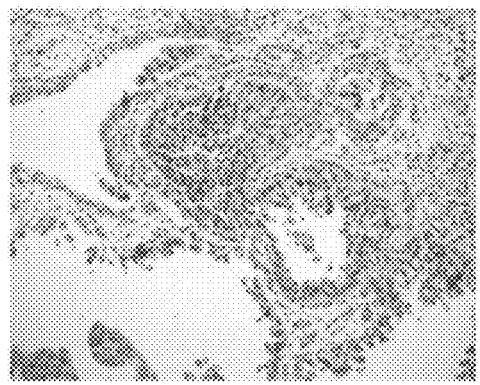
FIGS. 20A-20C show H&E staining of distinct histological sections obtained from the papillary urothelial kidney tumor.
Figure 20B:
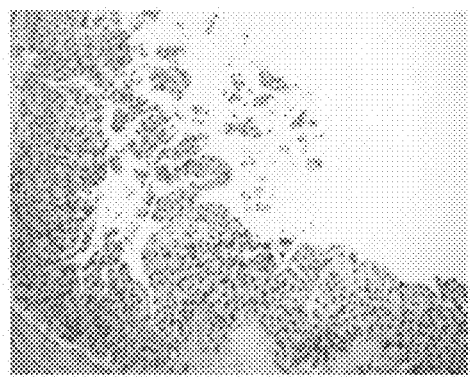
Figure 20C:
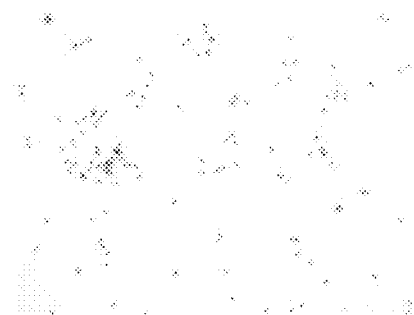

To determine if the diversity of cell types contained within the original sample, both histological sections and representative samples were stained with H&E (FIGS. 19 and 20. and 23). Here, FIG. 19A illustrates a first section obtained from the adenocarcinoma of the colon; while FIG. 19B illustrates a second and different section from the adenocarcinoma of the colon. Each of the sections in FIGS. 19A and 19B were each obtained by a pathologist. The difference in H&E staining shows the variation within the same tumor. FIG. 19C illustrates H&E staining of a representative sample prepared from the adenocarcinoma of the colon. FIGS. 20A-20C show H&E staining of distinct histological sections obtained from the papillary urothelial kidney tumor. FIG. 20A illustrates a first section taken from the papillary urothelial kidney tumor; FIG. 20B illustrates a second different section taken from the papillary urothelial kidney tumor. Each of the sections illustrated in FIGS. 10A and 20B were obtained by a pathologist. The difference in H&E staining shows the variation within the same tumor. FIG. 20C illustrates H&E staining of a representative sample prepared from the papillary urothelial kidney tumor.

Apparent from FIGS. 19 and 20, while the morphologies from the histological sections taken from different regions of the resected tumor have different histological appearances (A, B), the representative samples (C) recapitulate the heterogeneity in the cells that compose each tumor type (i.e. tumor, normal, immune).

Figure 21A:
FIG. 21A illustrates Alk DAB staining of a first distinct histological section taken from an adenocarcinoma of the colon.
Figure 21B:
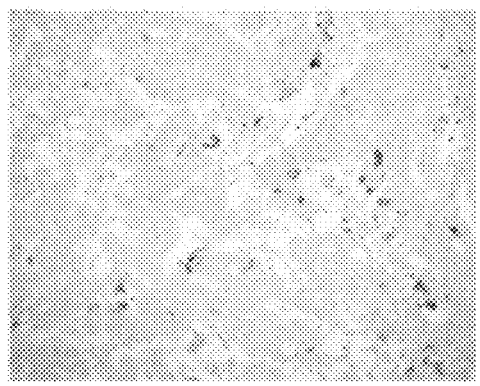
FIG. 21B illustrates Alk DAB staining of a second different section taken from an adenocarcinoma of the colon. Each of the sections illustrated in FIGS. 21A and 21B were obtained by a pathologist. The difference in Alk DAB staining shows the variation within the same tumor.
Figure 21C:
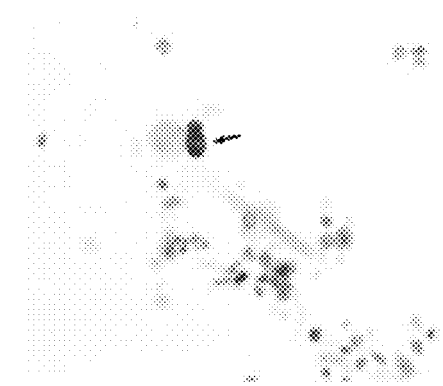
FIG. 21C illustrates Alk DAB staining of a representative sample prepared from the adenocarcinoma of the colon.

To determine whether any heterogeneity in biomarker expression was present in the histogical tissues that were recapitulated in the representative sample, all samples were analyzed for Alk expression, likely resulting from a genomic rearrangement with EML4. All slides were reviewed by a pathologist who determined positive vs negative expression of Alk DAB staining. FIGS. 21A-21C and FIGS. 22A-22C show that for both the kidney and the colon one histological section demonstrated punctate and infrequent positivity for Alk, whereas one section was negative. This discordance in staining between blocks while surprising, is indicative of the sampling bias inherent in the TNM staging system. The heterogeneity in Alk positivity (i.e. the low prevalence relative to the size of the entire tumor) was obvious in the representative samples stained with Alk IHC, as there were small clusters or single cells that were positive for Alk DAB. FIGS. 21A-21C show Alk DAB staining of distinct histological sections obtained from the adenocarcinoma of the colon. FIG. 21A illustrates a first section taken from the papillary urothelial kidney tumor; FIG. 21B illustrates a second different section taken from the papillary urothelial kidney tumor. Each of the sections illustrated in FIGS. 21A and 21B were obtained by a pathologist. The difference in Alk DAB staining shows the variation within the same tumor. FIG. 21C illustrates Alk DAB staining of a representative sample prepared from the adenocarcinoma of the colon.

Figure 22A:
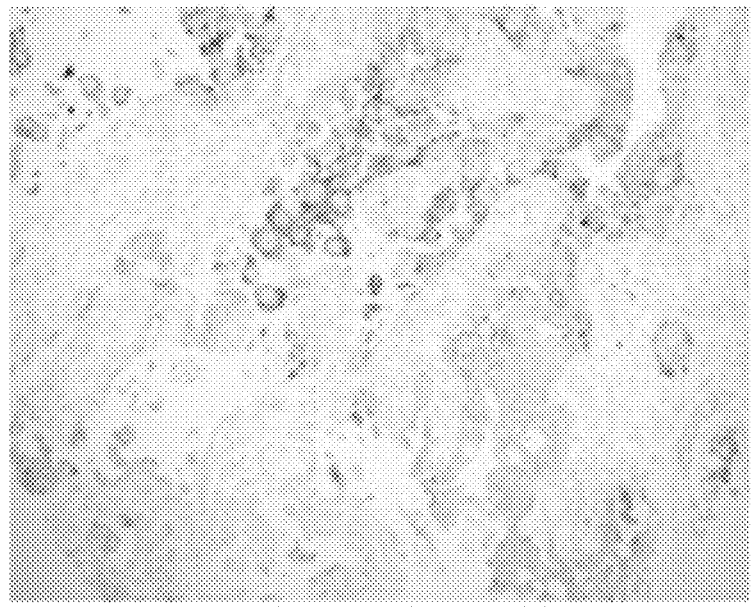
FIGS. 22A-C show Alk DAB staining of distinct histological sections obtained from the papillary urothelial kidney.
Figure 22B:
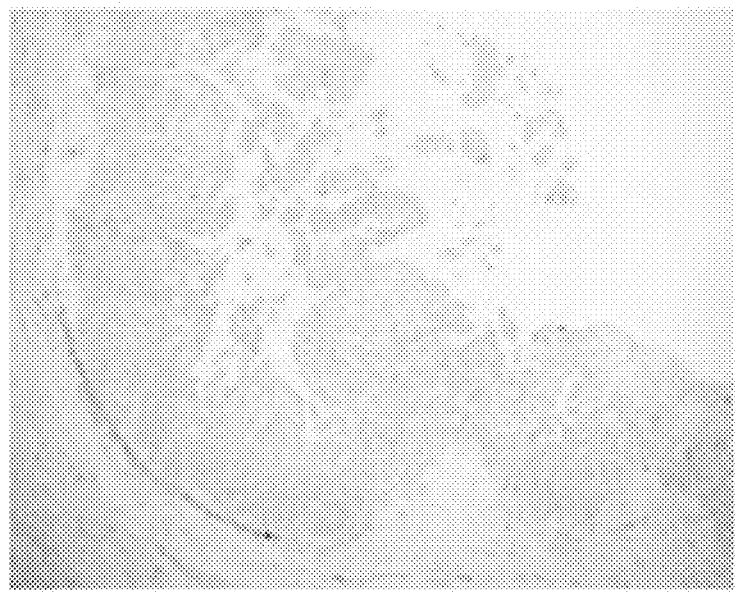
Figure 22C:
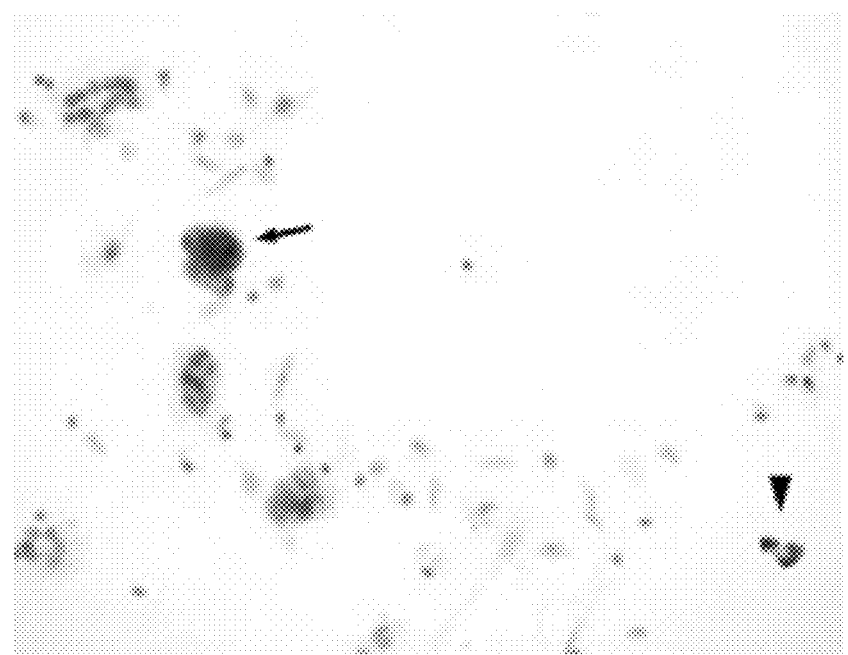
Figure 25A:
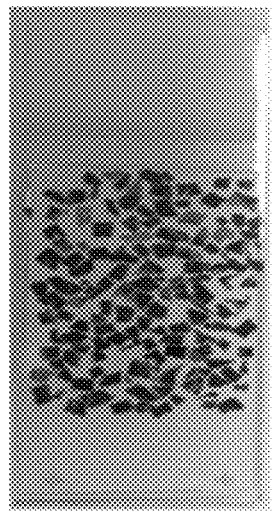
FIGS. 25A-D show images of H&E stained histological slides made of cut and minced tonsils.
Figure 25B:
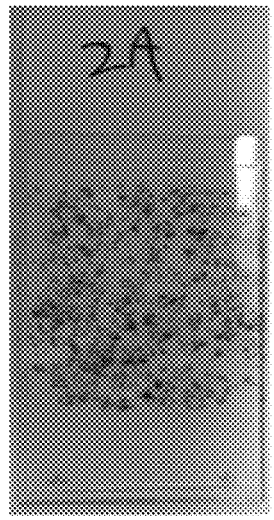
Figure 25C:
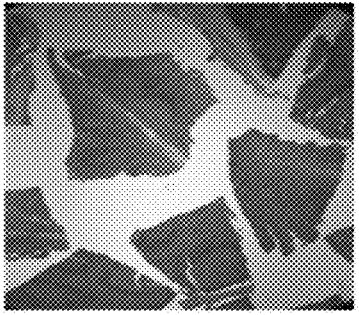

FIG. 21C shows a small cluster of three colon adenocarcinoma cells that are positive for Alk (arrow), and FIG. 25C shows a small cluster of six papillary urothelial kidney cancer cells (arrow) and a control lymphocyte that is positive (arrow head). FIGS. 22A-C show Alk DAB staining of distinct histological sections obtained from the papillary urothelial kidney. FIG. 22A illustrates a first section taken from the papillary urothelial kidney tumor; FIG. 22B illustrates a second different section taken from the papillary urothelial kidney tumor. Each of the sections illustrated in FIGS. 22A and 22B were obtained by a pathologist. The difference in Alk DAB staining shows the variation within the same tumor. FIG. 22C illustrates Alk DAB staining of a representative sample prepared from the papillary urothelial kidney tumor.

Example 6: Mechanical Dissociation and Homogenization of Tissue Samples

This example describes the step of mechanical dissociation and homogenization of tissue samples to produce the representative sample. The methods include cutting and mincing the tissue sample and single cell dissociation.
Methods The tissues were cut by hand (FIG. 25A) or minced using an appropriate food-processing instrument such as a "juicer" (FIG. 25B). Although this methods utilizes formalin fixed tonsils tissue (shown in FIGS. 25A-25B) other tissue types may also be used. The tonsils were ordered fresh, fixed in 10% neutral buffered formalin for 24 hours and then stored in pure ethanol. The tonsil was manually diced using a scalpel, or mechanically disassociated in a juicer. The resulting homogenates were then dehydrated and perfused with paraffin wax in a tissue processor (PROCESSOR NAME). Four micron sections were taken of the samples, and H&E staining was used to visualize the size distribution of the tissue fragments.
Results and Discussion To determine whether mincing, cutting, and juicing produced a uniform distribution of tissue fragments, a lymph node (tonsil) was diced by hand or mechanically disassociated using a juicer. As apparent in FIG. 25A and FIG. 25B, dicing a fixed tonsil by hand results in a mixture of tissue fragments with a very uniform size distribution. The tissue fragments contain tens of thousands to hundreds of thousands of cells, and maintain the structure of the organ in a histologically recognizable manner.

Figure 25D:
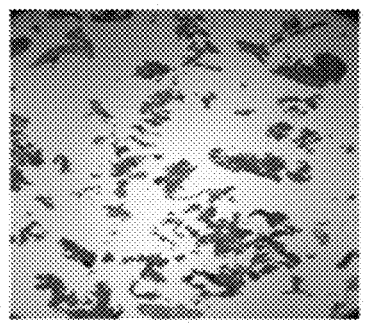

Disassociation of the lymph node using a juicer resulted in smaller fragments of tissue containing hundreds to thousands of cells (FIG. 25C and FIG. 25D). The tissue fragments produced by the juicer present the tissue homogenate in such a way that cell-to-cell interactions can be assessed by an anatomic pathologist.

It is contemplated that mincing, juicing, and blending can be used independently, or in combination. For instance, a resected tumor may first be minced producing a uniform population of tissue fragments for paraffin embedding and histological examination. A sample of the minced homogenate may then be juiced or blended to further disassociate the tissue in preparation for further enzymatic disassociation intended for single cell or single nuclei isolation.

Example 7: Disassociation of Homogenates (or Representative Samples) into Single Cells This example describes the further processing of representative samples derived from organs, tissues, or tumors (via blending, juicing, or mincing) into single cells for quantification, isolation, and biomarker analysis. Methods include mechanical disassociation, filtering, enzymatic disassociation, and sonication.
Mechanical Disassociation and Filtration Methods:

The clinical tumor sample used in this example is the afore mentioned large colon adenocarcinoma obtained from GLAS Tissue Consultants. A lymph node (tonsil), and the colon adenocarcinoma homogenates were prepared as described above. A sample of homogenate was filtering using a 1 mm sieve (Advantech Manufacturing, New Berlin, WI) and the material that unable to pass through the sieve was collected. The homogenate sample that passed through the 1 mm sieve was then filtered using a 20 micron filter (Pluriselect®, San Diego, CA). The material that was unable to pass through the 20 micron filter was collected. The homogenate that was able to pass through the 20 micron filter was then passed over a 10 micron filter and collecting the single cells that passed through. The single cells that passed through the 10 micron filter was centrifuge for 5 minutes at 800 g, and re-suspend in PBS with 3% BSA and 0.09% sodium azide, repeating three times, and discarding the supernatant. The single cells are ready to be stored at 4° C.

A Multisizer™ 4e Coulter Counter® (Beckman Coulter, Indianapolis IN) was used to characterize the size distribution of the single cells collected from the filtering steps. An Attune® focusing flow cytometer (ThermoFisher Scientific®) was used to characterize all single cells, and to sort and collect the single cells. A sonicator was used to mechanically disassociate the multicellular clusters into single cells. In some cases, 250 units of collagenase (TYPE & COMPANY) was used to biochemically disassociate the multicellular clusters by incubation at 37° C. for 1 hour in Hanks balanced salt buffer. Following the incubation, the mixture was centrifuged at centrifuged 800 g for 1 min and re-suspended in PBS.

EpCam antibody (Ventana® Medical Systems, Inc., Tucson, AZ) was used to stain the epithelial cells from the filtrate. Primary antibody was incubated with the sample nuclei for 1 h at 37° C. or for 24 h at 4° C. Control samples received no primary antibody. After incubation, samples were washed 6× with EZ prep buffer, and then resuspended in goat-anti-mouse Alexa-488 (Alexa Fluor®) antibody (1:500) in MACS buffer for 0.5-1 h at 37° C. Some samples were also stained with 3 µM DAPI for 10 min. Stained samples were washed 4× with reaction buffer at 4° C. A 50 µl sample was spread onto VWR plus slides and immediately imaged through a glass coverslip. Images of stained cells were acquired on a Zeiss Axio epifluorescent microscope controlled by in-house software, and images were analyzed using ImageJ. Stained nuclei were stored at 4° C. in MACS-T-STC.

Results and Discussion

Figure 26A:
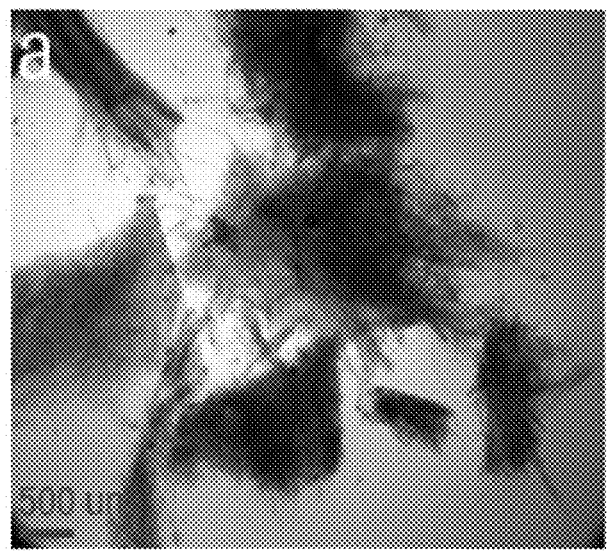
FIG. 26A is a brightfield image of collect 1 of a mechanically blended and filtered colon tumor sample.
Figure 26B:
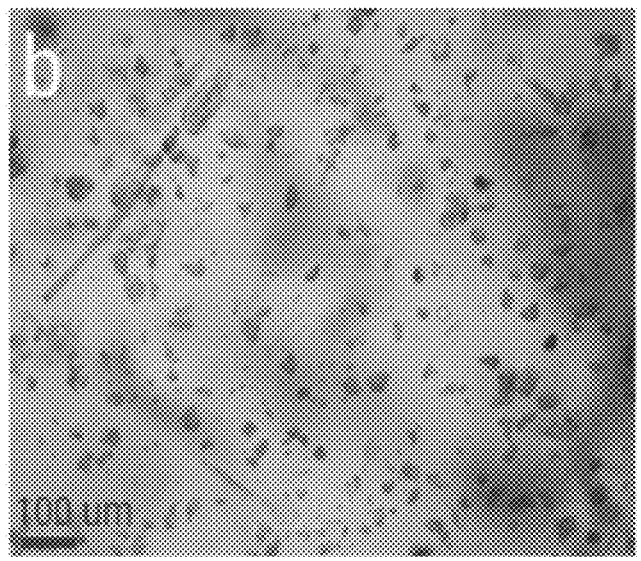
FIG. 26B is a brightfield image of collect 2 of a mechanically blended and filtered colon tumor sample.
Figure 26C:
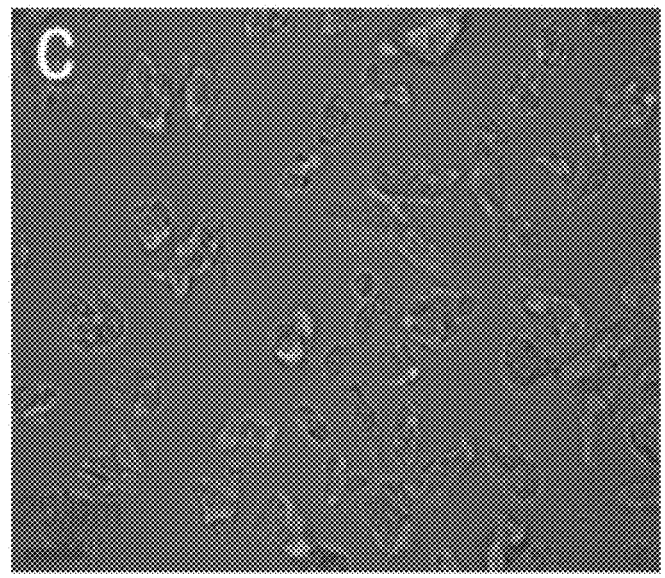
FIG. 26C is a brightfield image of collect 3 of a mechanically blended and filtered colon tumor sample.
Figure 26D:
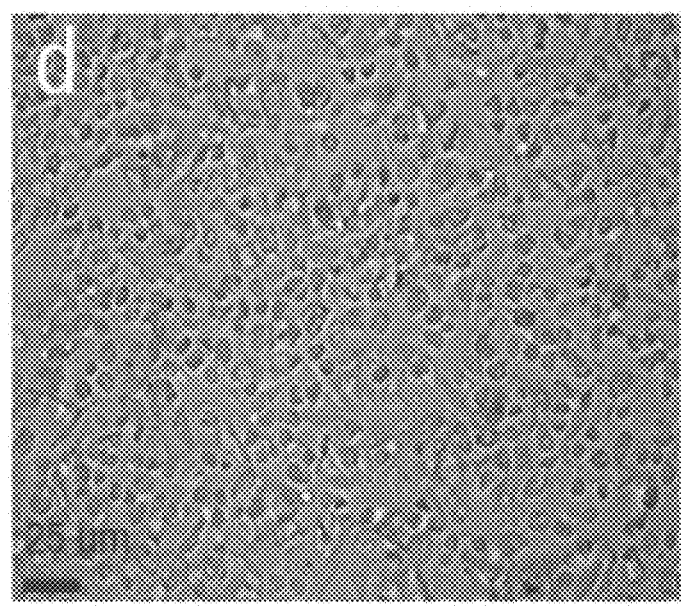
FIG. 26D is a brightfield image of filtrate is a brightfield image of collect 1 of a mechanically blended and filtered colon tumor sample.

The goal of the sequential filtration steps was to determine the composition of the various sized particles that comprise the homogenate. At each step, the tissue that was unable to pass through the filter was carefully analyzed by light microscopy (FIG. 29). As shown in FIG. 26A, the material that was unable to pass through the 1 mm sieve was primarily composed of connective tissue and muscle fibers. This material lacked cellularity, and was therefore discarded. The material that was unable to pass through the 20 micron filter was primarily composed of large multicellular clusters (FIG. 26B). The material unable to pass through the 10 micron filter was primarily composed of small multicellular clusters of tumor cells (FIG. 26C), while the material that passed through the 10 micron filter were the single cells that were liberated during the homogenization process (FIG. 26D). Therefore, homogenization of human tumors to create representative samples generates a distribution of tissue fragment sizes ranging from large multicellular clusters, to individual cells.

Figures 27A, 27B, 27C:
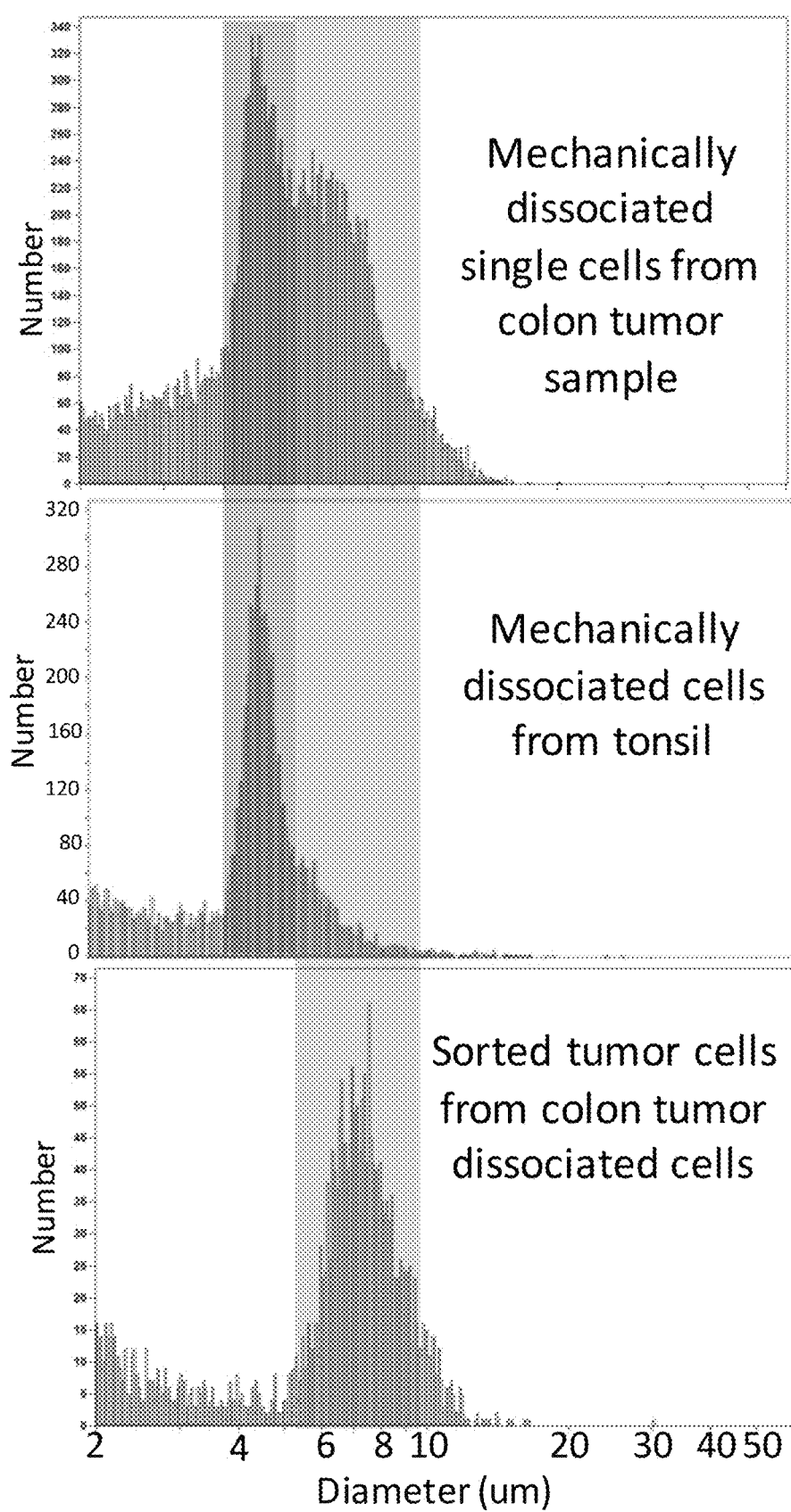
FIGS. 27A-FIG. 27C show size distribution of mechanically dissociated and filtered single cells.

A Multisizer™ 4e Coulter Counter® (Beckman Coulter, Indianapolis IN) was used to measure the yield (number of single cells per gram of homogenized tissue) as well as the size of the dissociated single cells isolated from the colon adenocarcinoma. Particles between 4 and 10 um were counted and considered as single cells. The yield per gram of tumor homogenate using the filtration method was approximately 320,106 cells/gram. The isolated cells from the tumor homogenate distribute into two distinct populations; cells ranging from 4-5.5 microns in diameter, and cells between 5.5-9.3 microns in diameter (FIG. 27A). The same analysis was done for the cells purified from the homogenized tonsil, and the majority of cells isolated from the tonsil were between 4 to 5.5 microns in diameter (FIG. 27B).

Figure 28:
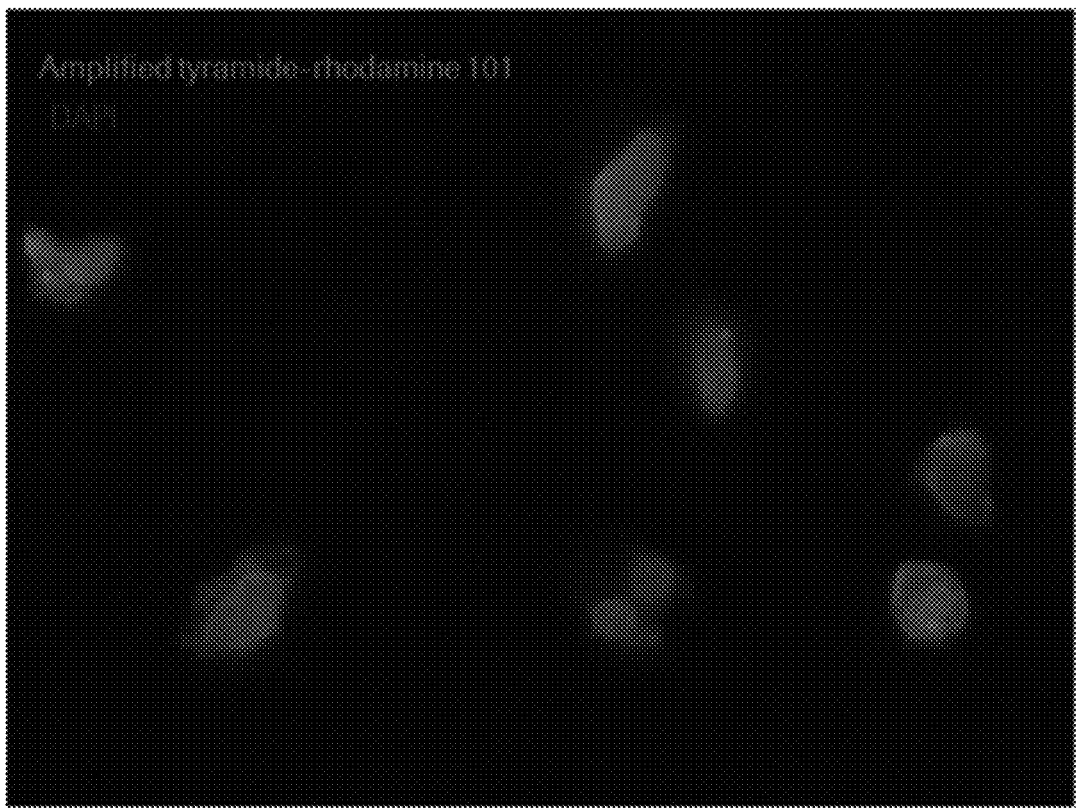
FIG. 28 shows a fluorescent image of EpCAM positive tumor cells mechanically dissociated and filtered from colon tumor sample and sorted with Sony® SH800 cell sorter.

The size distributions in the single cells isolated from the colon tumor and the tonsil suggest that the cells that are between 4 and 5.5 microns in diameter are immune cells, while the cells between 5.5 and 9.3 microns are tumor cells. To corroborate this finding, individual tumor cells isolated from the colon tumor were fluorescently stained for EpCam to determine the size of the tumor cell component. The fluorescently stained cells were first plated on a microscope slide and imaged using a fluorescent microscope to evaluate the staining procedure (FIG. 28). Following sorting on an Attune® Flow Sorting instrument, the size of the sorted EpCam positive cells was reassessed using the Coulter Counter. Accordingly, the size distribution of the EpCam positive tumor cells correlates to a cell population that is absent from the non-tumor containing tonsil, but present in the single cells from the homogenized colon tumor.

These data suggested that the mechanically dissociated and filtered cells from the homogenized colon tumor are composed of two distinct populations: normal immune cells and tumor cells. These two populations can be easily distinguished using a particle size analyzer and the isolated cells can be further analyzed using flow cytometry and sorting. The data further suggests that size-based separation methods (size-exclusion columns, microfluidic device, density centrifugation, etc.) can be adopted to separate the two populations yielding enriched tumor or immune cell samples.

Disassociation of Multicellular Fragments

Figure 35A:
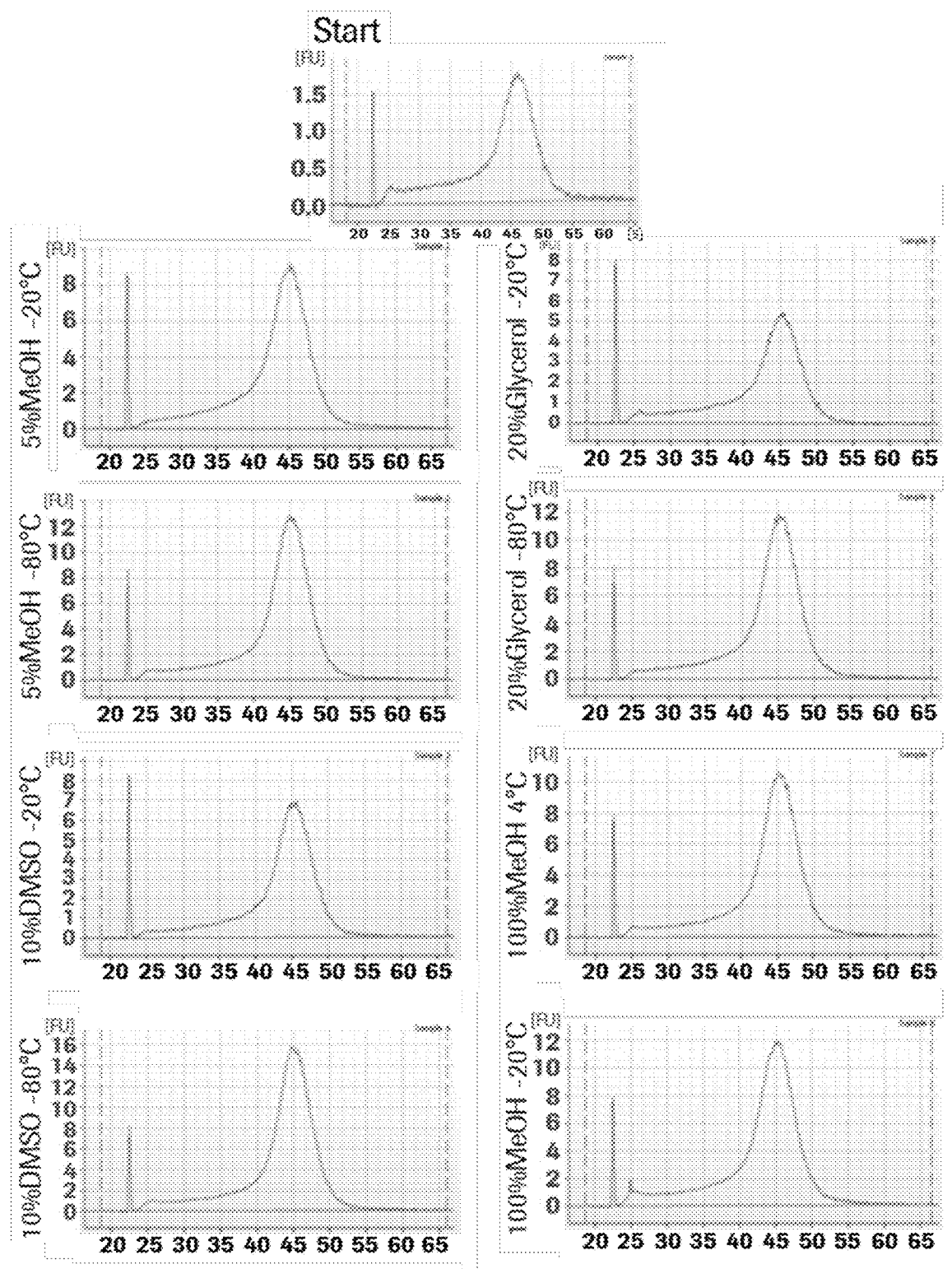
FIG. 35A illustrates six month stability of RNA isolated from a pancreatic well-differentiated neuroendocrine neoplasm and incubated in standard cell storage solutions as needed (20% glycerol, 10% DMSO, 5% MeOH, and 100% MeOH) at the indicated temperatures for 6 months).
Figure 35B:
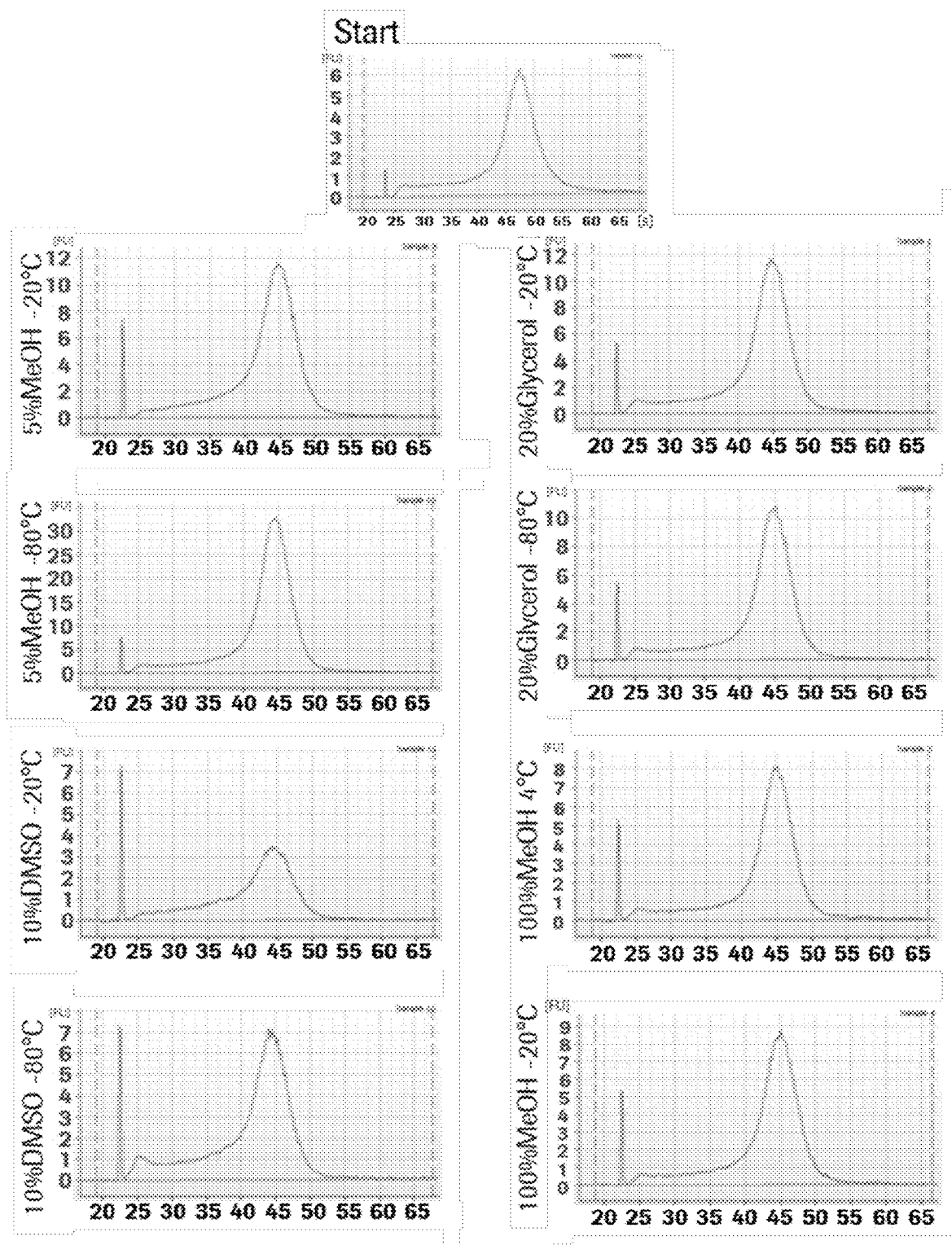
FIG. 35B illustrates six month stability of RNA isolated from a papillary urothelial carcinoma and incubated in standard cell storage solutions as needed (20% glycerol, 10% DMSO, 5% MeOH, and 100% MeOH) at the indicated temperatures for 6 months).
Figure 35C:
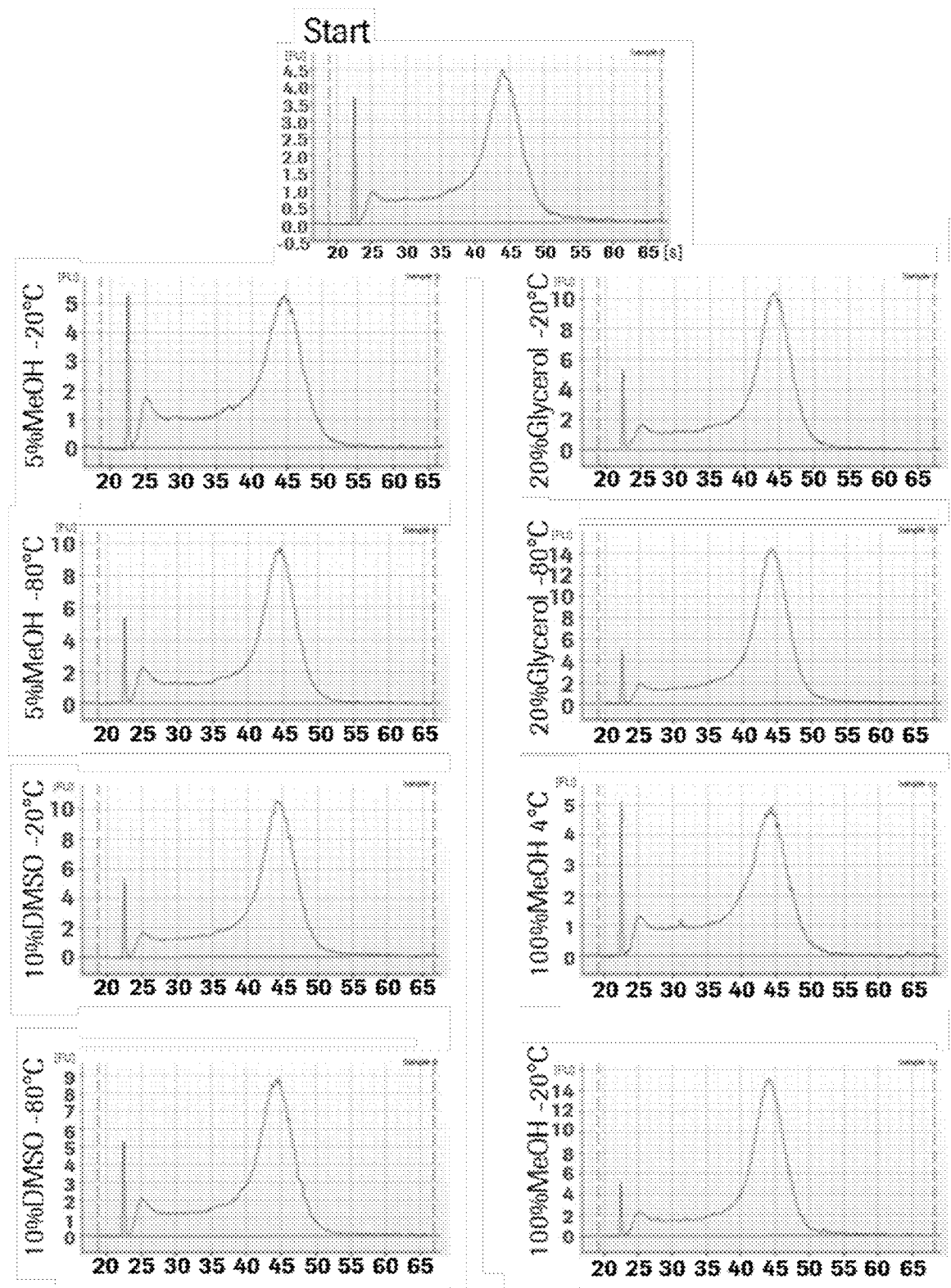
FIG. 35C illustrates six month stability of RNA isolated from a colon adenocarcinoma and incubated in standard cell storage solutions as needed (20% glycerol, 10% DMSO, 5% MeOH, and 100% MeOH) at the indicated temperatures for 6 months).

The multicellular fragments (or clusters) that did not pass through the 20 and 10 micron filters were further processed to generate single cells. Sonication using a probe sonicator was used in attempts to physically disassociate the multicellular fragments into singe cells. Multicellular fragments were exposed to increasing amounts of sonic energy, and the liberation of tumor cells was assessed by analyzing the size of the particles using a Coulter Counter. As shown in FIG. 35, increasing amounts of sonic energy leads to a release of particles that between 5.5 and 9.3 microns in diameter (arrow in 245 J panel). The physically liberated cells correlate with the tumor cells isolated from the homogenate from the above example, suggesting that the multicellular fragments are composed, primarily, of tumor cells.

Figure 33A:
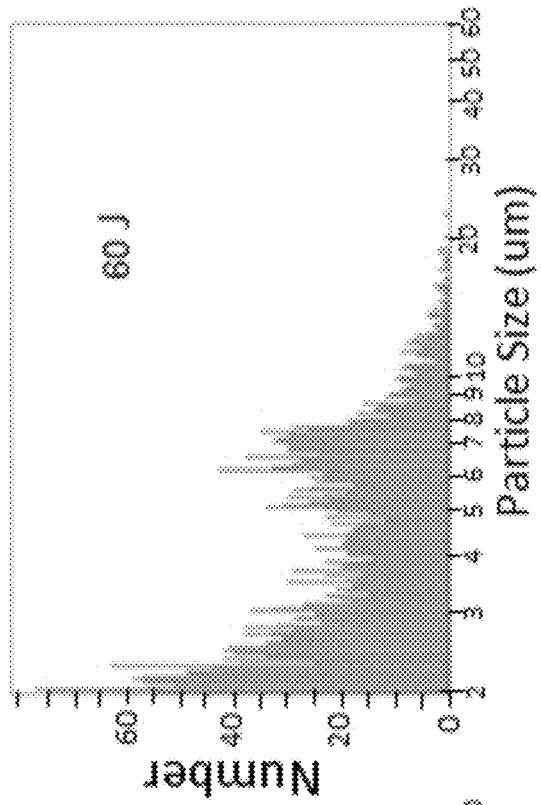
FIG. 33A-33D show multicellular aggregates treated with collagenase then sonicated.
Figure 33B:
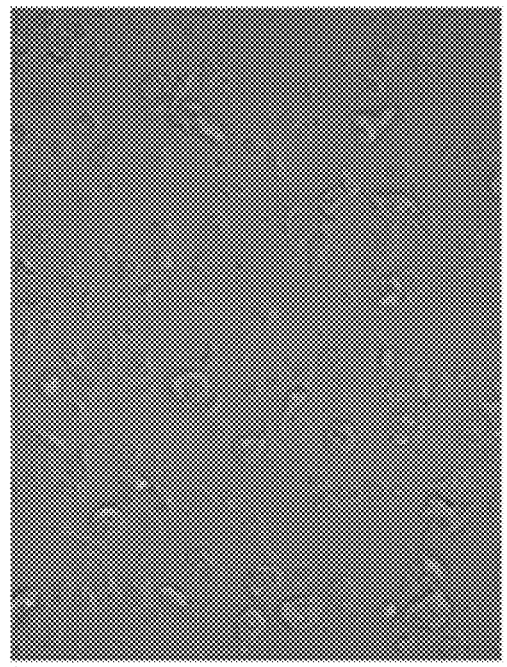
Figure 33C:
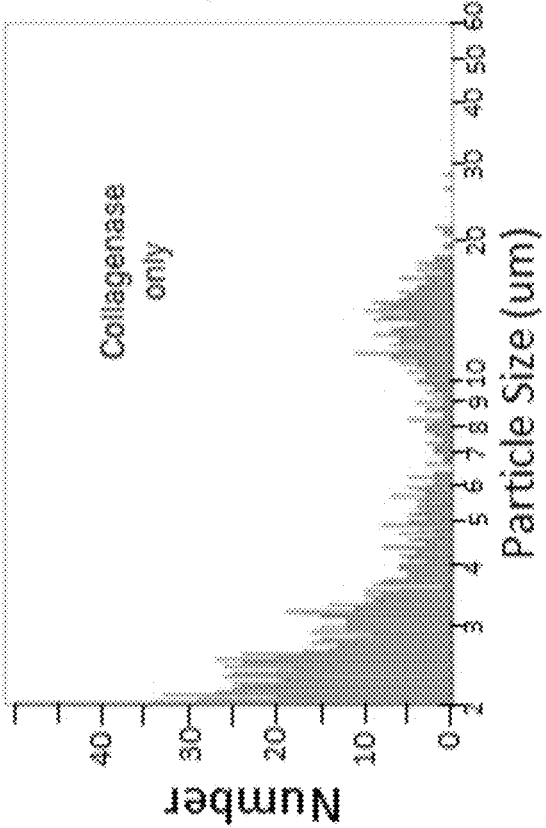
Figure 33D:
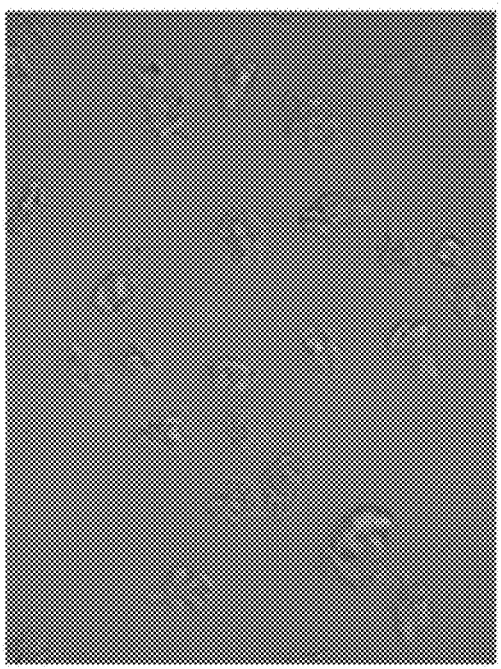

To further enhance the disassociation of multicellular fragments into single cells, a sample of multicellular fragments was incubated with collagenase. Following a 72 hour incubation in type 1 collagenase, the size distribution of the collagenase treated multicellular fragments was analyzed. As shown in FIGS. 33A and 33C, collagenase alone does not result in the liberation of single cells from multicellular fragments. When sonication was added following collagenase treatment, the majority of the multicellular fragments were disassociated into single particles within the size range of normal immune cells (4-5.5 microns in diameter) and tumor cells (5.5-9.3 microns in diameter). These data demonstrate that representative samples derived from human organs, tissues, and tumors can be further processed into single cells using mechanical, physical, and biochemical methods.

Biomarker Characterization of Single Cells From Representative Samples

The single cells from the representative sample of the colon tumor were further characterized for biomarker expression through fluorescent staining and FLOW cytometry analysis. FLOW cytometry is a common diagnostic analysis method for live cells taken from biopsy samples. Thousands to hundreds of thousands of cells can be interrogated for the presence or absence of biomarkers, simultaneously quantifying the number of cells and the biomarker expression level for each cell. One skilled in the art would recognize that formalin fixed tissue samples derived from resected organs, tissues, or tumors are not amenable to FLOW cytometry as current analysis methods for formalin fixed samples involve paraffin embedding and histological sectioning, rather than disassociation into single cells. The following example aimed to determine whether the processed cells produced from the colon tumor could be analyzed by FLOW cytometry.

Methods:

Cells were stained with CD3, CD8, CD45, CK8/18, EGFR, and PD-L1 antibodies from Ventana® Medical Systems, Inc. In some cases, tyramide signal amplification was used to improve the fluorescent staining. Cells (approximately $3 \times 10^7$ cells per tube) were centrifuged at 300×g for 2 min prior to resuspension in 0.3 ml 3% $H_2O_2$. After 15 min incubation, cells were washed 3 times with 0.1% Tween™ 20, 0.1% BSA in PBS. TSA blocking buffer (0.3 ml) was added for 5 min, followed by incubation in 0.2 ml primary antibody for 30 min at 37° C. Cells were then washed 3 times with 0.1% Tween™ 20, 0.1% BSA in PBS and then resuspended in 0.2 ml goat anti-species antibody conjugated to horseradish peroxidase for 30 min at 37° C. Cells were next diluted in 1.2 ml 20 µM Tyramide-Rhodamine 101 and incubated for 5 min, followed by 1.2 ml TSA $H_2O_2$ for 30 min. Cells were washed with 0.5% dextran, 0.1% Tween20, 0.1% BSA in PBS 3× and resuspended in MACS-T-STC for storage. Prior to imaging or flow cytometry, cells were stained with 3 µM DAPI for 10 min.

Biomarker Analysis by FLOW Cytometry

Figure 29A:
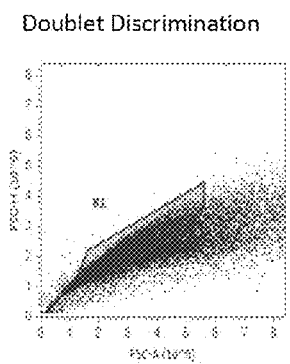
FIG. 29A illustrates mechanically dissociated and filtered colon tumor cells. FSC-A vs. FSC-H was used for doublet discrimination. Red: positively stained cells and violet: control (stained cells without primary Ab).
Figure 29B:
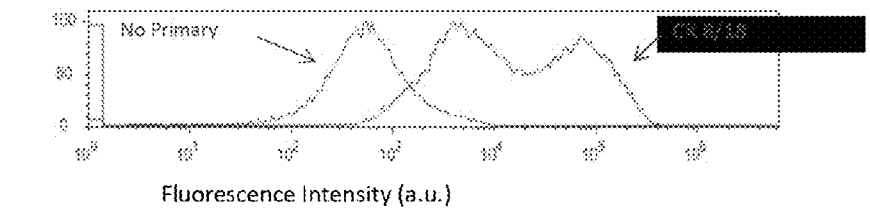
FIG. 29B shows mechanically dissociated and filtered colon tumor cells stained with CK8/18. Cell markers were analyzed with Attune® acoustic focusing flow cytometer.
Figure 29C:
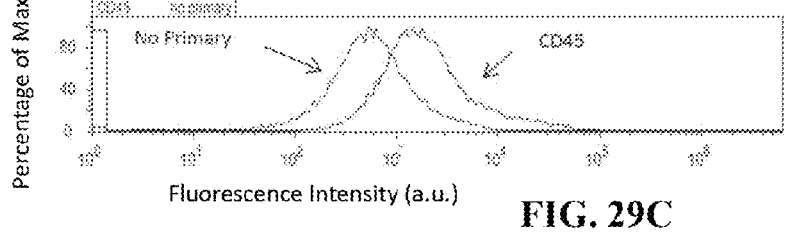
FIG. 29C shows mechanically dissociated and filtered colon tumor cells stained with CD45. Cell markers were analyzed with Attune® acoustic focusing flow cytometer.

An Attune® FLOW Cytometry system (ThermoFisher Scientific®) was used to quantify the percentages of cells expressing various biomarkers. The fluorescence intensity shift between control (cell stained with no primary Ab) and samples (cell stained with primary Ab) is proportional to the abundance of the target cells within the whole cell population and was used to calculate the percentage of positive cells in the population. As shown in FIGS. 29A-29E, fluorescent signals above background were detected for all biomarkers tested. Components of the immune systems and of the tumor were detected from the same sample; CD45 and CD8, compared to CK8/18 and EGFR (FIGS. 29A-29C). In some cases, both the immune cells and tumor cells can be simultaneously stained (PD-L1 in FIG. 29E). Moreover, the percentage of cells staining positive in the FLOW cytometry analysis is similar to the IHC staining of the embedded representative sample from the same clinical case (FIGS. 29A-29E).

Figure 29D:
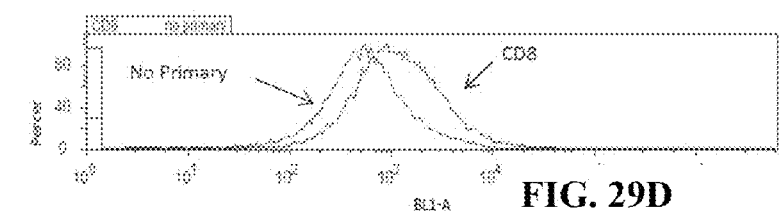
FIG. 29D shows mechanically dissociated and filtered colon tumor cells stained with CD8. Cell markers were analyzed with Attune® acoustic focusing flow cytometer.
Figure 29E:
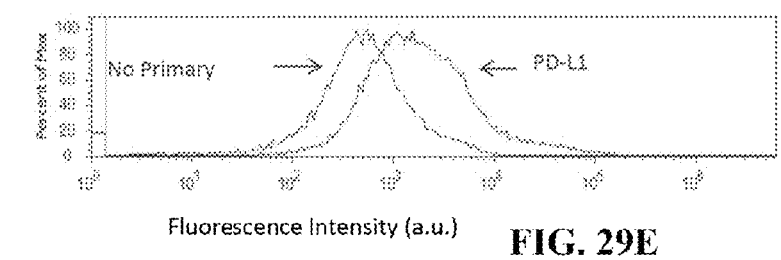
FIG. 29E shows mechanically dissociated and filtered colon tumor cells stained with PD-L1. Cell markers were analyzed with Attune® acoustic focusing flow cytometer.
Figure 29F:
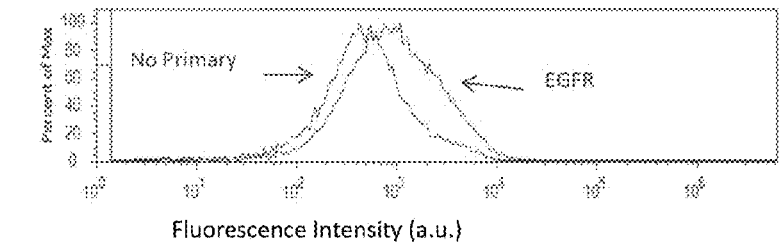
FIG. 29F shows mechanically dissociated and filtered colon tumor cells stained with EGFR. Cell markers were analyzed with Attune® acoustic focusing flow cytometer.

With these data, the inventors demonstrate the methods and workflow necessary to further disassociate homogenates derived from organs, tissues, and tumors into single cells for biomarker analysis via FLOW cytometry. One skilled in the art will recognize the quantitative nature of the data generated by FLOW cytometry. With this data it is now possible to calculate the percentages of the cellular components from resected tumors, by assessing the relative abundance of each cell type. For instance, from the above data, 33% of the cells in the colon tumor analyzed in this example are tumor cells. Further, approximately 33% of the tumor cells are PD-L1 positive (DAPI shift in PD-L1 FLOW analysis, FIG. 29E), and an even smaller percentage of the cells are EGFR positive (EGFR positive cells, FIG. 29F). Of the colon tumor, 20% of the cells are immune cells (CD45 positive cells, FIG. 29C-), and only a fraction of those cells are CD8 positive (FIG. 29D).

Isolation and Capture of Single Cells

The single cells from the representative sample of the colon tumor were isolated and captured to enable biomolecule analysis of specific cell populations. In this example, two types of isolation and capture were used, FLOW sorting and affinity sorting via magnetic beads.

Figures 30A, 30B, 30C:
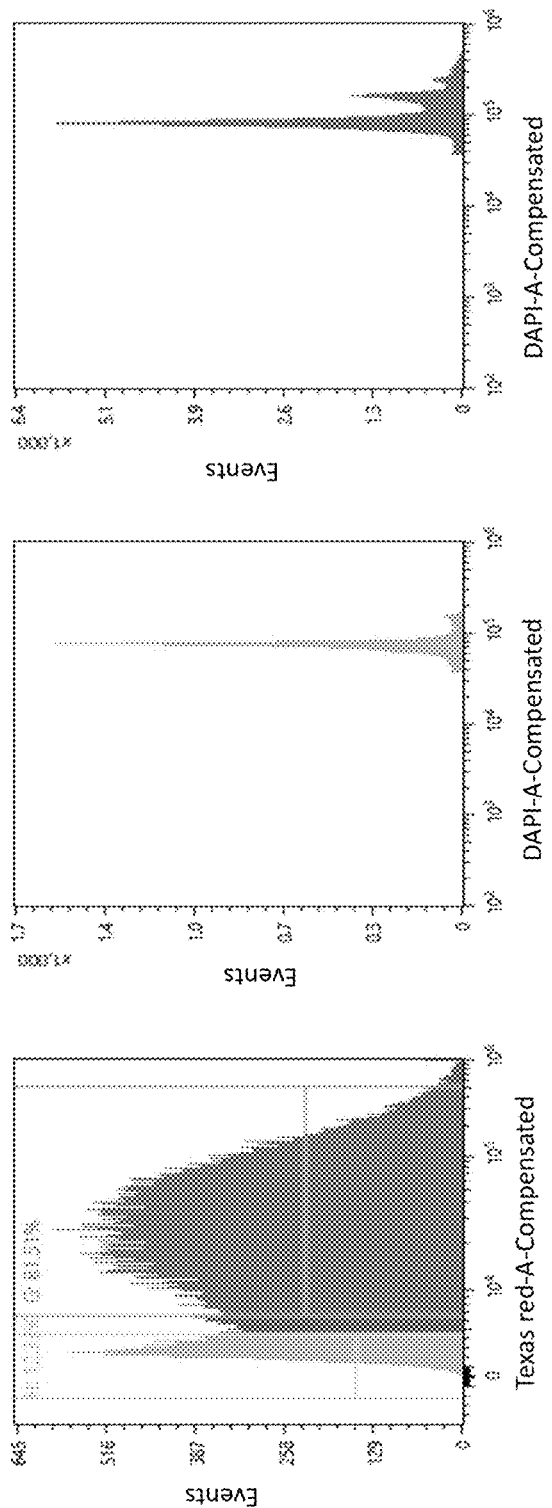
FIG. 30A illustrates analysis of sorted EpCAM positive cells using Sony® SH800 cell sorter and using utilizes Texas Red. EpCAM positive cells correspond to cells with higher DNA content based on the DAPI intensity plot.
FIG. 30B illustrates analysis of sorted EpCAM positive cells using Sony® SH800 cell sorter and utilizing DAPI. EpCAM positive cells correspond to cells with higher DNA content based on the DAPI intensity plot.
FIG. 30C illustrates analysis of sorted EpCAM positive cells using Sony® SH800 cell sorter utilizes DAPI. EpCAM positive cells correspond to cells with higher DNA content based on the DAPI intensity plot.

To identify and capture tumor cells from the single cells disassociated from the representative sample of the colon adenocarcinoma, cells were stained for EpCAM (Epithelial Cell Adhesion Molecule) using the previously described tyramide staining method, to deposit rhodamine 101 and stain DNA with DAPI. When analyzed on a Sony® SH800 cell sorter, the EpCAM positive tumor cells (green population in FIG. 30A) show a higher DNA content when back-gated to the DAPI intensity plot (FIG. 30B). The EpCAM negative cells with a diploid DAPI intensity are the normal cells. In this example, the cells that are both EpCAM positive and contain high DAPI levels were sorted. When the sorted cells are then analyzed for size on a Coulter Counter, the size range is between 5.5 and 9.3 microns in diameter (FIG. 27C). One skilled in the art will recognize that the EpCAM negative cells with diploid DAPI staining could also be sorted. These data demonstrate the ability to isolate and capture distinct populations of cells from representative samples derived from organs, tissues, and tumors using a FLOW sorter.

Figure 31A:
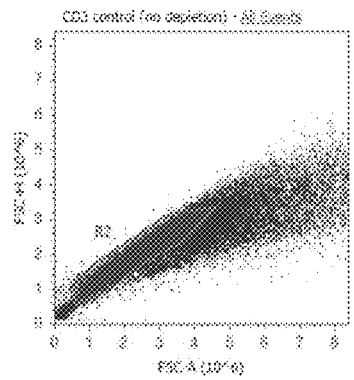
FIG. 31A and FIG. 31B show tonsil dissociated cells sorting using magnetic beads.
Figure 31B:
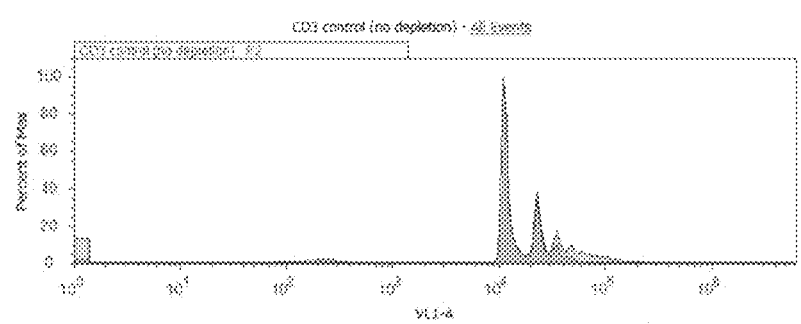
Figure 31C:
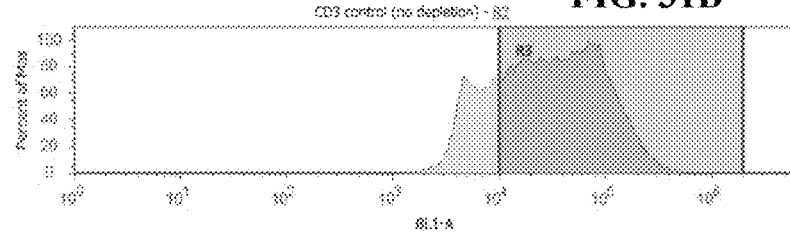
FIG. 31C illustrates bar graphs showing the percentage of fluorescent cells (CD3 or CD8 positive cells) in the total cell population (FIG. 31A) before and after depletion.
Figure 31D:
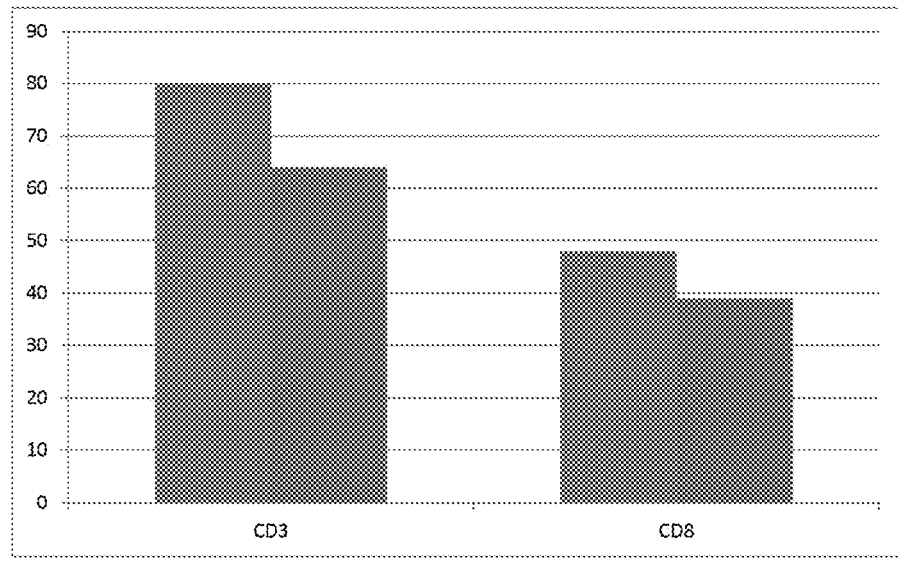
FIG. 31D illustrates bar graphs showing the percentage of fluorescent cells (CD3 or CD8 positive cells) in the total cell population (FIG. 31A) before and after depletion.
Figure 32G:
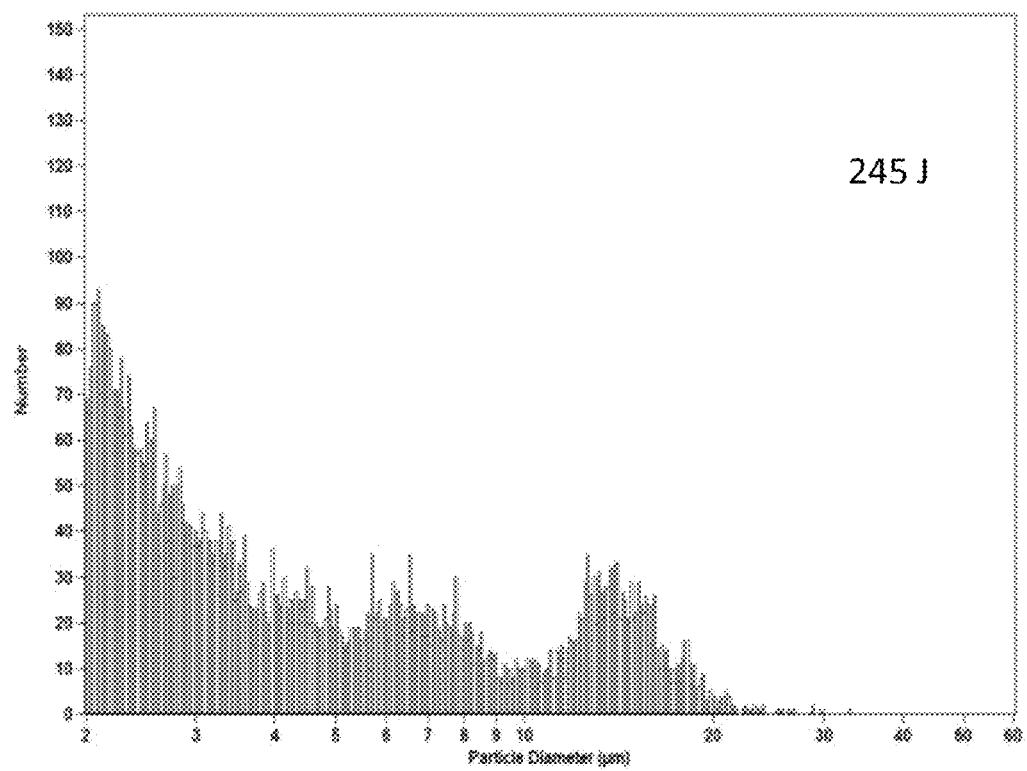
Figure 32H:
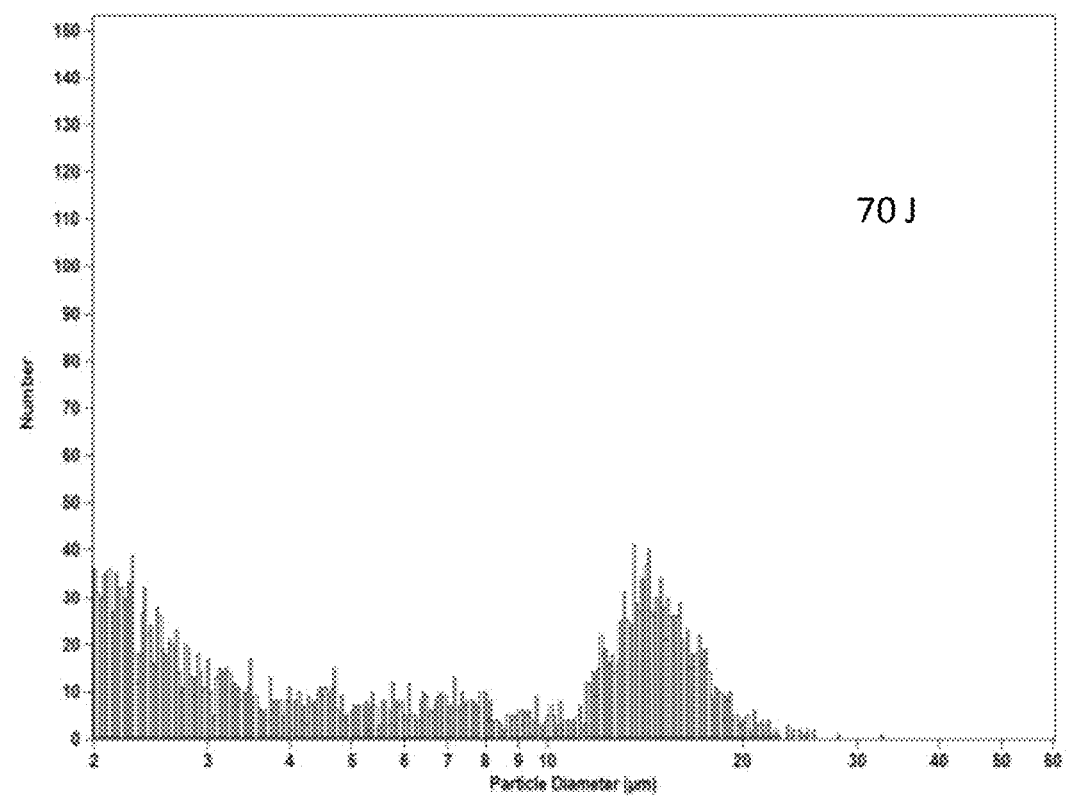
Figure 32I:
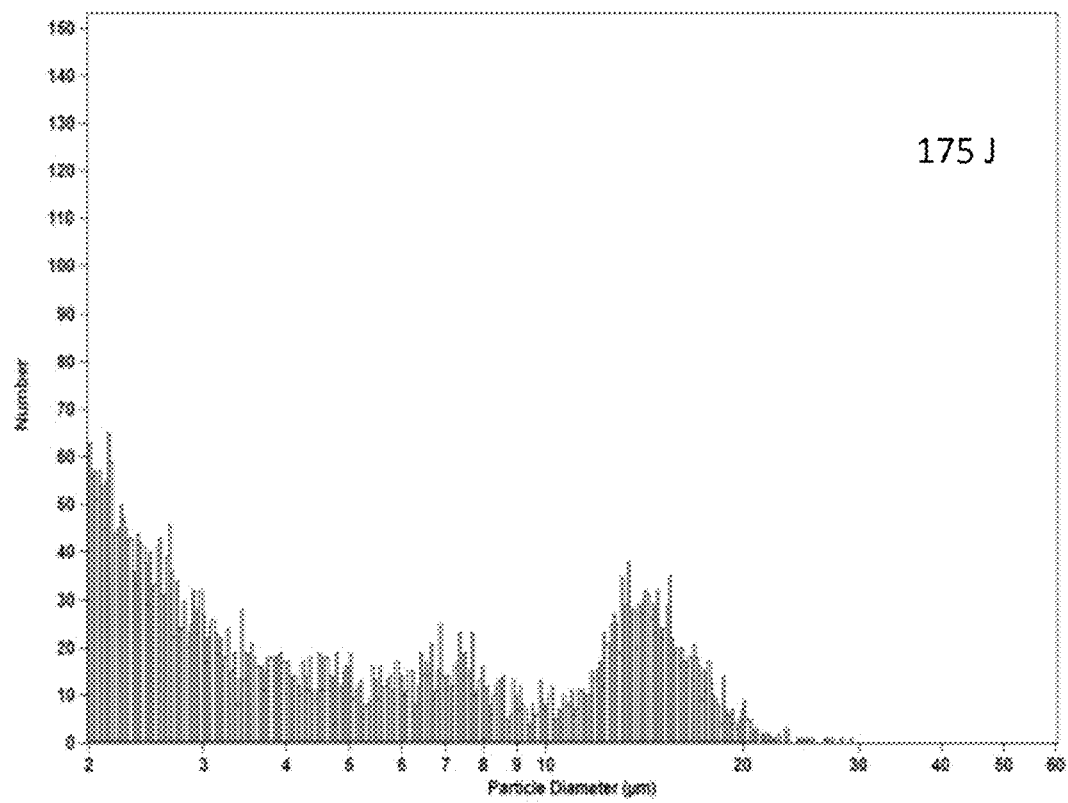
Figure 32J:
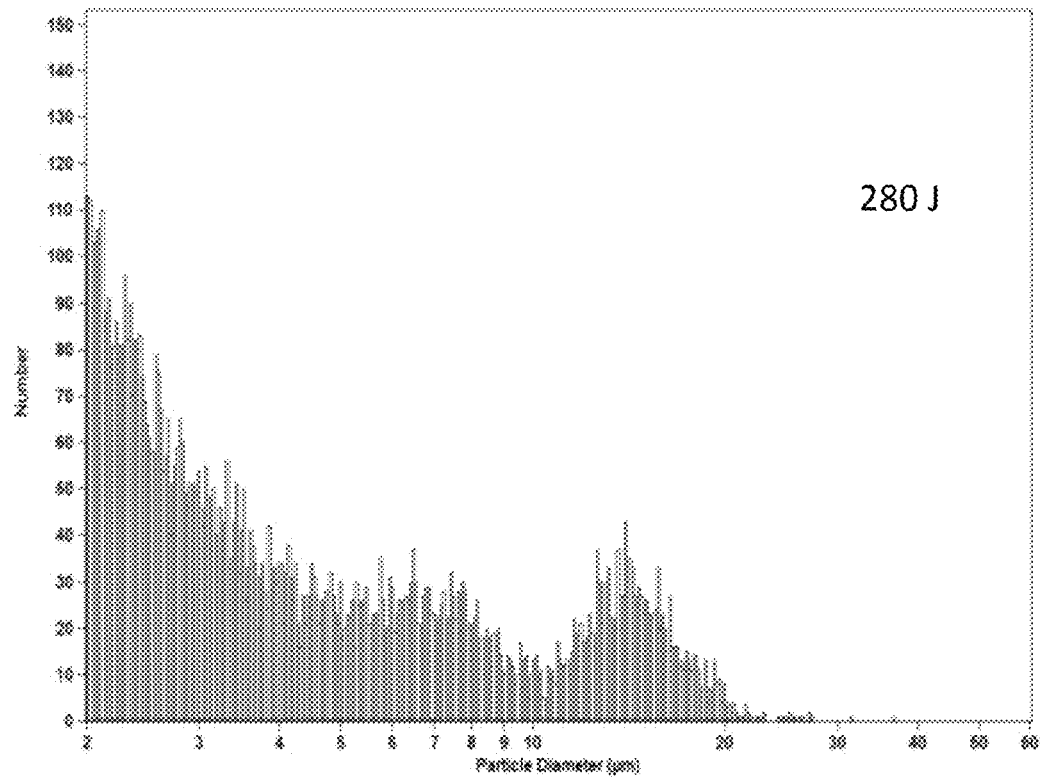

A separate method of isolation and capture of specific cell populations is removing populations of cells expressing specific cell surface markers through affinity selection using magnetic beads. In this example, the single cells from the lymph node were incubated with magnetic beads (Dynabeads®, ThermoFisher Scientific®), coupled to CD3 or CD8 primary antibodies. The cells are incubated with the antibody conjugated magnetic beads according to the manufactures protocol. Following the incubation, the magnetic beads are brought to the bottom of the tube via magnetism, and the liquid containing the unbound cells is removed from the tube. FLOW cytometry was used to demonstrate the depletion of CD3 or CD8 positive cells from the sample, similar to the analysis in FIG. 31A. The depletion of the specific cell types can be seen in FIG. 34B, where the percentage of cells expressing the CD3 or CD8 is decreased following incubation with the corresponding antibody conjugated magnetic beads.

With these data, the inventors demonstrate that single cells generated from representative samples derived from organs, tissues, and tumors can be isolated and captured for further diagnostic investigation. One skilled in the art will appreciate that any number of diagnostic methods could be used to analyze the purified cell populations, such as PCR, NGS, FLOW cytometry, single cell sequencing or transcriptomics, mass spectrometry based proteomic analysis, and other diagnostic methods.

Figure 34:
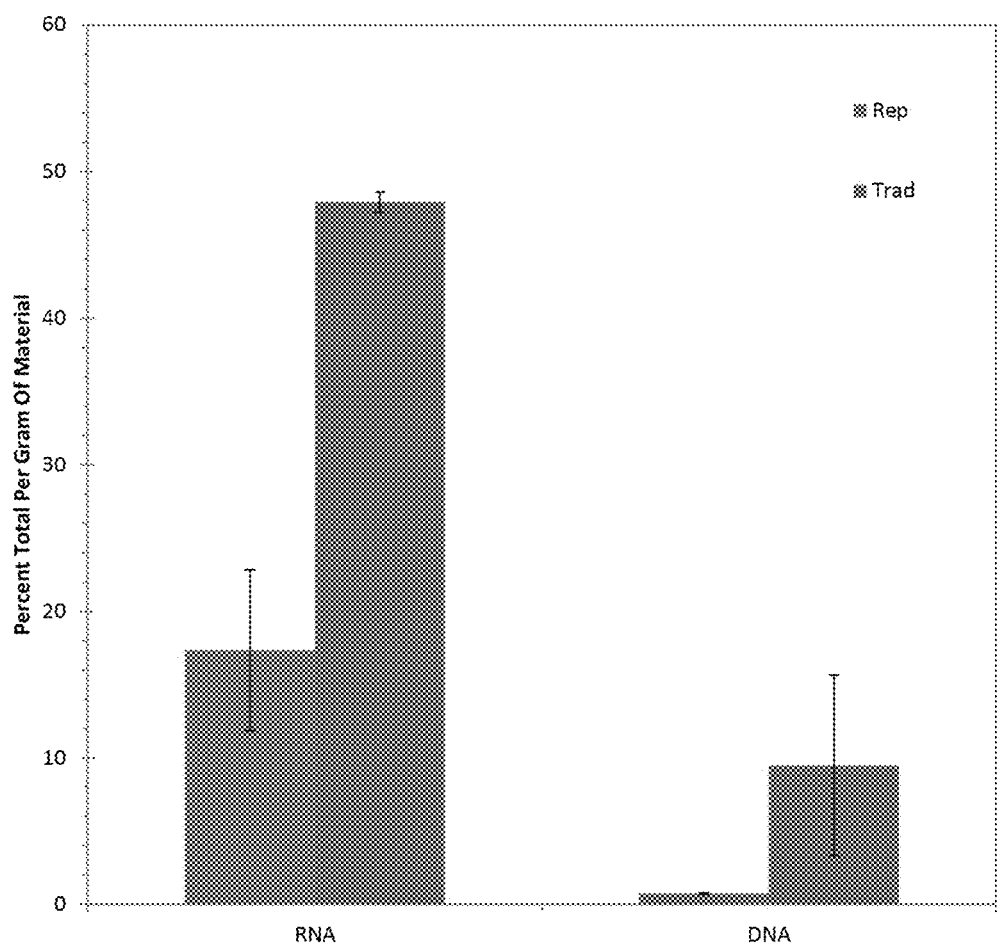
FIG. 34 shows RNA and DNA liberated from homogenates made from Representative samples (Rep) and fresh (Trad) tonsil tissue.

Example 8: Viability and Stability Studies of the Tissue Sample Fresh Tissue Viability Fresh tonsil was blended in an IKA® blender in 1:1 (w:v) DPBS without magnesium and without calcium at 3000 rpm for two minutes (Rep) and compared to tonsil prepped in the traditional method of mincing the tissue with a scalpel then collagenase digested for primary cell culture (Trad) (Donnenberg, et al., Methods Mol Biol., 568: 261-279, 2009). Tissue damage was assessed by measuring the release of RNA (cytoplasmic damage) and DNA (nuclear damage) into the supernatant (FIG. 34). Homogenization of the tonsil tissue is far more rapid than the traditional method of mincing followed by collagenase digestion, as the homogenization does not require any enzymatic treatment. As indicated in FIG. 37, homogenization of fresh tonsil generates less damage than the traditional method as measured by DNA and RNA liberation into the supernatant. Error bars represent the standard error of two experiments.

Figure 38A:
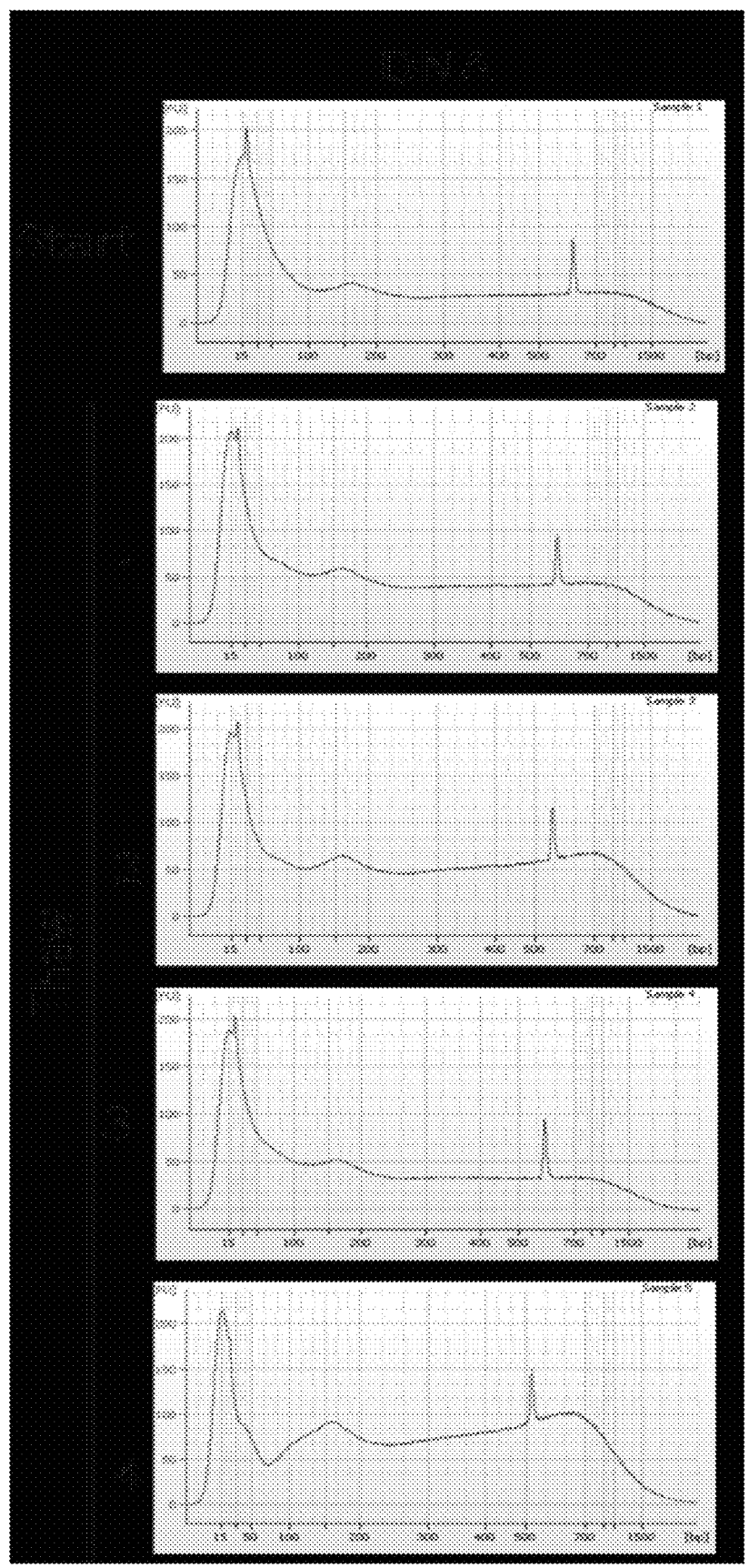
FIG. 38A shows nucleic acid (DNA and RNA) stability over repeated freeze/thaw cycles for a representative sample made from a colon adenocarcinoma.

Stability Studies of Nucleic Acids, Protein, and Cells from Formalin Fixed Tissues Tissue from a pancreatic well-differentiated neuroendocrine neoplasm, a papillary urothelial carcinoma, and a colon adenocarcinoma (FIGS. 35A, 35B and 35C respectively) were incubated in standard cell storage solutions (20% glycerol, 10% DMSO, 5% MeOH, and 100% MeOH) at the indicated temperatures for 6 months. RNA was isolated and analyzed on an Agilent® bio-analyzer. As indicated in Figure FIGS. 35A, 35B and 35C, all storage methods preserved RNA integrity, albeit at different levels as indicated by the subtle differences in the intensities of the 18S RNA peaks in the bio-analyzer traces (see 20% Glycerol sample in FIG. 38A). These data indicate that multiple storage methods for formalin fixed representative samples preserve the integrity of RNA over time.

Figure 36A:
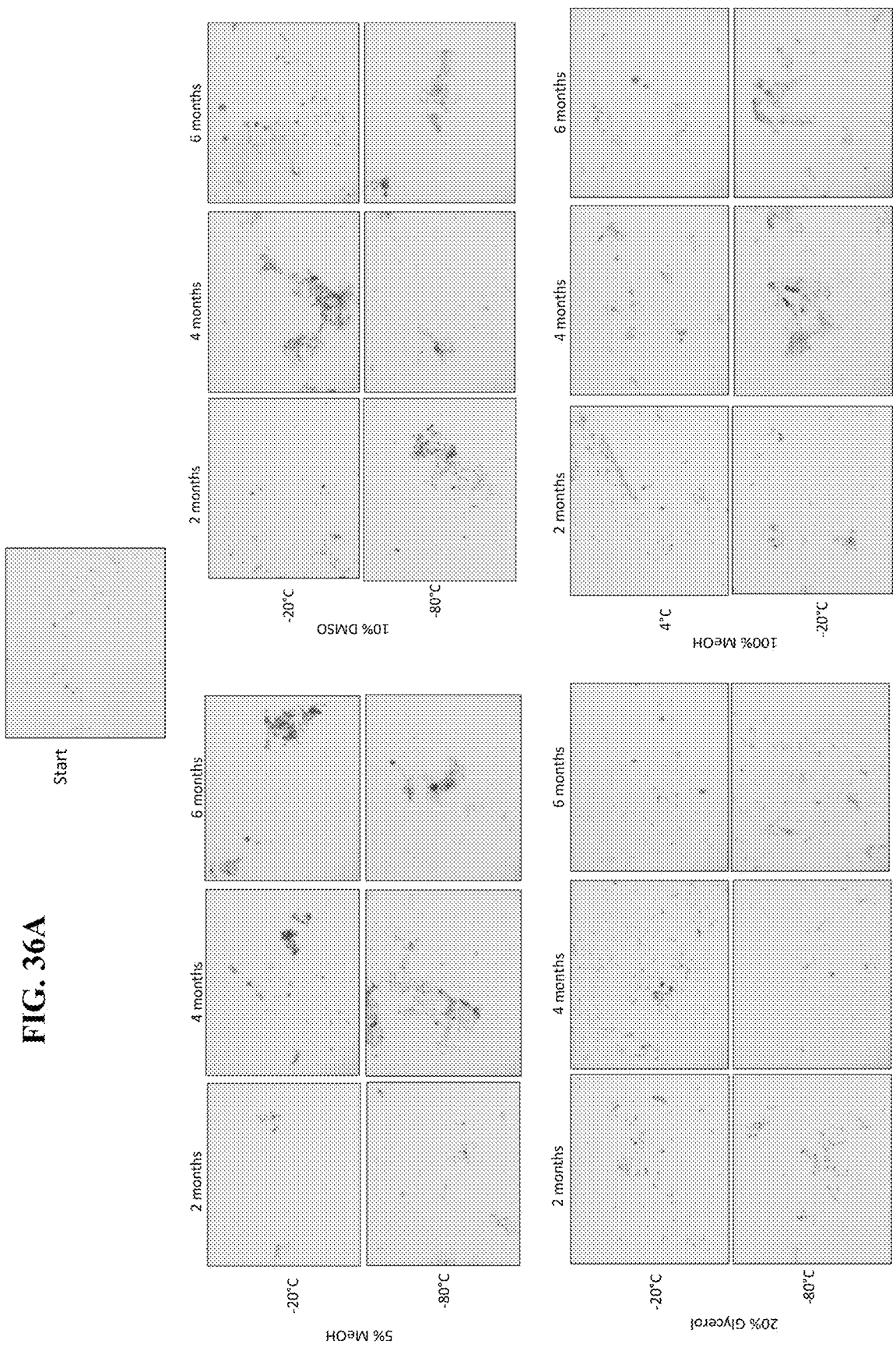
FIG. 36A illustrates six month stability of protein isolated from a papillary urothelial carcinoma, as measured by IHC for C-met.
Figure 36B:
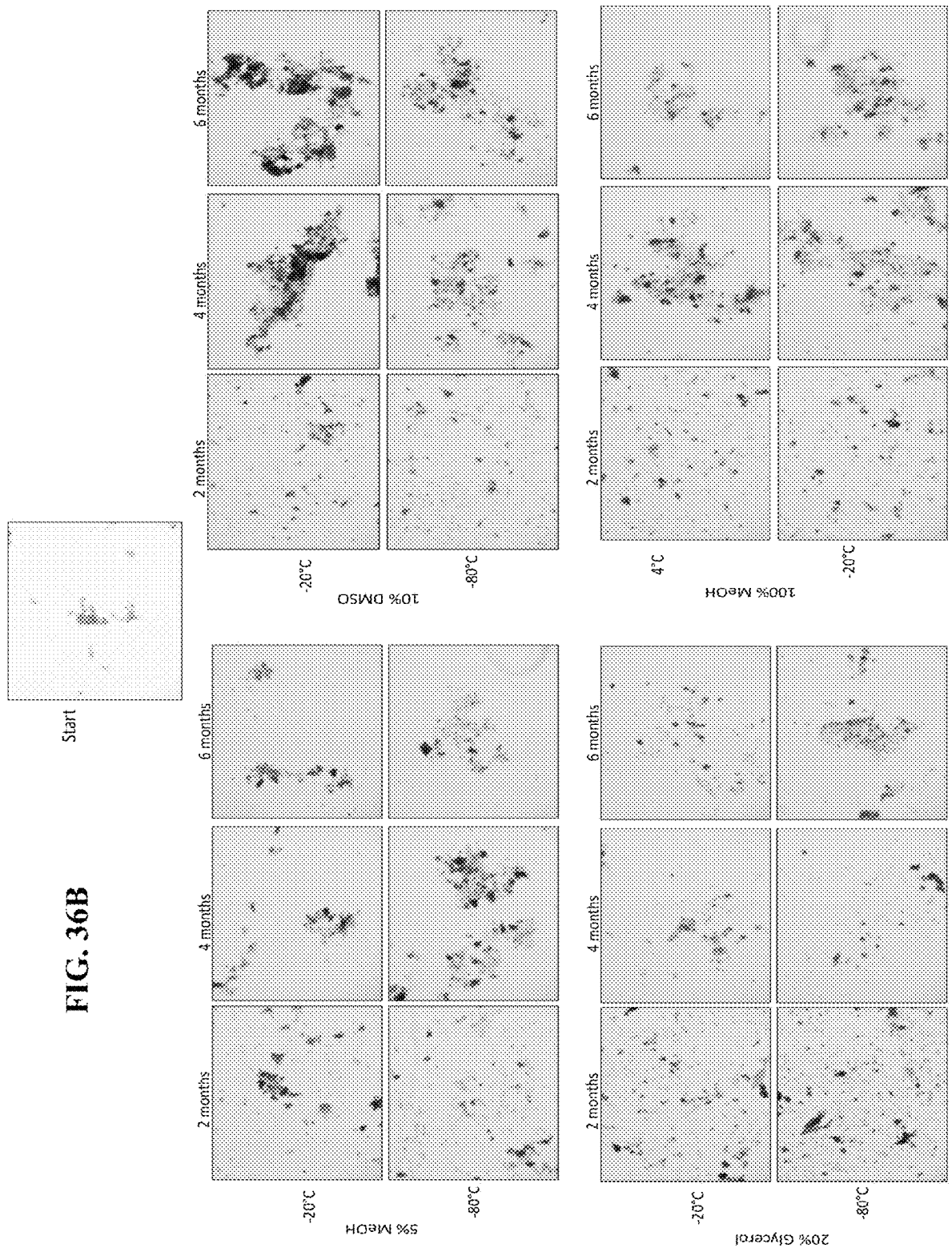
FIG. 36B illustrates six month stability of protein isolated from a colon adenocarcinoma, as measured by IHC for C-met.

Protein, as measured by IHC staining for c-Met, is fairly stable in both the papillary urothelial carcinoma and the colon adenocarcinoma (FIGS. 36A and 36B respectively) with all storage conditions and all temperatures throughout the 6 months test period. Following a six month storage period, samples were plated onto glass slides, stained for c-Met, and imaged using a bright field microscope. While some aggregation of the sample does occur, and the morphology of the cells may deteriorate over time, both positive and negative staining cells can be detected throughout the stability time course in all buffer compositions.

Figure 37A:
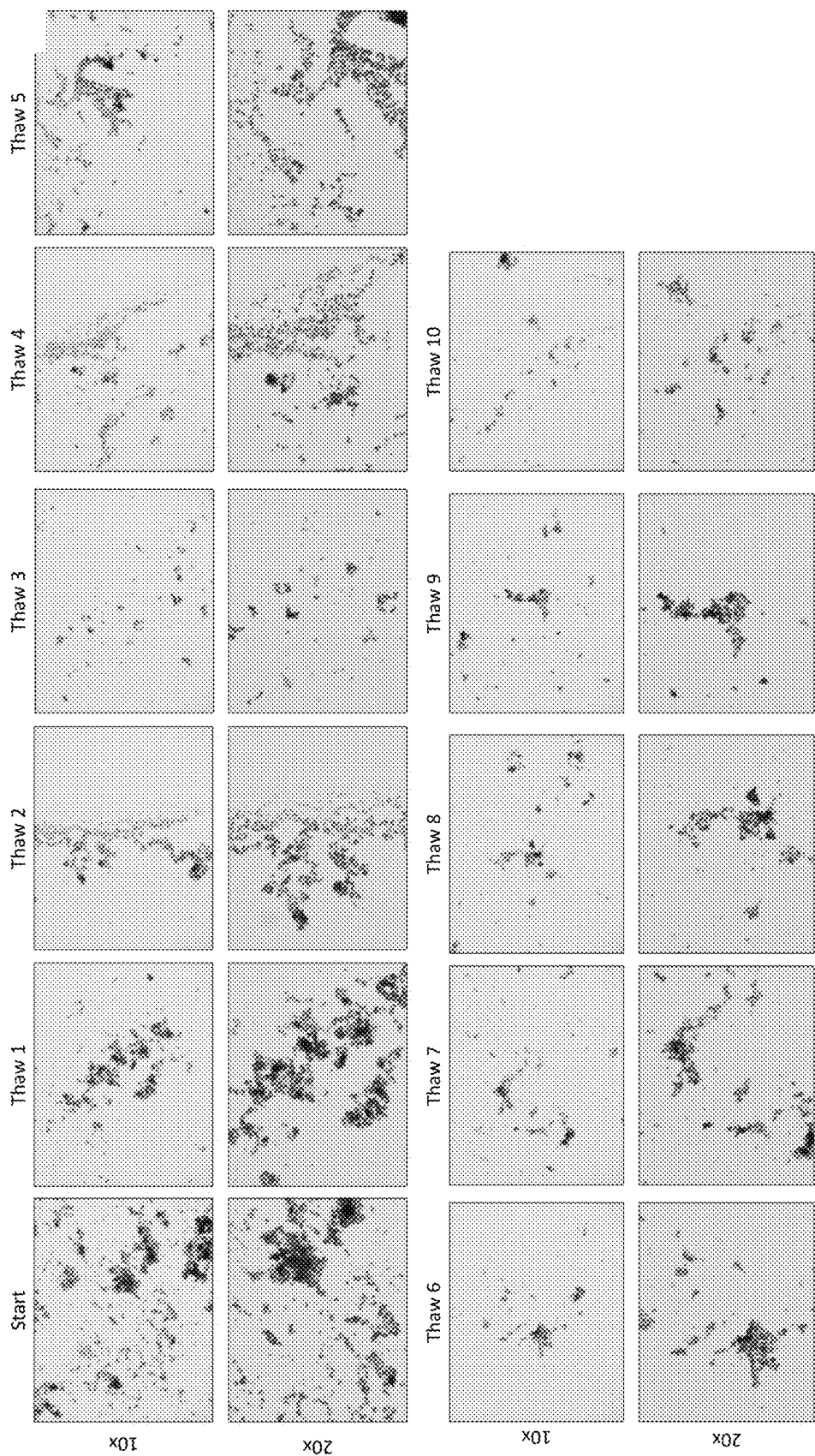
FIG. 37A illustrates the stability of cell morphology over repeated freeze/thaw cycles for a representative sample made from a colon adenocarcinoma, as assayed by H&E staining.
Figure 37B:
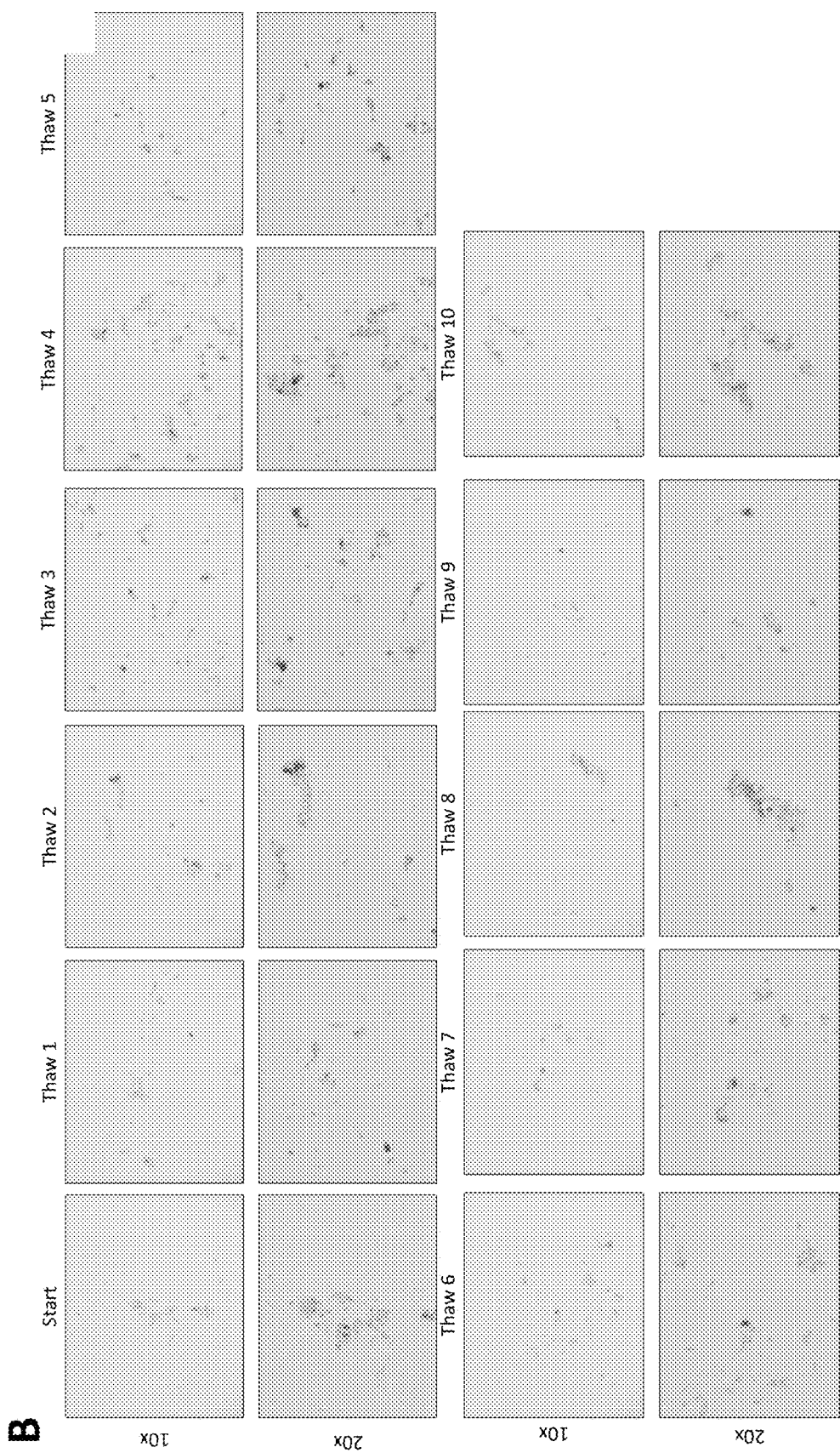
FIG. 37B illustrates protein stability over repeated freeze/thaw cycles for a representative sample made from a colon adenocarcinoma, as determined by staining the cells for C-met.

Storage of representative samples was further investigated by evaluating "flash freezing" in PBS. Thirty milliliters of the colon adenocarcinoma representative sample were flash frozen in PBs in a dry ice/alcohol bath and stored at −80° C. They were then thawed at 37° C. and an aliquot was taken on 10 subsequent freeze-thaw cycles. All samples taken following a freeze-thaw cycle was plated onto glass slides where H&E staining was used to evaluate the stability of cell morphology, and c-Met IHC was used to evaluate the stability of protein. As shown in FIG. 37A, cell morphology is very stable over all freeze-thaw cycles when samples are flash-frozen and stored at −80° C., as are protein based biomarkers (FIG. 37B).

Figure 38B:
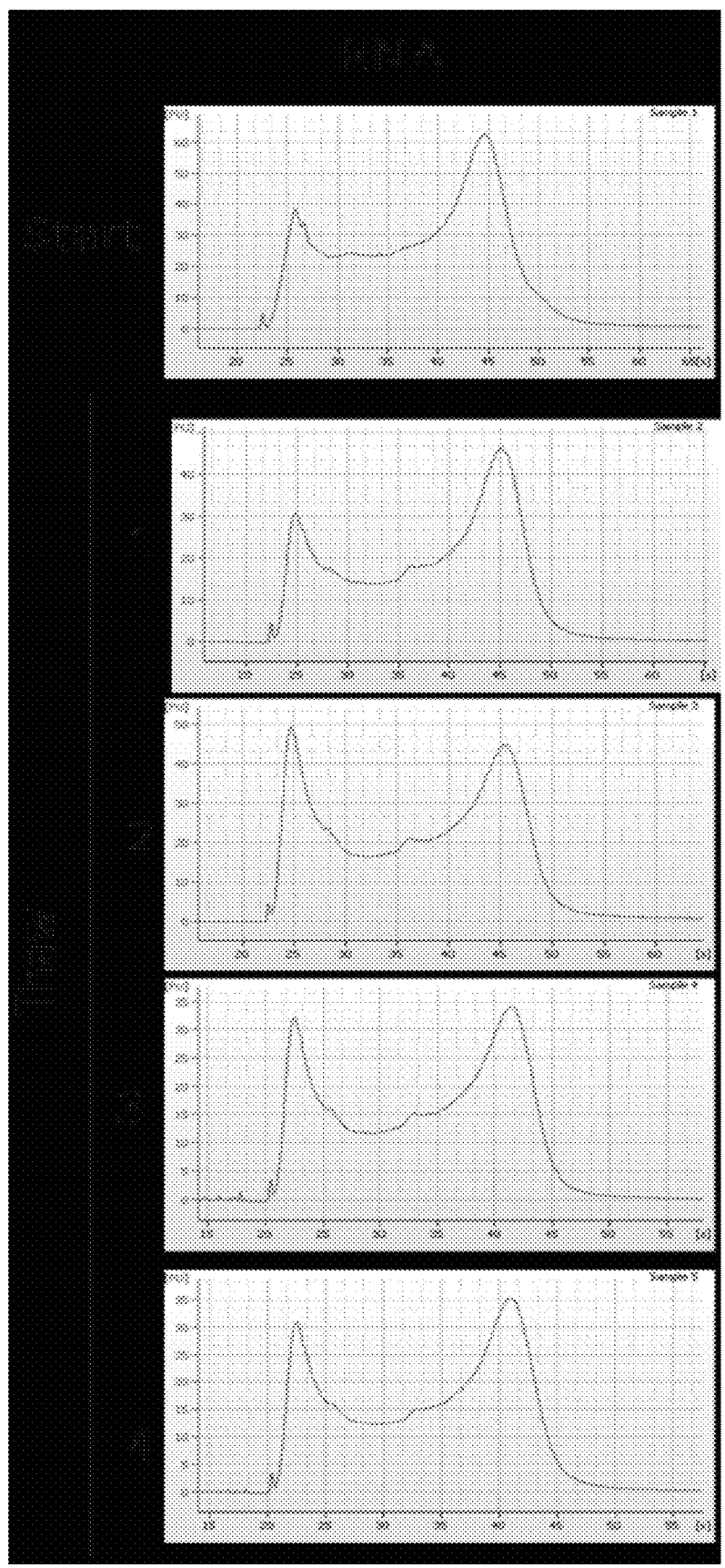
FIG. 38B shows nucleic acid (DNA and RNA) stability over repeated freeze/thaw cycles for a representative sample made from a colon adenocarcinoma.

The stability of RNA and DNA was assessed in the same samples over the 10 freeze-thaw cycles. Total DNA and RNA were extracted from the samples using standard phenol/chloroform methods and analyzed using an Agilent®bioanalyzer. Both DNA and RNA were stable over the course of the freeze-thaw cycles, with DNA being more resilient that RNA (FIG. 38).

With these data, the inventors have demonstrated multiple storage methods for representative samples made from organs, tissues, and tumors.

Example 9: Enrichment of Tumor Nuclei from a Representative Sample

This example describes the further processing of formalin fixed representative samples derived from organs, tissues, or tumors (via blending, juicing, or mincing) into individual nuclei for quantification, isolation, and biomarker analysis. Methods include mechanical disassociation, filtering, and enzymatic disassociation. Unique aspects of the methods include: 1) the establishment of a method to extract and dis-aggregate single particles containing nuclei from formalin-fixed representative samples; 2) assessment of the reproducibility of particle isolation from different aliquots of the same representative sample; 3) establishment of an approach for monitoring the extent of cellular destruction inflicted upon the sample by the mechanical dissociation and nuclear extraction methods; 4) the identification of markers that remain associated with nuclei extracted from representative samples that will serve to distinguish tumor and normal sub-populations; 5) the establishment of methodology to analyze extracted, stained material from fixed representative samples by flow cytometry; 6) The establishment of the number of tumor particles that will be required to: a) obtain sufficient DNA for sequencing, and b) retain analytic sensitivity for low-prevalence sub-clones.

Methods & Materials

Mechanical dissociation was performed with an IKA Works®S Tube Mill Control system from IKA-Works® (0004180001; Staufen im Breisgau, Germany) and gentleMACs™ Dissociator from Miltenyi Biotech (Teterow, Germany). All filters used were from Pluriselect® (San Diego, CA). Buffers used were from the following companies: CC1 (950-124; Ventana® Medical Systems, Tucson, AZ), EZ prep (950-102; Ventana® Medical Systems), Reaction Buffer (950-300; Ventana® Medical Systems), autoMACS® buffer (130-091-221, Miltenyi Biotech), dPBS (14190, Fisher Scientific®, USA). Tween™ 20 was purchased from Fisher Scientific®, USA (AC233362500). The following reagents were purchased from Sigma, USA: NP40 (74385), DNAse (AMPD1), Spermine tetrachloride (S2876), DAPI (D9542), Trypsin (59427C), Pepsin (P7012), Pronase® (P5147). Other enzymes were from the following companies: Proteinase K (0706, VWR, USA), Accumax™ (AM105, Innovative Cell Technologies, San Diego, CA), Collagenase H (11074032001, Roche, Basel, Switzerland). Tyramide-Rhodamine 101 was synthesized in house using chemicals purchased from Sigma. Mouse anti-cytokeratin 8/18 antibody (760-4344), Mouse anti-CD45 antibody (760-2505), and Goat anti-mouse HRP-conjugated antibody (760-4310) were from Ventana® Medical Systems. Goat-anti-Mouse conjugated with Alexa 488 (Alexa Fluor®) was purchased from Invitrogen (A-11001).

Tissue Models and Clinical Samples

Human tonsils were obtained from Northwest Medical Center (Tucson, AZ) and fixed in 10% neutral buffered formalin for 24 hours at Ventana® Medical Systems. Tumor samples were obtained from GLAS/(Winston-Salem, NC) and were previously fixed in formalin.

Hematoxylin and Eosin Staining

Representative samples were plated in autoMACS® buffer on VWR plus slides. Hematoxylin and Eosin (H&E) staining was performed using a Ventana® Medical Systems Symphony platform (Ventana® Medical Systems, Tucson, AZ) and the corresponding H&E Symphony Reagents (Ventana® Medical Systems, Tucson, AZ).

Immunohistochemistry

Tissue sections or paraffin embedded representative samples were subjected to brightfield DAB-based immunohistochemistry (IHC) using a Ventana® Medical Systems Benchmark® XT platform (Ventana® Medical Systems, Tucson, AZ). Visualization of biomarkers was performed using the OptiView® DAB Detection Kit from Ventana® (760-700). Antibodies were incubated for 4 minutes. Images were acquired on a Zeiss Axio brightfield microscope.

Flow Cytometry

For aggregation analysis, samples were filtered through a 40 μm filter prior to analysis on an Attune® Acoustic Focusing flow cytometer (Thermo Fisher Scientific® USA). Particles were incubated with DAPI (3 μM) for 10 min prior to filtration. If the flow rate was greater than 4,000 events per minute, the sample was diluted.

For flow-sorting, samples were filtered through a 40 μm filter prior to staining (see below) and analyzed on a Sony® SH800 cell sorter. Doublet discrimination was carried out using DAPI pulse width and height.

Method for Extracting Single Nuclei-Containing Particles from a Representative Sample Using formalin fixed tonsil as a model system, various enzymatic methods were investigated for disassociating aliquots of a representative sample into single particles. Prior to enzymatic steps, tonsil material was first mechanically dissociated in an IKA® blender in autoMACS® buffer, diluted 1:1 in CC1 buffer that had been heated to 85° C., and further blended in gentleMACs™ tubes using a gentleMACs™ dissociator. The sample underwent two rounds of heating at 85° C. for 5 min followed by blending. Subsequent to mechanical dissociation, different enzymatic conditions were evaluated qualitatively by visually monitoring H&E stained material that had been digested and filtered through a 100 μm filter. Enzyme inactivation was tested by incubating the material at 4° C. for 24 h after any inactivation step, plating material on VWR plus slides, staining with H&E, and monitoring the morphology of the cells, or the integrity of the nucleus. The conditions tested are summarized in Table 3.

liberated by each method per gram of starting material using a hemacytometer. Biological triplicate samples were analyzed where indicated.

Measuring Cellular Destruction

The supernatants from each step during the dissociation preps were retained and analyzed for DNA liberated into solution, as an indicator of nuclear destruction. The supernatants were divided into three for technical replicates. Where necessary, samples were concentrated using a GeneVac (SP Scientific). DNA was extracted from the remaining residue using a Roche High pure FFPE kit according to the manufacturer's instructions. DNA was also extracted from a 0.1 g aliquot, together with reserved processing liquids, taken from the bulk homogenate to serve as a reference sample. DNA yields were assessed using a Nanodrop-1000 Spectrophotometer (Thermo Scientific). DNA extracted from the processing liquids was expressed as a percentage of the DNA extracted from the reference sample to serve as a surrogate for damage to cellular nuclei, with the assumption that the percentage of released DNA is proportional to the percentage of damaged nuclei.

Minimization of Particle Aggregation

Particles isolated from representative tonsil samples using the proteinase K-pepsin method were stained using DAPI (3 μM, 10 min) to visualize DNA content, and analyzed by flow cytometry. Aggregation was evidenced by particles containing doublet, triplet, and >triplet DNA levels. The following conditions were tested to determine additives that would assist with de-aggregation of the particles: 1% Tween™ 20, 1% NP40, DNAse, 1.5 mM Spermidine Tetrachloride, 5 mM $CaCl_2$. Flow cytometry was used to assess the percentages

TABLE 3

Different conditions tested for mechanical and enzymatic digestion methods

| Method | Conditions | Dissociation | Quenching | Combined with other methods? |
|---|---|---|---|---|
| Metchanical + CC1 + heat | 15 min alternating heat (85° C.) and blending in CC1 buffer | ++ | None | Base step for all methods |
| Trypsin (tryp) | 0.25% 0 0.025%, 10 min, 30 min, 1 h, 24 h, dPBS buffer, 37° C. | ++ | Trypsin inhibitor - somewhat effective | Tryp_acc/col_pep worked better than tryp alone |
| Pepsin (pep) | 0.1, 0.5, 1, 5, mg/mL; 2, 5, 30, min, 1 h, 24 h; 150 mM NaCl; pH 1.5, 37° C. | ++ | pH - effective auto-degradation may contribute | Effective as a last step to quench other proteases |
| Pronase | 0.1%; 10 min, 30 min; dPBS buffer, 50° C. | ++++ | Heat-ineffective | |
| Proteinase K (protK) | 0.1 mg/mL, 1 mg/mL; 10 min, 1 h; dPBS buffer; 50° C. | ++++ | Heat-ineffective; Pepsin digestion of enzyme - effective | *Best method when followed with pepsin quench |
| Accumax/collagenase (acc/col) | 1 h; 1 mg/1 mL; dPBS buffer; 1 h at RT, 1 h at 40°C. | ++ | Heat | Tyrp_acc/col_pep worked better than acc/col alone |

Comparing the Yield of Particles from Each Dissociation Method

The different enzymatic and mechanical dissociation methods were compared side-by-side from sequential aliquots of a representative tonsil sample. The methods compared are summarized in Table 6. The effectiveness of each method was assessed by counting the number of particles of singlet, doublet, and >triplet DNA levels using DAPI histograms from normal tonsil preps in the presence of each additive.

Isolating Nuclei from Representative Samples Using the Optimized-Proteinase K-Pepsin Digestion Method Representative samples prepared from tonsil tissue were subjected to mechanical dissociation using CC1 buffer as described above. For tumor tissue, bulk mechanical dissociation was first carried out in MACS buffer in an IKA® blender at a 1:1 tumor:MACS ratio, and then aliquots of the total homogenate were taken and further blended in an IKA® blender at a 1 g tumor tissue: 5 ml solution ratio. The diluted blended material was filtered through a 1 mm×1 mm metal sieve, and the filtered material was CC1 conditioned in a 1 g tumor tissue: 5 ml CC1 buffer ratio as described in the above. For both tonsil and tumor samples, CC1 buffer was exchanged for dPBS (1:1) by centrifugation at 300×g for 1 min in a benchtop microcentrifuge (Eppendorf); all subsequent liquid exchanges were performed in the same manner. After centrifugation, the pellet was resuspended 1:1 in dPBS containing 1 mg/ml proteinase K and incubated at 50° C. for 10 min. To quench proteinase K and for further dissociation, the sample was exchanged into 5 mg/ml pepsin in 150 mM NaCl, pH 1.5. The pH of the solution was tested with pH strips and re-adjusted to 1.5-2 using 5 M HCl as needed. The sample was incubated for 30 min at 37° C., with gentle mixing every 10 min. For tumor tissue, yields were improved by agitation of the tube at 600 rpm in a Thermo-Mixer F1.5 (Eppendorf) during both enzymatic digestion steps. Pepsin was inactivated by the adjustment of the pH to above 8 with 5 M NaOH, and then the solution containing the pepsin was exchanged for autoMACS® buffer, 1% Tween™ 20 and 1.5 mM spermidine tetrachloride (MACS-T-STC). The digested sample was filtered through a 40 micron filter using 10 ml of MACS-T-STC, collected by centrifugation, and resuspended in 500 µl MACS-T-STC for storage prior to downstream applications. Reproducibility of the tumor nuclei preps was assessed by monitoring the yields of particles in the 3-30 micron range, measured on a Multisizer 4e® (Beckman Coulter), normalized to the starting "dry" weight of the tumor tissue, across multiple preps for the same tumor. Reproducibility was further assessed by monitoring the size distribution of the particles from different preps for the same tumor.

Staining Material Isolated from Representative Samples
Standard Immunofluorescence Nuclei prepared from 1 g of a representative tumor sample using the proteinase K-pepsin method were collected by centrifugation at 300×g for 1 min prior to resuspension in 200 ul of mouse anti-cytokeratin 8/18 primary antibody. Primary antibody was incubated with the sample nuclei for 1 h at 37° C. or for 24 h at 4° C. Control samples received no primary antibody. After incubation, samples were washed 6× with EZ prep™ buffer, and then resuspended in goat-anti-mouse Alexa-488 (Alexa Fluor®) antibody (1:500) in MACS buffer for 0.5-1 h at 37° C. Some samples were also stained with 3 µM DAPI for 10 min. Stained samples were washed 4× with reaction buffer at 4° C. A 50 µl sample was spread onto VWR plus slides and immediately imaged through a glass coverslip. Images of stained cells were acquired on a Zeiss Axio epifluorescent microscope controlled by in-house software, and images were analyzed using ImageJ. Stained nuclei were stored at 4° C. in MACS-T-STC.

Staining Using Tyramide Signal Amplification (TSA)

Particles nuclei isolated by mechanical homogenization or by the proteinase k-pepsin method (3×10$^7$ particles per tube) were centrifuged at 300×g for 2 min prior to resuspension in 0.3 ml 3% H$_2$O$_2$. After 15 min incubation, nuclei were washed three times with 0.1% Tween™ 20, 0.1% BSA in PBS. TSA blocking buffer (0.3 ml) was added for five minutes, followed by incubation in 0.2 ml primary antibody for 30 minutes at 37° C. The nuclei were washed 3 times with 0.1% Tween™ 20, 0.1% BSA in PBS and then resuspended in 0.2 ml goat anti-species antibody conjugated to horseradish peroxidase for 30 min at 37° C. Nuclei were diluted in 1.2 ml 20 µM Tyramide-Rhodamine 101 and incubated for 5 min, followed by 1.2 ml TSA H$_2$O$_2$ for 30 min. Nuclei were washed with 0.5% dextran, 0.1% Tween20, 0.1% BSA in PBS 3× and resuspended in MACS-T-STC for storage. Prior to imaging or flow cytometry, nuclei were stained with 3 µM DAPI for 10 min. Images of stained nuclei were acquired on an Olympus BX63 epifluorescent microscope and analyzed using ImageJ.

Calibrating the DNA Yield Per Number of Particles Isolated by Mechanical and Enzymatic Methods Nuclei were isolated from tonsil using the proteinase K-pepsin method as described above. Particles were counted using a hemacytometer. DNA was prepared from 10$^5$, 10$^6$, and 10$^7$ particles using a Roche High pure FFPE kit according to the manufacturer's instructions. DNA yields were assessed using a Nanodrop-1000 Spectrophotometer (Thermo Scientific).

Results
Further Processing of Representative Samples into Individual Nuclei

Further processing of representative samples into individual nuclei requires the removal of the cell membrane. Current nuclear isolation methods for fresh cells do not require enzymes to liberate nuclei, and nuclear isolation from formalin fixed sample is not a common method. To efficiently isolate individual nuclei, while maintaining cytoskeletal markers that would enable differentiation between normal and tumor nuclei, an enzymatic method was developed to reveal nuclei without undue damage that would liberate DNA from the treated nuclei.

Multiple enzymes were evaluated for their ability to digest the cell membrane away from nuclei, including pronase, proteinase K, pepsin, trypsin, Accumax, collagenase H. FIG. 43 shows examples of samples that have been digested by pepsin or trypsin under different conditions. The swollen, fragmented nuclei present in the lower right panel, are indicative of over-digestion.

After determining the conditions and quenching for each enzyme, a side-by-side comparison of each method was carried out on parallel aliquots from a representative sample from formalin-fixed tonsil tissue. See Table 3. Each method was also compared to mechanical homogenization alone, as described in the methods section. FIG. 43 shows that proteinase K treatment, followed by digestion with pepsin, liberates the most particles from a representative sample. Although this experiment shows little difference between 0.1 mg/ml and 1 mg/ml proteinase K, further experiments with tumor samples have demonstrated that 1 mg/ml proteinase K yields the most consistent results (not shown).

Enzymatic Dissociation Increases the Particle Yield Compared to Mechanical Dissociation The dissociation method of proteinase K-pepsin was compared alongside mechanical dissociation alone for three independent tonsil samples. FIGS. 44A-44C shows that the proteinase K-pepsin method significantly improves the number of particles liberated from a representative sample. Interestingly, the H&E staining results show that many of the particles liberated by the proteinase K-pepsin method consist of nuclei with or without cytoplasmic fragments attached, while the mechanically dissociated sample contains more intact cellular material (FIG. 48, lower panels).

Nuclear Preps from Tumors are Reproducible in Yield and Size Distribution

To determine the reproducibility of nuclear preps from the same representative tumor sample, the consistency of the methods and consistency of populations present in individual aliquots were assessed. From different aliquots (~1 gram) taken from the total homogenate, nuclei were prepared using the Proteinase K-pepsin method as described above. FIG. 45A shows that the yield of nuclei prepared from two different tumors (colon and lung) is highly consistent across multiple aliquots taken from the same representative sample. The size distribution of the particles isolated from the colon tumor was further analyzed to identify a very reproducible and characteristic size distribution across three different preps (FIG. 45B). Notably, the nuclei distribute into two populations of characteristic sizes (FIG. 45B). These data support that different aliquots of the same representative sample contain a consistent cellular composition, and that the developed methods to extract nuclei produce consistent yields of two different nuclear populations.

Estimation of Cellular Damage Due to Dissociation

The further processing of representative samples into individual nuclei could result in the liberation of DNA from the nuclear compartment. The release of DNA into the supernatant is a potential readout of damage to the nuclei. FIG. 46 shows that around 4% of the total DNA is released during processing of tonsil material by mechanical or Proteinase K-Pepsin methods. Processing of three different tumors results in less than 10% of the DNA released (FIG. 46). Interestingly, similar percentages of nuclear damage occur with both the mechanical and enzymatic methods, supporting that the Proteinase K-Pepsin method isolates intact nuclei without damaging them.

Decreasing Aggregation of Nuclei

Initial flow cytometry experiments revealed that ~35% of the particles existed in an aggregated state, as evidenced by the presence of particles in peaks of higher DAPI staining intensity (FIG. 47, panel (ii), R2 (green) and R3 (pink)). When back-gated onto the dot plot of side scatter vs. forward scatter (panel (i), green and pink populations), these particles falling in peaks of higher DAPI intensity map to regions with higher forward and side scatter, indicating a larger size. Although routine doublet discrimination can allow one to specifically analyze singlet nuclei (R1, red), the number of singlet nuclei present in the sample were increased. Several additives (see methods) were added to decrease the aggregation of the isolated nuclei. It was discovered that the addition of 1% Tween™ 20 reduced the number of aggregated particles from ~35% to ~23% (compare R2+R3 of plots in B to the same regions of plots in A). Other additives were ineffective at reducing the number of aggregated particles; however, the addition of 1.5 mM Spermine Tetrachloride maintained the integrity of the nuclei over time (not shown). Notably, unlike fresh tissue, DNAse cannot be used to disaggregate fixed tissue, as there are no functional cell or nuclear membranes to prevent DNAse from gaining access to nuclear DNA in the cell and destroy it (data not shown).

Figure 48A:
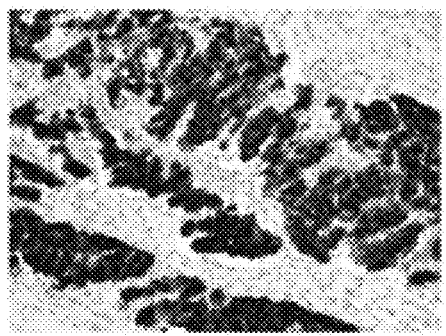
FIG. 48A illustrates a brightfield image of a colon adenocarcinoma (ADC) tissue section stained for CK-8/18 using immunohistochemistry (IHC). ADC tissues visualized with CK-8/18 are stained brown.
Figure 48B:
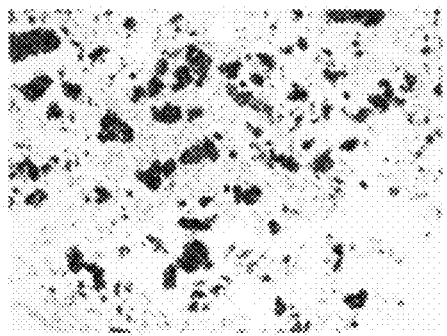
FIG. 48B illustrates a brightfield image of a representative sample that was mechanically dissociated, embedded in paraffin wax, sectioned and stained for CK-8/18 using IHC. CK-8/18-positive tissues are stained brown.
Figure 48C:
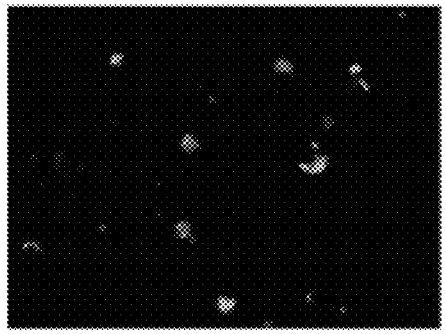
FIG. 48C illustrates a fluorescent image of a representative sample dissociated using the proteinase K-pepsin method and stained in solution for DAPI and CK-8/18, visualized with Alexa 488 (Alexa Fluor®. Pseudocolored images reflect CK-8/18 (green) and DAPI (blue) staining.
Figure 48D:
FIG. 48D illustrates a negative control samples of the tissues described in FIG. 48C, incubated without CK-8/18 antibody. All samples were prepared from the same colon ADC tumor.

Cytokeratins Remain Associated with Nuclei Isolated from Representative Tumor Samples In order to sort isolated nuclei from the representative sample, markers that remain associated with nuclei were identified to distinguish tumor from normal. Intermediate filaments (cytokeratins, vimentin) are often intimately associated with the nucleus, and they are also often used to identify carcinomas from the surrounding normal stroma. It was hypothesized that these may be lineage-specific markers that could be stained in the isolated nuclear particles that were collected using the proteinase K-pepsin method. FIG. 48A shows a section from a colon adenocarcinoma with characteristic strong immunohistochemistry staining for cytokeratin 8/18; and a section taken from a representative sample from the same fixed tumor embedded in paraffin wax shows similar staining (FIG. 52B). FIG. 48C shows material isolated from the representative sample of this tumor using the proteinase K-pepsin method, stained for CK8/18 and visualized with a fluorescently conjugated secondary antibody. Notably, this marker is retained when the sample is disassociated with the proteinase K-pepsin method, and a negative control sample incubated without primary antibody shows little background staining (FIG. 48D). Vimentin remains associated with many nuclei isolated from tonsil. However the surface marker CD45, which stains positive in the mechanically dissociated sample, is lost with the proteinase K-pepsin treatment (not shown). Thus, cytokeratins and vimentin will serve as lineage-specific nuclei-associated markers for flow cytometry analysis and cell sorting, even when surface markers are destroyed. Other nuclear markers, such as lineage specific transcription factors, can also be stained for specific tumor types. This is a unique feature of nuclear isolation from formalin fixed samples.

Improvement in marker staining using Tyramide Signal Amplification

Conventional immunofluorescence (IF) staining (FIG. 48C) did not provide a bright and stable enough signal to consistently resolve positively stained populations by flow cytometry (not shown). Analysis of stained samples by flow cytometry often requires the use of antibodies that are directly conjugated to fluorophores to obtain a more stable signal. The challenge for material isolated from representative samples is that it is derived from tumors that are often heavily formalin fixed. To enable the routine analysis of fixed representative samples by flow cytometry, tyramide signal amplification (TSA) was used for antibody staining using antibodies used on formalin fixed tissues. For TSA, Tyramide-conjugated fluorophores are activated by HRP conjugated to a secondary antibody that binds to a marker-specific primary antibody. The activated fluorescent dyes covalently link to proteins in the vicinity of the marker recognized by the primary antibody, which produces a bright and stable signal. FIG. 53A shows a comparison of mechanically dissociated tonsil stained for CD45 using conventional immunofluorescence vs. TSA. FIG. 53B shows cytokeratin staining for two different tumor types, amplified by TSA. Note the presence of DAPI stained cytokeratin-negative cells within the cytokeratin stained sample, showing the specificity of TSA In solution.

Cytokeratin Staining Allows for Distinction of Tumor and Normal Nuclei by Flow Cytometry Next, cytokeratin (CK)- and DAPI-stained nuclei from representative samples of colon and lung tumors using flow cytometry were analyzed (FIG. 50). In both cases, CK-positive (teal green) and CK-negative (pink) populations were discerned (FIG. 50, panel i). The CK-negative populations were associated with diploid DNA content (FIG. 50, panel ii), confirming that these are nuclei deriving from a population of normal cells (likely immune cells) residing within the tumor. For the CK-positive populations, the DAPI staining revealed a fraction of nuclei with aneuploid DNA (FIG. 50, panel iii), supporting that these are likely derived from tumor cells. For each sample, nuclei were successfully sorted into fractions that were enriched for normal nuclei (FIG. 50, panel iv) or tumor nuclei (panel v). DNA was successfully extracted from these collected populations and can be analyzed by next-generation sequencing (NGS), PCR, in situ hybridization, or other downstream analysis.

In addition, FIGS. 51A and 51B show that the percentage of tumor and normal nuclei from different tumors varies. For the colon tumor sample, the entire tumor was assigned to different bins. The undefined fraction (grey) corresponds to the percent by weight of material that was removed by filtration (see methods). The percentage of red blood cells was estimated by subtracting the total particle counts after enzymatic digestion, which destroys red blood cells, from the total particle counts prior to enzymatic digestion. The remaining fraction was designated tumor and normal according to flow cytometric analysis of the tumor nuclei. Analysis of the tumor composition at the cellular level may be diagnostically relevant, particularly when one tries to identify populations of immune cells that are present in the tumor homogenate.

Establishment of the DNA Yield from Particles Isolated from the Representative Sample A defined number of particles having specific characteristics were collected using FLOW sorting. Calibration of the DNA yield from different numbers of particles will determine how much material to collect from the representative samples for specific downstream analysis, such as NGS. FIG. 52 shows the DNA yield from mechanically dissociated and proteinase K-pepsin dissociated particles from representative tonsil samples. Importantly, these data show that particles isolated from the proteinase K-pepsin method provide similar DNA yield as particles isolated from mechanical dissociation alone, indicating that the enzymatic method maintains DNA integrity. In addition, the number of particles was calculated to determine the number required to detect a clone present at 5% prevalence (Table 8). These results will guide efforts to collect a sufficient number of particles from specific populations from the representative sample to power variant detection in downstream sequencing applications.

TABLE 4

Calculation of the number of particles required to identify a 5% prevalence sub-clone

| Sample Size | Threshold (5%) | Confidence | Actual Prevalence Detection Power |
|---|---|---|---|
| 30000 | 1500 | 99.1% | 5.30% |
| 300000 | 15000 | 99.4% | 5.10% |
| 500000 | 25000 | 99.9% | 5.10% |
| 500000 | 25000 | 99.5% | 5.08% |
| 1000000 | 50000 | 99.7% | 5.06% |

Example 10 In Situ Hybridization on Isolated Nuclei

Background

Isolating nuclei from a representative sample allows the opportunity to perform in situ hybridization (ISH) on a tumor sample that is representative of the diversity of the whole tumor, in an automated manner on a VENTANA® BenchMark® automated stainer platform. The interpretation of ISH staining of isolated nuclei is likely to be easier, with less non-specific background due to the lack of the paraffin embedded tissue.

Materials

Mechanical dissociation was performed as described in Example 9.

Clinical Samples

Clinical samples were described in Example 9.

Hematoxylin and Eosin Staining

Representative samples were plated in autoMACS® buffer on VWR plus slides.

Hematoxylin and Eosin (H&E) staining was performed using a Ventana® Medical Systems Symphony platform (Ventana® Medical Systems, Tucson, AZ) and the corresponding H&E Symphony Reagents (Ventana® Medical Systems, Tucson, AZ).

In-Situ Hybridization

Isolated nuclei were prepared as per Example 8, plated on slides at $2 \times 10^7$ particles per mL and allowed to air-dry overnight. Samples were assayed using the Her2/Chr17 Dual in-situ hybridization (ISH) protocol using a Ventana® Medical Systems Benchmark® XT platform (Ventana® Medical Systems, Tucson, AZ). Visualization of biomarkers were performed using the silver HRP detection and Alkaline Phosphatase (AP) Red detection, respectively. Cocktailed antibodies were incubated for 8 minutes. Images were acquired on a Zeiss Axio brightfield microscope.

Results

Figure 39:
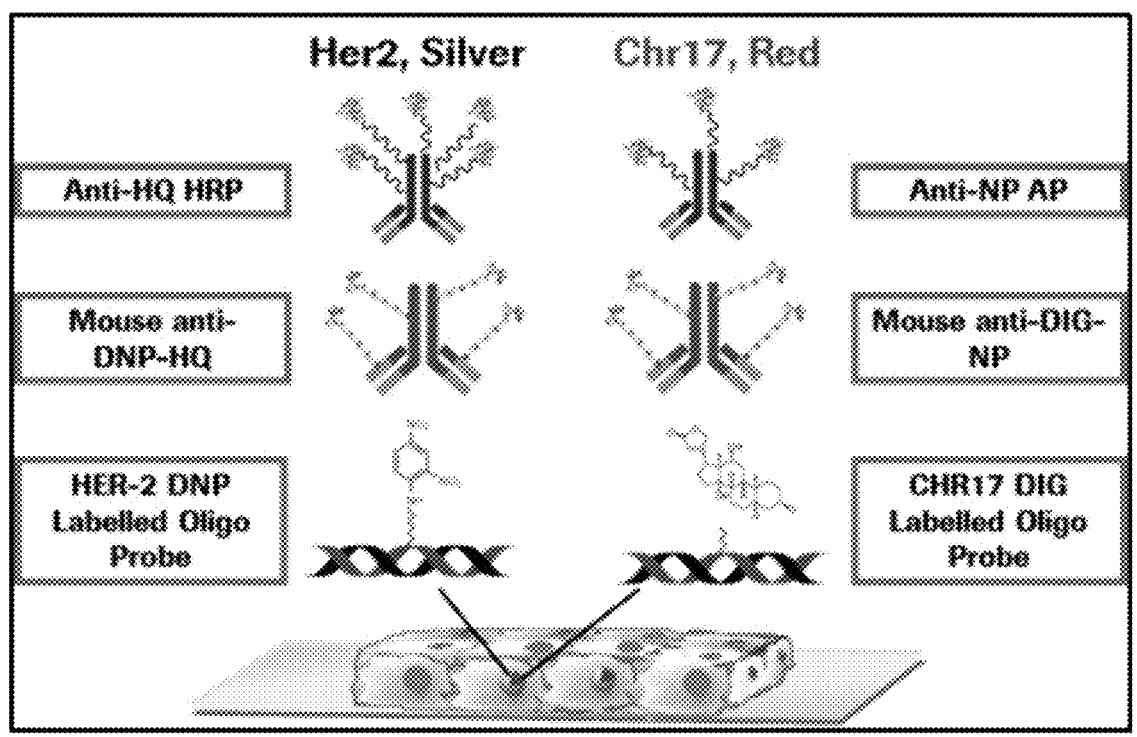
FIG. 39 shows an illustration of the Her2/Chr17 Detection stack.
Figure 40:
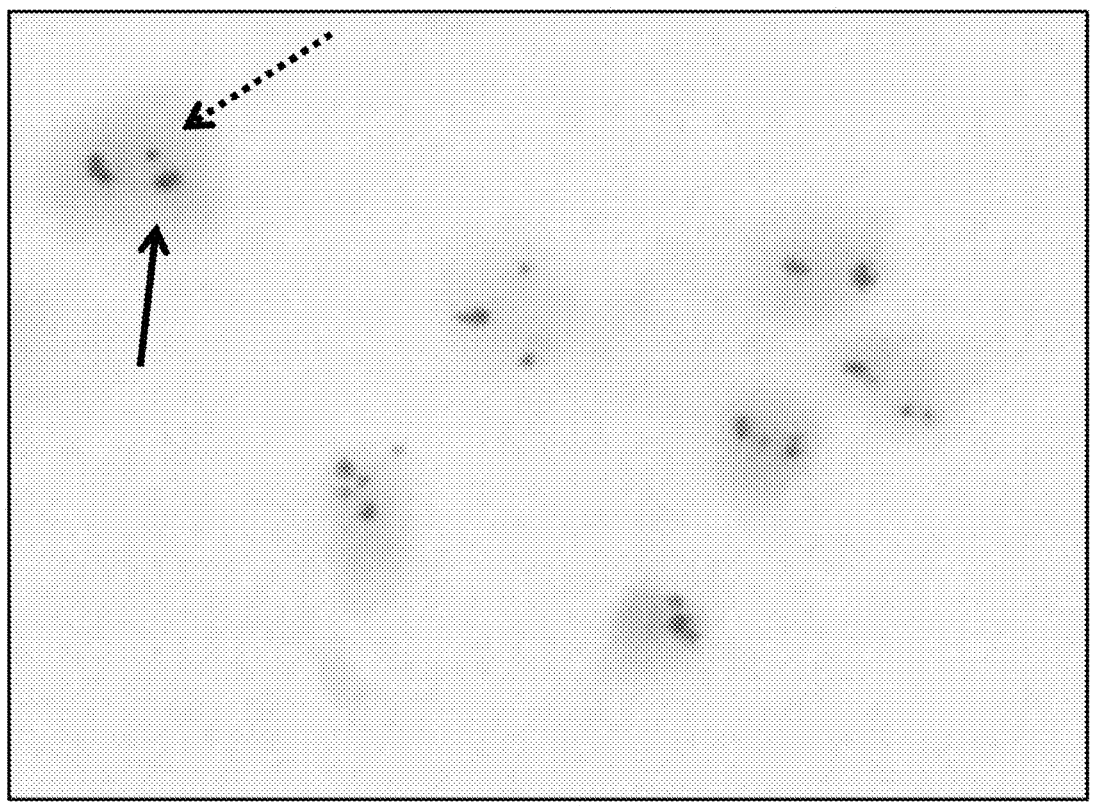
FIG. 40 shows a deparaffinization study. Images of isolated nuclei prepared from colon tissue and stained for Her2 (silver) and Chromosome 17 (red) (40×). Deparaffinization options explored were A LCS deparaffinization, B EZ prep deparaffinization, and C wet load option in place of deparaffinization.
Figure 41:
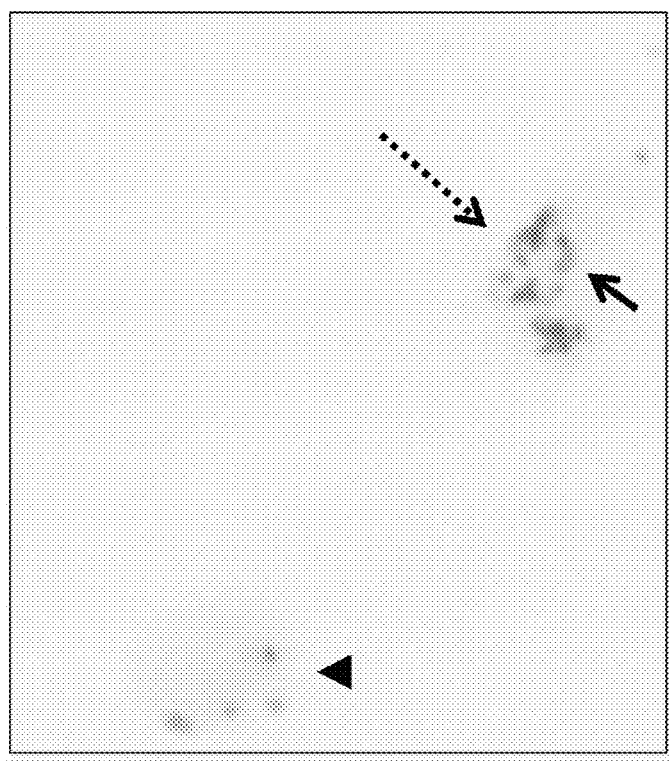
FIG. 41 shows a hybridization incubation study. Images of isolated nuclei prepared from colon tissue and stained for Her2 (silver) and Chromosome 17 (red) (40×). Hybridization options explored were A 1 hour hybridization, B 2 hour hybridization, and C 4 hour hybridization.

Isolation of nuclei from a colon and lung tumor creates a novel sample for ISH analysis of formalin fixed tissue samples. Isolation of the nuclei enables the rapid assessment of gene copy number, as the surrounding tissue does not complicate signal acquisition and interpretation, the detection scheme is shown in FIG. 39. As shown in FIG. 39, when Her2/Chr17 DNA oligo probes are hybridized to nuclei isolated from a representative sample derived from a colon tumor, two Her2 genes and two chromosome 17 alpha satellite regions (black Her2 SISH and red Chr17 alkaline phosphatase signals, dashed arrow and arrow, respectively) are readily detectable. Interestingly, a fraction of the nuclei isolated from a representative sample derived from a lung tumor have amplification of the Her2 locus, as evidenced by the ample SISH signal in a percentage of the nuclei (FIG. 40, Her2 SISH signal at dashed arrow).

With these data, the inventors demonstrate the ability to interrogate individual nuclei derived from representative samples of formalin fixed human tumors using ISH. Isolated nuclei provide an improved substrate for ISH as there is no residual paraffin wax in the tissue, a common reason for background staining in ISH procedures.

Example 11: Next Generation Sequencing Analysis of Representative Samples

Background

Next Generation Sequencing (NGS) is a high throughput DNA sequencing technology that enables the simultaneous analysis of millions to billions of fragments of DNA. In the past decade, significant advances in NGS technology have enabled researchers and clinicians to link DNA mutations with tumor heterogeneity, resistance to targeted therapy, and the efficacy of caner immuno-therapy. However, the tumor samples used for NGS in the clinic are exclusively FFPE tissues that are biased as described above. NGS analysis of representative samples from tumors will significantly improve the clinical relevance of NGS data.

Materials and Methods

Mechanical disassociation of the tumors was performed using a Hamilton Beach® Single Serve blender purchased from Walmart (Tucson, AZ) or by using an IKA® Works Tube Mill Control System (0004180001) from IKA-Works® (Staufen im Breisgau, Germany). All library preparation (TruSeq® Amplicon Cancer Panel) and MiSeq® reagent kits (MiSeq® Reagent Kit V2) were purchased from Illumina Inc (San Diego, CA). Sequencing was performed upon a MiSeq® (Illumina, San Diego, CA).

Colon, lung, and the papillary urothelial carcinoma tissue samples were obtained from GLAS (Winston-Salem, NC), the clear cell renal carcinoma was obtained from Northwest Hospital (Tucson, AZ), and the translocation renal carcinoma sample was obtained from Chandler Regional Hospital (Chandler, AZ). All tissues arrived at Ventana® Medical Systems in 10% neutral buffered formalin.

All tissues were removed from packaging material and examined by a pathologist. The tissue was dissected to separate tumor from normal, and blocks were taken for traditional histological examinations. Tumor and normal specimens for each clinical sample were mechanically disassociated by first weighing the tissue and then blending in a 1:1 or 1:1.25 (weight:volume) solution of MACS PBS (Miltenyi Biotec; Teterow, Germany). Representative samples were stored in MACS PBS at 4° C.

TRIzol® (Thermo-Fisher; Waltham, MA) was used to isolated DNA from the representative samples according to the standard protocol with one modification. The samples were incubated overnight at 60° C. in TRIzol® with 2 mg/ml Proteinase K (VWR; Radnor, PA). In some cases, histological sections taken from FFPE blocks were used to compare the current sampling methodology to representative sampling. For cases where FFPE tissue blocks were generated, five 10 µM sections were cut from the blocks of the colon, lung, and translocation kidney specimens along with a single 4 µM section that was stained for hematoxylin and eosin (H&E). The H&E stained slide was reviewed by a pathologist who identified tumor regions. The tumor regions were isolated from the remaining slides using a Millisect mesodissection instrument (Roche; Basel, Switzerland). The DNA was then isolated using a High Pure FFPET DNA Isolation Kit (Roche; Basel, Switzerland).

DNA concentration was determined using a Quant-iT PicoGreen dsDNA kit (Thermo-Fisher; Waltham, MA). DNA quality was assessed using the Illumina TruSeq® FFPE DNA Library Prep QC Kit (San Diego, CA). For each sample, 400 ng of DNA was used as template for the TruSeq® Amplicon-Cancer Panel Library preparation kit according to the manufacturer's protocol (Illumina; San Diego, CA). After amplification the PCR reactions were cleaned up using a Qiaquick® PCR purification kit (Qiagen; Duesseldorf, Germany). DNA concentrations were then measured using a Quant-iT® PicoGreen dsDNA kit (Thermo-Fisher; Waltham, MA). Libraries were mixed in equal amounts to create a 4 nM pooled library. The libraries were then denatured using an equal amount of 0.2N NaOH, and then diluted to 20 pM in HT1 buffer (Illumina; San Diego, CA). Each library was then further diluted to 15 pM in HT1 buffer prior to loading on the sequencing cartridge.

Sequencing was performed on a MiSeq® instrument using MiSeq® V2 reagent kits (Illumina; San Diego, CA) and loading 600 µL of a 15 pM pooled library. Paired end sequencing was performed according to manufacturer's protocol.

Raw sequencing data was analyzed by using the TruSeq® Amplicon App from Illumina (San Diego, CA) and through a modified CAVA (Clinical Annotation of Variants) (The Wellcome Trust Center for Human Genetics; Oxford, UK) database. Only variants above 5% prevalence were included in the data set, as the 5% mutant allele frequency is the common cut-off for reporting NGS data.

Results and Discussion

A small, targeted gene panel of 48 known cancer genes was used to deep sequence representative samples derived from formalin fixed human tumors. To demonstrate the significant improvement in the detection of mutations from cancer tissues, representative samples were compared to histological sections taken from the same tumors. In all cases, the representative samples delivered significantly more tumor mutations than did the current and historical sampling method of acquiring small, FFPE blocks.

TABLE 5

List of Tumor Samples

| Organ | Diagnosis | Weight |
|---|---|---|
| Colon | Adenocarcinoma | 125.2 g |
| Kidney | Translocation Renal Carcinoma | 56.73 g |
| Lung | Squamous Cell Carcinoma | 78.6 g |

Table 5 summarizes the clinical samples that were used to generate representative samples for NGS analysis in this example. The NGS data was first analyzed using the TRUSeq Amplicon app from Illumina in order to identify variants. This program aligns the sequencing reads with the Homo sapiens hg19 reference genome in order to identify point mutations and deletions that are present at or above a 5% prevalence threshold. Following this initial data analysis, all mutations identified in the representative samples that were not found in any FFPE blocks taken from the same tumor were annotated as unique to the representative sample, and are listed in tables 6-11 for each tumor tested. For every tumor tested, the representative samples contained far more mutations than did the FFPE blocks taken from the same tumors.

TABLE 6

Unique Mutations in the Representative Sample of the Colon Adenocarcinoma

| Gene | Chr | Mutation | Consequence | Prevalence |
|---|---|---|---|---|
| ERBB4 | 2 | 212530121 C--T | Missense | 9.50% |
| ERBB4 | 2 | 212530151 C--T | Missense | 12.30% |
| ERBB4 | 2 | 212587186 G--A | Missense | 6.90% |
| ERBB4 | 2 | 212587258 G--A | Missense | 9.80% |
| ERBB4 | 2 | 212652807 C--T | Missense | 7.20% |

TABLE 6-continued

Unique Mutations in the Representative Sample of the Colon Adenocarcinoma

| Gene | Chr | Mutation | Consequence | Prevalence |
|---|---|---|---|---|
| VHL | 3 | 10191507 G--T | Missense | 29.50% |
| MLH1 | 3 | 37067254 CG--C | Frameshift/truncation | 8% |
| MLH1 | 3 | 37067333 A--T | Missense | 8.10% |
| CTNNB1 | 3 | 41266086 A--G | Missense | 19.30% |
| PIK3CA | 3 | 178916954 A--G | Missense | 16.60% |
| PIK3CA | 3 | 178921573 A--T | Missense | 6.30% |
| PIK3CA | 3 | 178938878 A--G | Missense | 6.60% |
| PIK3CA | 3 | 178951928 G--A | Missense | 7.30% |
| PIK3CA | 3 | 178952018 A--T | Missense | 6% |
| FGFR3 | 4 | 1803675 A--G | Missense | 12.50% |
| FGFR3 | 4 | 1808371 GC--G | Frameshift/truncation | 18.30% |
| PDGFRA | 4 | 551152076 G--A | Missense | 5.90% |
| KIT | 4 | 55593675 A--T | Stop gained | 9.20% |
| KIT | 4 | 55602697 A--T | Missense | 7.90% |
| KDR | 4 | 55946146 G--A | Missense | 16% |
| KDR | 4 | 55953829 C--T | Missense | 15.90% |
| KDR | 4 | 55953844 G--A | Missense | 13.40% |
| KDR | 4 | 55980419 A--T | Stop gained | 7% |
| KDR | 4 | 55980429 TA--T | Frameshift | 5.70% |
| FBXW7 | 4 | 153245503 A--T | Missense | 6.40% |
| FBXW7 | 4 | 153249442 A--T | Missense | 12.40% |
| APC | 5 | 1121173944 G--A | Missense | 8.10% |
| APC | 5 | 112174005 G--T | Missense | 8.90% |
| APC | 5 | 112175150 A--G | Missense | 15.90% |
| APC | 5 | 1121175468 C--A | Missense | 9.70% |
| APC | 5 | 112175573 G--T | Stop gained | 5.50% |
| APC | 5 | 112175604 CA--C | Frameshift/truncation | 8.30% |
| CSF1R1 | 5 | 149453052 A--T | Missense | 9.20% |
| EGFR | 7 | 55211125 G--T | Missense | 32.50% |
| EGFR | 7 | 55249026 G--A | Missense | 5.80% |
| EGFR | 7 | 55259539 A--T | Missense | 11.30% |
| MET | 7 | 116339672 CG--C | Frameshift/truncation | 5.40% |
| MET | 7 | 116417508 G--A | Missense | 11.70% |
| MET | 7 | 116423476 G--C | Missense | 7.10% |
| MET | 7 | 116423492 A--T | Missense | 6.30% |
| SMO2 | 7 | 128846157 CTCACCTGG--C | Frameshift/truncation | 23% |
| BRAF | 7 | 140453136 A--T | Missense | 27.90% |
| GNAQ | 9 | 80336367 G--T | Missense | 12.30% |

TABLE 6-continued

Unique Mutations in the Representative Sample of the Colon Adenocarcinoma

| Gene | Chr | Mutation | Consequence | Prevalence |
|---|---|---|---|---|
| GNAQ | 9 | 80336373 G--T | Missense | 10.10% |
| GNAQ | 9 | 80343534 G--T | Missense | 6% |
| GNAQ | 9 | 80343546 A--T | Missense | 5.80% |
| ABL1 | 9 | 133748292 T--A | Missense | 8.20% |
| ABL1 | 9 | 133750433 G--T | Missense | 11.60% |
| NOTCH1 | 9 | 139399407 A--G | Missense | 19.70% |
| RET | 10 | 43609986 C--A | Missense | 18.90% |
| PTEN | 10 | 89711909 A--T | Missense | 21.50% |
| PTEN | 10 | 89711941 G--T | Missense | 19.60% |
| PTEN | 10 | 89711995 A--T | Missense | 21.40% |
| PTEN | 10 | 89717647 A--G | Missense | 8.40% |
| PTEN | 10 | 89717651 T--A | Missense | 6.80% |
| PTEN | 10 | 89720718 TAGAAAAT--T | Inframe Deletion | 10.70% |
| PTEN | 10 | 89720811 CA--C | Frameshift | 6.70% |
| FGFR2 | 10 | 123279566 A--G | Missense | 7.70% |
| FGFR2 | 10 | 123279579 G--A | Stop gained | 5.80% |
| FGFR2 | 10 | 123279623 A--G | Missense | 11.60% |
| ATM | 11 | 108123557 C--T | Missense | 6.80% |
| ATM | 11 | 108137974 A--T | Missense | 19.50% |
| ATM | 11 | 108155191 G--C | Missense | 9.20% |
| ATM | 11 | 108170487 TA--T | Frameshift/truncation | 7.60% |
| ATM | 11 | 108180976 ACTTTACAG--A | Frameshift/truncation | 7.70% |
| ATM | 11 | 108181023 A--T | Missense | 6.40% |
| ATM | 11 | 108181038 A--G | Missense | 7.20% |
| ATM | 11 | 108204684 A--T | Missense | 6.70% |
| ATM | 11 | 108206627 A--T | Missense | 5.10% |
| ATM | 11 | 108206678 G--T | Missense | 11.50% |
| KRAS | 12 | 25380317 A--T | Missense | 7.40% |
| HNF1A | 12 | 121432158 A--G | Missense | 9% |
| FLT3 | 13 | 28602402 C--T | Missense | 5.50% |
| RB1 | 13 | 48955568 G--T | Missnese | 44.70% |
| RB1 | 13 | 49033886 G--T | Stop gained | 8.50% |
| CDH1 | 16 | 68835678 G--T | Missense | 7.60% |
| CDH1 | 16 | 68847279 G--T | Missense | 16.10% |
| TP53 | 17 | 7578222 T--A | Missense | 15.20% |
| TP53 | 17 | 7578274 T--A | Missense | 8.50% |
| TP53 | 17 | 7578277 G--T | Missense | 6.50% |

TABLE 6-continued

Unique Mutations in the Representative Sample of the Colon Adenocarcinoma

| Gene | Chr | Mutation | Consequence | Prevalence |
|---|---|---|---|---|
| TP53 | 17 | 7578289 C--A | Missense | 9.70% |
| TP53 | 17 | 7578413 C--T | Missense | 13.90% |
| TP53 | 17 | 7578473 G--A | Missense | 7.70% |
| SMAD4 | 18 | 48584590 G--A | Missense | 9.70% |
| SMAD4 | 18 | 48593474 G--A | Missense | 6.20% |
| GNA11 | 19 | 3118937 GGGCCAGCGGTC--G | Frameshift/truncation | 6.60% |
| GNA11 | 19 | 3121086 G--A | Missense | 27.90% |
| GNA11 | 19 | 3121149 T--A | Missense | 18.80% |
| SMARCB1 | 22 | 24134072 A--T | Missense | 21.20% |
| SMARCB1 | 22 | 24145588 G--T | Missense | 9% |

TABLE 7

Unique Mutations in the Representative Sample of the Translocation Renal Carcinoma

| Gene | Chr | Mutation | Consequence | Prevalence |
|---|---|---|---|---|
| Alk2 | 2 | 29443700 TG--T | Frameshift/truncation | 7.10% |
| Idh1 | 2 | 209113193 C--T | Missense | 5.70% |
| Idh1 | 2 | 209113204 A--T | Missense | 7.20% |
| ERBB4 | 2 | 212587162 T--C | Missense | 6.90% |
| ERBB4 | 2 | 212652750 A--T | Missense | 9.40% |
| ERBB4 | 2 | 212812160 A--T | Stop gained | 5.40% |
| Vh1 | 3 | 10191561 A--G | Missense | 56.90% |
| Vh1 | 3 | 10191576 A--T | Missense | 100% |
| PIK3CA | 3 | 178951953 C--T | Missense | 6% |
| PIK3CA | 3 | 178952019 C--T | Missense | 5.20% |
| FGFR3 | 4 | 1806212 G--T | Missense | 38.20% |
| FGFR3 | 4 | 1807996 G--A | Missense | 7.20% |
| PDGFRA | 4 | 55141065 G--T | Stop gained | 8.80% |
| Kit | 4 | 55595549 AT--A | Frameshift/truncation | 5% |
| Kit | 4 | 55597504 A--T | Missense | 10.50% |
| Kit | 4 | 55597549 C--T | Missense | 11.40% |
| Kdr | 4 | 55946181 C--A | Missense | 7.90% |
| Kdr | 4 | 55946244 T--A | Missense | 6.60% |
| Kdr | 4 | 55960995 G--T | Missense | 13.60% |
| Kdr | 4 | 55961082 C--T | Missense | 9.10% |
| APC | 5 | 112173935 A--G | Missense | 13.20% |
| APC | 5 | 112174708 G--T | Missense | 14.90% |
| APC | 5 | 112175094 C--A | Missense | 7.10% |

TABLE 7-continued

Unique Mutations in the Representative Sample of the Translocation Renal Carcinoma

| Gene | Chr | Mutation | Consequence | Prevalence |
|---|---|---|---|---|
| APC | 5 | 112175115 G--A | Missense | 8.70% |
| APC | 5 | 112175285 AC--A | Frameshift/truncation | 6.30% |
| APC | 5 | 112175432 C--A | Missense | 7.10% |
| APC | 5 | 112175440 G--T | Missense | 7.60% |
| APC | 5 | 112175469 T--A | Missense | 25.60% |
| APC | 5 | 112175565 A--T | Missense | 7.30% |
| CSF1 | 5 | 149433748 TG--T | Frameshift/truncation | 25.90% |
| EGFR | 7 | 55211090 G--C | Missense | 24.80% |
| EGFR | 7 | 55211109 G--T | Missense | 24.60% |
| EGFR | 7 | 55211136 G--T | Missense | 24.40% |
| EGFR | 7 | 55233075 A--T | Stop gained | 16.40% |
| EGFR | 7 | 55241699 A--T | Missense | 33.20% |
| EGFR | 7 | 55249058 G--A | Missense | 31.70% |
| Met | 7 | 116340265 A--T | Missense | 14.50% |
| Smo2 | 7 | 128846133 G--A | Missense | 13% |
| GNAQ | 9 | 80343454 C--T | Missense | 7% |
| GNAQ | 9 | 80343534 G--T | Missense | 6% |
| GNAQ | 9 | 80343549 G--A | Missense | 6.60% |
| GNAQ | 9 | 80343581 G--T | Missense | 6.10% |
| GNAQ | 9 | 80412458 C--T | Missense | 7.20% |
| GNAQ | 9 | 80412505 A--T | Missense | 19.50% |
| ABL1 | 9 | 133748272 C--A | Missense | 8.40% |
| ABL1 | 9 | 133748285 G--A | Missense | 8.40% |
| ABL1 | 9 | 133748409 A--C | Missense | 20.10% |
| NOTCH1 | 9 | 139399419 A--G | Missense | 5.60% |
| RET | 10 | 43617418 G--T | Missense | 6.90% |
| FGFR2 | 10 | 123258067 C--T | Missense | 5% |
| FGFR2 | 10 | 123279502 C--A | Missense | 5.30% |
| HRAS | 11 | 533884 TA--T | Frameshift/truncation | 12.30% |
| ATM | 11 | 108123557 C--T | Missense | 7.10% |
| ATM | 11 | 108123568 G--T | Missense | 5.60% |
| ATM | 11 | 108137982 G--T | Missense | 9.10% |
| ATM | 11 | 108170488 A--T | Missense | 6.90% |
| ATM | 11 | 108170585 A--T | Missense | 8.50% |
| ATM | 11 | 108173701 T--C | Missense | 8.60% |
| ATM | 11 | 108205796 G--A | Missense | 8.60% |
| ATM | 11 | 108206622 G--C | Missense | 12.40% |

TABLE 7-continued

Unique Mutations in the Representative Sample of the Translocation Renal Carcinoma

| Gene | Chr | Mutation | Consequence | Prevalence |
|---|---|---|---|---|
| KRAS | 12 | 25380316 C--T | Missense | 8.40% |
| KRAS | 12 | 25380343 A--T | Missense | 6.10% |
| KRAS | 12 | 25398297 C--T | Missense | 5.70% |
| HNF1A | 12 | 121431499 G--T | Stop gained | 100% |
| HNF1A | 12 | 121432091 A--G | Missense | 16.30% |
| FLT3 | 13 | 28592702 TGGCG--T | Frameshift/truncation | 9.60% |
| FLT3 | 13 | 28602410 G--T | Missense | 9.20% |
| FLT3 | 13 | 28608332 TGG--T | Frameshift/truncation | 10.80% |
| RB1 | 13 | 48919223 A--T | Stop gained | 5% |
| RB1 | 13 | 48955572 G--A | Stop gained | 6.10% |
| RB1 | 13 | 4903386 G--T | Stop gained | 7.30% |
| RB1 | 13 | 49033898 A--T | Missense | 5.70% |
| RB1 | 13 | 49033923 C--T | Missense | 5% |
| AKT1 | 14 | 105246509 T--C | Missense | 25.20% |
| CDH1 | 16 | 68835741 C--T | Missense | 8.90% |
| TP53 | 17 | 7574032 A--T | Missense | 8.10% |
| TP53 | 17 | 7577091 G--A | Missense | 11% |
| TP53 | 17 | 7577597 G--T | Missense | 87.30% |
| TP53 | 17 | 7578227 C--A | Missense | 6.80% |
| TP53 | 17 | 7578242 C--T | Missense | 16.60% |
| TP53 | 17 | 7578424 ATGTGC--A | Frameshift/truncation | 7.30% |
| TP53 | 17 | 7578520 A--T | Missense | 19.60% |
| SMAD4 | 18 | 48575195 C--A | Missense | 7.20% |
| SMAD4 | 18 | 48581231 A--T | Missense | 5.40% |
| SMAD4 | 18 | 48581243 C--T | Stop gained | 6.20% |
| SMAD4 | 18 | 48581255 A--C | Missense | 6.50% |
| SMAD4 | 18 | 48584596 C--T | Missense | 11.60% |
| SMAD4 | 18 | 48603131 A--T | Missense | 100% |
| STK11 | 19 | 1221324 T--A | Missense | 13.70% |
| GNA11 | 19 | 3119344 C--A | Missense | 23.50% |
| JAK3 | 19 | 17945730 GCC--G | Frameshift/truncation | 6% |
| GNAS | 20 | 57484462 G--T | Missense | 7.50% |

TABLE 8

Unique Mutations in the Representative Sample of the Lung Squamous Cell Carcinoma

| Gene | Chr | Mutation | Consequence | Prevalence |
|---|---|---|---|---|
| IDH1 | 2 | 209113181 C--T | Missense | 15.90% |
| ERBB4 | 2 | 212530085 G--A | Missense | 13% |
| ERBB4 | 2 | 212652782 A--T | Stop gained | 38.10% |
| MLH1 | 3 | 37067282 A--T | Missense | 49.40% |
| PIK3CA | 3 | 178951914 C--T | Missense | 42.80% |
| PIK3CA | 3 | 178951997 G--T | Missense | 42.60% |
| PDGFRA | 4 | 55152101 C--A | Missense | 13.60% |
| KIT | 4 | 55594230 A--T | Missense | 18.80% |
| FBXW7 | 4 | 153249460 C--T | Missense | 58.90% |
| APC | 5 | 112173975 C--T | Missense | 35.70% |
| APC | 5 | 112175438 A--G | Missense | 14.30% |
| EGFR | 7 | 55242438 G--T | Missense | 50.10% |
| EGFR | 7 | 55249008 T--C | Missense | 68% |
| ABL1 | 9 | 133748411 A--T | Missense | 14.60% |
| RET | 10 | 43615616 GT--G | Frameshift | 47.60% |
| PTEN | 10 | 89685304 A--G | Missense | 24.50% |
| PTEN | 10 | 89720801 C--T | Missense | 28.10% |
| FGFR2 | 10 | 123258043 A--T | Missense | 8.30% |
| ATM | 11 | 108138014 C--G | Stop gained | 10.10% |
| ATM | 11 | 108172427 A--T | Stop gained | 97.80% |
| ATM | 11 | 108206665 A--T | Stop gained | 42.20% |
| ATM | 11 | 108236095 A--T | Missense | 56% |
| ATM | 11 | 108236170 A--G | Missense | 9.90% |
| FLT3 | 13 | 28608258 C--G | Missense | 17.50% |
| CDH1 | 16 | 68847337 G--T | Missense | 16.40% |
| TP53 | 17 | 7577072 A--G | Missense | 12.40% |
| TP53 | 17 | 7578449 C--T | Missense | 10.40% |
| TP53 | 17 | 7579398 C--T | Missense | 26.20% |
| TP53 | 17 | 7579472 G--C | Missense | 100% |
| ERBB2 | 17 | 37880240 A--T | Stop gained | 24.50% |
| SMAD4 | 18 | 48575213 T--C | Missense | 8.30% |
| SMAD4 | 18 | 48591887 TG--T | Frameshift | 98.40% |
| SMAD4 | 18 | 48591942 A--G | Missense | 96.40% |
| SMAD4 | 18 | 48593432 G--T | Missense | 8.50% |
| SMAD4 | 18 | 48593456 A--T | Missense | 8.70% |
| SMAD4 | 18 | 48593472 T--C | Missense | 7.30% |
| JAK3 | 19 | 17945758 G--T | Missense | 35.70% |
| SMARCB1 | 22 | 24145603 A--T | Missense | 99.70% |

Mutations were found in the FFPE blocks that were not found in the representative samples, however there were far fewer mutations unique to the blocks compared to the representative samples (Tables 9-12).

TABLE 9

Block only mutations in the colon adenocarcinoma

| Gene | Chr | Mutation | Consequence | Blocks |
|---|---|---|---|---|
| FGFR3 | 4 | 1803649 A--T | Missense | 3 |
| HNF1A | 12 | 121432178 C--T | Missense | 3 |

TABLE 10

Block only mutations in the Translocation Renal Cell Carcinoma

| Gene | Chr | Mutation | Consequence | Blocks |
|---|---|---|---|---|
| FGFR3 | 4 | 1808386 A--T | Missense | 2 |
| TP53 | 17 | 7577538 C--T | Missense | 2, 5 |
| STK11 | 19 | 1207093 G--T | Missense | 5 |
| GNA11 | 19 | 3121154 C--T | Missense | 2 |

TABLE 11

Mutations Unique to FFPE Blocks in the Lung Squamous Cell Carcinoma

| Gene | Chr | Mutation | Consequence | Blocks |
|---|---|---|---|---|
| FGFR3 | 4 | 1808329 C--T | Missense | 4 |
| FGFR3 | 4 | 1808376 C--T | Missense | 4 |
| PDGFRA | 4 | 55144643 A--T | Missense | 3 |
| PTEN | 10 | 89711891 G--A | Missense | 4 |

TABLE 12

Number of Unique Mutations Per Sample Type

| Tumor Type | # Unique Mutations in Rep. Sample | # Unique Mutations in FFPE Blocks |
|---|---|---|
| Colon | 90 | 2 |
| Kidney | 92 | 4 |
| Lung | 38 | 4 |

The NGS data was further analyzed for the colon adenocarcinoma, translocation renal cell carcinoma, and the lung squamous cell carcinoma using a CAVA database to determine the number of mutations resulting in a coding region changes (egg. missense mutation resulting in an amino acid change). Tables 13-15 show the mutations resulting in coding changes, suggesting that these mutations may be of research and/or clinical import.

TABLE 13

Pathogenic Mutations in the Representative Sample of the Colon Adenocarcinoma

| Gene | Chr | Mutation | Consequence | Prevalence | Protein Type | Amino Acid Change |
|---|---|---|---|---|---|---|
| RB1 | 13 | 48955568 G--T | Missense | 44.70% | tumor suppressor | Ala562Ser |
| EGFR | 7 | 55211125 C--T | Missense | 32.50% | Oncogene | Ser123Phe |
| VHL | 3 | 10191507 G--T | Missense | 29.50% | tumor suppressor | Arg167Leu |
| BRAF | 7 | 140453136 A--T | Missense | 27.90% | Oncogene | Val600Glu |
| GNA11 | 19 | 3121086 G--A | Missense | 27.90% | Oncogene | Cys330Tyr |
| PTEN | 10 | 89711909 A--T | Missense | 21.50% | tumor suppressor | Tyr176Phe |
| PTEN | 10 | 89711995 A--T | Missense | 21.40% | tumor suppressor | Met205Leu |
| SMARCB1 | 22 | 24134072 A--T | Missense | 21.20% | tumor suppressor | Asn75Tyr |
| PTEN | 10 | 89711941 G--T | Missense | 19.60% | tumor suppressor | Asp187Tyr |
| CTNNB1 | 3 | 41266086 A--G | Missense | 19.30% | Oncogene | Gln28Arg |

TABLE 14

Pathogenic Mutations in the Representative Sample of the Translocation Renal Carcinoma

| Gene | Chr | Mutation | Consequence | Prevalence | Protein Type | Amino Acid Change |
|---|---|---|---|---|---|---|
| Vhl | 3 | 10191576 A--T | Missense variant | 100% | tumor suppressor | Asp190Val |
| HNF1A | 12 | 121431499 G--T | Stop gained | 100% | tumor suppressor | Glu235Stop |
| SMAD4 | 18 | 48603131 A--T | Missense variant | 100% | tumor suppressor | Ile478Leu |
| TP53 | 17 | 7577597 G--T | Missense variant | 87.30% | tumor suppressor | Asp228Glu |
| Vhl | 3 | 10191561 A--G | Missense variant | 56.90% | tumor suppressor | Tyr185Cys |
| FGFR3 | 4 | 1806212 G--T | Missense variant | 38.20% | Oncogene | Val413Leu |
| EGFR | 7 | 55241699 A--T | Missense variant | 33.20% | Oncogene | Lys716Ile |

TABLE 14-continued

Pathogenic Mutations in the Representative Sample of the Translocation Renal Carcinoma

| Gene | Chr | Mutation | Consequence | Prevalence | Protein Type | Amino Acid Change |
|---|---|---|---|---|---|---|
| EGFR | 7 | 55249058 G--A | Missense variant | 31.70% | Oncogene | Val786Met |
| CSF1 | 5 | 149433748 TG--T | Frameshift/Truncation | 25.90% | Oncogene | deletion |
| APC | 5 | 112175469 T--A | Missense variant | 25.60% | tumor suppressor | Leu1393His |
| AKT1 | 14 | 105246509 T--C | Missense variant | 25.20% | Oncogene | Asn314Asp |
| EGFR | 7 | 55211090 G--C | Missense variant | 24.80% | Oncogene | Met111Ile |
| EGFR | 7 | 55211109 G--T | Missense variant | 24.60% | Oncogene | Ala118Ser |
| EGFR | 7 | 55211136 G--T | Missense variant | 24.40% | Oncogene | Ala127Ser |
| GNA11 | 19 | 3119344 C--A | Missense variant | 23.50% | Oncogene | Phe292Leu |
| ABL1 | 9 | 133748409 A--C | Missense variant | 20.10% | Oncogene | Lys376Thr |
| GNAQ | 9 | 80412505 A--T | Missense variant | 19.50% | Oncogene | Val179Glu |

TABLE 15

Pathogenic Mutations in the Representative Sample of the Lung Squamous Cell Carcinoma

| Gene | Chr | Mutation | Consequence | Prevalence | Protein Type | Amino Acid Change |
|---|---|---|---|---|---|---|
| TP53 | 17 | 7579472 G--C | Missense | 100% | Tumor suppressor | Pro72Arg |
| SMARCB1 | 22 | 24145603 A--T | Missense | 99.70% | Tumor suppressor | Met208Leu |
| SMAD4 | 18 | 48591887 TG--T | Frameshift | 98.40% | Tumor suppressor | |
| ATM | 11 | 108172427 A--T | Stop gained | 97.80% | Oncogene | Lys1744Stop |
| SMAD4 | 18 | 48591942 A--G | Missense | 96.40% | Tumor suppressor | Asn369Asp |
| EGFR | 7 | 55249008 T--C | Missense | 68% | Oncogene | Val769Ala |
| FBXW7 | 4 | 153249460 C--T | Missense | 58.90% | Tumor suppressor | Asp440Asn |
| ATM | 11 | 108236095 A--T | Missense | 56% | Oncogene | Met3011Leu |
| EGFR | 7 | 55242438 G--T | Missense | 50.10% | Oncogene | Glu736Asp |
| MLH1 | 3 | 37067282 A--T | Missense | 49.40% | Tumor suppressor | Gln398Leu |
| RET | 10 | 43615616 GT--G | Frameshift | 47.60% | Oncogene | |
| PIK3CA | 3 | 178951914 C--T | Missense | 42.80% | Oncogene | Ala990Val |
| PIK3CA | 3 | 178951997 G--T | Missense | 42.60% | Oncogene | Asp1018Tyr |
| ATM | 11 | 108206665 A--T | Stop gained | 42.20% | Oncogene | Lys2749Stop |
| ERBB4 | 2 | 212652782 A--T | Stop gained | 38.10% | Tumor suppressor | Leu175X |
| APC | 5 | 112173975 C--T | Missense | 35.70% | Tumor suppressor | Ser895Leu |
| JAK3 | 19 | 17945758 G--T | Missense | 35.70% | Oncogene | Thr701Lys |
| PTEN | 10 | 89720801 C--T | Missense | 28.10% | Tumor suppressor | Leu318Phe |
| TP53 | 17 | 7579398 C--T | Missense | 26.20% | Tumor suppressor | Val97Ile |
| PTEN | 10 | 89685304 A--G | Missense | 24.50% | Tumor suppressor | Ile67Val |
| ERBB2 | 17 | 37880240 A--T | Stop gained | 24.50% | Oncogene | Lys762X |

TABLE 15-continued

Pathogenic Mutations in the Representative Sample of the Lung Squamous Cell Carcinoma

| Gene | Chr | Mutation | Consequence | Prevalence | Protein Type | Amino Acid Change |
|------|-----|----------|-------------|------------|--------------|-------------------|
| APC | 5 | 112175438 A--G | Missense | 14.30% | Tumor suppressor | Met1383Val |
| ATM | 11 | 108236170 A--G | Missense | 9.90% | Oncogene | Ile3036Val |

With these data the inventors have demonstrated that representative samples are superior to current the current sampling techniques in clinical pathology and oncology. Moreover, that the prevalence rates of the mutations vary demonstrates that NGS analysis from representative samples of tumors enables the detection of clonal and sub-clonal mutations within human tumors. Together, these data demonstrate that representative samples from human resected tumors can be used to interrogate the genomic diversity of cancer.

Example 12: Embedding of Representative Samples into Paraffin Wax an Histological Analysis Background Representative samples derived from organs, tissues, or tumors can be embedded in paraffin wax to generate a sample type that contains cellular fragments of tissue, thereby preserving the anatomic relationships between the structures contained within the original organ, tissue, or tumor. Histological sections taken from embedded representative samples can be analyzed by an anatomic pathologist, or using a digital microscope scanning system. Data from digital scanning systems can be further interrogated to quantify the level of heterogeneity between biomarkers, or between patients. Moreover, the output from scanning systems can be used as input to a mathematical analysis of heterogeneity as illustrated below.

Materials and Methods:

Fresh tonsils were acquired from Northwest Hospital (Oro Valley, AZ) and were fixed in 10% neutral buffered formalin upon arrival. Some tonsil samples were processed into FFPE blocks by placing the entire tonsil into a tissue cassette, followed by dehydration and paraffin perfusion. Representative samples of tonsils were done as described in previous examples. The representative samples derived from a human lung and colon tumor were the same samples as described in Example 11. A sample of the representative samples from the tonsil, colon tumor, and lung tumor were wrapped in microscope lens paper and placed in a tissue cassette. The tissue cassette was placed into xylene and dehydrated in a tissue processor (Leica Biosystems, Wetzlar, Germany) and then embedded in wax. Four micron sections were taken from all blocks analyzed.

For IHC, slides were stained using the OptiView® DAB IHC protocol using a Ventana® Medical Systems Benchmark® XT platform (Ventana® Medical Systems, Tucson, AZ). Visualization of the antibodies was performed using the OptiView® DAB Detection kit. Antibodies were incubated per package insert instructions.

For digital image analysis, full slide scans were acquired on a Aperio AT2 scanner and image analysis was performed using Aperio ImageScope® algorithm 'Positive Pixel Count v9'.

Results and Discussion

The interpretation of many histological stains requires the preservation of tissue architecture, for instance the orientation of immune cells to tumor cells. Therefore, the disassociation of tumors into individual cells may not work for all histological assays. To determine whether mechanically disassociated representative samples derived from an intact organ could be embedded in wax, histologically sectioned, and assessed for specific architectural features, whole tonsils were mechanically disassociated in an IKA® Tube Mill. A sample of the tonsil homogenate was dehydrated and embedded in wax, four micron sections were taken and placed on glass slides, and stained for various biomarkers on a Ventana® BenchMark® XT.

FIGS. 53A and 53B are whole slide images of a histological section taken from an intact tonsil stained with a pan-keratin antibody. FIG. 53A depicts a traditional histological section of a normal tonsil detected by DAB for Pan-Keratin. FIG. 53B is a section from a representative sample of tonsil detected by DAB for Pan-Keratin. The organization and structure of the tonsil is further highlighted in the box in figure FIG. 53A, where the epithelial tissue in brown is adjacent to multiple germinal centers containing the many different types of lymphocytes. This tissue organization is preserved when a sample of homogenized tonsil is embedded in paraffin and sectioned (FIGS. 54A and 54B). FIG. 54A depicts a traditional histological section of a normal tonsil detected by DAB for CD8. FIG. 54B depicts a section from a representative sample of tonsil detected by DAB for CD8. When stained with for the presence of CD8 positive cells, both the section of the whole tonsil and the homogenized tonsil demonstrate CD8 positive cells surrounding the circular germinal centers. These data demonstrate the ability to paraffin embed representative samples derived from organs, tissues, and tumors to generate a histological sample that preserves the anatomic and tissue architecture for further analysis.

Two representative samples derived from the colon and a lung tumor from example 9 were embedded in paraffin wax for histological analysis. Thin, four-micron sections were cut from and stained for multiple tumor and immune specific biomarkers (Met, Alk, bRaf, EGFR, PD-L1, CD8, and CK 8/18. The slides read and the intensity scores were analyzed by an anatomical pathologist. Standard FFPE blocks made from samples taken to mimic the current TNM staging system were included in this analysis (blocks in Table 16). As shown in Table 16, anatomic pathologist can read and interpret staining from both FFPE blocks and representative samples.

TABLE 16

Pathologist Scoring of IHC

| Biomarker | Block 1 | Block 2 | Block 3 | Block 4 | Rep. Sample |
|---|---|---|---|---|---|
| MET | 2+ | 1+ | 1+ | 1+ | 1+ |
| ALK | Neg | Neg | Neg | Neg | Neg |
| EGFR | 3+ | 3+ | 3+ | 3+ | 2+ |
| bRAF | Neg | Neg | Neg | Neg | Neg |
| PD-L1 | Neg | Neg | Neg | Neg | Neg |
| CD8 | Present | Present | Present | Present | Present |

The interpretation of the representative sample by the pathologist did not appear to address the heterogeneity in signal intensity and staining across the entire slide. To generate a mathematical representation of the heterogeneity in IHC staining from representative samples the IHC stained slides were analyzed using a digital slide scanner. Following whole slide scanning, the DAB intensity was quantified using the Aperio ImageScope® algorithm 'Positive Pixel Count v9'. For all blocks and representative samples CD8, PD-L1, EGFR, and MET signal intensity was divided by the signal intensity of CK 8/18 to mathematically express the heterogeneity of biomarker signal, relative to tumor content. As shown in Tables 16-23, while the averages of the CD8 relative to CK 8/18 for the histological blocks from the colon and lung tumor equal that of the representative sample, there is significant differences in the averages of the relative signal intensities between the samples stained with PD-L1, EGFR, and MET. These data suggest that IHC staining of histological sections made from samples of representative samples better represent the heterogeneity in biomarker signals, and decrease the variance in IHC results as the blocks varied significantly between each other.

TABLE 17

Digital Imaging and Analysis of CD8 IHC from Colon Samples

| | Block | CD8/CK8:18 | |
|---|---|---|---|
| Standard TNM Blocks | Block-1 | 32.8 | Average |
| | Block 2 | 66.3 | 52.7 |
| | Block 3 | 44.6 | |
| | Block 4 | 67.0 | |
| Rep. Sample | Rep 1 | 52.8 | Average |
| | Rep 4 | 56.5 | 54.7 |

TABLE 18

Digital Imaging and Analysis of PD-L1 IHC from Colon Samples

| | Block | PD-L1/CK8:18 | |
|---|---|---|---|
| Standard TNM Blocks | Block-1 | 14.8 | Average |
| | Block 2 | 20.4 | 21.7 |
| | Block 3 | 26.8 | |
| | Block 4 | 24.8 | |
| Rep. Sample | Rep 1 | 32.1 | Average |
| | Rep 4 | 25.2 | 28.6 |

TABLE 19

Digital Imaging and Analysis of EGFR IHC from Colon Samples

| | Block | EGFR/CK8:18 | |
|---|---|---|---|
| Standard TNM Blocks | Block-1 | 0.3 | Average |
| | Block 2 | 2.9 | 2.2 |
| | Block 3 | 3.6 | |
| | Block 4 | 1.9 | |
| Rep. Sample | Rep 1 | 1.6 | Average |
| | Rep 4 | 2.0 | 1.8 |

TABLE 20

Digital Imaging and Analysis of MET IHC from Colon Samples

| | Block | MET/CK8:18 | |
|---|---|---|---|
| Standard TNM Blocks | Block-1 | 76.7 | Average |
| | Block 2 | 54.4 | 56.0 |
| | Block 3 | 48.6 | |
| | Block 4 | 44.4 | |
| Rep. Sample | Rep 1 | 38.1 | Average |
| | Rep 4 | 32.3 | 35.2 |

TABLE 21

Digital Imaging and Analysis of CD8 IHC from Lung Samples

| | Block | CD8/CK8:18 | |
|---|---|---|---|
| Standard TNM Blocks | Block-1 | 118.7 | Average |
| | Block 2 | 89.6 | 123.5 |
| | Block 3 | 154.2 | |
| | Block 4 | 131.4 | |
| Rep. Sample | Rep 1 | 123.1 | 123.1 |

TABLE 22

Digital Imaging and Analysis of PD-L1 IHC from Lung Samples

| | Block | PD-L1/CK8:18 | |
|---|---|---|---|
| Standard TNM Blocks | Block-1 | 58.0 | Average |
| | Block 2 | 47.5 | 54.2 |
| | Block 3 | 51.7 | |
| | Block 4 | 59.7 | |
| Rep. Sample | Rep 1 | 39.0 | 39.0 |

TABLE 23

Digital Imaging and Analysis of EGFR IHC from Lung Samples

| | Block | EGFR/CK8:18 | |
|---|---|---|---|
| Standard TNM Blocks | Block-1 | 109.7 | Average |
| | Block 2 | 65.9 | 79.3 |
| | Block 3 | 69.7 | |
| | Block 4 | 71.9 | |
| Rep. Sample | Rep 1 | 45.6 | 45.6 |

TABLE 24

Digital Imaging and Analysis of MET IHC from Lung Samples

| | Block | MET/CK8:18 | |
|---|---|---|---|
| Standard TNM Blocks | Block-1 | 32.3 | Average |
| | Block 2 | 39.6 | 37.1 |
| | Block 3 | 40.6 | |
| | Block 4 | 36.0 | |
| Rep. Sample | Rep 1 | 49.2 | 49.2 |

All patent and non-patent references cited herein are incorporated by reference in their entireties.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The disclosures illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

OTHER EMBODIMENTS

1. A method for preparing a representative sample for analysis, comprising:
   a. obtaining a surgical resection tissue sample from at least one subject; and,
   b. homogenizing the surgical resection tissue sample to obtain a homogenized sample.

2. The method of embodiment 1, further comprising fixing at least a portion of the surgical resection tissue sample.

3. The method of embodiment 1, further comprising processing a first portion of the surgical resection sample and generating one or more fixed, embedded tissue blocks.

4. The method of embodiment 3, further comprising homogenizing a second portion of the remaining surgical tissue resection sample.

5. The method of embodiment 3 or 4, further comprising processing at least a portion of the one or more fixed, embedded tissue blocks by micrototomy to produce one or more tissue thin sections for morphological analysis.

6. The method of embodiment 5, further comprising deparaffinizing at least one of the one or more fixed, embedded tissue blocks and homogenizing the tissue from the one or more deparaffinized fixed, embedded tissue blocks.

7. The method of embodiment 1, wherein the surgical resection tissue sample includes one or more separate pieces of tissue.

8. The method of embodiment 7, wherein the one or more separate pieces of tissue comprise at least a portion of one or more primary solid tumor tissue masses resected from a subject to obtain the surgical resection sample.

9. The method of embodiment 8, wherein the one or more separate pieces of tissue comprise at least a portion of one or more lymph nodes resected from the subject.

10. The method of embodiment 7, 8 or 9, further comprising separately homogenizing at least a portion of the separate pieces of tissue to yield separate homogenized samples.

11. The method of embodiment 1, wherein the surgical resection tissue sample comprises a single tissue mass.

12. The method of embodiment 11, wherein the single tissue mass is further divided into two or more pieces of the single tissue mass.

13. The method of embodiment 12, further comprising homogenizing at least one of the two or more pieces of the single tissue mass and preserving at least one of the remaining two or more pieces of the single tissue mass.

14. The method of embodiment 1, wherein the homogenizing comprises physical separation.

15. The method of embodiment 14 wherein the physical separation is by cutting, dicing, or mincing.

16. The method of embodiment 1, wherein the homogenizing comprises mechanical disassociation.

17. The method of embodiment 16, wherein the mechanical dissociation is by blending or juicing.

18. The method of embodiment 1, wherein the homogenizing is by biochemical disassociation 19. The method of embodiment 18, wherein the biochemical dissociation is by a protease.

20. The method of embodiment 1, further comprising purifying one or more biomolecules from at least a portion of the homogenate.

21. The method of embodiment 20, wherein the one or more biomolecules are selected from the group consisting of DNA, RNA, proteins, lipids, and metabolites.

22. The method of embodiment 21, further comprising analyzing the one or more biomolecules.

23. The method of embodiment 22, wherein the analyzing the one or more biomolecules is by PCR, mass spectrometry, next generation sequencing, or ELISA.

24. The method of embodiment 22 wherein the analyzing produces at least one dataset.

25. The method of embodiment 1, further comprising embedding at least a portion of the homogenized sample in paraffin.

26. The method of embodiment 25, further comprising preparing one or more thin sections of the paraffin embedded homogenized sample.

27. The method of embodiment 26, further comprising performing histological analysis on thin sections of the paraffin embedded homogenized sample.

28. The method of embodiment 27, wherein the histological analysis is by H&E staining, IHC staining, ISH staining, and FISH staining.

29. The method of embodiment 27, wherein the histological analysis on thin sections of the paraffin embedded homogenized sample is interpreted by a human.

30. The method of embodiment 27, wherein the histological analysis on thin sections of the paraffin embedded homogenized sample is quantified by an automated device.

31. The method of embodiment 29, wherein the interpretation produces at least one dataset.

32. The method of embodiment 30, wherein the quantification produces at least one dataset.

33. The method of embodiment 1, further comprising further processing at least a portion of the homogenate to generate cellular fragments.

34. The method of embodiment 32, wherein the processing of at least a portion of the homogenate is by physical, mechanical, chemical, or enzymatic methods.

35. The method of embodiment 33, wherein the cellular fragments are selected from the group consisting of nuclei, cellular membranes, and cellular organelles.

36. The method of embodiment 33, wherein at least a portion of the cellular fragments are affixed to at least one glass slide.

37. The method of embodiment 36, wherein the at least a portion of the cellular fragments affixed to at least one glass slide are subjected to histological analysis.

38. The method of embodiment 37, wherein the histological analysis is by H&E staining, IHC staining, ISH staining, or FISH staining.

39. The method of embodiment 36, wherein the histological analysis on at least a portion of the cellular fragments affixed to at least one glass slide is interpreted by a human.

40. The method of embodiment 36, wherein the histological analysis on at least a portion of the cellular fragments affixed to at least one glass slide is quantified by an automated device.

41. The method of embodiment 39, wherein the interpretation produces at least one dataset.

42. The method of embodiment 40, wherein the quantification produces at least one dataset.

43. The method of embodiment 33, wherein at least a portion of the cellular fragments is analyzed by flow cytometry, FACS, or particle analyzer.

44. The method of embodiment 43 wherein the analysis produces a data set.

45. The method of embodiment 33, further comprising purifying at least one cellular fragment from the at least a portion of the cellular fragments.

46. The method of embodiment 45 wherein the purifying is by FACS, affinity purification, size exclusion differential centrifugation, filtration, or electrophoresis.

47. The method of embodiment 45, further comprising isolating biomolecules from the purified at least one cellular fragment from the at least a portion of the cellular fragments.

48. The method of embodiment 47, further comprising analyzing the biomolecules from the purified at least one cellular fragment from the at least a portion of the cellular fragments.

49. The method of embodiment 48, wherein the analyzing comprises is PCR, mass spectrometry, next generation sequencing, or ELISA.

50. The method of embodiment 49, wherein the analysis produces at least one dataset.

51. The method of embodiment 1, further comprising further processing at least a portion of the homogenate to generate at least one disassociated cell.

52. The method of embodiment 51, wherein the processing of at least a portion of the homogenate is physical, mechanical, chemical, or enzymatic.

53. The method of embodiment 51, wherein the at least one disassociated cell is a normal cell, a cancer cell, or a bacterial cell.

54. The method of embodiment 51, wherein the at least one disassociated cell is affixed to at least one glass slide.

55. The method of embodiment 54, wherein the at least one disassociated cell affixed to at least one glass slide is subjected to histological analysis.

56. The method of embodiment 55, wherein the histological analysis is H&E staining, IHC staining, ISH staining, or FISH staining.

57. The method of embodiment 55, wherein the histological analysis on the at least one disassociated cell affixed to at least one glass slide is interpreted by a human.

58. The method of embodiment 55, wherein the histological analysis on the at least one disassociated cell affixed to at least one glass slide is quantified by an automated device.

59. The method of embodiment 57, wherein the interpretation produces at least one dataset.

60. The method of embodiment 58, wherein the quantification produces at least one dataset.

61. The method of embodiment 51, wherein the at least one disassociated cell is analyzed by flow cytometry, FACS, or particle analyzer.

62. The method of embodiment 61 wherein the analysis produces a data set.

63. The method of embodiment 51, further comprising purifying at least one cell from the at least one disassociated cell.

64. The method of embodiment 63 wherein the purifying is FACS, affinity purification, size exclusion differential centrifugation, filtration, or electrophoresis.

65. The method of embodiment 63, further comprising isolating biomolecules from the purified at least one cell from the at least one disassociated cell.

66. The method of embodiment 65, further comprising analyzing the biomolecules from the purified at least one cell from the at least one disassociated cell.

67. The method of embodiment 66, wherein the analyzing is PCR, mass spectrometry, next generation sequencing, or ELISA.

68. The method of embodiment 67, wherein the analysis produces at least one dataset.

69. The method of embodiment 63, wherein the purified at least one cell from the at least one disassociated cell is affixed to at least one glass slide.

70. The method of embodiment 69, wherein the purified at least one cell from the at least one disassociated cell affixed to at least one glass slide is subjected to histological analysis.

71. The method of embodiment 70, wherein the histological analysis is H&E staining, IHC staining, ISH staining, or FISH staining.

72. The method of embodiment 70, wherein the histological analysis on the purified at least one cell from the at least one disassociated cell affixed to at least one glass slide is interpreted by a human.

73. The method of embodiment 70, wherein the histological analysis on the purified at least one cell from the at least one disassociated cell affixed to at least one glass slide is quantified by an automated device.

74. The method of embodiment 72, wherein the interpretation produces at least one dataset.

75. The method of embodiment 73, wherein the quantification produces at least one dataset.

76. The method of any one of embodiments 24, 31, 32, 41, 42, 44, 50, 59, 60, 62, 68, 74 and 75, further comprising analyzing the at least one dataset from the at least one subject.

77. The method of embodiment 76, wherein the analyzing comprises the determination of a biomarker diversity or phenotypic diversity data set.

78. The method of embodiment 76, wherein the analyzing comprises the determination of the prevalence of at least one distinct biomarker or phenotype.

79. The method of embodiment 76, wherein the analyzing comprises the determination of at least one clinical decision.

80. The method of embodiment 79, wherein the clinical decision is determining disease prognosis, predicting recurrence of disease, predicting targets of therapy of disease, inclusion of subjects of clinical trials, or therapeutic treatment strategy for at least one subject.

2. The method of claim 1, further comprising further processing at least a portion of the representative sample to generate a single cell solution, and wherein at least a portion of the single cell solution is analyzed by flow cytometry, fluorescence-activated cell sorter (FACS), or particle analyzer.

3. The method of claim 1, further comprising further processing at least a portion of the representative sample to generate at least one disassociated cell, wherein the at least one disassociated cell is a normal cell, a cancer cell, or a bacterial cell, and wherein the at least one disassociated cell is affixed to at least one glass slide.

4. The method of claim 3, wherein the at least one disassociated cell affixed to at least one glass slide is subjected to histological analysis, wherein the histological analysis is hematoxylin and eosin ("H&E") staining, immunohistochemical ("IHC") staining, in situ hybridization ("ISH") staining, or fluorescent in situ hybridization ("FISH") staining.

5. The method of claim 1, wherein cells within the representative sample are intact.

6. The method of claim 1, wherein the obtained surgical resection tissue sample is at least 2 cm in diameter at its widest point.

7. The method of claim 1, wherein the obtained surgical resection tissue sample is at least 10 cm in diameter at its widest point.

8. The method of claim 1, wherein the obtained surgical resection tissue samples comprises at least 1 trillion cells.

9. The method of claim 1, wherein the obtained surgical resection tissue sample has a volume of at least 10 cm$^3$.

What is claimed is:

1. A method for preparing a representative sample for analysis, comprising:
   a) obtaining a surgical resection tissue sample from a tumor of a subject, wherein the obtained surgical resection tissue sample is at least 1 cm in diameter at its widest point, and wherein the obtained surgical resection tissue sample is fixed; and wherein the obtained surgical resection tissue sample is not derived from a formalin-fixed paraffin-embedded sample; and
   b) mechanically blending the obtained surgical resection tissue sample to provide the representative sample, wherein any heterogeneity of cells within the obtained surgical resection tissue sample is substantially homogeneously distributed within the representative sample, and wherein any aliquot removed from the representative sample comprises one or more populations of subclones at a proportion at which they existed within the obtained surgical resection tissue sample.

10. The method of claim 1, wherein the obtained surgical resection tissue sample comprises an entire intact solid tumor.

11. The method of claim 1, further comprising (c) extracting genomic material from at least a portion of the representative sample; and (d) sequencing the extracted genomic material.

12. The method of claim 11, wherein the sequencing comprises next generation sequencing.

13. The method of claim 11, further comprising identifying one or more subclones within the sequenced genomic material.

14. The method of claim 13, wherein the one or more identified subclones are one or more low prevalence subclones.

15. The method of claim 14, wherein the one or more low prevalence subclones have a prevalence of 0.0001% to 0.00001% within the sequenced genomic material.

16. The method of claim 11, further comprising determining a relative frequency of one or more subclones in the sequenced genomic material.

17. The method of claim 1, further comprising staining at least a portion of the representative sample for the presence of one or more biomarkers, and quantifying a number of tumor cells and a number of immune cells within the at least the portion of the representative sample.

18. The method of claim 1, further comprising (i) isolating intact cells from at least a portion of the representative sample; (ii) staining at least a portion of the isolated intact cells; and (iii) sorting the stained isolated intact cells into two or more populations of stained isolated intact cells.

19. The method of claim 18, wherein the isolated intact cells are immunoenzymatically stained for the presence of one or more biomarkers.

20. The method of claim 18, further comprising extracting genomic material from at least one of the two or more populations of stained isolated intact cells, and sequencing the extracted genomic material.

21. The method of claim 1, further comprising detecting one or more neoantigens within at least a portion of the representative sample.

22. A method of sequencing genomic material, comprising:
a) obtaining a residual surgical tumor sample having a diameter of at least 1 cm at its widest point from a human subject, wherein the residual surgical tumor material is fixed but not embedded within paraffin, and wherein the residual surgical tumor material has not been deparaffinized;
b) mechanically blending the obtained residual surgical tumor material to provide representative sample, wherein any subpopulations of cells that were originally spatially segregated within the residual surgical tumor material are homogeneously distributed throughout the representative sample, and wherein any aliquot removed from the representative sample comprises one or more populations of subclones at a proportion at which they existed within the obtained residual surgical tumor sample;
c) extracting the genomic material from at least a first aliquot of the representative homogenized sample; and
d) sequencing the extracted genomic material.

23. The method of claim 22, further comprising (i) isolating intact cells from at least a portion of the representative sample; (ii) staining at least a portion of the isolated intact cells; and (iii) sorting the stained isolated intact cells into two or more populations of stained isolated intact cells.

24. The method of claim 22, wherein the sequencing comprises next generation sequencing.

25. The method of claim 22, further comprising identifying one or more subclones within the sequenced genomic material.

26. The method of claim 25, wherein the one or more identified subclones are one or more low prevalence subclones.

27. The method of claim 26, wherein the one or more low prevalence subclones have a prevalence of 0.0001% to 0.00001% within the sequenced genomic material.

28. The method of claim 22, further comprising determining a relative frequency of one or more subclones in the sequenced genomic material.

29. The method of claim 22, wherein the obtained residual surgical tumor sample is a specimen that would have otherwise been destroyed.

30. The method of claim 22, wherein the entire obtained residual surgical tumor sample is fixed in a fixative agent fixative, and wherein all of the fixed but not paraffin embedded residual surgical sample is homogenized.

31. The method of claim 22, wherein the obtained residual surgical tumor sample is not derived from tissue specimens used for diagnostic purposes.

32. The method of claim 22, wherein the obtained residual surgical tumor sample is not derived from tissue specimens used TNM staging.

33. A method for preparing a representative sample for analysis, comprising:
a) obtaining a fresh residual surgical sample having a diameter of at least 1 cm at its widest point;
b) preparing a fixed but not paraffin embedded residual surgical sample for homogenization, wherein the preparation consists essentially of contacting the obtained fresh residual surgical material with a fixative; and
c) mechanically blending the prepared fixed but not paraffin embedded residual surgical sample to provide the representative sample, wherein any heterogeneity of cells within the prepared fixed residual surgical sample is substantially homogeneously distributed within the representative sample, and wherein any aliquot removed from the representative sample comprises one or more populations of subclones at a proportion at which they existed within the obtained fresh residual surgical sample.

34. The method of claim 33, further comprising (d) extracting genomic material from at least a portion of the representative sample; and (e) sequencing the extracted genomic material.

35. The method of claim 34, wherein the sequencing comprises next generation sequencing.

36. The method of claim 34, further comprising identifying one or more subclones within the sequenced genomic material.

37. The method of claim 36, wherein the one or more identified subclones are one or more low prevalence subclones.

38. The method of claim 37, wherein the one or more low prevalence subclones have a prevalence of 0.0001% to 0.00001% within the sequenced genomic material.

39. The method of claim 35, further comprising determining a relative frequency of one or more subclones in the sequenced genomic material.

40. The method of claim 33, wherein the obtained fresh residual surgical sample is a specimen that would have otherwise been destroyed.

41. The method of claim 33, wherein the entire obtained fresh residual surgical sample is fixed in a fixative agent fixative, and wherein all of the fixed but not paraffin embedded residual surgical sample is homogenized.

42. The method of claim 33, wherein the obtained fresh residual surgical sample is not derived from tissue specimens used for diagnostic purposes.

43. The method of claim 33, wherein the obtained fresh residual surgical sample is not derived from tissue specimens used TNM staging.

* * * * *

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Synthetic: Flow-Fish probe

<400> SEQUENCE: 1
ccctaaccct aaccctaa                                             18